US011584756B2

(12) United States Patent
Pham et al.

(10) Patent No.: US 11,584,756 B2
(45) Date of Patent: Feb. 21, 2023

(54) HETEROCYCLIC COMPOUNDS AS BET INHIBITORS

(71) Applicant: NUVATION BIO INC., New York, NY (US)

(72) Inventors: Son Minh Pham, San Francisco, CA (US); Sarvajit Chakravarty, Edmond, OK (US); Jayakanth Kankanala, Plymouth, MN (US); Jiyun Chen, Moraga, CA (US); Chris P. Miller, San Mateo, CA (US); Jeremy D. Pettigrew, Vancouver (CA); Anjan Kumar Nayak, Uttar Pradesh (IN); Anup Barde, Uttar Pradesh (IN)

(73) Assignee: NUVATION BIO INC., New York, NY (US)

( * ) Notice: Subject to any disclaimer, the term of this patent is extended or adjusted under 35 U.S.C. 154(b) by 338 days.

(21) Appl. No.: 16/918,997

(22) Filed: Jul. 1, 2020

(65) Prior Publication Data

US 2021/0002293 A1   Jan. 7, 2021

Related U.S. Application Data

(60) Provisional application No. 62/870,020, filed on Jul. 2, 2019, provisional application No. 63/017,547, filed on Apr. 29, 2020.

(51) Int. Cl.
C07D 495/04   (2006.01)

(52) U.S. Cl.
CPC .................. *C07D 495/04* (2013.01)

(58) Field of Classification Search
CPC .................................. C07D 495/04
USPC ....................................... 514/301
See application file for complete search history.

(56) References Cited

U.S. PATENT DOCUMENTS

| 9,034,900 | B2 * | 5/2015 | Bennett | C07D 471/04 |
| | | | | 546/141 |
| 9,050,346 | B2 | 6/2015 | Hasvold | |
| 9,115,114 | B2 | 8/2015 | Bennett | |
| 9,663,533 | B2 | 5/2017 | Amans et al. | |
| 10,034,881 | B2 | 7/2018 | Amans | |
| 10,035,800 | B2 | 7/2018 | Fidanze | |
| 10,053,454 | B2 | 8/2018 | Poss | |
| 10,059,699 | B2 | 8/2018 | Atkinson | |
| 10,077,259 | B2 | 9/2018 | Samajdar | |
| 10,253,044 | B2 | 4/2019 | Wang | |
| 10,292,968 | B2 | 5/2019 | Brown | |
| 10,307,407 | B2 | 6/2019 | Wang | |
| 10,328,074 | B2 | 6/2019 | Engelhardt | |
| 10,336,697 | B2 | 7/2019 | Ujjinamatada | |
| 10,336,722 | B2 | 7/2019 | Bair | |
| 10,363,257 | B2 | 7/2019 | Quinn | |
| 10,370,356 | B2 | 8/2019 | Atkinson | |
| 10,370,374 | B2 | 8/2019 | Ibrahim | |
| 10,377,769 | B2 | 8/2019 | Bair | |
| 10,391,175 | B2 | 8/2019 | Wang | |
| 10,633,379 | B2 | 4/2020 | Hasvold et al. | |
| 10,807,982 | B2 | 10/2020 | Bennett et al. | |
| 10,941,160 | B2 | 3/2021 | Boloor | |
| 2004/0067955 | A1 | 4/2004 | Tabuchi | |
| 2009/0093456 | A1 | 4/2009 | Arnold | |
| 2016/0016966 | A1 | 1/2016 | Amans et al. | |
| 2016/0318916 | A1 | 11/2016 | Tanaka | |
| 2017/0029418 | A1 | 2/2017 | Kawasaki | |
| 2017/0158709 | A1 | 6/2017 | Boloor | |
| 2017/0298040 | A1 | 10/2017 | Bennett et al. | |
| 2018/0273547 | A1 | 9/2018 | Boloor | |
| 2019/0247509 | A1 | 8/2019 | Buckley et al. | |
| 2019/0263799 | A1 | 8/2019 | Brown | |
| 2020/0140459 | A1 | 5/2020 | Pham | |
| 2022/0213122 | A1 | 7/2022 | Pham et al. | |

FOREIGN PATENT DOCUMENTS

| AU | 2019205984 A1 | 8/2019 |
| CN | 110041253 A | 7/2019 |
| EP | 0751132 A1 | 1/1997 |
| EP | 3230277 B1 | 9/2019 |
| WO | 2009054952 A2 | 4/2009 |
| WO | 2009054952 A3 | 4/2009 |
| WO | 2013097052 A1 | 7/2013 |
| WO | 2013097601 A1 | 7/2013 |
| WO | 2014139324 A1 | 9/2014 |
| WO | 2014206150 A1 | 12/2014 |
| WO | 2014206345 A1 | 12/2014 |
| WO | 2015058160 A1 | 4/2015 |
| WO | 2017083431 A2 | 5/2017 |
| WO | 2017083431 A3 | 8/2017 |
| WO | 2017177955 A1 | 10/2017 |
| WO | 2017197056 A1 | 11/2017 |
| WO | 2018086604 A1 | 5/2018 |
| WO | 2018130174 A1 | 7/2018 |

(Continued)

OTHER PUBLICATIONS

Abedin, S.M. et al. (2016). "BET Inhibitors in the Treatment of Hematologic Malignancies: Current Insights and Future Prospects," OncoTargets and Therapy 9:5943-5953.

Alqahtani, A. et al. (2019, e-pub. January 29, 2019). "Bromodomain and Extra-Terminal Motif Inhibitors: A Review of Preclinical and Clinical Advances in Cancer Therapy," Future Science OA ISO372:1-19.

Andrieu, G. et al. (2016). "Clinical Trials for BET inhibitors Run Ahead of the Science," Drug Discovery Today: Technologies 19:45-50.

Asangani, I.A. et al. (Apr. 2016, e-pub. Jan. 20, 2016). "BET Bromodomain Inhibitors Enhance Efficacy and Disrupt Resistance to AR Antagonists in the Treatment of Prostate Cancer," Mo. Cancer Res. 14(4):324-331.

(Continued)

*Primary Examiner* — Niloofar Rahmani

(74) *Attorney, Agent, or Firm* — Morrison & Foerster LLP

(57) ABSTRACT

Novel bromodomain and extraterminal domain (BET) inhibitors and to therapeutic methods of treating conditions and diseases using these novel BET inhibitors are provided.

31 Claims, No Drawings

(56) References Cited

FOREIGN PATENT DOCUMENTS

| | | |
|---|---|---|
| WO | 2019120234 A2 | 6/2019 |
| WO | 2019141131 A1 | 7/2019 |
| WO | 2019120234 A3 | 8/2019 |
| WO | 2020020288 A1 | 1/2020 |
| WO | 2020063976 A1 | 4/2020 |
| WO | 2020092638 A1 | 5/2020 |
| WO | 2020160193 A2 | 8/2020 |
| WO | 2020160193 A3 | 9/2020 |
| WO | 2020187123 A1 | 9/2020 |
| WO | 2020253711 A1 | 12/2020 |
| WO | 2021222466 A1 | 11/2021 |

OTHER PUBLICATIONS

Asangani, I.A. et al. (Jun. 12, 2014). "Therapeutic Targeting of BET Bromodomain Proteins in Castration-Resistant Prostate Cancer," HHS Public Access Author Manuscript 510(7504):278-282, 44 pages.

Attwell, S. et al. (2015). "The Clinical Candidate ZEN-3694, a BET Bromodomain Inhibitor, is Efficacious in the Treatment of a Variety of Solid Tumor and Hematological Malignancies, Alone or in Combination With Several Standard of Care Therapies," Zenith Epigenetics, Poster, 1 page.

Attwell, S. et al. (Jul. 2016). "Abstract LB-207: Preclinical Characterization of ZEN-3694, a Novel BET Bromodomain Inhibitor Entering Phase I Studies For Metastatic Castration-Resistance Prostate Cancer (mCRPC)," Cancer Research, 4 pages.

Aitwell, S. et al. (Jul. 2016). "Abstract LB-207: Preclinical Characterization of ZEN-3694, a Novel BET Bromodomain Inhibitor Entering Phase I Studies for Metastatic Castration-Resistance Prostate Cancer (mCRPC)," Cancer Research, Poster, 1 page.

Banerjee, C. et al. (2012), "BET Bromodomain Inhibition as a Novel Strategy for Reactivation of HIV-1" J. Leukocyte Biol. 92:1147-1154.

Bates, J. et al. (2016). "Combination of the BET Inhibitors GS-5829 and a BCL2 Inhibitor Resulted in Broader Activity in DLBCL and MCL Cell Lines," Blood 128,5104, 7 pages.

Bernasconi, E. et al. (2017, e-pub. Jun. 27, 2017). "Preclinical Evaluation of the BET Bromodomain Inhibitor BAY 1238097 for the Treatment of Lymphoma," British Journal of Haematology 178:936-948.

Bhattacharya, S. et al. (Jul. 2018). "Bromodomain Inhibitors: What Does the Future Hold?" Clinical Advances in Hematology & Oncolocy 16(7):504-515.

Boi, M. et al. (Apr. 1, 2015, e-pub. Jan. 26, 2015). "The BET Bromodomain Inhibitor OTX015 Affects Pathogenetic Pathways in Preclinical B-Cell Tumor Models and Synergizes With Targeted Drugs," Clinical Cancer Research 21 (7):1628-1638.

Boi, M. et al. (Oct. 25, 2016). "Therapeutic Efficacy of the Bromodomain Inhibitor OTX015/MK-8628 in ALK-Positive Anaplastic Large Cell Lymphoma: An Alternative Modality to Overcome Resistant Phenotypes," Oncotarget 7 (48):79637-79653.

Bui, M.H. et al. (Jun. 1, 2017). "Preclinical Characterization of BET Family Bromodomain Inhibitor ABBV-075 Suggests Combination Therapeutic Strategies," Cancer Research 77(11):2976-2989.

Cai, T. et al. (Jul. 2018). "Abstract LB-261: Targeting BET Family Bromodomain With ABBV-075 and BCL-2 With Venetoclax (ABT-199) is Synergistic in Primary Acute Myeloid Leukemia Models," Cancer Research, 4 pages.

Carrà, G. et al. (2017). "BET Inhibitors in Chronic Lymphocytic Leukemia: JQ1 Synergizes With Venetoclax in Promoting Apoptosis," Blood 130:2542, 6 pages.

Chen, Y, et al. (Jun. 9, 2016, e-pub. Sep. 28, 2015). "Identification of an Orally Available Compound With Potent and Broad FLT3 Inhibition Activity," Oncogene 35:2971-2978, 17 pages.

Conery, A.R. et al. (2016, e-pub. Jan. 12, 2016). "Preclinical Anticancer Efficacy of BET Bromodomain Inhibitors is Determined by the Apoptotic Response," Cancer Research 76(6):1313-1319.

Da Costa, D. et al. (2013). "BET Inhibition as a Signal or Combined Therapeutic Approach in Primary Pediatric B-Precursor Acute Lymphoblastic Leukemia," Blood Cancer Journal 3:e126, 11 pages.

Dawson, M.A. et al. (Jun. 12, 2013). "Inhibition of BET Recruitment to Chromatin as an Effective Treatment for MLL-Fusion Leukemia," Europe PMC Funders Group 478(73701:529-533.

Delmore, J.E. et al. (Sep. 16, 2011). "BET Bromodomain Inhibition as a Therapeutic Strategy to Target c-Myc," Cell 146:904-917.

Denis, G.V. (Dec. 2010). "Bromodomain Coactivators in Cancer, Obesity, Type 2 Diabetes, and Inflammation," Discovery Medicine 10(55):489-499, 17 pages.

Derenzini, E. et al. (Aug. 21, 2018). "BET Inhibition-Induced GSK3β Feedback Enhances Lymphoma Vulnerability to PI3K Inhibitors," Cell Reports 24:2155-2166, 37 pages.

Doroshow, D.B. et al. (2017, e-pub. Jul. 21, 2017). "BET Inhibitors: A Novel Epigenetic Approach," Annals of Oncology 28:1776-1787.

Du, Z. et al., (2018). "Genome-Wide Transcriptional Analysis of BRD4-Regulated Genes and Pathways in Human Glioma U251 Cells," International Journal of Oncology 52:1415-1426.

Esteve-Arenys, A. et al. (2018, e-pub. Jan. 22, 2018). "The BET Bromodomain Inhibitor CPI203 Overcomes Resistance to ABT-199 (Venetoclax) by Downregulation of BFLL-1/A1 In in vitro and in vivo Models of MYC+/BCL2+ Double Hit Lymphoma," Oncogene 19 pages.

Faivre, E.J. et al. (Jul. 2018). "Abstract 4960: First-In-Class, Highly BDII-Selective BET Family Inhibitor ABBV-744 Displays Potent Anti-Tumor Activity in Androgen Receptor Positive Prostate Cancer Models and an Improved Tolerability Profile," Cancer Research, 4 pages.

Fidanze, S.D. et al. (2018, e-pub. Apr. 11, 2018). "Discovery and Optimization of Novel Constrained Pyrrolopyridone BET Family Inhibitors," Bioorganic & Medicinal Chemistry Letters 28:1804-1810.

Gaudio, E. et al. (Aug. 1, 2016). "Bromodomain Inhibitor OTX015 (MK-8628) Combined With Targeted Agents Shows Strong in vivo Antitumor Activity in Lymphoma," Oncotarget 7(36):58142-58147.

Gayle, S.S. et al. (2018, e-pub. Nov. 27, 2018). "Targeting BCL~xL Improves the Efficacy of Bromodomain and Extra-Terminal Protein Inhibitors in Triple-Negative Breast Cancer by Eliciting the Death of Senescent Cells," J. Biol Chem. 20 pages.

Gerlach, D. et al. (2018). "The Novel BET Bromodomain Inhibitor BI 894999 Represses Super-Enhancer-Associated Transcription and Synergizes With CDK9 Inhibition in AML," Oncogene 37:2687-2701.

Ghoshal, A. et al. (2016, e-pub. Feb. 29, 2016). "BET Inhibitors in Cancer Therapeutics: A Patent Review," Expert Opinion on Therapeutic Patents, 44 pages.

Gopalakrishnan, R. et al. (Apr. 7, 2016). "Immunomodulatory Drugs Target IKZF1-IRF4-MYC Axis in Primary Effusion Lymphoma in a Cereblon-Dependent Manner and Display Synergistic Cytotoxicity With BRD4 Inhibitors," HHS Public Access Author Manuscript 34(14):1797-1810.

Gosmini, R. et al. (2014). "The Discovery of I-BET726 (GSK1324726A), A Potent Tetrahydroquinoline ApoA1 Up-Regulator and Selective BET Bromodomain Inhibitor," J. of Medicinal Chemistry, 21 pages.

Greene, T.W. et al. (1999), Protective Groups in Organic Synthesis, 3rd edition, Wiley.

Guo, Y, et al. (Dec. 6, 2012). "SU11652 Inhibits Tyrosine Kinase Activity of FLT3 and Growth of MV-4-11 Cells," J Hematol Oncol 5:72, 6 pages, Hogg, S.J. et al. (Feb. 28, 2017). "BET-Bromodomain Inhibitors Engage the Host Immune System and Regulate Expression of the Immune Checkpoint Ligand PD-L1," Cell Reports 18:2162-2174.

Huang, B. et al. (Mar. 2009, e-pub. Dec. 22, 2008). "Brd4 Coactivates Transcriptional Activation of NF-κB Via Specific Binding to Acetylated RelA," Mol. Cell. Bioi. 29(5):1375-1387.

International Search Report and Written Opinion, dated Oct. 5, 2020, for PCT Application No. PCT/US2020/40566, filed Jul. 1, 2020, 12 pages.

(56) References Cited

OTHER PUBLICATIONS

Jang, M.K. et al. (Aug. 19, 2005). "The Bromodomain Protein Brd4 is a Positive Regulatory Component of P-TEFb and Stimulates RNA Polymerase II-Dependent Transcription," Mol. Cell 19(4):523-534.

Jauset, T. et al. (2018). "BET Inhibition is an Effective Approach Against KRAS-Driven PDAC and NSCLC," Oncotarget 9(27):18734-18746.

Jin, X. et al. (Aug. 16, 2018). "DUBS Promotes BET Inhibitor Resistance and Cancer Progression by Deubiquitinating BRD4," Molecular Cell 71:1-14.

Johnson-Farley, N. et al. (2014). "ABT-199, a BhS Mimetic That Specifically Targets Bcl-2, Enhances the Antitumor Activity of Chemotherapy, Bortezomib, and JQ1 in 'Double Hit' Lymphoma Cells," Leukemia & Lymphoma, 12 pages.

Karakashev, S. et al. (Dec. 19, 2017). "BET Bromodomain Inhibition Synergizes With PARP Inhibitor in Epithelial Ovarian Cancer," Cell Reports 21:3308-3405.

Kati, W. (Apr. 15, 2018). "ABBV-744: A Highly BDII-Selective BET Bromodomain Inhibitor," AACR 2018, 23 pages.

Kharenko, O. et al. "Discovery and Characterization of Covalent BET Bromodomain Inhibitors," Poster, 1 page, No Date.

Kharenko, O. et al. (2018). "Design and Characterization of Novel Covalent Bromodomain and Extra-Terminal Domain (BET) Inhibitors Targeting a Methionine," J. of Medicinal Chemistry, 44 pages.

Kim, S.R. et al. (2018). "BET Inhibition in Advanced Cutaneous T Cell Lymphoma is Synergistically Potentiated by BCL2 Inhibition or HDAC Inhibition," Oncotarget 9(49):29193-29207.

Lacasce, A.S. (Nov. 3, 2014). "Targeting Bromodomain Proteins in DLBCL," Hematologist 11(6):1-3.

Lam, L.T. et al. (2017, e-pub. May 3, 2017). "Vulnerability of Small-Cell Lung Cancer to Apoptosis Induced by the Combination of BET Bromodomain Proteins and BCL2 Inhibitors," Molecular Cancer Therapeutics 16(8):1-10.

Lasorsa, E. et al. (2015, e-pub, Dec. 10, 2015). "Mitochondrial Protection Impairs BET Bromodomain Inhibitor-Mediated Cell Death and Provides Rationale for Combination Therapeutic Strategies," Cell Death and Disease 6: e2014, 8 pages.

Liu, Z. et al. (2018, e-pub. Apr. 3, 2018). "Discovery of Potent and Selective BRD4 Inhibitors Capable of Blocking TLR3-Induced Acute Airway Inflammation," European Journal of Medicinal Chemistry 151:450-461.

Liu, Z. et al. (Feb. 14, 2017). "Drug Discovery Targeting Bromodomain-Containing Protein 4," J. of Medicinal Chemistry, 26 pages.

Lovén, J. et al. (Apr. 11, 2013). "Selective Inhibition of Tumor Oncogenes by Disruption of Super-Enhancers," Cell 153(2):320-334, 27 pages.

Lu, J. et al. (Jun. 18, 2015). "Hijacking the E3 Ubiquitin Ligase Cerebion to Efficiently Target BRD4," Chemistry & Biology 22:755-763.

Matzuk, M.M. et al. (Aug. 17, 2012). "Small-Molecule Inhibition of BRDT for Male Contraception," Cell 150 (4):673-684.

McDaniel, K.F. et al. (Sep. 26, 2017). "Discovery of N-(2,4-Difluorophenoxy)-3-(6-methyl-7-oxo-6,y-dihydro-1H-pryrrolo[2,3-c]pyridin-4-yl)phenyl_ethaneesulfonamide (ABBV-075/Miverbresib). A Potent and Orally Available Bromodomain and Extra terminal Domain (BET) Family Bromodomain Inhibitor," J. of Medicinal Chemistry 60:8369-8384.

Mensah, A.A. et al. (2018, e-pub. (Aug. 3, 2018), "Bromodomain and Extra-Terminal Domain Inhibition Modulates the Expression of Pathologically Relevant MictroRNAs in Diffuse Large B-Cell Lymphoma," J. of the European Hematology Association, 21 pages.

Mertz, J.A. et al. (Oct. 4, 2011). "Targeting MYC Dependence in Cancer by Inhibiting BET Bromodomains," PNAS 108(40): 16669-16674.

Middleton, S.A. et al. (2018, e-pub. Nov. 22, 2018). "BET Inhibition Improves NASH and Liver Fibrosis," Scientific Reports 8:17257, 13 pages.

Mottok, A. et al. (Jan. 1, 2015, e-puyb. Aug. 27, 2014). "Bromodomain Inhibition in Diffuse Large B-Cell Lymphoma-Giving MYC a Brake," Clinical Cancer Research 21(1):4-6, 4 pages.

Nicodeme, E. et al. (Dec. 23, 2010, e-pub. Nov. 10, 2010). "Suppression of Inflammation by a Synthetic Histone Mimic," Nature 468(7327):1119-1123, 13 pages.

Nueuvolution (2016). "NUE7770—ABET-BD1 Selective Chemical Probe With Potent Cellular and in vivo Anti-Inflammatory Activity," 14th Discovery on Target, 18 pages.

Peirs, S. et al. (2017). "Targeting BET Proteins Improves the Therapeutic Efficacy of BCL-2 Inhibition in T-Cell Acute Lymphoblastic Leukemia," University of Zurich, 36 pages.

PubChem 86591759 (Feb. 2, 2015) "2-Chloro-5-(1-isopropyl-6-oxo-1,6-dihydro-3-pyridazinyl)-6-phenyinicotinonitrile," 9 pages.

PubChem CID: 53245731 (Jul. 17, 2011). "-(4-Hydroxyphenyl)-Pyridin-4-Yl-5h-Thieno[3,2-C]pyrdin-4-One," 11 pages.

PubChem CID: 91668542 (Apr. 23, 2015). "7-(3,4-Dimethoxyphenyl_-5-methyl-2-(4-methylsuifonylpiperazine-1-carbonyl)thienol[3,2-c]pyridin-4-one," 11 pages.

Pérez-Salvia, M. et al. (2017). "Bromodomain Inhibitors and Cancer Therapy: From Structures to Applications," Epigenetics 12(5):323-339.

Ramadoss, M. et al. (Jan. 2018). "Targeting the Cancer Epigenome: Synergistic Therapy With Bromodomain Inhibitors," Drug Discovery Today 28(1)76-89.

Ramsey, H. et al. (Dec. 3, 2018). "4074—The BET Inhibitor INCB054329 Primes AML Ceils for Venetoclas-Inducted Apoptosis," 616 Acute Myeloid Leukemia: Novel Therapy, Excluding Transplantation: Post III Hematology Disease Topics & Pathways, 2 pages.

Remington's Pharmaceutical Sciences, Mack Publishing Company, Philadelphia, PA, 21th ed. (2000) TOC, 4 Pages.

Rhyssen, G.W. et al. (Jul. 23, 2018). "BRD4 Amplification Facilities an Oncogenic Gene Expression Program in High-Grade Serous Ovarian Cancer and Confers Sensitivity to BET Inhibitors," PLoS One 13(7):e0200826, 23 pages.

Shah, N. et al. (Sep. 11, 2017). "Regulation of the Glucocorticoid Receptor Via a BET-Dependent Enhancer Drives Antiandrogen Resistance in Prostate Cancer," eLife 6:e27861, 19 pages.

Shimamura, T. et al. (2013, e-pub. Sep. 17, 2013). "Efficacy of BET Bromodomain Inhibition in Kras-Mutant Non-Small Cell Lung Cancer," Clinical Cancer Research, 37 pages.

Stubbs, M. et al. (Jul. 2016). "Abstract 3780: Activity of the BET Inhibitor INCB054329 in Models of Lymphoma," Cancer Research, 4 pages.

Sun, B. et al. (Sep. 24, 2015, e-pub. Aug. 7, 2015). "Synergistic Activity of BET Protein Antagonist-Based Combinations in Mantle Cell Lymphoma Cells Sensitive or Resistant to Ibrutinib," Blood 126(13):1565-1574.

Sun, C. et al. (Mar. 12, 2018). BRD4 Inhibition is Synthetic Lethal With PARP Inhibitors Through the Induction of Homologous Recombination Deficiency,: Cancer Cell 33:401-416, 25 pages.

Takimoto-Shimomura, T. et al. (2018, e-pub. Jun. 21, 2018). "Dual Targeting of Bromodomain-Containing 4 by AZD5153 and BCL2 by AZD4320 Against B-Cell Lymphomas Concomitantly Overexpressing c-MYC and BCL2," Investigational New Drugs, 13 pages.

Tan, Y. et al. (2018). "Inhibition of BRD4 Suppresses Tumor Growth in Prostate Cancer Via the Enhancement of FOXO1 Expression," International Journal of Oncology 53:2503-2517.

Taniguchi, Y. (2016). "The Bromodomain and Extra-Terminal Domain (BET) Family: Functional Anatomy of BET Paralogous Proteins," International J. of Molecular Sciences 17:1849, 24 pages.

Tarantelli, C. et al. (2018). "BET Bromodomain Inhibitor Birabresib in Mantle Cell Lymphoma: in vivo Activity and Identification of Novel Combinations to Overcome Adaptive Resistance," BMJ 3:e000387, 7 pages.

Tontsch-Grunt, U. et al. (2018). "Synergistic Activity of BET Inhibitor BI 894999 With PLK Inhibitor Volasertib in AML in vitro and in vivo," Cancer Letters 421:112-120.

Trabucco, S. E. et al. (2014, e-pub. Jul. 9, 2014). "Inhibition of Bromodomain Proteins for the Treatment of Human Diffuse Large B-Cell Lymphoma," Clinical Cancer Research 21(1):113-122.

(56) References Cited

OTHER PUBLICATIONS

Tsujikawa, L. et al. (Apr. 2017). "Abstract LB-038: Preclinical Development and Clinical Validation of a Whole Blood Pharmacodynamic Marker Assay for the BET Bromodomain Inhibitor ZEN-3694 in Metastatic Castration-Resistant Prostate Cancer (mCRPC) Patients," Cancer Research, Poster, 2 pages.

Urbanucci, A. et al. (2018, e-pub. Jun. 15, 2017). "Bromodomain-Containing Proteins in Prostate Cancer," Molecular and Cellular Endocrinology 462:31-40.

Urbanucci, A. et al. (Jun. 6, 2017). "Androgen Receptor Deregulation Drives Bromodomain-Mediated Chromatin Alterations in Prostate Cancer," Cell Reports 19:2045-2049.

Villar-Prados, A. (2018). "Identifying Molecular Targets and Validating Novel Therapies for Ovarian Cancer," UT GSBS Dissertations and Theses (Open Access) 840, 127 pages.

Vis, D.J. et al. (May 2016, e-pub. May 16, 2016). "Multilevel Models Improve Precision and Speed of IC50 Estimates," Pharmacogenomics 17(7):691-700, 14 pages.

Wahlestedt, C. et al. (Sep. 20, 2018). "PLX51107, A Promising Novel Bromodomain and Extra-Terminal Inhibitor in Chronic Lymphoid Leukemia Treatment," Precis. Cancer Med. 8:458-477.

Welti, J. et al. (2018, e-pub. Mar. 19, 2018). "Targeting Bromodomain and Extra-Terminal (BET) Family Proteins in Castration-Resistant Prostate Cancer (CRPC)," Clinical Cancer Research 24(13):3149-3162.

Wyce, A. et al. (2018). "MEK Inhibitors Overcome Resistance to BET Inhibition Across a Number of Solid and Hematologic Cancers," Oncogenesis 7:35, 12 pages.

Yang, L. et al. (Jul. 26, 2017). "Repression of BET Activity Sensitizes Homologous Recombination-Proficient Cancers to PARP Inhibition," Science Translational Medicine 9:eaal1645, 13 pages.

Zenith Epigenetics (Feb. 2019). "Zenith Epigenetic: Advanced Epigenetic Technology," 24 pages.

Zhang, G. et al. (Aug. 17, 2012, e-pub. May 29, 2012). "Down-Regulation of NF-κB Transcriptional Activity in HIV-Associated Kidney Disease by BRD4 Inhibition," J. Biol. Chem. 287(34):28840-28851.

Zuber, J. et al. (2011). "RNAi Screen Identifies Brdr4 as a Therapeutic Target in Acute Myeioid Leukemia," Nature, 8 pages.

Extended European Search Report, dated Jun. 15, 2022, for European Patent Application No. 19879449.7, 8 pages.

International Preliminary Report on Patentability, dated Dec. 28, 2021, for PCT Application No. PCT/US2020/40566, filed Jul. 1, 2020, 5 pages.

International Preliminary Report on Patentability, dated Apr. 27, 2021, and Written Opinion, dated Feb. 10, 2020, for PCT Application No. PCT/US2019/58952, filed Oct. 30, 2019, 7 pages.

International Search Report and Written Opinion, dated Feb. 10, 2020, for PCT Application No. PCT/US2019/58952, filed Oct. 30, 2019, 12 pages.

International Search Report and Written Opinion, dated Sep. 8, 2021, for PCT Application No. PCT/US2021/29738, filed Apr. 28, 2021, 11 pages.

International Preliminary Report on Patentability, dated Oct. 27, 2022, for PCT Application No. PCT/US2021/29738, filed Apr. 28, 2021, 7 pages.

\* cited by examiner

HETEROCYCLIC COMPOUNDS AS BET INHIBITORS

CROSS REFERENCE TO RELATED APPLICATIONS

This application claims priority to U.S. Provisional Application No. 62/870,020, filed Jul. 2, 2019, and U.S. Provisional Application No. 63/017,547, filed Apr. 29, 2020, each of which is incorporated herein by reference in its entirety.

FIELD OF THE INVENTION

The present invention relates to novel bromodomain and extraterminal domain (BET) inhibitors and to therapeutic methods of treating conditions and diseases using these novel BET inhibitors.

BACKGROUND OF THE INVENTION

Epigenetic dysregulation has a crucial role in driving aberrant gene expressions leading to various types of cancers. Many components involved in epigenetic regulation have been attractive targets for therapeutic interventions. Among them, the bromodomain and extra-terminal (BET) family of proteins attracted much attention in recent years. The BET family proteins include BRD2, BRD3, BRD4, and the testis-specific BRDT. Via their bromodomains (BRDs), they bind with a high affinity to acetylation motifs, including acetylated histones in chromatin, thereby regulating gene transcription. The genes regulated by BET family proteins include many important oncogenes responsible for cell survival and cell cycle progression.

BET proteins are emerging targets in cancer, directly regulating the expression of oncogenes in hematological and solid tumors. BRD4, in addition to occupying gene promoters, has a strong preference for enhancers and super-enhancers in key driver genes such as c-MYC (Loven et al, Cell 2013; 153(2):320-34). BET family proteins have also been implicated in mediating acute inflammatory responses through the canonical NF-KB pathway (Huang et al., Mol. Cell. Biol. 29: 1375-1387 (2009)) resulting in the upregulation of genes associated with the production of cytokines (Nicodeme et al., Nature 468: 1119-1123, (2010)). In addition, bromodomain function has been implicated in kidney disease (Zhang, et al., J. Biol. Chem. 287: 28840-28851 (2012)). BRD2 function has also been linked to a predisposition for dyslipidemia or improper regulation of adipogenesis, elevated inflammatory profiles and increased susceptibility to autoimmune diseases (Denis, Discovery Medicine 10: 489-499 (2010)). The human immunodeficiency virus utilizes BRD4 to initiate transcription of viral RNA from stably integrated viral DNA (Jang et al., Mol. Cell, 19: 523-534 (2005)). BET bromodomain inhibitors have also been shown to reactivate HIV transcription in models of latent T cell infection and latent monocyte infection (Banerjee, et al., J. Leukocyte Biol, doi: 10.1189/jlb.0312165). BRDT has an important role in spermatogenesis (Matzuk, et al., Cell 150: 673-684 (2012)).

Due to this potential as an epigenetic target, a number of small molecule compounds that inhibit the function of BET family proteins have been developed, and many of them have demonstrated promising anti-cancer activities with both solid and hematologic malignancies in preclinical studies. This has led to several early-phase clinical trials. Included among these are RO6870810 (formerly TEN-010), ZEN003694, BMS-986158, CPI-0610, I-BET762, OTX015, FT-1101, INCB054329, PLX51107, GS-5829, and ABBV-075. While these efforts are promising, there is need for better selectivity and improved durability of BET inhibitors that provide enhanced efficacy while reducing toxicity related to off-target effects. The present invention relates to novel BET inhibitors.

SUMMARY OF THE INVENTION

In one aspect, provided is a compound of Formula (J):

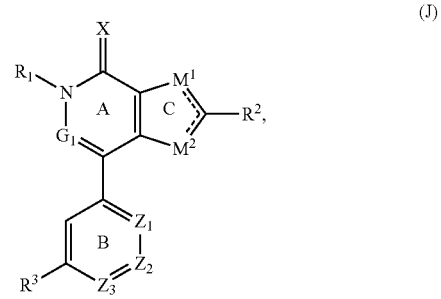

(J)

or a tautomer or isomer thereof, or a pharmaceutically acceptable salt of any of the foregoing, wherein $=\!=\!=\!=$, X, $G_1$, $R^1$, $R^2$, $R^3$, $M^1$, $M^2$, $Z_1$, $Z_2$, and $Z_3$ are defined herein.

In some embodiments, the compounds provided herein are BET inhibitors that selectively target and covalently bind the protein of interest. In some embodiments, the BET inhibitors comprise a compound of the Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a tautomer or isomer thereof, or a pharmaceutically acceptable salt of any of the foregoing.

In some embodiments, provided herein is a pharmaceutical composition comprising a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a tautomer or isomer thereof, or a pharmaceutically acceptable salt of any of the foregoing, in combination with at least one pharmaceutically acceptable carrier, diluent, or excipient.

In some embodiments, use of a compound having the structure of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a tautomer or isomer thereof, or a pharmaceutically acceptable salt of any of the foregoing, for the manufacture of a medicament is provided.

In some embodiments, provided herein is a method of treating a disease mediated by inhibition of the BET family of proteins in an individual. In some embodiments, such method comprises administering to the subject an effective amount of a compound having the structure of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a tautomer or isomer thereof, or a pharmaceutically acceptable salt of any of the foregoing, or a pharmaceutical composition comprising the same, at a frequency and for duration sufficient to provide a beneficial effect to the subject.

In some embodiments, provided herein are methods for treating or preventing disorders that are ameliorated by inhibition of BET. In some embodiments, such methods comprise of administering to the subject a therapeutically effective amount of a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a tautomer or isomer thereof, or a pharmaceutically acceptable salt of any of the foregoing, alone, or in combination with a pharmaceutically acceptable carrier.

In another aspect, the methods are directed to methods of treating or preventing an inflammatory disease or cancer or AIDS. In some embodiments, such methods comprise of administering to the subject a therapeutically effective amount of a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a tautomer or isomer thereof, or a pharmaceutically acceptable salt of any of the foregoing, alone, or in combination with a pharmaceutically acceptable carrier.

In another aspect, provided herein is the use of a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a tautomer or isomer thereof, or a pharmaceutically acceptable salt of any of the foregoing, alone or in combination with a second active pharmaceutical agent, in the manufacture of a medicament for treating or preventing conditions and disorders disclosed herein, with or without a pharmaceutically acceptable carrier.

In another aspect, a method of synthesis is provided for a compound having the structure of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a tautomer or isomer thereof, or a pharmaceutically acceptable salt of any of the foregoing, as detailed herein.

DETAILED DESCRIPTION OF THE INVENTION

Definitions

"Alkyl" refers to and includes saturated linear and branched univalent hydrocarbon structures and combination thereof, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_{20}$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of alkyl include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkenyl" as used herein refers to an unsaturated linear or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). The alkenyl group may be in "cis" or "trans" configurations, or alternatively in "E" or "Z" configurations. Particular alkenyl groups are those having 2 to 20 carbon atoms (a "$C_2$-$C_{20}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

"Alkylene" as used herein refers to the same residues as alkyl but having bivalency. Particular alkylene groups are those having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), butylene (—$CH_2CH_2CH_2CH_2$—), and the like.

"Alkynyl" as used herein refers to an unsaturated linear or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Aryl" refers to and includes polyunsaturated aromatic hydrocarbon groups. Aryl may contain additional fused rings (e.g., from 1 to 3 rings), including additionally fused aryl, heteroaryl, cycloalkyl, and/or heterocyclyl rings. In one variation, the aryl group contains from 6 to 14 annular carbon atoms. Examples of aryl groups include, but are not limited to, phenyl, naphthyl, biphenyl, and the like.

"Carbonyl" refers to the group C=O.

"Cycloalkyl" refers to and includes cyclic univalent hydrocarbon structures, which may be fully saturated, mono- or polyunsaturated, but which are non-aromatic, having the number of carbon atoms designated (e.g., $C_1$-$C_{10}$ means one to ten carbons). Cycloalkyl can consist of one ring, such as cyclohexyl, or multiple rings, such as adamantyl, but excludes aryl groups. A cycloalkyl comprising more than one ring may be fused, spiro or bridged, or combinations thereof. A preferred cycloalkyl is a cyclic hydrocarbon having from 3 to 13 annular carbon atoms. A more preferred cycloalkyl is a cyclic hydrocarbon having from 3 to 8 annular carbon atoms (a "$C_3$-$C_8$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

"Halo" or "halogen" refers to elements of the Group 17 series having atomic number 9 to 85. Preferred halo groups include fluoro, chloro, bromo and iodo. Where a residue is substituted by more than one halogen, it may be referred to by using a prefix corresponding to the number of halogen moieties attached, e.g., dihaloaryl, dihaloalkyl, trihaloaryl etc. refer to aryl and alkyl substituted by two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or at an annular heteroatom. Heteroaryl may contain additional fused rings (e.g., from 1 to 3 rings), including additionally fused aryl, heteroaryl, cycloalkyl, and/or heterocyclyl rings. Examples of heteroaryl groups include, but are not limited to, pyridyl, pyrimidyl, pyridazinyl, thiophenyl, furanyl, thiazolyl, pyrrolyl, pyrazolyl, oxazolyl, isooxazolyl, imidazolyl, quinolyl, isoquinolyl, benzimidazolyl, benzopyrazolyl, benzotriazolyl, indole, benzothiazyl, benzoxazolyl, benzisoxazolyl, imidazopyridinyl and the like.

"Heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl or heteroaryl. Examples of heterocyclyl groups include, but are not limited to, tetrahydropyranyl, dihydropyranyl, piperidinyl, piperazinyl, pyrrolidinyl, thiazolinyl, thiazolidinyl, tetrahydrofuranyl, dihydrooxazolyl, dihydroisoxazolyl, dioxolanyl, morpholinyl, dioxanyl, tetrahydrothiophenyl, and the like.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 2 to 5, 3 to 5, 2 to 3, 2 to 4, 3 to 4, 1 to 3, 1 to 4 or 1 to 5 substituents.

Term "BET" refers to bromodomain and extraterminal domain family.

As used herein "BRD" refers to one or more bromodomain extraterminal domain family proteins (BRD2, BRD3, BRD4, and BRDT).

"Disease" specifically includes any unhealthy condition of an animal or part thereof. "Optional" or "optionally" means that the subsequently described event or circumstance may or may not occur, and that the description includes instances where the event or circumstance occurs and instances in which it does not.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary-butylacetic acid, lauryl sulfuric acid, gluconic acid, glutamic acid, hydroxynaphthoic acid, salicylic acid, stearic acid, muconic acid, and the like.

In addition, pharmaceutically acceptable salts may be formed when an acidic proton present is capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Therapeutically effective amount" means that amount which, when administered to an animal for treating a disease, is sufficient to affect such treatment for the disease.

"Treatment" or "treating" is an approach for obtaining beneficial or desired results including clinical results. For purposes of this disclosure, beneficial or desired results include, but are not limited to, one or more of the following: decreasing one or more symptoms resulting from the disease or disorder, diminishing the extent of the disease or disorder, stabilizing the disease or disorder (e.g., preventing or delaying the worsening of the disease or disorder), delaying the occurrence or recurrence of the disease or disorder, delaying or slowing the progression of the disease or disorder, ameliorating the disease or disorder state, providing a remission (whether partial or total) of the disease or disorder, decreasing the dose of one or more other medications required to treat the disease or disorder, enhancing the effect of another medication used to treat the disease or disorder, delaying the progression of the disease or disorder, increasing the quality of life, and/or prolonging survival of a patient. Also encompassed by "treatment" is a reduction of pathological consequence of the disease or disorder. The methods of the disclosure contemplate any one or more of these aspects of treatment.

Compounds that have identical molecular formulae but differ in the nature or sequence of bonding of their atoms or in the arrangement of their atoms in space are termed "isomers." Isomers that differ in the nature or sequence of bonding of their atoms are termed "constitutional isomers." Isomers that differ only in the arrangement of their atoms in space are termed "stereoisomers." Stereoisomers that are not mirror images of one another are termed "diasteromers" and stereoisomers that are mirror images are termed "enantiomers" or sometimes "optical isomers." Stereoisomers that are superimposable upon their mirror images are termed "achiral" and those not superimposable are termed "chiral." A carbon atom bonded to four different groups is termed a "chiral center" or alternatively an "asymmetric carbon."

When a compound has a chiral center, a pair of enantiomers of opposite chirality is possible. An enantiomer can be characterized by the absolute configuration of its chiral center and described by the R- and S-sequencing rules of Cahn and Prelog (i.e., as (R)- and (S)-isomers) or by the manner in which the molecule rotates the plane of polarized light and designated as dextrorotatory or levorotatory (i.e., as (+)- and (−)-isomers, respectively). A chiral compound can exist as either individual enantiomer or as a mixture thereof. A mixture containing equal proportions of the enantiomers is termed a "racemic mixture" or "racemate" and may be described as the (RS)- or (±)-mixture thereof. Unless indicated otherwise, the description or naming of a particular compound in the specification and claims is intended to include both individual enantiomers and mixtures, racemic or otherwise, thereof. Conventions for stereochemical nomenclature, methods for the determination of stereochemistry and the separation of stereoisomers are well-known in the art (see discussion in Chapter 4 of "Advanced Organic Chemistry", 3rd edition March, Jerry, John Wiley and Sons, New York, 1985).

Compounds

In some embodiments, provided is a compound of Formula (J):

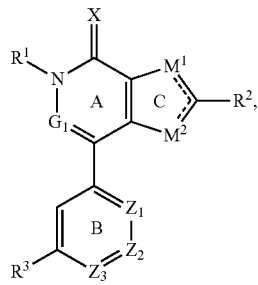

(J)

or a tautomer or isomer thereof, or a pharmaceutically acceptable salt of any of the foregoing, wherein:

each ==== is independently a single bond or double bond;

X is O or S;

$R^1$ is hydrogen, $C_1$-$C_3$ alkyl, —($C_1$-$C_3$ alkylene)OH, $C_1$-$C_3$ haloalkyl, or $C_3$-$C_4$ cycloalkyl;

$G_1$ is $CR^a$ or N, wherein:
$R^a$ is hydrogen, halogen, or $C_1$-$C_4$ alkyl;

$Z_1$ is C—$W_1$—$R^c$; wherein:
each $W_1$ is independently —O— or —$NR^{w1}$—, wherein:
$R^{w1}$ is hydrogen, $C_3$-$C_6$ cycloalkyl, or $C_1$-$C_4$ alkyl optionally substituted by oxo, —OH, or halogen, and
$R^c$ is independently $C_3$-$C_6$ cycloalkyl, 4- to 6-membered heterocyclyl, $C_6$-$C_{14}$ aryl, or 5- or 6-membered heteroaryl, each of which is independently optionally substituted by $R^{c1}$, wherein each $R^{c1}$ is independently halogen, $C_1$-$C_4$ alkyl, $C_3$-$C_6$ cycloalkyl, 3- to 6-membered heterocyclyl, cyano, oxo, $C_1$-$C_4$ alkoxy, $C_1$-$C_4$ haloalkoxy, $C_1$-$C_4$ haloalkyl, —$OR^{10}$, —$NR^{10}R^{11}$, —$C(O)NR^{10}R^{11}$, —$NR^{10}C(O)R^{11}$, —$S(O)_2R^{10}$, —$NR^{10}S(O)_2R^{11}$, or —$S(O)_2NR^{10}R^{11}$;

$Z_2$ is C—$W_2$—$R^d$ or N, wherein:
$W_2$ is —O—, —$NR^{w2}$—, or a bond, wherein:
$R^{w2}$ is hydrogen, $C_3$-$C_6$ cycloalkyl, or $C_1$-$C_4$ alkyl optionally substituted by oxo, —OH, or halogen, and
$R^d$ is independently hydrogen, halogen, cyano, 3- to 6-membered heterocyclyl, or $C_1$-$C_4$ alkyl;

$Z_3$ is C—$R^e$ or N, wherein:
$R^e$ is independently hydrogen, cyano, 3- to 6-membered heterocyclyl, or $C_1$-$C_4$ alkyl;

$M^1$ is S or $CR^{1a}$;

$M^2$ is S or $CR^{2a}$, provided that
(1) when $M^1$ is S, then the ==== adjacent to $M^1$ is a single bond and the ==== adjacent to $M^2$ is a double bond, (2) when $M^2$ is S, then the ==== adjacent to $M^2$ is a single bond and the ==== adjacent to $M^1$ is a double bond, and
(3) either $M^1$ or $M^2$ is S;

$R^{1a}$ and $R^{2a}$ are each independently hydrogen, halogen, $C_1$-$C_4$ alkyl, $C_3$-$C_6$ cycloalkyl, 3- to 6-membered heterocyclyl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is independently optionally substituted by $R^{12}$;

$R^2$ is hydrogen, halogen, $C_1$-$C_4$ alkyl, $C_3$-$C_6$ cycloalkyl, 3- to 6-membered heterocyclyl, —($C_1$-$C_3$ alkylene)3- to 6-membered heterocyclyl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{11}$, —$C(O)NR^{10}R^{11}$, —$NR^{10}C(O)R^{11}$, —$S(O)_2R^{10}$, —$NR^{10}S(O)_2R^{11}$, or —$S(O)_2 NR^{10}R^{11}$, each of which is independently optionally substituted by $R^{12}$;

$R^3$ is —$(CH_2)_m NR^{13}S(O)_2R^{14}$ wherein m is 0, 1, 2 or 3; $C_3$-$C_6$ cycloalkyl optionally substituted by halogen, oxo, —CN, or —OH; $C_1$-$C_4$ alkyl substituted by halogen, oxo, —CN, or —OH; or $C_2$-$C_6$ alkenyl;

$R^{10}$ and $R^{11}$ are each independently hydrogen, $C_1$-$C_4$ alkyl, $C_1$-$C_4$ alkoxy, $C_1$-$C_4$ alkenyl, $C_3$-$C_6$ cycloalkyl, $C_6$-$C_{14}$ aryl, 3- to 6-membered heterocyclyl, —($C_1$-$C_3$ alkylene)$C_3$-$C_6$ cycloalkyl, —($C_1$-$C_3$ alkylene) 3- to 6-membered heterocyclyl, —($C_1$-$C_3$ alkylene) $C_6$-$C_{14}$ aryl, —$NR^{15}R^{16}$, or —$C(O)R^{12}$, wherein each of $R^{10}$ and $R^{11}$ is independently optionally substituted by halogen, oxo, —CN, —$CF_3$, —OH, —$NR^{13}R^{14}$, —$C(O)NR^{13}R^{14}$, or $C_1$-$C_4$ alkyl optionally substituted by halogen, oxo, —CN, —$CF_3$, or —OH, or $R^{10}$ and $R^{11}$ are taken together with the atom or atoms to which they are attached to form a 3- to 6-membered heterocyclyl ring optionally substituted by halogen, oxo, —CN, —$CF_3$, —OH, or $C_1$-$C_4$ alkyl optionally substituted by halogen, oxo, —CN, or —OH;

each $R^{12}$ is independently halogen, cyano, $C_1$-$C_4$ haloalkyl, $C_1$-$C_4$ alkoxy, $C_1$-$C_4$ haloalkoxy, —$OR^{15}$, —$NR^{15}R^{16}$, —$C(O)NR^{15}R^{16}$, —$NR^{15}C(O)R^{16}$, —$S(O)_2R^{15}$, —$NR^{15}S(O)_2R^{16}$, —$S(O)_2NR^{15}R^{16}$, $C_3$-$C_6$ cycloalkyl, 3- to 6-membered heterocyclyl, or $C_1$-$C_4$ alkyl, each of which is independently optionally substituted by halogen, oxo, —$CF_3$, —CN, —OH, —$NR^{13}R^{14}$, or —$NR^{13}C(O)R^{14}$;

$R^{13}$ and $R^{14}$ are independently hydrogen, $C_1$-$C_4$ alkyl $C_3$-$C_6$ cycloalkyl, or 3- to 6-membered heterocyclyl, each of which is independently optionally substituted by halogen, oxo, —CN, or —OH, or $R^{13}$ and $R^{14}$ are taken together with the atom or atoms to which they are attached to form a 3- to 6-membered heterocyclyl ring optionally substituted by halogen, oxo, —CN, —OH, or $C_1$-$C_4$ alkyl optionally substituted by halogen, oxo, —CN, or —OH; and each $R^{15}$ and $R^{16}$ are independently hydrogen, $C_1$-$C_4$ alkyl, $C_3$-$C_6$ cycloalkyl, or 3- to 6-membered heterocyclyl, each of which is independently optionally substituted by halogen, oxo, —CN, or —OH, or $R^{15}$ and $R^{16}$ are taken together with the atoms to which they are attached to form a 3- to 6-membered heterocyclyl ring optionally substituted by halogen, oxo, —CN, —OH, or $C_1$-$C_4$ alkyl optionally substituted by halogen, oxo, —CN, or —OH.

In some embodiments, provided is a compound of Formula (I):

$$\text{(I)}$$

[Chemical structure showing a bicyclic compound with N-R¹, X, A ring fused with C ring containing M¹, M² positions and R², connected via G₁ to B ring with Z₁, Z₂, Z₃ positions and R³]

or a tautomer or isomer thereof, or a pharmaceutically acceptable salt of any of the foregoing, wherein:
each ---- is independently a single bond or double bond;
X is O or S;
$R^1$ is hydrogen, $C_1$-$C_3$ alkyl, —($C_1$-$C_3$ alkylene)OH, $C_1$-$C_3$ haloalkyl, or $C_3$-$C_4$ cycloalkyl;
$G_1$ is $CR^a$ or N, wherein:
 $R^a$ is hydrogen, halogen, or $C_1$-$C_4$ alkyl;
$Z_1$ is C—$W_1$—$R^c$; wherein:
 each $W_1$ is independently —O— or —$NR^{w1}$—, wherein:
  $R^{w1}$ is hydrogen, $C_3$-$C_6$ cycloalkyl, or $C_1$-$C_4$ alkyl optionally substituted by oxo, —OH, or halogen, and
 $R^c$ is independently 4- to 6-membered heterocyclyl, $C_6$-$C_{14}$ aryl, or 5- or 6-membered heteroaryl, each of which is independently optionally substituted by $R^{c1}$, wherein each $R^{c1}$ is independently halogen, $C_1$-$C_4$ alkyl, $C_3$-$C_6$ cycloalkyl, 3- to 6-membered heterocyclyl, cyano, oxo, $C_1$-$C_4$ alkoxy, $C_1$-$C_4$ haloalkoxy, $C_1$-$C_4$ haloalkyl, —$OR^{10}$, —$NR^{10}R^{11}$, —$C(O)NR^{10}R^{11}$, —$NR^{10}C(O)R^{11}$, —$S(O)_2R^{11}$, —$NR^{10}S(O)_2R^{11}$, or —$S(O)_2NR^{10}R^{11}$;
$Z_2$ is C—$W_2$—$R^d$ or N, wherein:
 $W_2$ is —O—, —$NR^{w2}$—, or a bond, wherein:
  $R^{w2}$ is hydrogen, $C_3$-$C_6$ cycloalkyl, or $C_1$-$C_4$ alkyl optionally substituted by oxo, —OH, or halogen, and
 $R^d$ is independently hydrogen, halogen, cyano, 3- to 6-membered heterocyclyl, or $C_1$-$C_4$ alkyl;
$Z_3$ is C—$R^e$ or N, wherein:
 $R^e$ is independently hydrogen, halogen, cyano, 3- to 6-membered heterocyclyl, or $C_1$-$C_4$ alkyl;
$M^1$ is S or $CR^{1a}$;
$M^2$ is S or $CR^{2a}$, provided that
 (1) when $M^1$ is S, then the ---- adjacent to $M^1$ is a single bond and the ---- adjacent to $M^2$ is a double bond,
 (2) when $M^2$ is S, then the ---- adjacent to $M^2$ is a single bond and the ---- adjacent to $M^1$ is a double bond, and
 (3) at least one of $M^1$ and $M^2$ is not S;
$R^{1a}$ and $R^{2a}$ are each independently hydrogen, halogen, $C_1$-$C_4$ alkyl, $C_3$-$C_6$ cycloalkyl, 3- to 6-membered heterocyclyl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{11}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is independently optionally substituted by $R^{12}$;
$R^2$ is halogen, $C_1$-$C_4$ alkyl, $C_3$-$C_6$ cycloalkyl, 3- to 6-membered heterocyclyl, —($C_1$-$C_3$ alkylene)3- to 6-membered heterocyclyl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{11}$, —$C(O)NR^{10}R^{11}$, —$NR^{10}C(O)R^{11}$, —$S(O)_2R^{10}$, —$NR^{10}S(O)_2R^{11}$, or —$S(O)_2NR^{10}R^{11}$, each of which is independently optionally substituted by $R^{12}$;
$R^3$ is —$(CH_2)_mNR^{13}S(O)_2R^{14}$, $C_3$-$C_6$ cycloalkyl, or $C_1$-$C_4$ alkyl substituted by halogen, oxo, —CN, or —OH, wherein m is 0, 1, 2 or 3;
$R^{10}$ and $R^{11}$ are each independently hydrogen, $C_1$-$C_4$ alkyl, $C_1$-$C_4$ alkoxy, $C_1$-$C_4$ alkenyl, $C_3$-$C_6$ cycloalkyl, 3- to 6-membered heterocyclyl, —($C_1$-$C_3$ alkylene)$C_3$-$C_6$ cycloalkyl, —($C_1$-$C_3$ alkylene) 3- to 6-membered heterocyclyl, —$NR^{15}R^{16}$, or —$C(O)R^{12}$, wherein each of $R^{10}$ and $R^{11}$ is independently optionally substituted by halogen, oxo, —CN, —$CF_3$, —OH, —$NR^{13}R^{14}$, —$C(O)NR^{13}R^{14}$, or $C_1$-$C_4$ alkyl optionally substituted by halogen, oxo, —CN, —$CF_3$, or —OH,
or $R^{10}$ and $R^{11}$ are taken together with the atom or atoms to which they are attached to form a 3- to 6-membered heterocyclyl ring optionally substituted by halogen, oxo, —CN, —$CF_3$, —OH, or $C_1$-$C_4$ alkyl optionally substituted by halogen, oxo, —CN, or —OH;
each $R^{12}$ is independently halogen, cyano, $C_1$-$C_4$ haloalkyl, $C_1$-$C_4$ alkoxy, $C_1$-$C_4$ haloalkoxy, —$OR^{15}$, —$NR^{15}R^{16}$, —$C(O)NR^{15}R^{16}$, —$NR^{15}C(O)R^{16}$, —$S(O)_2R^{15}$, —$NR^{15}S(O)_2R^{16}$, —$S(O)_2NR^{15}R^{16}$, $C_3$-$C_6$ cycloalkyl, 3- to 6-membered heterocyclyl, or $C_1$-$C_4$ alkyl, each of which is independently optionally substituted by halogen, oxo, —$CF_3$, —CN, —OH, —$NR^{13}R^{14}$, or —$NR^{13}C(O)R^{14}$;
$R^{13}$ and $R^{14}$ are independently hydrogen, $C_1$-$C_4$ alkyl $C_3$-$C_6$ cycloalkyl, or 3- to 6-membered heterocyclyl, each of which is independently optionally substituted by halogen, oxo, —CN, or —OH,
or $R^{13}$ and $R^{14}$ are taken together with the atom or atoms to which they are attached to form a 3- to 6-membered heterocyclyl ring optionally substituted by halogen, oxo, —CN, —OH, or $C_1$-$C_4$ alkyl optionally substituted by halogen, oxo, —CN, or —OH; and
each $R^{15}$ and $R^{16}$ are independently hydrogen, $C_1$-$C_4$ alkyl, $C_3$-$C_6$ cycloalkyl, or 3- to 6-membered heterocyclyl, each of which is independently optionally substituted by halogen, oxo, —CN, or —OH,
or $R^{15}$ and $R^{16}$ are taken together with the atoms to which they are attached to form a 3- to 6-membered heterocyclyl ring optionally substituted by halogen, oxo, —CN, —OH, or $C_1$-$C_4$ alkyl optionally substituted by halogen, oxo, —CN, or —OH.

In some embodiments of compound of Formula (I), $M^1$ is S. In some embodiments, $M^1$ is $CR^{1a}$. In some embodiments, $R^{1a}$ is hydrogen, halogen, or $C_1$-$C_4$ alkyl optionally substituted by $R^{12}$. In some embodiments, $R^{1a}$ is hydrogen. In some embodiments, $R^{1a}$ is halogen such as fluoro or chloro. In some embodiments, $R^{1a}$ is $C_1$-$C_4$ alkyl such as methyl or ethyl. In some embodiments, $M^1$ is $CR^{1a}$ and $R^{1a}$ is hydrogen.

In some embodiments of compound of Formula (I), $M^2$ is S. In some embodiments, $M^2$ is $CR^{2a}$. In some embodiments, $R^{2a}$ is hydrogen, halogen, or $C_1$-$C_4$ alkyl optionally substituted by $R^{12}$. In some embodiments, $R^{2a}$ is hydrogen. In some embodiments, $R^{2a}$ is halogen such as fluoro or chloro. In some embodiments, $R^{2a}$ is $C_1$-$C_4$ alkyl such as methyl or ethyl. In some embodiments, $M^2$ is $CR^{2a}$ and $R^{2a}$ is hydrogen.

In some embodiments of a compound of Formula (I), $M^1$ is S and $M^2$ is $CR^{2a}$. In some embodiments, $M^1$ is S and $M^2$ is $CR^{2a}$, wherein $R^{2a}$ is hydrogen. In some embodiments, $M^1$ is $CR^{1a}$ and $M^2$ is S. In some embodiments, $M^1$ is $CR^{1a}$, wherein $R^{1a}$ is hydrogen, and $M^2$ is S.

In some embodiments, provided is a compound of Formula (II),

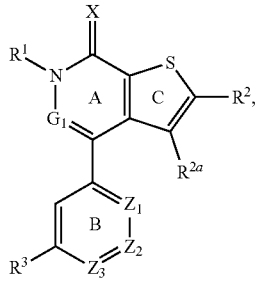
(II)

or a tautomer or isomer thereof, or a pharmaceutically acceptable salt of any of the foregoing, wherein X, $G_1$, $R^1$, $R^2$, $R^3$, $R^{2a}$, $Z_1$, $Z_2$, and $Z_3$ are defined herein for Formula (I).

In some embodiments, provided is a compound of any one of Formula (IIa-1) to (IIa-8):

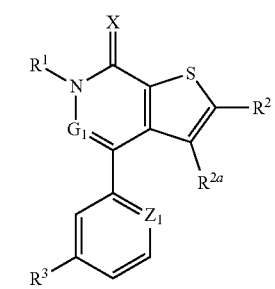
(IIa-1)

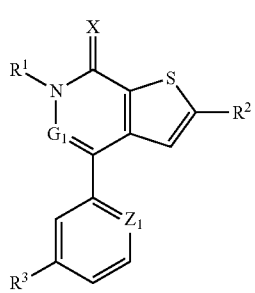
(IIa-2)

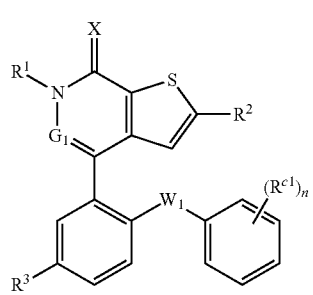
(IIa-3)

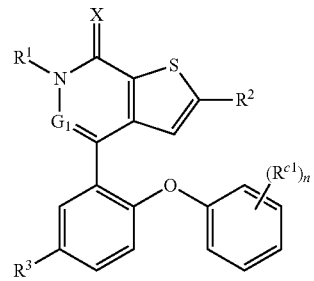
(IIa-4)

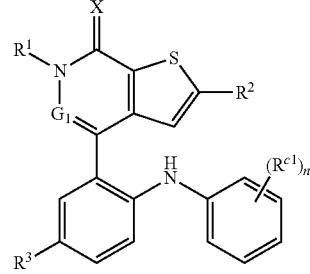
(IIa-5)

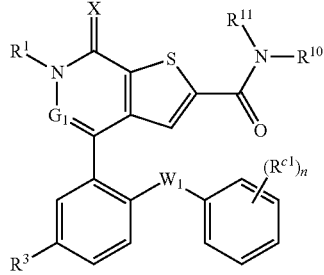
(IIa-6)

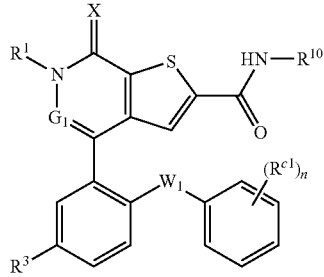
(IIa-7)

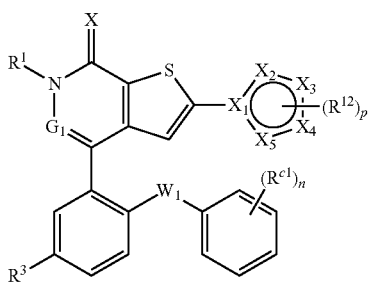
(IIa-8)

or a tautomer or isomer thereof, or a pharmaceutically acceptable salt of any of the foregoing, wherein X, $G_1$, $R^1$, $R^2$, $R^3$, $R^{2a}$, $R^{c1}$, $R^{10}$, $R^{11}$, $R^2$, $Z_1$ and $W_1$ are defined herein for Formula (I), and n is 0, 1, 2, 3, 4, or 5;
p is 0, 1, 2, 3, or 4;
$X_1$ is N or C;
$X_2$, $X_3$, $X_4$ and $X_5$ are each independently C, CH, $CR^{12}$, S, O, N, NH, $NR^{12}$;

provided that:

1. not more than one of $X_2$, $X_3$, $X_4$ and $X_5$ is S or O,
2. not more than three of $X_1$, $X_2$, $X_3$, $X_4$ and $X_5$ are N; and
3. at least one of $X_2$, $X_3$, $X_4$ and $X_5$ is $CR^{12}$ or $NR^{12}$.

In some embodiments, a compound of Formula (I) is of Formula (IIa-1). In some embodiments, a compound of Formula (I) is of Formula (IIa-2). In some embodiments, a compound of Formula (I) is of Formula (IIa-3). In some embodiments, a compound of Formula (I) is of Formula (IIa-4). In some embodiments, a compound of Formula (I) is of Formula (IIa-5). In some embodiments, a compound of Formula (I) is of Formula (IIa-6). In some embodiments, a compound of Formula (I) is of Formula (IIa-7). In some embodiments, a compound of Formula (I) is of Formula (IIa-8).

In some embodiments, provided is a compound of Formula (III),

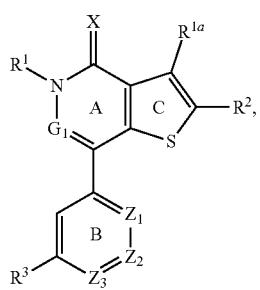

(III)

or a tautomer or isomer thereof, or a pharmaceutically acceptable salt of any of the foregoing, wherein X, $G_1$, $R^1$, $R^2$, $R^3$, $R^{1a}$, $Z_1$, $Z_2$, and $Z_3$ are defined herein for Formula (I).

In some embodiments, provided is a compound of any one of Formula (IIIa-1) to (IIIa-8):

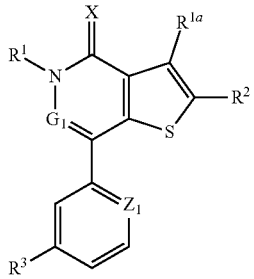

(IIIa-1)

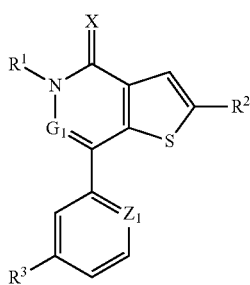

(IIIa-2)

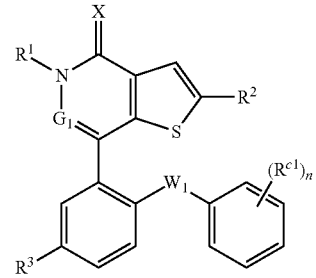

(IIIa-3)

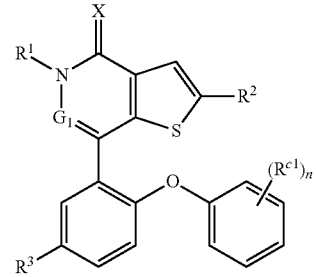

(IIIa-4)

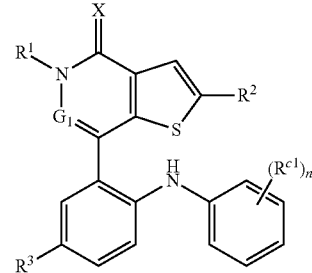

(IIIa-5)

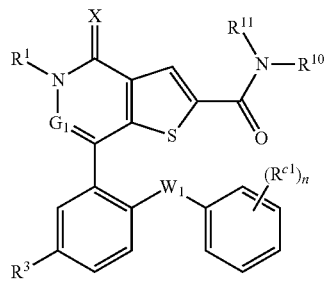

(IIIa-6)

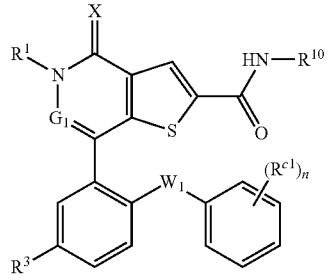

(IIIa-7)

-continued

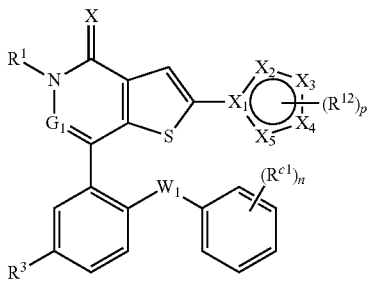
(IIIa-8)

or a tautomer or isomer thereof, or a pharmaceutically acceptable salt of any of the foregoing, wherein X, $G_1$, $R^1$, $R^2$, $R^3$, $R^{2a}$, $R^{c1}$, $R^{10}$, $R^{11}$, $R^{12}$, $Z_1$ and $W_1$ are defined herein Formula (I), and n is 0, 1, 2, 3, 4, or 5;
p is 0, 1, 2, 3, or 4;
$X_1$ is N or C;
$X_2$, $X_3$, $X_4$ and $X_5$ are each independently C, CH, $CR^{12}$, S, O, N, NH, or $NR^{12}$;
provided that
1. not more than one of $X_2$, $X_3$, $X_4$ and $X_5$ is S or O;
2. not more than three of $X_1$, $X_2$, $X_3$, $X_4$ and $X_5$ are N; and
3. at least one of $X_2$, $X_3$, $X_4$ and $X_5$ is $CR^{12}$ or $NR^{12}$.

In some embodiments, a compound of Formula (I) is of Formula (IIIa-1). In some embodiments, a compound of Formula (I) is of Formula (IIIa-2). In some embodiments, a compound of Formula (I) is of Formula (IIIa-3). In some embodiments, a compound of Formula (I) is of Formula (IIIa-4). In some embodiments, a compound of Formula (I) is of Formula (IIIa-5). In some embodiments, a compound of Formula (I) is of Formula (IIIa-6). In some embodiments, a compound of Formula (I) is of Formula (IIIa-7). In some embodiments, a compound of Formula (I) is of Formula (IIIa-8).

In some embodiments, provided is a compound of Formula (IV):

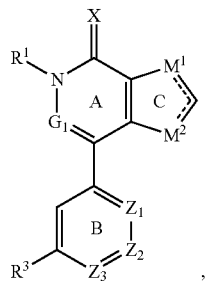
(IV)

or a tautomer or isomer thereof, or a pharmaceutically acceptable salt of any of the foregoing, wherein:
each ==== is independently a single bond or double bond;
X is O or S;
$R^1$ is hydrogen, $C_1$-$C_3$ alkyl, —($C_1$-$C_3$ alkylene)OH, $C_1$-$C_3$ haloalkyl, or $C_3$-$C_4$ cycloalkyl;
$G_1$ is $CR^a$ or N, wherein:
  $R^a$ is hydrogen, halogen, $C_1$-$C_6$ alkyl, or $C_1$-$C_6$ haloalkyl;
$Z_1$ is C—$W_1$—$R^c$, wherein:
  each $W_1$ is independently —O— or —$NR^{w1}$—, wherein:
    $R^{w1}$ is hydrogen, $C_3$-$C_6$ cycloalkyl, or $C_1$-$C_4$ alkyl optionally substituted by oxo, —OH, or halogen, and $R^c$ is independently $C_3$-$C_6$ cycloalkyl, 4- to 6-membered heterocyclyl, $C_6$-$C_{14}$ aryl, or 5- or 6-membered heteroaryl, each of which is independently optionally substituted by $R^{c1}$, wherein each $R^{c1}$ is independently halogen, $C_1$-$C_4$ alkyl, $C_3$-$C_6$ cycloalkyl, 3- to 6-membered heterocyclyl, cyano, oxo, $C_1$-$C_4$ alkoxy, $C_1$-$C_4$ haloalkoxy, $C_1$-$C_4$ haloalkyl, —$OR^{10}$, —$NR^{10}R^{11}$, —$C(O)NR^{10}R^{11}$, —$NR^{10}C(O)R^{11}$, —$S(O)_2R^{10}$, —$NR^{10}S(O)_2R^{11}$, or —$S(O)_2NR^{10}R^{11}$;

$Z_2$ is C—$W_2$—$R^d$ or N, wherein:
  $W_2$ is —O—, —$NR^{w2}$—, or a bond, wherein:
    $R^{w2}$ is hydrogen, $C_3$-$C_6$ cycloalkyl, or $C_1$-$C_4$ alkyl optionally substituted by oxo, —OH, or halogen, and
  $R^d$ is independently hydrogen, halogen, cyano, 3- to 6-membered heterocyclyl, or $C_1$-$C_4$ alkyl;
$Z_3$ is C—$R^e$ or N, wherein:
  $R^e$ is independently hydrogen, halogen, cyano, 3- to 6-membered heterocyclyl, or $C_1$-$C_4$ alkyl;
$M^1$ is S or $CR^{1a}$;
$M^2$ is S or $CR^{2a}$, provided that
  (1) when $M^1$ is S, then the ==== adjacent to $M^1$ is a single bond and the ==== adjacent to $M^2$ is a double bond,
  (2) when $M^2$ is S, then the ==== adjacent to $M^2$ is a single bond and the ==== adjacent to $M^1$ is a double bond, and
  (3) at least one of $M^1$ and $M^2$ is S;
$R^{1a}$ and $R^{2a}$ are each independently hydrogen, halogen, $C_1$-$C_4$ alkyl, $C_3$-$C_6$ cycloalkyl, 3- to 6-membered heterocyclyl, 5- to 10-membered heteroaryl, cyano, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{11}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is independently optionally substituted by $R^{12}$;
$R^3$ is —$(CH_2)_m NR^{13}S(O)_2R^{14}$, wherein m is 0, 1, 2 or 3; $C_3$-$C_6$ cycloalkyl optionally substituted by halogen, oxo, —CN, or —OH; or $C_1$-$C_4$ alkyl substituted by halogen, oxo, —CN, or —OH;
$R^{10}$ and $R^{11}$ are each independently hydrogen, $C_1$-$C_4$ alkyl, $C_1$-$C_4$ alkoxy, $C_1$-$C_4$ alkenyl, $C_3$-$C_6$ cycloalkyl, 3- to 6-membered heterocyclyl, —($C_1$-$C_3$ alkylene) $C_3$-$C_6$ cycloalkyl, —($C_1$-$C_3$ alkylene) 3- to 6-membered heterocyclyl, —$NR^{15}R^{16}$, or —$C(O)R^{12}$, wherein each of $R^{10}$ and $R^{11}$ is independently optionally substituted by halogen, oxo, —CN, —$CF_3$, —OH, —$NR^{13}R^{14}$, —$C(O)NR^{13}R^{14}$, or $C_1$-$C_4$ alkyl optionally substituted by halogen, oxo, —CN, —$CF_3$, or —OH,
or $R^{10}$ and $R^{11}$ are taken together with the atom or atoms to which they are attached to form a 3- to 6-membered heterocyclyl ring optionally substituted by halogen, oxo, —CN, —$CF_3$, —OH, or $C_1$-$C_4$ alkyl optionally substituted by halogen, oxo, —CN, or —OH;
each $R^{12}$ is independently halogen, cyano, $C_1$-$C_4$ haloalkyl, $C_1$-$C_4$ alkoxy, $C_1$-$C_4$ haloalkoxy, —$OR^{15}$, —$NR^{15}R^{16}$, —$C(O)NR^{15}R^{16}$, —$NR^{15}C(O)R^{16}$, —$S(O)_2R^{15}$, —$NR^{15}S(O)_2R^{16}$, —$S(O)_2NR^{15}R^{16}$, $C_3$-$C_6$ cycloalkyl, 3- to 6-membered heterocyclyl, or $C_1$-$C_4$ alkyl, each of which is independently optionally substituted by halogen, oxo, —$CF_3$, —CN, —OH, —$NR^{13}R^{14}$, or —$NR^{13}C(O)R^{14}$;
$R^{13}$ and $R^{14}$ are independently hydrogen, $C_1$-$C_4$ alkyl $C_3$-$C_6$ cycloalkyl, or 3- to 6-membered heterocyclyl, each of which is independently optionally substituted by halogen, oxo, —CN, or —OH,
or $R^{13}$ and $R^{14}$ are taken together with the atom or atoms to which they are attached to form a 3- to 6-membered heterocyclyl ring optionally substituted by halogen, oxo, —CN, —OH, or $C_1$-$C_4$ alkyl optionally substituted by halogen, oxo, —CN, or —OH; and each $R^{15}$ and $R^{16}$ are independently hydrogen, $C_1$-$C_4$ alkyl, $C_3$-$C_6$ cycloalkyl, or 3- to 6-membered heterocyclyl, each of which is independently optionally substituted by halogen, oxo, —CN, or —OH, or $R^{15}$ and $R^{16}$ are taken together with the atoms to which they are attached to form a 3- to 6-membered heterocyclyl ring optionally substituted by halogen, oxo, —CN, —OH, or $C_1$-$C_4$ alkyl optionally substituted by halogen, oxo, —CN, or —OH.

In some embodiments of compound of Formula (IV), or a tautomer or isomer thereof, or a pharmaceutically acceptable salt of any of the foregoing, $M^1$ is S. In some embodiments, $M^1$ is $CR^{1a}$. In some embodiments, $R^{1a}$ is hydrogen, halogen, or $C_1$-$C_4$ alkyl optionally substituted by $R^{12}$. In some embodiments, $R^{1a}$ is hydrogen. In some embodiments, $R^{1a}$ is halogen such as fluoro or chloro. In some embodiments, $R^{1a}$ is $C_1$-$C_4$ alkyl such as methyl or ethyl. In some embodiments, $M^1$ is $CR^{1a}$ and $R^{1a}$ is hydrogen.

In some embodiments of compound of Formula (IV), or a tautomer or isomer thereof, or a pharmaceutically acceptable salt of any of the foregoing, $M^2$ is S. In some embodiments, $M^2$ is $CR^{2a}$. In some embodiments, $R^{2a}$ is hydrogen, halogen, or $C_1$-$C_4$ alkyl optionally substituted by $R^{12}$. In some embodiments, $R^{2a}$ is hydrogen. In some embodiments, $R^{2a}$ is halogen such as fluoro or chloro. In some embodiments, $R^{2a}$ is $C_1$-$C_4$ alkyl such as methyl or ethyl. In some embodiments, $M^2$ is $CR^{2a}$ and $R^{2a}$ is hydrogen.

In some embodiments of a compound of Formula (IV), or a tautomer or isomer thereof, or a pharmaceutically acceptable salt of any of the foregoing, $M^1$ is S and $M^2$ is $CR^{2a}$. In some embodiments, $M^1$ is S and $M^2$ is $CR^{2a}$, wherein $R^{2a}$ is hydrogen. In some embodiments, $M^1$ is $CR^{1a}$ and $M^2$ is S. In some embodiments, $M^1$ is $CR^{1a}$, wherein $R^{1a}$ is hydrogen, and $M^2$ is S.

In some embodiments, provided is a compound of Formula (V),

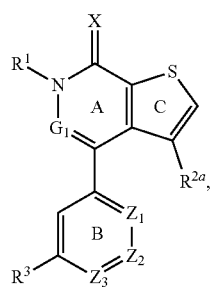

(V)

or a tautomer or isomer thereof, or a pharmaceutically acceptable salt of any of the foregoing, wherein X, $G_1$, $R^1$, $R^3$, $R^{2a}$, $Z_1$, $Z_2$, and $Z_3$ are as detailed herein for Formula (IV).

In some embodiments, provided is a compound of any one of Formula (Va-1) to (Va-11):

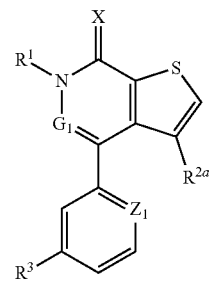

(Va-1)

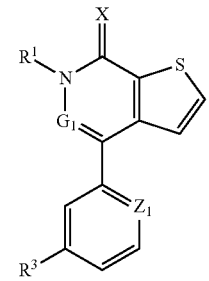

(Va-2)

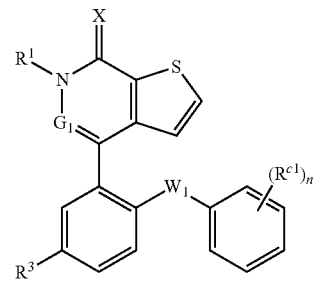

(Va-3)

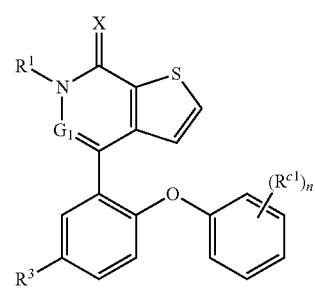

(Va-4)

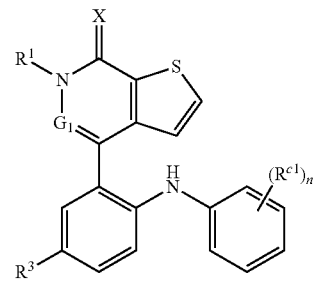

(Va-5)

(Va-6)
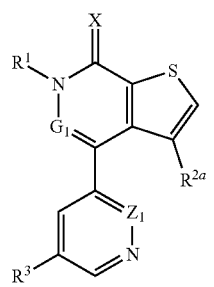

(Va-7)
(Va-8)
(Va-9)
(Va-10)
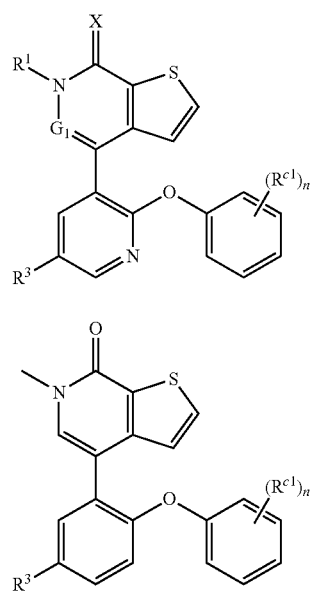

(Va-11)
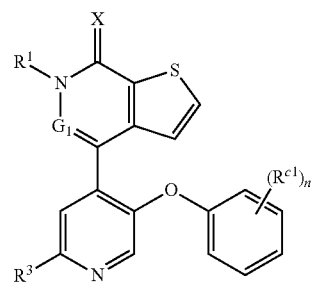

or a tautomer or isomer thereof, or a pharmaceutically acceptable salt of any of the foregoing, wherein X, $G_1$, $R^1$, $R^3$, $R^{2a}$, $R^{c1}$, $Z_1$ and $W_1$ are as detailed herein for Formula (IV), and n is 0, 1, 2, 3, 4, or 5. In some embodiments, a compound of Formula (IV) is of Formula (Va-1). In some embodiments, a compound of Formula (IV) is of Formula (Va-2). In some embodiments, a compound of Formula (IV) is of Formula (Va-3). In some embodiments, a compound of Formula (IV) is of Formula (Va-4). In some embodiments, a compound of Formula (IV) is of Formula (Va-5). In some embodiments, a compound of Formula (IV) is of Formula (Va-6). In some embodiments, a compound of Formula (IV) is of Formula (Va-7). In some embodiments, a compound of Formula (IV) is of Formula (Va-8). In some embodiments, a compound of Formula (IV) is of Formula (Va-9). In some embodiments, a compound of Formula (IV) is of Formula (Va-10). In some embodiments, a compound of Formula (IV) is of Formula (Va-11).

In some embodiments, provided is a compound of Formula (VI), (VI)
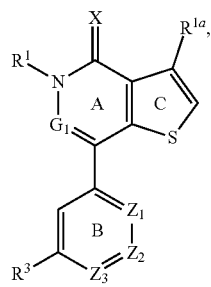

or a tautomer or isomer thereof, or a pharmaceutically acceptable salt of any of the foregoing, wherein X, $G_1$, $R^1$, $R^3$, $R^{1a}$, $Z_1$, $Z_2$, and $Z_3$ are as detailed herein for Formula (IV).

In some embodiments, provided is a compound of any one of Formula (VIa-1) to (VIa-11):

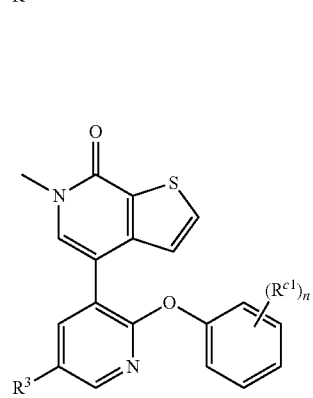
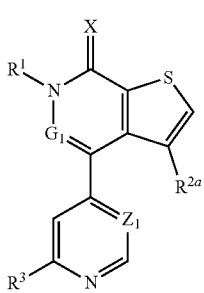

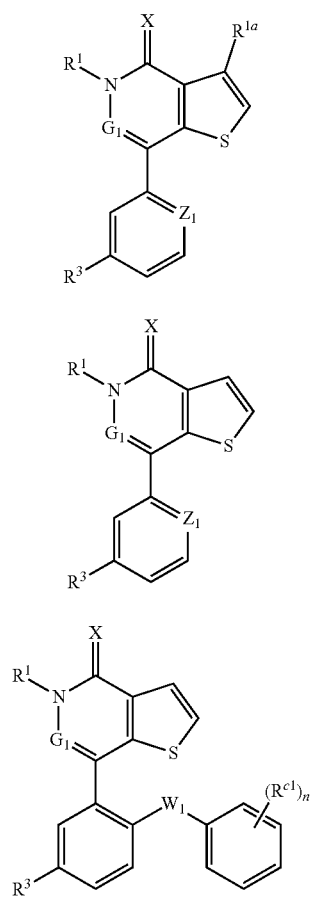 (VIa-1)
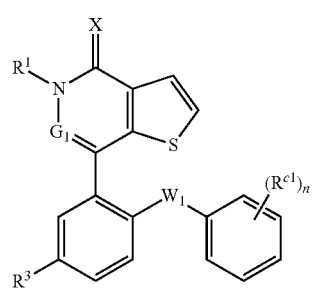 (VIa-2)
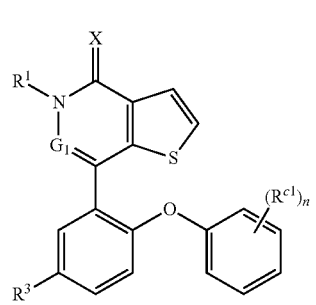 (VIa-3)
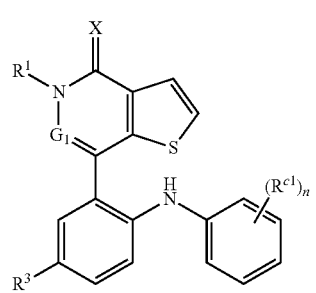 (VIa-4)
(VIa-5)
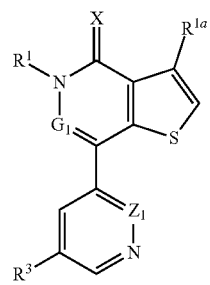 (VIa-6)
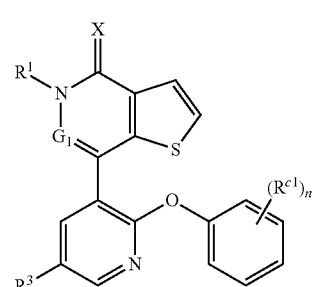 (VIa-7)
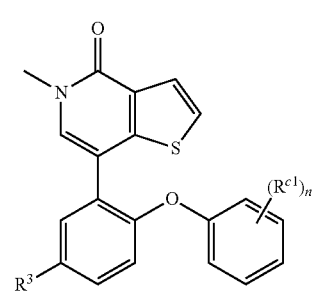 (VIa-8)
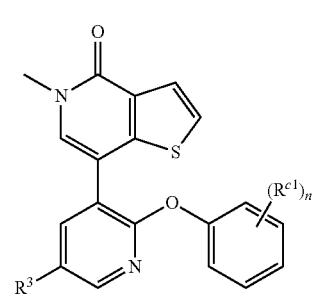 (VIa-9)
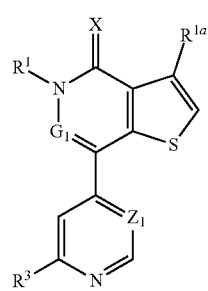 (VIa-10)

-continued (VIa-11)

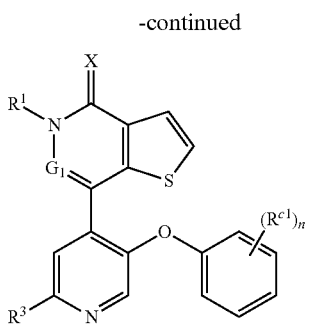

or a tautomer or isomer thereof, or a pharmaceutically acceptable salt of any of the foregoing, wherein X, $G_1$, $R^1$, $R^3$, $R^{1a}$, $R^{c1}$, $Z_1$ and $W_1$ are as detailed herein for Formula (IV), and
n is 0, 1, 2, 3, 4, or 5.

In some embodiments, a compound of Formula (IV) is of Formula (VIa-1). In some embodiments, a compound of Formula (IV) is of Formula (VIa-2). In some embodiments, a compound of Formula (IV) is of Formula (VIa-3). In some embodiments, a compound of Formula (IV) is of Formula (VIa-4). In some embodiments, a compound of Formula (IV) is of Formula (VIa-5). In some embodiments, a compound of Formula (IV) is of Formula (VIa-6). In some embodiments, a compound of Formula (IV) is of Formula (VIa-7). In some embodiments, a compound of Formula (IV) is of Formula (VIa-8). In some embodiments, a compound of Formula (IV) is of Formula (VIa-9). In some embodiments, a compound of Formula (IV) is of Formula (VIa-10). In some embodiments, a compound of Formula (IV) is of Formula (VIa-11).

Specific values described herein are values for a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt or pharmaceutically acceptable tautomer thereof. It is to be understood that two or more values may combined. It is to be understood that any variable for a compound of Formula (J) or any related formulae may be combined with any other variable the same as if each and every combination of variables were specifically and individually listed. Thus, it is to be understood that any variable for a compound of Formula (I) or any related formulae may be combined with any other variable for a compound of Formula (I) or any related formulae the same as if each and every combination of variables were specifically and individually listed. Any embodiment provided for Formula (I) is equally applicable to other formulae where applicable, such as Formula (J), the same as if each and every embodiment were specifically and individually listed.

In some embodiments of a compound of Formula (I), X is O. In some embodiments of a compound of Formula (I), X is S. In some embodiments of a compound of Formula (J) or any related formulae where applicable, X is as provided herein to the same extent as is described for Formula (I).

In some embodiments of a compound of Formula (I), $R^1$ is hydrogen, $C_1$-$C_3$ alkyl, —($C_1$-$C_3$ alkylene)OH, $C_1$-$C_3$ haloalkyl or $C_3$-$C_4$ cycloalkyl. In some embodiments of a compound of Formula (I), $R^1$ is hydrogen. In some embodiments of a compound of Formula (I), $R^1$ is $C_1$-$C_3$ alkyl, such as methyl, ethyl, n-propyl, or isopropyl. In some embodiments of a compound of Formula (I), $R^1$ is methyl. In some embodiments of a compound of Formula (I), $R^1$ is $C_3$-$C_4$ cycloalkyl, such as cyclopropyl or cyclobutyl. In some embodiments of a compound of Formula (I), $R^1$ is cyclopropyl. In some embodiments of a compound of Formula (I), $R^1$ is —($C_1$-$C_3$ alkylene)OH, such as methanol, ethanol, 1-propanol, or 2-propanol. In some embodiments of a compound of Formula (J) or any related formulae where applicable, $R^1$ is as provided herein to the same extent as is described for Formula (I).

In some embodiments of a compound of Formula (I), $G_1$ is N. In some embodiments of a compound of Formula (I), $G_1$ is $CR^a$. In some embodiments of a compound of Formula (I), $R^a$ is hydrogen. In some embodiments, $R^a$ is $C_1$-$C_4$ alkyl such methyl or ethyl. In some embodiments, $G_1$ is $CR^a$ and $R^a$ is hydrogen. In some embodiments of a compound of Formula (J) or any related formulae where applicable, $G_1$ is as provided herein to the same extent as is described for Formula (I).

In some embodiments of a compound of Formula (J) or any related formulae where applicable, $R^2$ is as provided herein to the same extent as is described for Formula (I). In some embodiments of a compound of Formula (I), $R^2$ is —$OR^{10}$ such as —$OCH_3$ or —$OCF_3$. In some embodiments of a compound of Formula (I), $R^2$ is cyano. In some embodiments of a compound of Formula (I), $R^2$ is halogen such as fluoro or chloro. In some embodiments of a compound of Formula (I), $R^2$ is $C_1$-$C_4$ alkyl such as methyl or ethyl. In some embodiments of a compound of Formula (I), $R^2$ is $C_1$-$C_4$ haloalkyl such as —$CF_3$. In some embodiments of a compound of Formula (I), $R^2$ is ethyl. In some embodiments, $R^2$ is methyl. In some embodiments of a compound of Formula (I), $R^2$ is —$OCF_3$. In some embodiments, $R^2$ is —$OCH_3$. In some embodiments, $R^2$ is —$C(O)NR^{10}R^{11}$, 5- to 10-membered heteroaryl, —($C_1$-$C_3$ alkylene)3- to 6-membered heterocyclyl, or $C_1$-$C_4$ alkyl, each of which is independently optionally substituted by $R^{12}$. In some embodiments, $R^2$ is —$C(O)NR^{10}R^{11}$ which is optionally substituted by $R^{12}$. In some embodiments, when $R^2$ is —$C(O)NR^{10}R^{11}$ which is optionally substituted by $R^{12}$, then $R^3$ is $C_3$-$C_6$ cycloalkyl or $C_1$-$C_4$ alkyl substituted by halogen, oxo, —CN, or —OH. In some embodiments, $R^2$ is —$C(O)NR^{10}R^{11}$ which is optionally substituted by $R^{12}$, wherein $R^{10}$ and $R^{11}$ are each independently hydrogen, $C_1$-$C_4$ alkyl, or $C_3$-$C_6$ cycloalkyl, or $R^{10}$ and $R^{11}$ are taken together with the atom or atoms to which they are attached to form a 3- to 6-membered heterocyclyl ring optionally substituted by halogen. In some embodiments, $R^2$ is

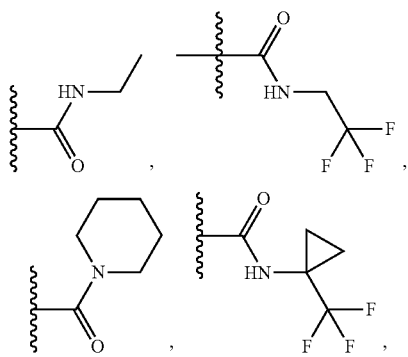

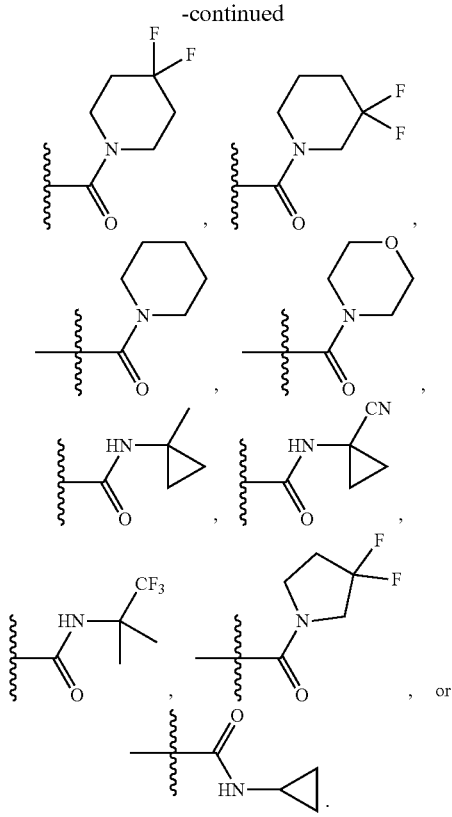

In some embodiments, $R^2$ is 5- to 10-membered heteroaryl optionally substituted by $R^{12}$. In some embodiments, $R^2$ is 5- to 10-membered heteroaryl which is unsubstituted. In some embodiments, $R^2$ is a 5- or 6-membered heteroaryl optionally substituted by $R^{12}$. In some embodiments, $R^2$ is a 5- or 6-membered heteroaryl which is unsubstituted. In some embodiments, $R^2$ is a 6-membered heteroaryl optionally substituted by $R^{12}$. In some embodiments, $R^2$ is a 6-membered heteroaryl which is unsubstituted. In some embodiments, $R^2$ is a 5-membered heteroaryl optionally substituted by $R^{12}$. In some embodiments, $R^2$ is a 5-membered heteroaryl which is unsubstituted. In some embodiments, $R^2$ is

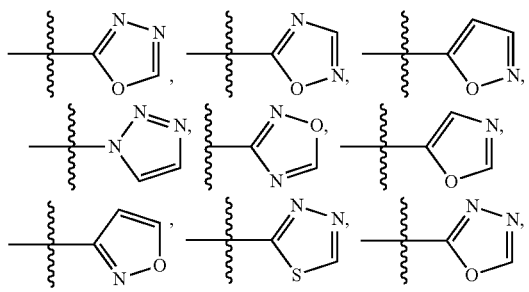

each of which is independently optionally substituted by $R^{12}$. In some embodiments, $R^2$ is

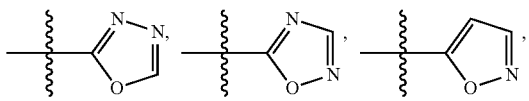

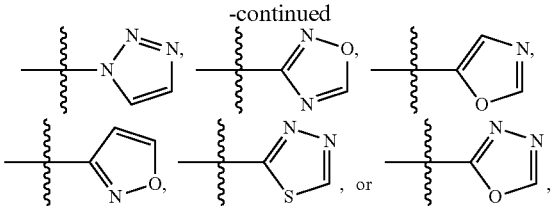

each of which is optionally substituted by $R^{12}$, wherein each $R^{12}$ is independently $C_1$-$C_4$ haloalkyl, $C_1$-$C_4$ alkoxy, —$NR^{15}R^{16}$, or $C_1$-$C_4$ alkyl. In some embodiments, $R^2$ is

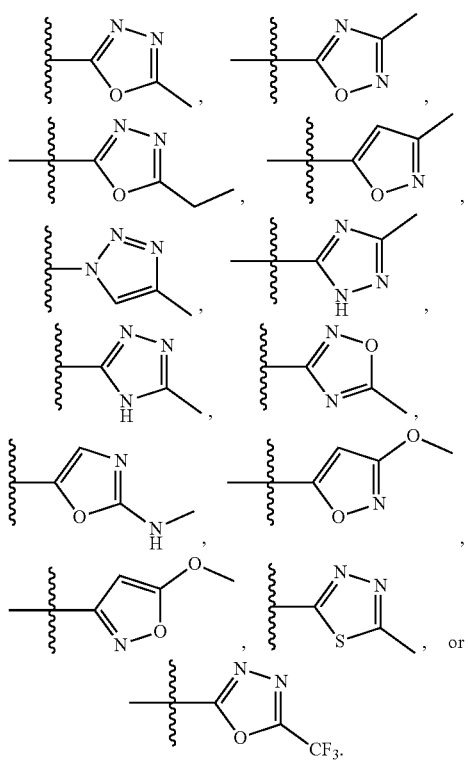

In some embodiments, $R^2$ is $C_1$-$C_4$ alkyl optionally substituted by $R^{12}$. In some embodiments, $R^2$ is —($C_1$-$C_3$ alkylene)3- to 6-membered heterocyclyl optionally substituted by $R^{12}$. In some embodiments, $R^2$ is —($C_1$-$C_3$ alkylene)3- to 6-membered heterocyclyl which is unsubstituted. In some embodiments, $R^2$ is

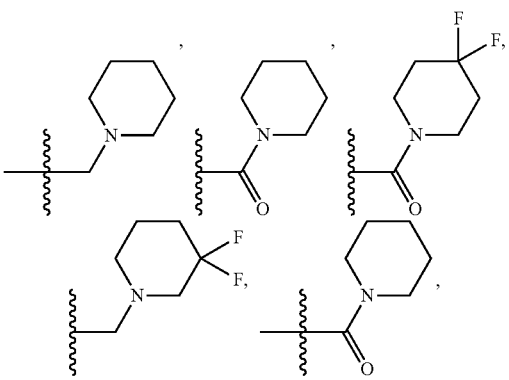

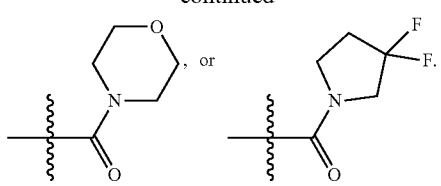
In some embodiments, R² is
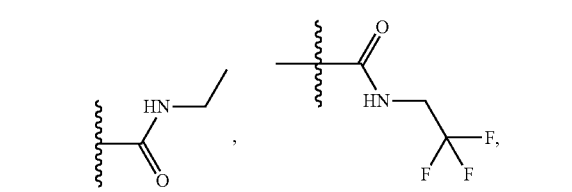
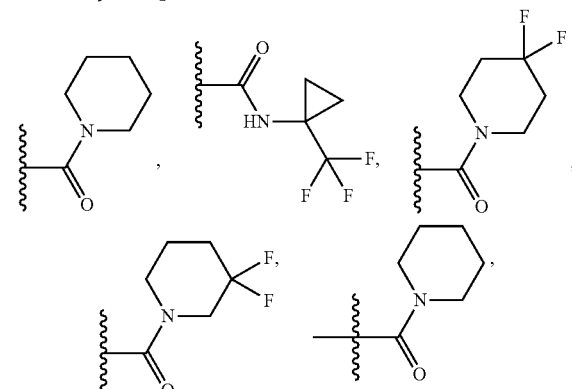
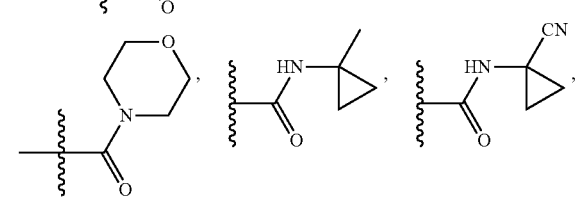
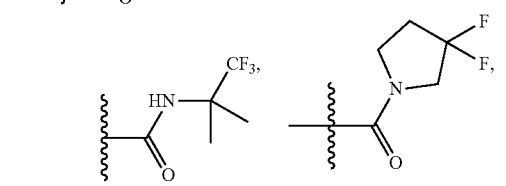
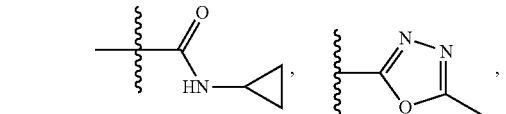
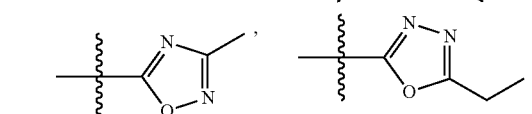
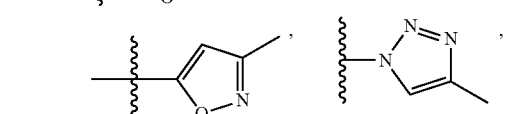
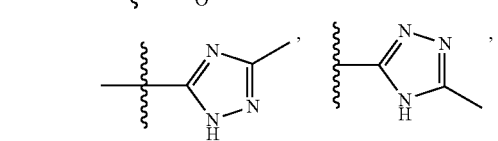
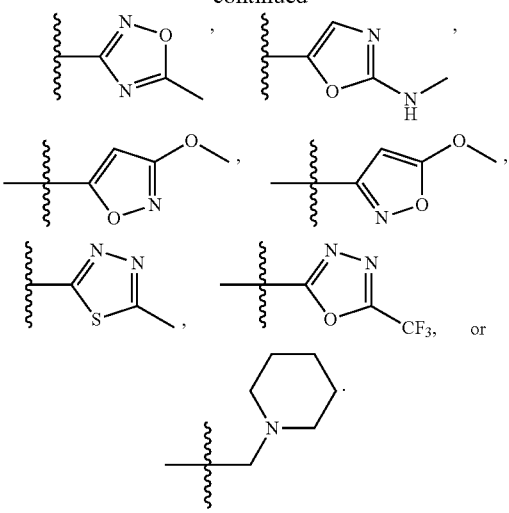
In some embodiments, R² is
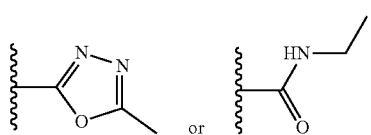
In some embodiments, R² is
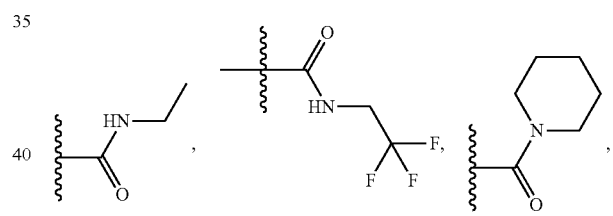
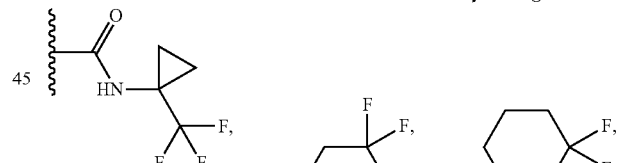
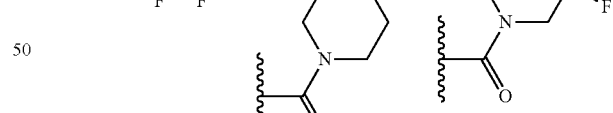
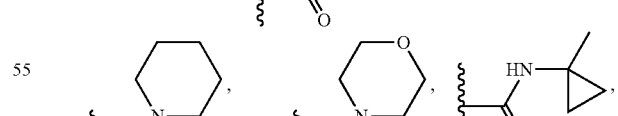
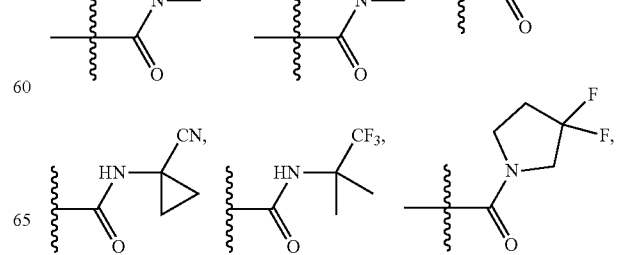

-continued
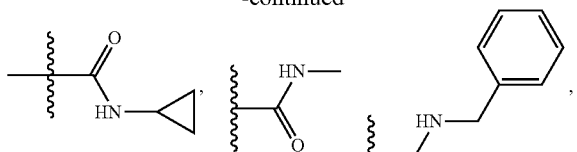
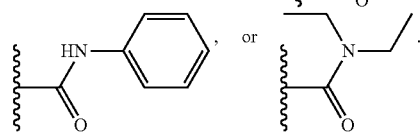
In some embodiments, R² is
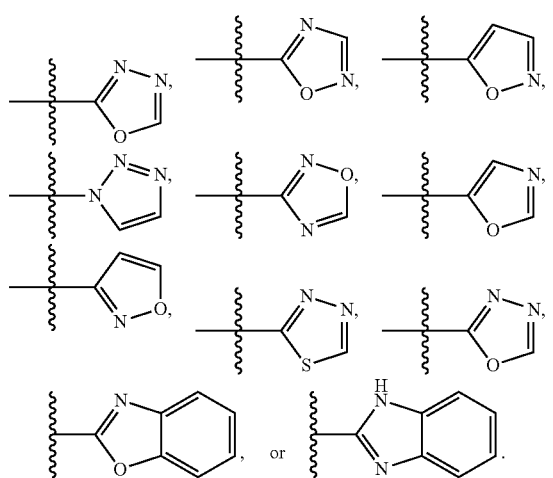
In some embodiments, R² is
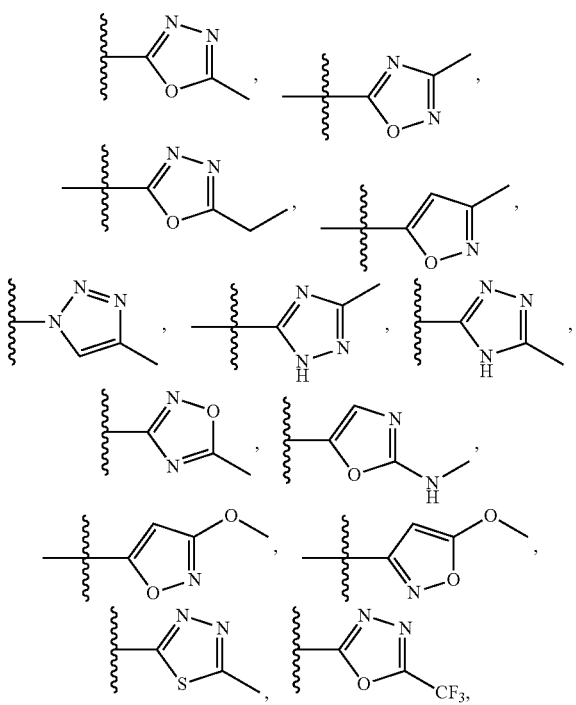
-continued
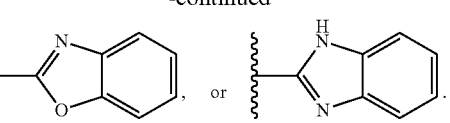
In some embodiments, R² is H. In some embodiments, R² is H,
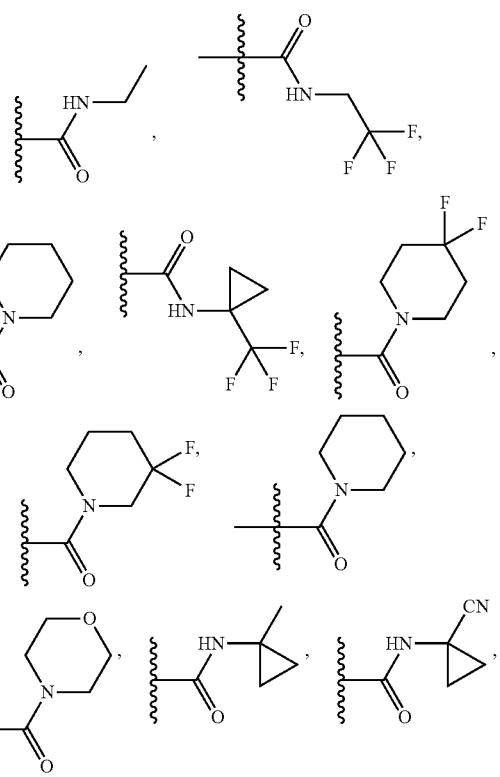
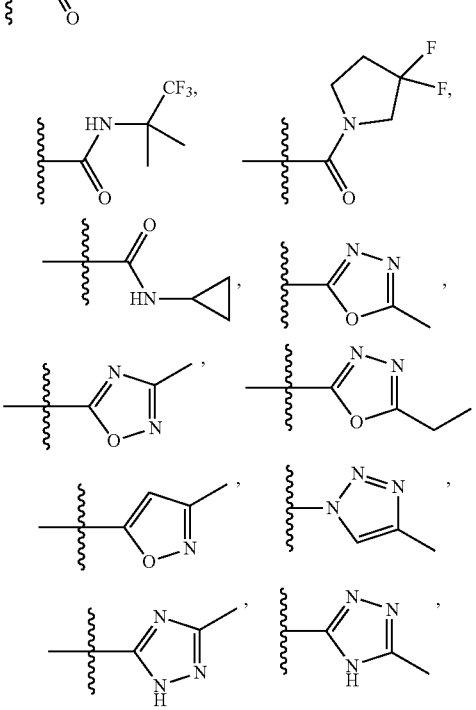

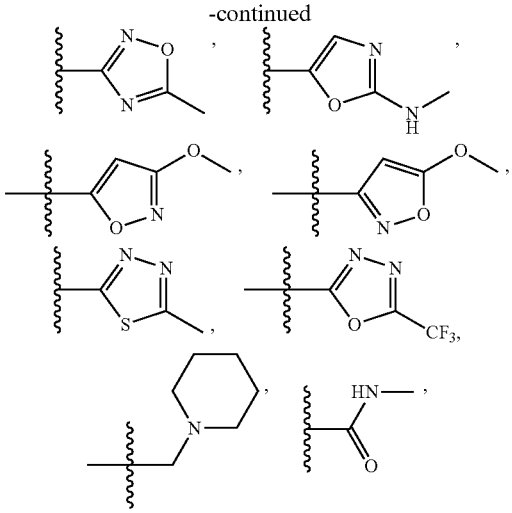

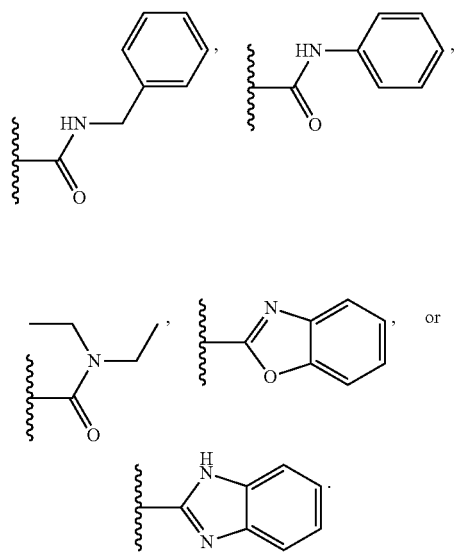

In some embodiments of a compound of Formula (J) or any related formulae where applicable, C ring is as provided herein to the same extent as is described for Formula (I).

In some embodiments of a compound of Formula (I), C ring is thiophenyl substituted by $R^2$, wherein $R^2$ is halogen, $C_1$-$C_4$ alkyl, $C_3$-$C_6$ cycloalkyl, 3- to 6-membered heterocyclyl, $C_6$-$C_{14}$ aryl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{11}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is independently optionally substituted by $R^{12}$. In some embodiments, $R^2$ is —$C(O)NR^{10}R^{11}$, 5- to 10-membered heteroaryl, or $C_1$-$C_4$ alkyl, each of which is independently optionally substituted by $R^{12}$. In some embodiments, $R^2$ is —$C(O)NR^{10}R^{11}$, 5- to 10-membered heteroaryl optionally substituted by —$NR^{15}R^{16}$, $OR^{15}$, or $C_1$-$C_4$ alkyl optionally substituted by halogen, or $C_1$-$C_4$ alkyl optionally substituted by —$NR^{13}R^{14}$.

In some embodiments of a compound of Formula (I), the C ring is

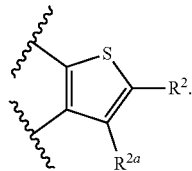

In some embodiments of a compound of Formula (I), the C ring is

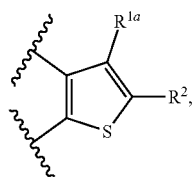

wherein the wavy lines denote attachment points with the A ring.

In some embodiments of a compound of Formula (I), the C ring is selected from the group consisting of:

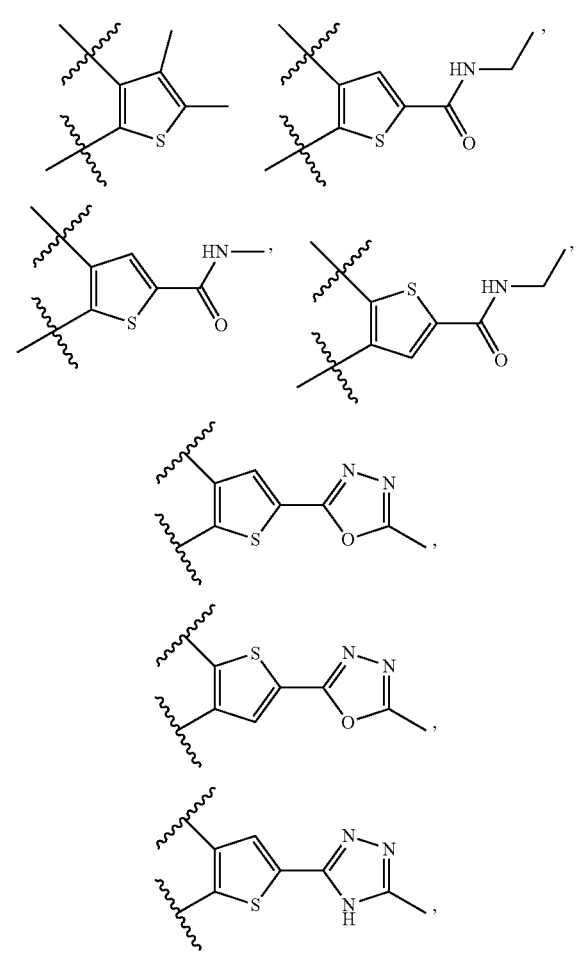

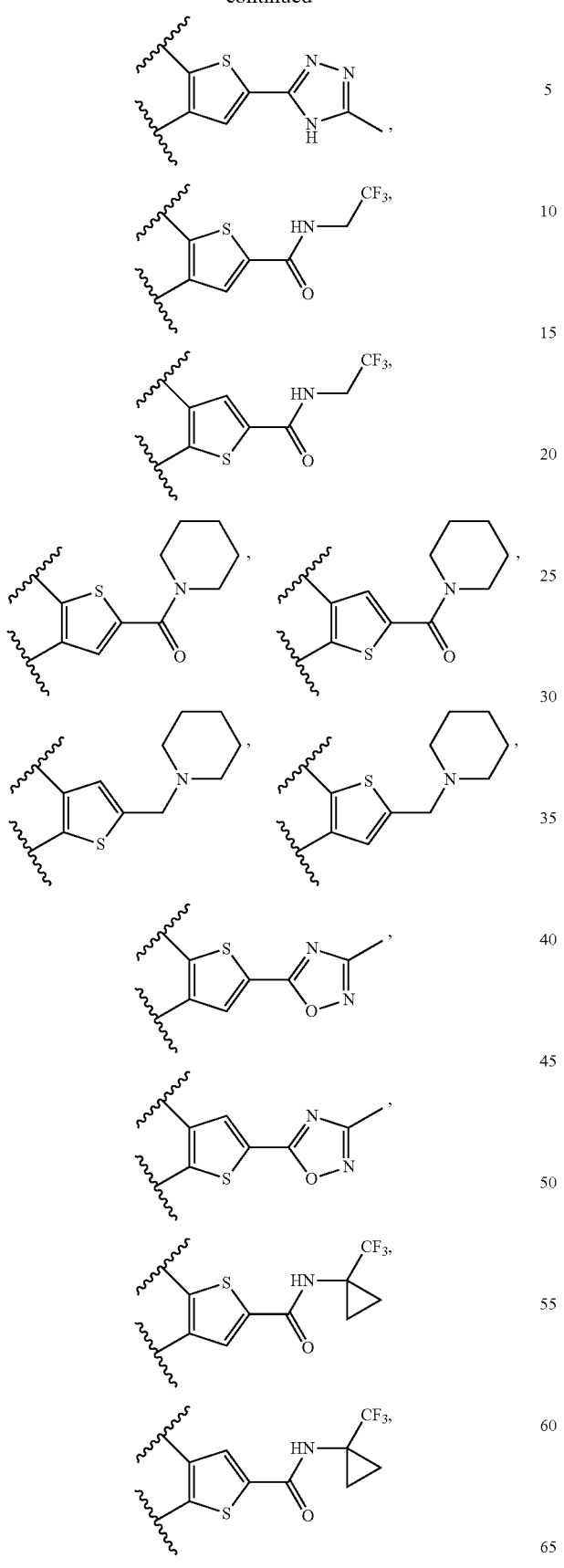
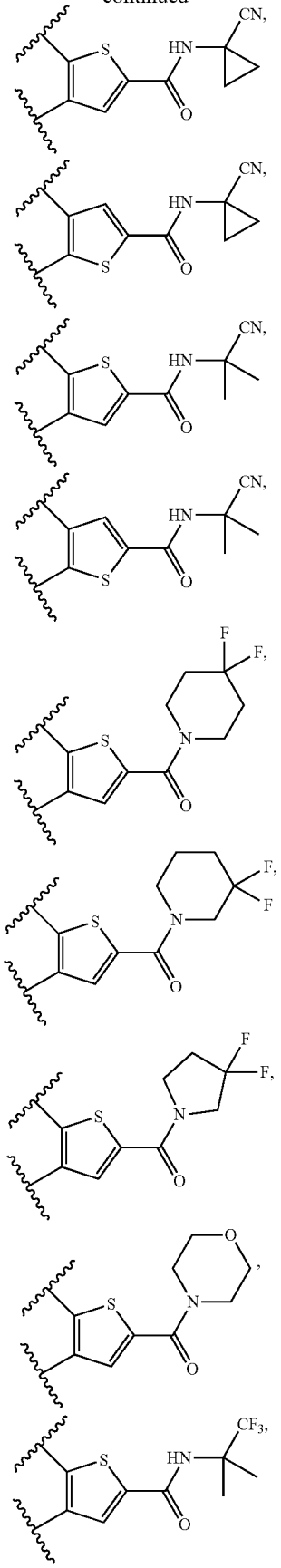

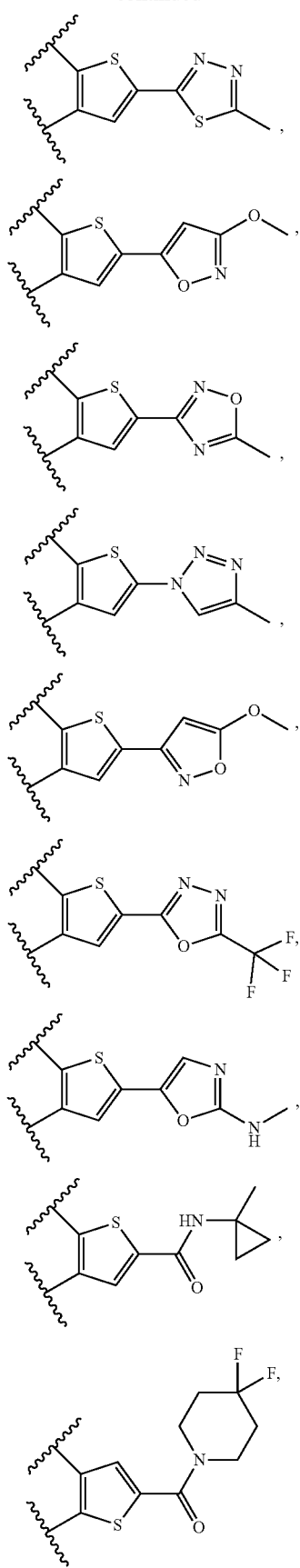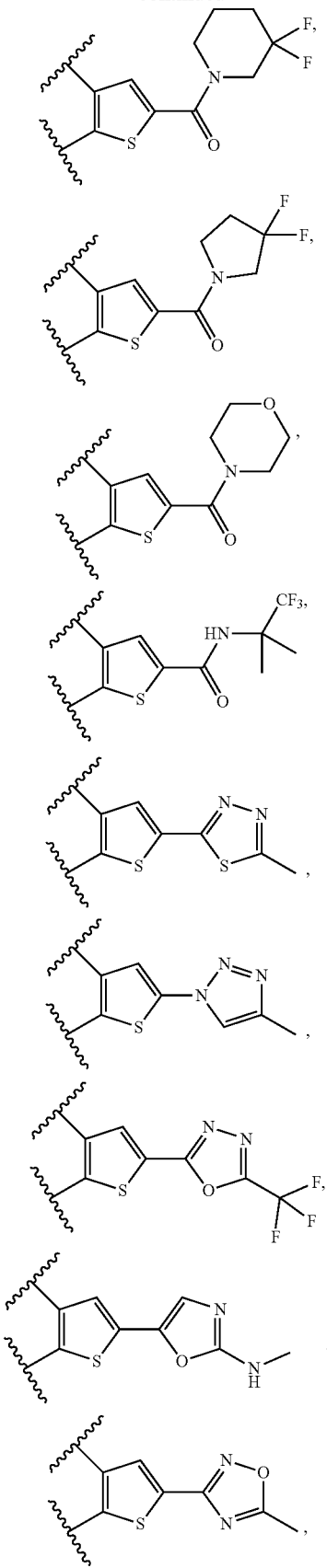

wherein the wavy lines denote attachment points with the A ring. In some embodiments of a compound of Formula (I), the C ring is selected from the group consisting of:
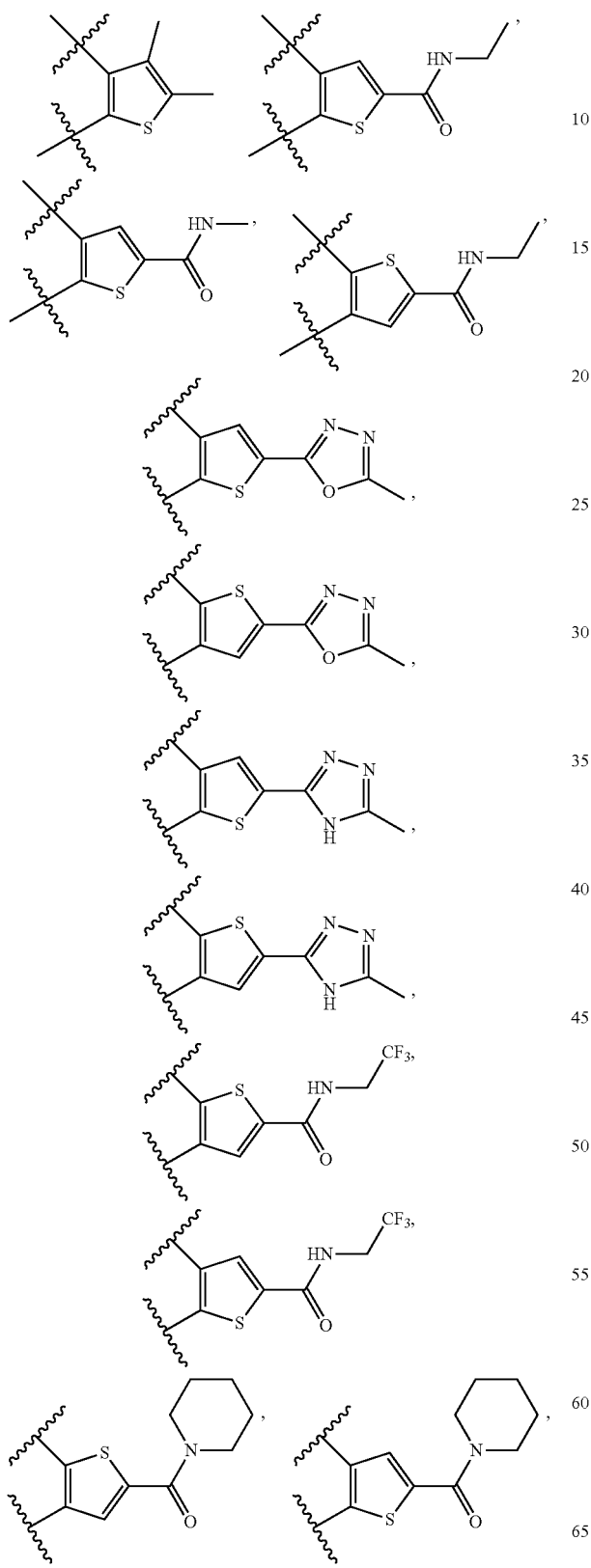
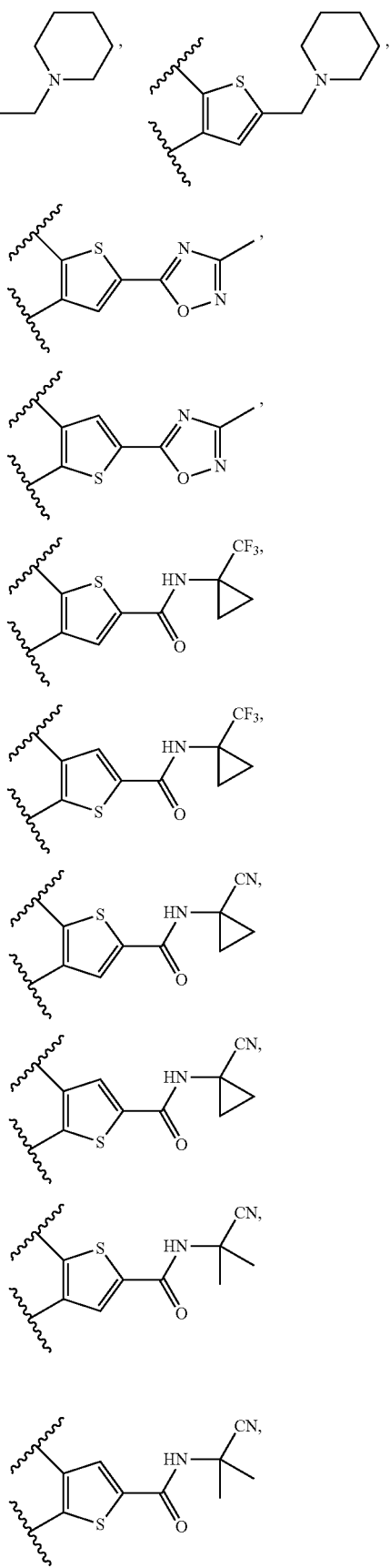

-continued
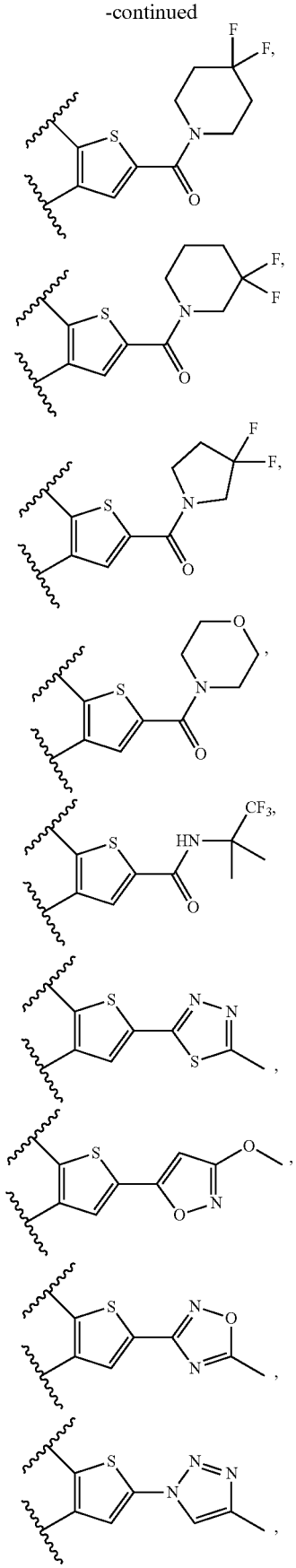
-continued
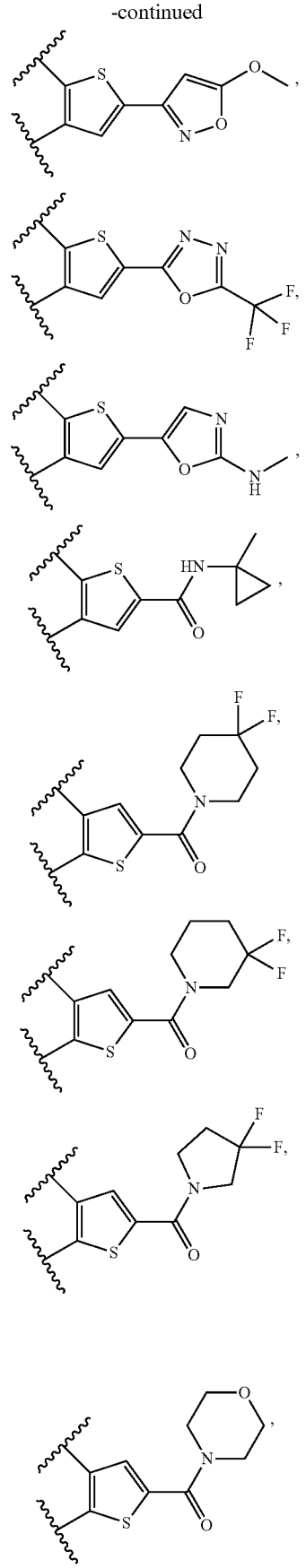

-continued

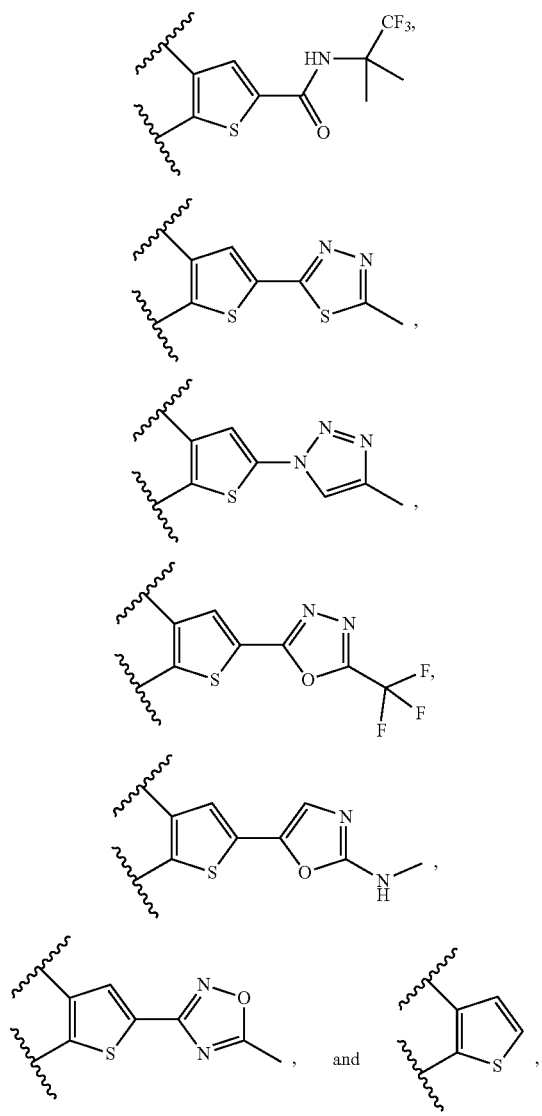

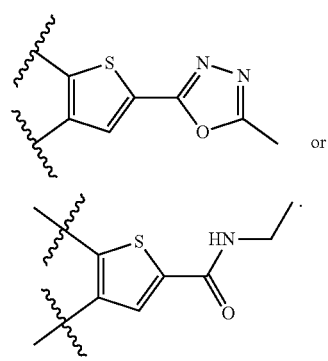

wherein the wavy lines denote attachment points with the A ring.

In some embodiments of a compound of Formula (I), the C ring is

In some embodiments, the C ring is

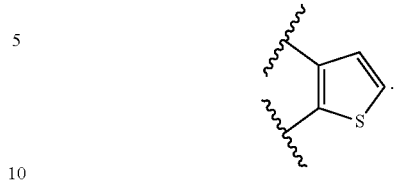

In some embodiments, the C ring

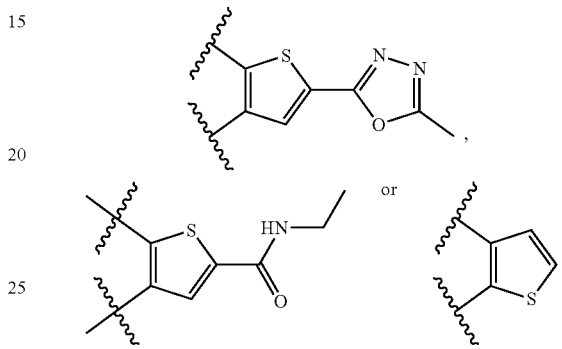

In some embodiments of a compound of Formula (I), $W_1$ is O and $Z_1$ is C—O—$R^c$. In some embodiments of a compound of Formula (I), $W_1$ is —$NR^{w1}$— and $Z_1$ is C—$NR^{w1}$—$R^c$. In some embodiments of a compound of Formula (I), $R^{w1}$ is hydrogen, $C_3$-$C_6$ cycloalkyl or $C_1$-$C_4$ alkyl optionally substituted by oxo, OH or halogen. In some embodiments of a compound of Formula (I), $R^{w1}$ is hydrogen. In some embodiments of a compound of Formula (I), $R^{w1}$ is $C_3$-$C_6$ cycloalkyl. In some embodiments of a compound of Formula (I), $R^{w1}$ is $C_1$-$C_4$ alkyl optionally substituted by oxo, OH or halogen. In some embodiments of a compound of Formula (I), $R^{w1}$ is methyl. In some embodiments of a compound of Formula (I), $W_1$ is —NH— and $Z_1$ is C—NH—$R^c$. In some embodiments of a compound of Formula (I) or any related formulae where applicable, $W_1$ and $Z_1$ are as provided herein to the same extent as is described for Formula (I).

In some embodiments of a compound of Formula (I), $R^c$ is $C_6$-$C_{14}$ aryl or 5- or 6-membered heteroaryl, wherein the $C_6$-$C_{14}$ aryl and 5- or 6-membered heteroaryl of $R^c$ are independently optionally substituted by $R^{c1}$. In some embodiments, each $R^{c1}$ is independently halogen or $C_1$-$C_4$ alkyl. In some embodiments of a compound of Formula (I), $R^c$ is $C_6$-$C_{14}$ aryl optionally substituted by $R^{c1}$. In some embodiments of a compound of Formula (I), $R^c$ is $C_6$-$C_{14}$ aryl which is unsubstituted. In some embodiments of a compound of Formula (I), $R^c$ is phenyl optionally substituted by $R^{c1}$. In some embodiments, $R^c$ is phenyl which is unsubstituted. In some embodiments, $R^c$ is phenyl optionally substituted by $R^{c1}$, wherein each $R^{c1}$ is independently halogen or $C_1$-$C_4$ alkyl. In some embodiments, $R^c$ is phenyl optionally substituted by $R^{c1}$, wherein each $R^{c1}$ is independently methyl or fluoro. In some embodiments of a compound of Formula (I), $R^c$ is 5- or 6-membered heteroaryl optionally substituted by $R^{c1}$. In some embodiments, $R^c$ is 5- or 6-membered heteroaryl which is unsubstituted, such as pyridinyl, pyrazinyl, pyridazinyl, primidinyl, triazinyl, pyrrolyl, pyrazolyl, imidazolyl, triazolyl, tetrazolyl, oxazolyl, thiazolyl, thiazolyl, or furanyl, each of which is unsubstituted. In some embodiments, $R^c$ is 5- or 6-membered heteroaryl optionally substituted by $R^{c1}$, such as pyridinyl, pyrazinyl, pyridazinyl, primidinyl, triazinyl, pyrrolyl, pyrazolyl, imidazolyl, triazolyl, tetrazolyl, oxazolyl, thiazolyl, thiazolyl, or furanyl, each of which is independently optionally substituted by $R^{c1}$. In some embodiments of a compound of Formula (J) or any related formulae where applicable, $R^c$ is as provided herein to the same extent as is described for Formula (I).

In some embodiments, $R^c$ is $C_3$-$C_6$ cycloalkyl optionally substituted by $R^{c1}$, wherein each $R^{c1}$ is independently halogen or $C_1$-$C_4$ alkyl. In some embodiments, each $R^{c1}$ is halogen. In some embodiments, $R^c$ is $C_6$-$C_{14}$ aryl, 5- to 6-membered heteroaryl, or $C_3$-$C_6$ cycloalkyl, wherein each $R^c$ is optionally substituted by $R^{c1}$.

In some embodiments of a compound of Formula (I), $R^c$ is

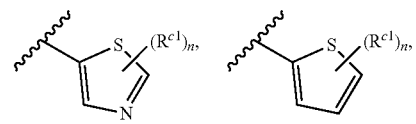

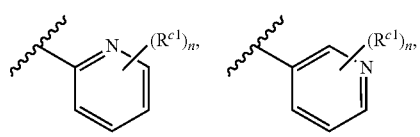

wherein the wavy lines denote attachment points and n is 0, 1, 2, 3, 4, or 5. In some embodiments, $R^c$ is

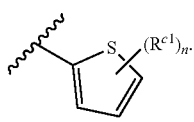

In some embodiments, $R^c$ is

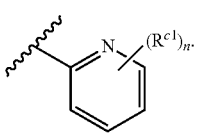

In some embodiments, $R^c$ is

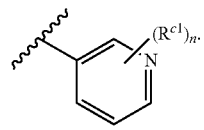

In some embodiments, $R^c$ is

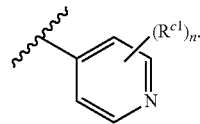

In some embodiments, $R^c$ is

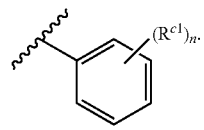

In some embodiments, $R^c$ is

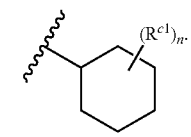

In some embodiments, $R^c$ is

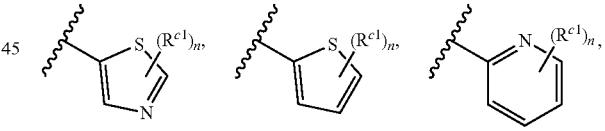

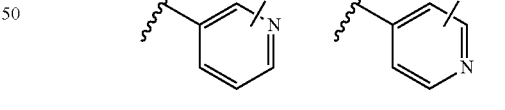

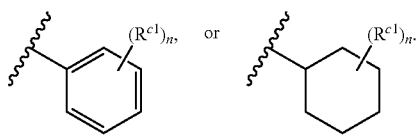

In some embodiments, each $R^{c1}$ is independently halogen or $C_1$-$C_4$ alkyl.

In some embodiments of a compound of Formula (I), $R^c$ is selected from the group consisting of:

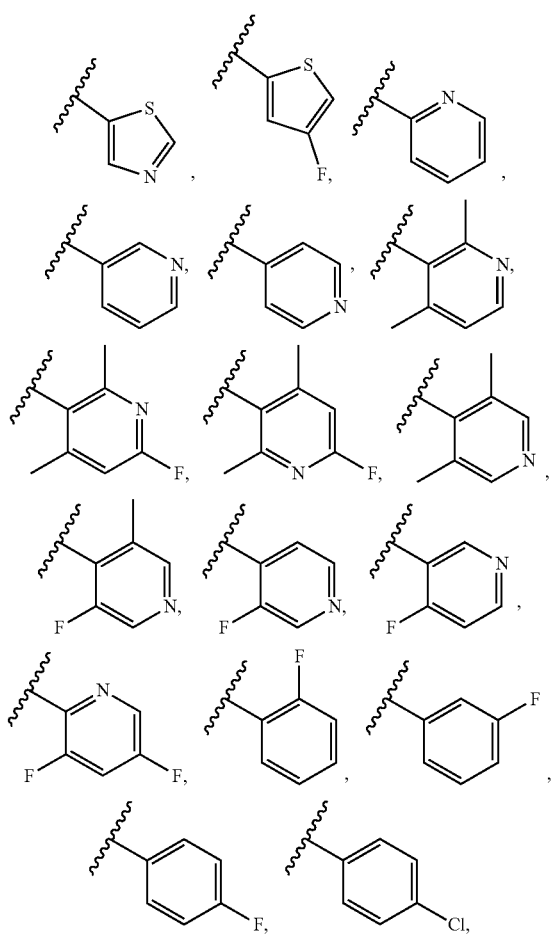
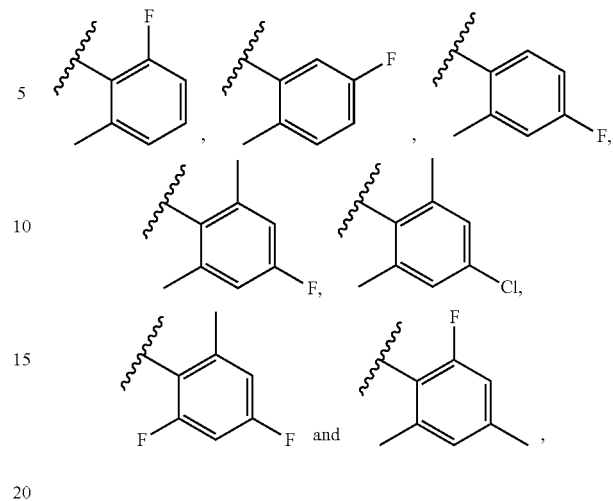
wherein the wavy lines denote attachment points. In some embodiments, $R^c$ is
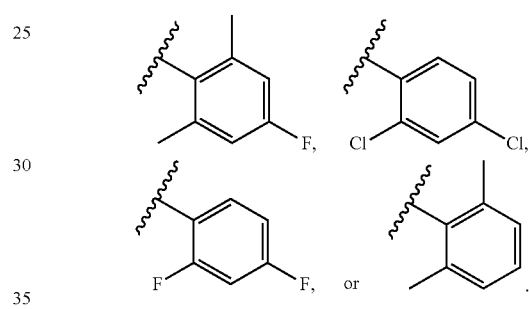
In some embodiments, $R^c$ is
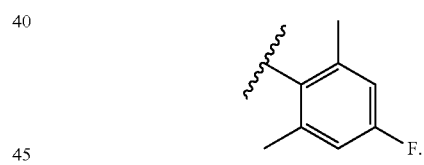
In some embodiments, $R^c$ is
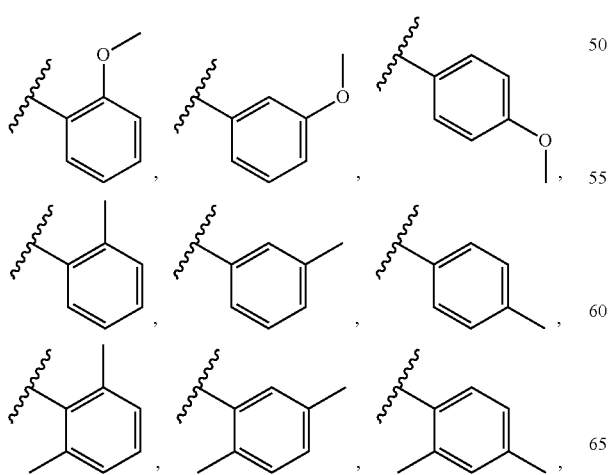
In some embodiments, $R^c$ is
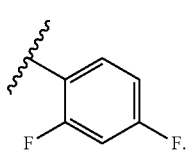 [SMILES: *c1ccc(F)cc1F]

In some embodiments, $R^c$ is
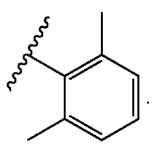
In some embodiments, $R^c$ is selected from the group consisting of:
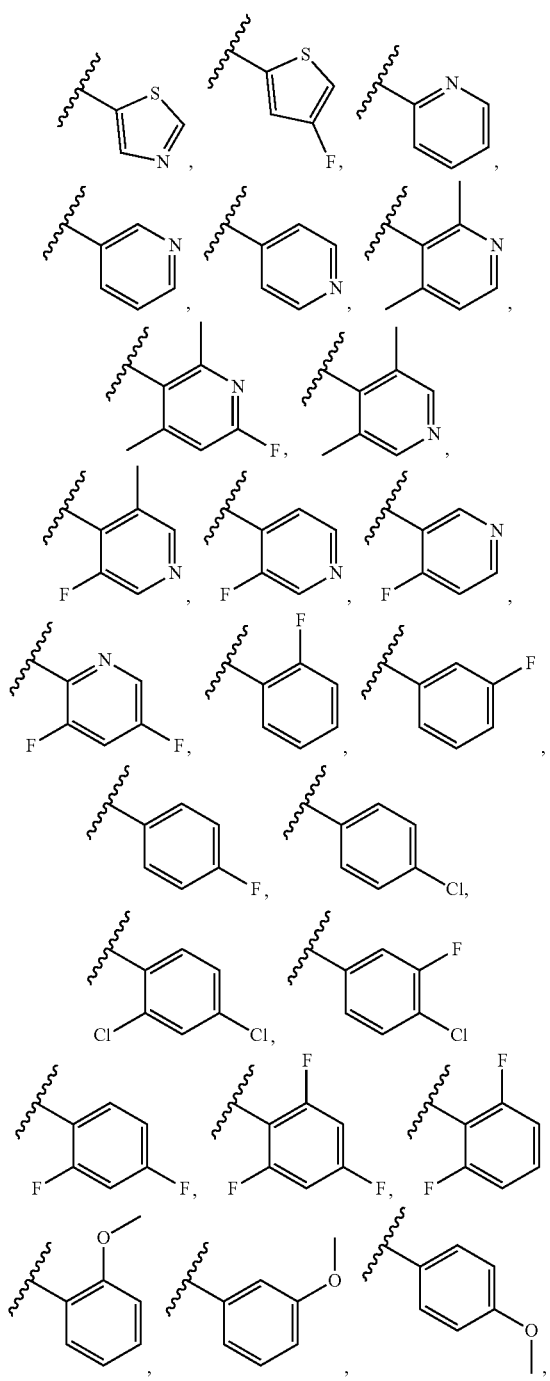
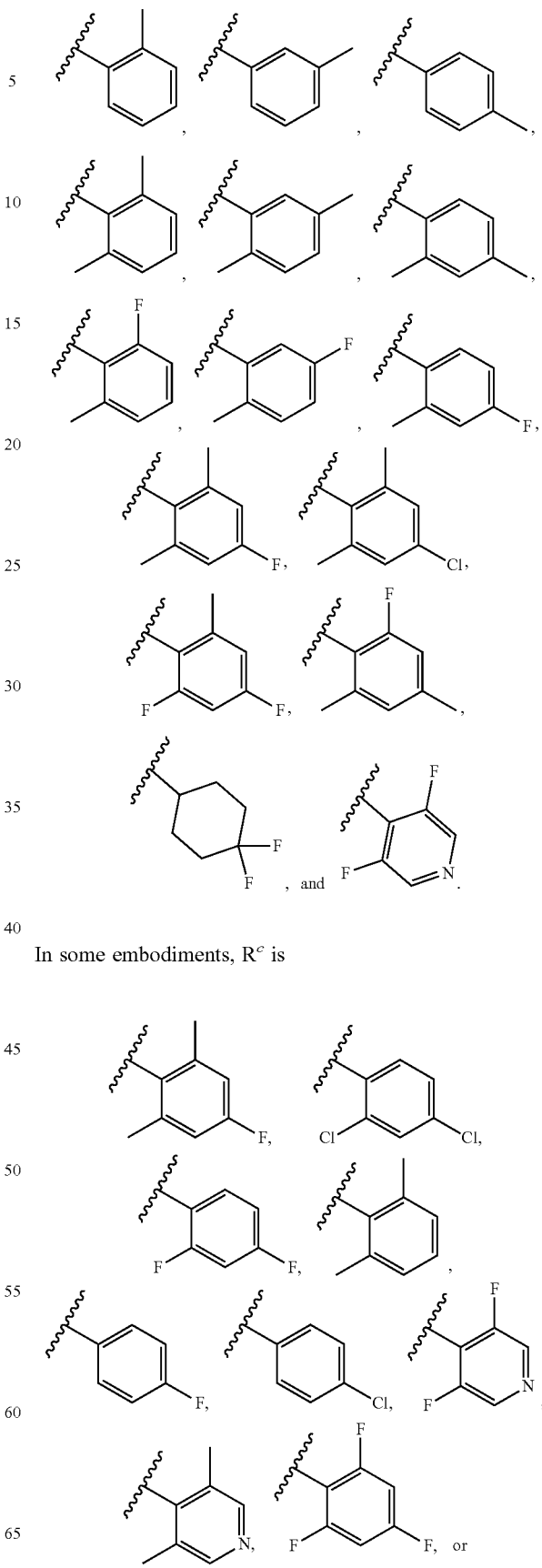
In some embodiments, $R^c$ is -continued In some embodiments, $R^c$ is

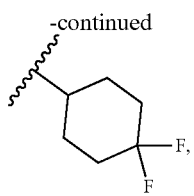

In some embodiments, $R^c$ is

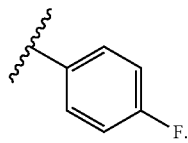 [SMILES: *c1ccc(F)cc1]

In some embodiments, $R^c$ is

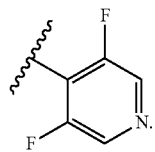

In some embodiments, $R^c$ is

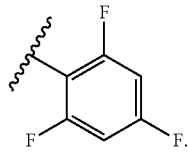 [SMILES: *c1c(F)cc(F)cc1F]

In some embodiments, $R^c$ is

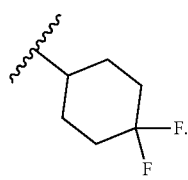 [SMILES: *C1CCC(F)(F)CC1]

In some embodiments of a compound of Formula (I), $Z_2$ is N. In some embodiments of a compound of Formula (I), $Z_2$ is C—$W_2$—$R^d$. In some embodiments of a compound of Formula (I), $W_2$ is —O—. In some embodiments of a compound of Formula (I), $W_2$ is a bond. In some embodiments of a compound of Formula (I), $W_2$ is —$NR^{w2}$—. In some embodiments of a compound of Formula (I), $R^{w2}$ is hydrogen or $C_1$-$C_4$ alkyl optionally substituted by oxo, OH or halogen. In some embodiments of a compound of Formula (I), $W_2$ is —$NR^{w2}$— and $R^{w2}$ is hydrogen. In some embodiments, $R^{w2}$ is $C_1$-$C_4$ alkyl optionally substituted by oxo, OH or halogen. In some embodiments of a compound of Formula (I), $R^{w2}$ is methyl. In some embodiments of a compound of Formula (I), $R^{w2}$ is $C_3$-$C_6$ cycloalkyl. In some embodiments of a compound of Formula (I), $W_2$ is —$NR^{w2}$— and $R^{w2}$ is —$CH_3$—. In some embodiments of a compound of Formula (I), $W_2$ is —$NR^{w2}$— and $R^{w2}$ is hydrogen. In some embodiments of a compound of Formula (J) or any related formulae where applicable, $Z_2$ is provided herein to the same extent as is described for Formula (I).

In some embodiments of a compound of Formula (I), $R^d$ is hydrogen. In some embodiments of a compound of Formula (I), $R^d$ is $C_1$-$C_4$ alkyl, such as methyl, ethyl, n-propyl, or isopropyl. In some embodiments, $R^d$ is methyl. In some embodiments, $Z_2$ is C—$W_2$—$R^d$, wherein $W^2$ is a bond and $R^d$ is hydrogen.

In some embodiments of a compound of Formula (I), $Z_3$ is N. In some embodiments of a compound of Formula (I), $Z_3$ is C—$R^e$. In some embodiments of a compound of Formula (I), $R^e$ is hydrogen. In some embodiments of a compound of Formula (I), $R^e$ is halogen, such as fluoro, chloro, bromo, or iodo. In some embodiments of a compound of Formula (I), $R^e$ is cyano. In some embodiments, $R^e$ is 3- to 6-membered heterocyclyl, such as tetrahydrofuranyl, pyrrolidinyl, piperidinyl, piperazinyl, morpholinyl, or thiomorpholinyl. In some embodiments, $R^e$ is $C_1$-$C_4$ alkyl such as methyl, ethyl, n-propyl, or isopropyl. In some embodiments, $Z_3$ is C—$R^e$ and $R^e$ is hydrogen. In some embodiments of a compound of Formula (J) or any related formulae where applicable, $Z_3$ is provided herein to the same extent as is described for Formula (I).

In some embodiments of a compound of Formula (I), $R^3$ is —$(CH_2)_m NR^{13}S(O)_2R^{14}$ or $C_1$-$C_4$ alkyl substituted by halogen, oxo, —CN or —OH. In some embodiments, $R^3$ is —$(CH_2)_m NR^{13}S(O)_2R^{14}$. In some embodiments of a compound of Formula (I), m is 0. In some embodiments of a compound of Formula (I), m is 1. In some embodiments of a compound of Formula (I), m is 2. In some embodiments of a compound of Formula (I), m is 3. In some embodiments, $R^3$ is —$(CH_2)_m NR^{13}S(O)_2R^{14}$, wherein m is 0. In some embodiments, $R^3$ is —$(CH_2)_m NR^{13}S(O)_2R^{14}$, wherein m is 0 and $R^{13}$ and $R^{14}$ are each independently hydrogen or $C_1$-$C_4$ alkyl. In some embodiments, $R^3$ is —$(CH_2)_m NR^{13}S(O)_2R^{14}$, wherein m is 0, $R^{13}$ is hydrogen, and $R^{14}$ is $C_1$-$C_4$ alkyl such as methyl, ethyl, n-propyl, or isopropyl. In some embodiments, $R^3$ is

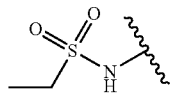 [SMILES: *NS(=O)(=O)CC]

In some embodiments of a compound of Formula (I), $R^3$ is $C_1$-$C_4$ alkyl optionally substituted by halogen, oxo, —CN or —OH. In some embodiments of a compound of Formula (I), $R^3$ is $C_1$-$C_4$ alkyl substituted by —OH. In some embodiments of a compound of Formula (I), $R^3$ is.

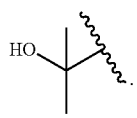

In some embodiments of a compound of Formula (I), $R^3$ is

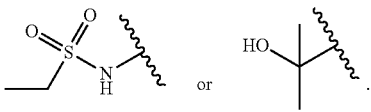

In some embodiments, $R^3$ is

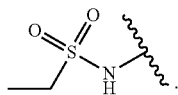

In some embodiments, $R^3$ is

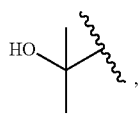

wherein the wavy lines denote attachment points. In some embodiments of a compound of Formula (J) or any related formulae where applicable, $R^3$ is provided herein to the same extent as is described for Formula (I).

In some embodiments of a compound of Formula (J) or any related formulae where applicable such as compound of Formula (I), $R^3$ is

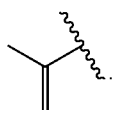

In some embodiments, $R^3$ is $C_3$-$C_6$ cycloalkyl optionally substituted by halogen, oxo, —CN, or —OH. In some embodiments, $R^3$ is $C_3$-$C_6$ cycloalkyl optionally substituted by —CN or —OH. In some embodiments, $R^3$ is unsubstituted $C_3$-$C_6$ cycloalkyl. In some embodiments, $R^3$ is

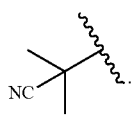

In some embodiments, $R^3$ is

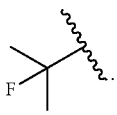

In some embodiments, $R^3$ is

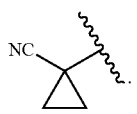

In some embodiments, $R^3$ is

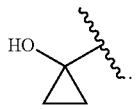

In some embodiments, $R^3$ is

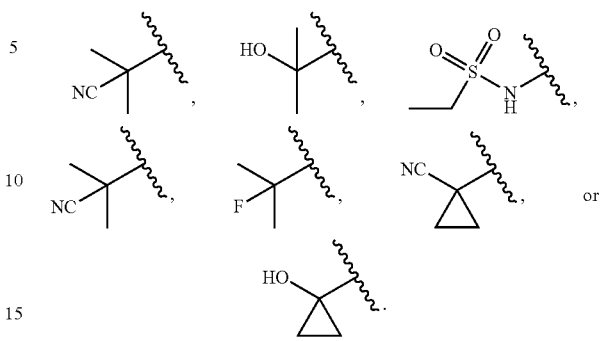

In some embodiments. $R^3$ is

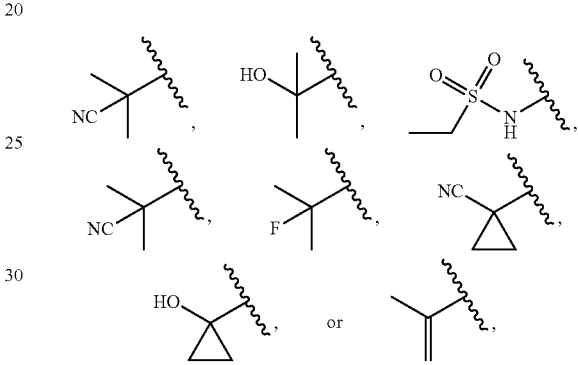

wherein the wave lines denote attachments points.

In some embodiments of a compound of Formula (J) or any related formulae where applicable such as a compound of Formula (I), the compound has one or more of the following features:

(I) X is O;

(II) $R^1$ is $C_1$-$C_3$ alkyl, such as methyl;

(III) $G_1$ is $CR^a$, wherein $R^a$ is hydrogen;

(IV) $Z_2$ is CH;

(V) $Z_3$ is CH;

(VI) $R^2$ is (1) —C(O)$NR^{10}R^{11}$ optionally substituted by $R^{12}$, such as

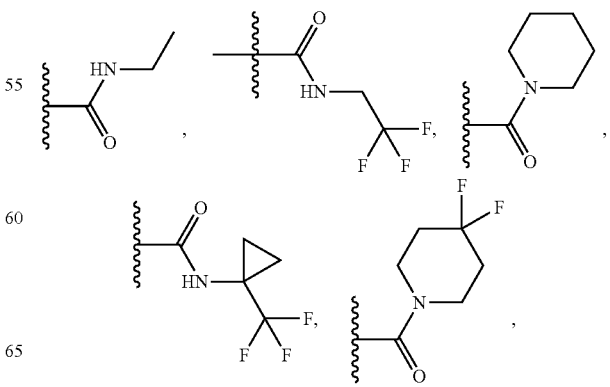

(2) 5- to 10-membered heteroaryl optionally substituted by $R^{12}$, such as or (3) —($C_1$-$C_3$ alkylene)3- to 6-membered heterocyclyl optionally substituted by $R^{12}$, such as (VII) $R^3$ is (4) —$(CH_2)_m NR^{13}S(O)_2R^{14}$, such as or (5) $C_1$-$C_4$ alkyl substituted by —OH, such as and (VIII) $Z_1$ is C—O—$R^c$, wherein $R^c$ is phenyl optionally substituted by $R^{c1}$, such as F, In some embodiments, (I) applies. In some embodiments, (II) applies. In some embodiments, (III) applies. In some embodiments, (IV) applies. In some embodiments, (V) applies. In some embodiments, (VI) applies. In some embodiments, (VII) applies. In some embodiments, (VIII) applies. In some embodiments, (1) applies. In some embodiments, (2) applies. In some embodiments, (3) applies. In some embodiments, (4) applies. In some embodiments, (5) applies. In some embodiments, (I), (II), (III), (IV), (V), (VI), (VII), and (VIII) apply. In some embodiments, (I), (II), (III), (IV), (V), and (1) apply. In some embodiments, (I), (II), (III), (IV), (V), and (4) apply. In some embodiments, (I), (II), (III), (IV), (V), and (5) apply. In some embodiments, (I), (II), (III), (IV), (V), and (VIII) apply. In some embodiments, (I), (II), (III), (IV), (V), and (2) apply. In some embodiments, (I), (II), (III), (IV), (V), and (3) apply. In some embodiments, (I), (II), (III), (IV), (V), (1), (VII), and (VIII) apply. In some embodiments, (I), (II), (III), (IV), (V), (2), (VII), and (VIII) apply. In some embodiments, (I), (II), (III), (IV), (V), (3), (VII), and (VIII) apply. In some embodiments, (I), (II), (III), (IV), (V), (VI), (4), and (VIII) apply. In some embodiments, (I), (II), (III), (IV), (V), (VI), (5), and (VIII) apply. In some embodiments, (VIII) and (4) apply. In some embodiments, (VIII) and (5) apply. In some embodiments, (1) and (VIII) apply. In some embodiments, (2) and (VIII) apply. In some embodiments, (3) and (VIII) apply. In some embodiments, (1) and (4) apply. In some embodiments, (1) and (5) apply. In some embodiments, (2) and (4) apply. In some embodiments, (2) and (5) apply. In some embodiments, (3) and (4) apply. In some embodiments, (3) and (5) apply.

In some embodiments of a compound of Formula (J) or any related formulae where applicable such as a compound of Formula (I), the compound has one or more of the following features:

(I-1) X is O;
(II-1) $R^1$ is $C_1$-$C_3$ alkyl, such as methyl;
(III-1) $G_1$ is $CR^a$, wherein $R^a$ is hydrogen;
(IV-1) $Z_2$ is CH;
(V-1) $Z_3$ is CH;
(VI-1) $R^2$ is
(1-1) —C(O)$NR^{10}R^{11}$ optionally substituted by $R^{12}$, such as

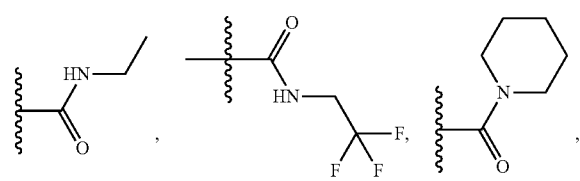

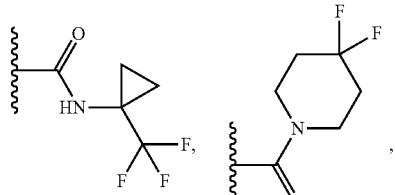

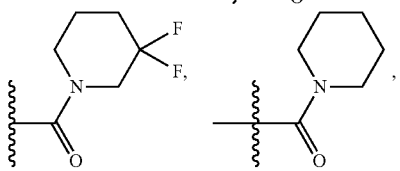

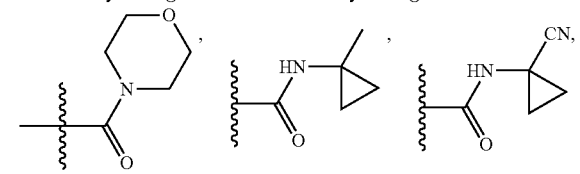

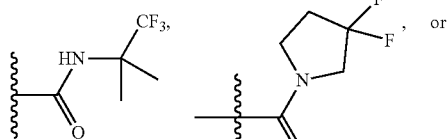

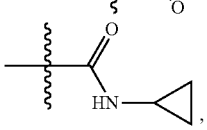

(2-1) 5- to 10-membered heteroaryl optionally substituted by $R^{12}$, such as

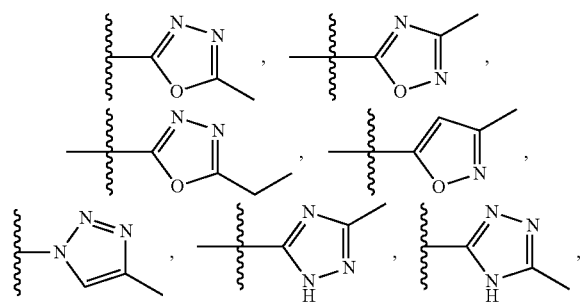

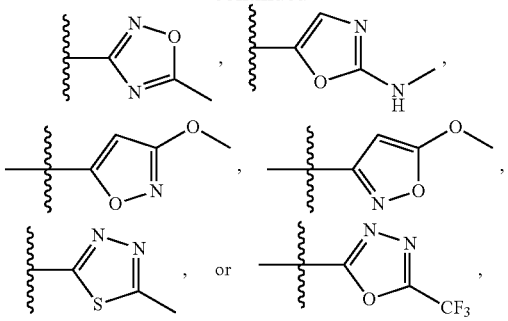

(3-1) —($C_1$-$C_3$ alkylene)3- to 6-membered heterocyclyl optionally substituted by $R^{12}$, such as

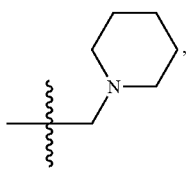 [SMILES: *CN1CCCCC1]

or
(4-1) hydrogen;
(VII) $R^3$ is
(5-1) —$(CH_2)_m NR^{13}S(O)_2R^{14}$, such as

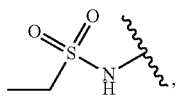

(6-1) $C_1$-$C_4$ alkyl substituted by —OH, such as

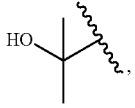 [SMILES: *C(C)(C)O]

(7-1) $C_3$-$C_6$ cycloalkyl optionally substituted by halogen, oxo, —CN, or —OH, such as

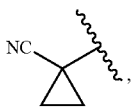

or
(8-1) $C_2$-$C_6$ alkenyl; and
(VIII-1) $Z_1$ is C—O—$R^c$, wherein $R^c$ is phenyl optionally substituted by $R^{c1}$, such as

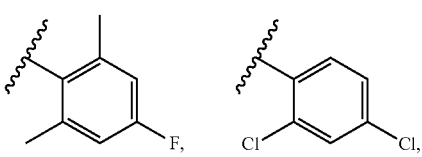

-continued

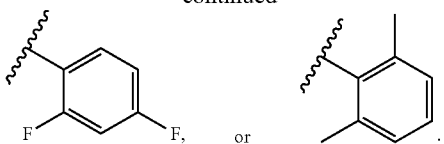

In some embodiments, (1-1) applies. In some embodiments, (II-1) applies. In some embodiments, (III-1) applies. In some embodiments, (IV-1) applies. In some embodiments, (V-1) applies. In some embodiments, (VI-1) applies. In some embodiments, (VII-1) applies. In some embodiments, (VIII-1) applies. In some embodiments, (1-1) applies. In some embodiments, (2-1) applies. In some embodiments, (3-1) applies. In some embodiments, (4-1) applies. In some embodiments, (5-1) applies. In some embodiments, (6-1) applies. In some embodiments, (7-1) applies. In some embodiments, (8-1) applies. In some embodiments, (I-1), (II-1), (III-1), (IV-1), (V-1), (VI-1), (VII-1), and (VIII-1) apply. In some embodiments, (1-1), (II-1), (III-1), (IV-1), (V-1), (VII-1) and (VIII-1) apply. In some embodiments, (I-1), (II-1), (III-1), (IV-1), (V-1), and (VIII-1) apply. In some embodiments, (I-1), (II-1), (III-1), (IV-1), (V-1), and (1-1) apply. In some embodiments, (I-1), (II-1), (III-1), (IV-1), (V-1), and (5-1) apply. In some embodiments, (1-1), (II-1), (III-1), (IV-1), (V-1), and (6-1) apply. In some embodiments, (I-1), (II-1), (III-1), (IV-1), (V-1), and (VIII-1) apply. In some embodiments, (I-1), (II-1), (III-1), (IV-1), (V-1), and (2-1) apply. In some embodiments, (I-1), (II-1), (III-1), (IV-1), (V-1), and (3-1) apply. In some embodiments, (I-1), (II-1), (III-1), (IV-1), (V-1), (1-1), (VII-1), and (VIII-1) apply. In some embodiments, (1-1), (II-1), (III-1), (IV-1), (V-1), (2-1), (VII-1), and (VIII-1) apply. In some embodiments, (1-1), (II-1), (III-1), (IV-1), (V-1), (3-1), (VII-1), and (VIII-1) apply. In some embodiments, (1-1), (II-1), (III-1), (IV-1), (V-1), (VI-1), (5-1), and (VIII-1) apply. In some embodiments, (1-1), (II-1), (III-1), (IV-1), (V-1), (VI-1), (6-1), and (VIII-1) apply. In some embodiments, (VIII-1) and (5-1) apply. In some embodiments, (VIII-1) and (6-1) apply. In some embodiments, (1-1) and (VIII-1) apply. In some embodiments, (2-1) and (VIII-1) apply. In some embodiments, (3-1) and (VIII-1) apply. In some embodiments, (1-1) and (5-1) apply. In some embodiments, (1-1) and (6-1) apply. In some embodiments, (2-1) and (5-1) apply. In some embodiments, (2-1) and (6-1) apply. In some embodiments, (3-1) and (5-1) apply. In some embodiments, (3-1) and (6-1) apply In some embodiments, (I-1), (II-1), (III-1), (IV-1), (V-1), and (7-1) apply. In some embodiments, (I-1), (II-1), (III-1), (IV-1), (V-1), and (6-1) apply. In some embodiments, (I-1), (II-1), (III-1), (IV-1), (V-1), (1-1), and (VIII-1) apply. In some embodiments, (1-1), (II-1), (III-1), (IV-1), (V-1), (7-1), and (VIII-1) apply. In some embodiments, (I-1), (II-1), (III-1), (IV-1), (V-1), (6-1), and (VIII-1) apply. In some embodiments, (1-1) and (VIII-1) apply. In some embodiments, (7-1) and (VIII-1) apply. In some embodiments, (6-1) and (VIII-1) apply. In some embodiments, (I-1), (VII-1), and (8-1) apply. It is to be understood that any variable for a compound of Formula (J) or any related formulae where applicable such as a compound of formula (I) may be combined with any other variable for a compound of Formula (J) or any related formulae where applicable such as a compound of Formula (I) the same as if each and every combination of variables were specifically and individually listed. For example, it is understood that each description of $R^3$ may be combined with each description of other variation on B ring ($Z_1$, $Z_2$, $Z_3$) the same as if each and every combination were specifically and individually listed. It is similarly understood that each description of $R^3$ may be combined with each description of every variation on A ring (X, $R^1$, $G_1$) and/or each description of every variation on C ring the same as if each and every combination were specifically and individually listed. It is also understood that each description of every variation on B ring ($R^3$, $Z_1$, $Z_2$, $Z_3$) may be combined with each description of every variation on A ring (X, $R^1$, $G_1$) the same as if each and every combination were specifically and individually listed. It is similarly understood that each description of every variation on B ring ($R^3$, $Z_1$, $Z_2$, $Z_3$) may be combined with each description of every variation on C ring ($M^1$, $M^2$, $R^2$) the same as if each and every combination were specifically and individually listed. For example, in one aspect, it is understood that each description of every variation on B ring may be combined in one aspect with a variation of A ring in which X is O; $G_1$ is CH; and $R^1$ is methyl. In one such variation, B ring is as defined in any variation herein, A ring is with the variables such as X is O; $G_1$ is hydrogen; $R^1$ is methyl; and C ring is substituted thiophenyl. As another example, in another aspect, provided is a compound, or a tautomer or isomer thereof, or a pharmaceutically acceptable salt of any of the foregoing, wherein $R^3$ is

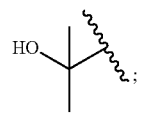

$Z_2$ and $Z_3$ are CH; and $Z_1$ is C—$W_1$—$R^c$, wherein —$W_1$—$R^c$ is

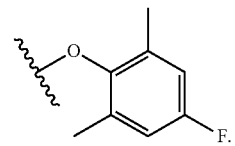 [SMILES: *Oc1c(C)cc(F)cc1C]

As another example, provided is a compound, or a tautomer or isomer thereof, or a pharmaceutically acceptable salt of any of the foregoing, wherein $R^3$ is

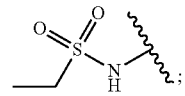 [SMILES: *NS(=O)(=O)CC]

$Z_2$ and $Z_3$ are CH; and $Z_1$ is C—$W_1$—$R^c$, wherein —$W_1$—$R^c$ is

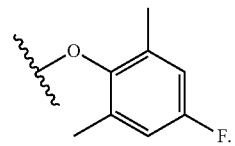 [SMILES: *Oc1c(C)cc(F)cc1C]

Also provided are salts of compounds referred to herein, such as pharmaceutically acceptable salts. The invention also includes any or all of the stereochemical forms, including any enantiomeric or diastereomeric forms, and any tautomers or other forms of the compounds described.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

Representative compounds are listed in Tables 1 and 2. It is understood that individual enantiomers and diastereomers are included in the tables below by Compound No. and their corresponding structures can be readily determined therefrom.

TABLE 1

Representative Compounds

| Com. No. | Structure |
|---|---|
| 1 | 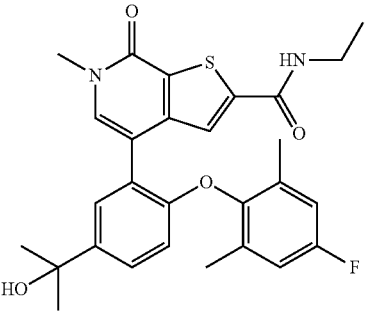 [SMILES: CCNC(=O)c1cc2c(-c3cc(C(C)(C)O)ccc3Oc3c(C)cc(F)cc3C)cn(C)c(=O)c2s1] |
| 2 | 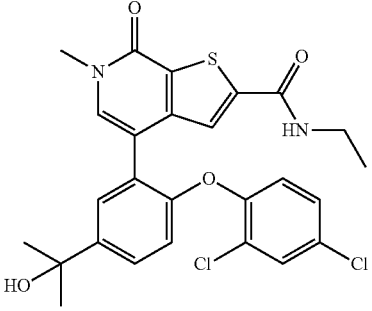 [SMILES: CCNC(=O)c1cc2c(-c3cc(C(C)(C)O)ccc3Oc3ccc(Cl)cc3Cl)cn(C)c(=O)c2s1] |

TABLE 1-continued

Representative Compounds

| Com. No. | Structure |
|---|---|
| 3 | 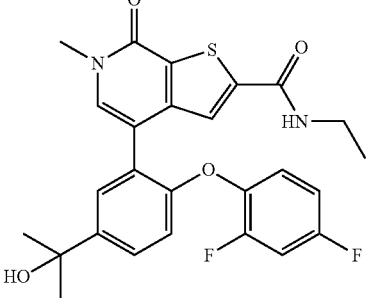 |
| 4 | 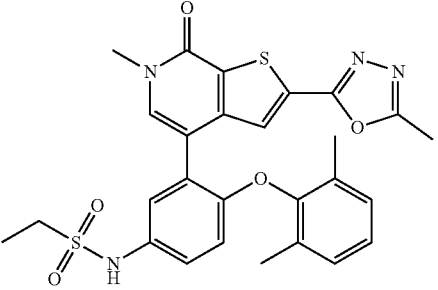 [SMILES: CCS(=O)(=O)Nc1ccc(Oc2c(C)cccc2C)c(-c2cn(C)c(=O)c3sc(-c4nnc(C)o4)cc23)c1] |
| 5 | 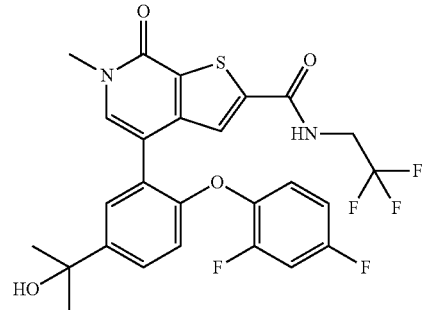 [SMILES: Cn1cc(-c2cc(C(C)(C)O)ccc2Oc2ccc(F)cc2F)c2cc(C(=O)NCC(F)(F)F)sc2c1=O] |
| 6 | 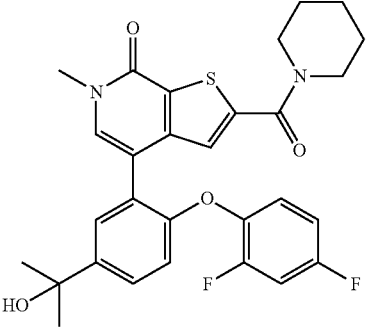 |

TABLE 1-continued

Representative Compounds

| Com. No. | Structure |
|---|---|
| 7 | (structure) |
| 8 | (structure) |
| 9 | (structure) |
| 10 | (structure) |
| 11 | (structure) |
| 12 | (structure) |
| 13 | (structure) |
| 14 | (structure) |

TABLE 1-continued
Representative Compounds
| Com. No. | Structure |
|---|---|
| 15 | 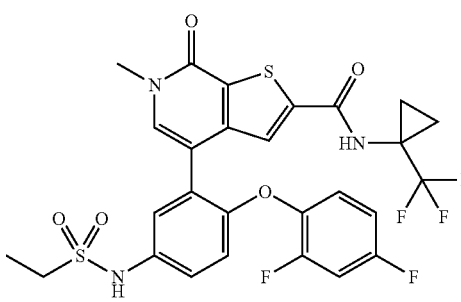 |
| 16 | 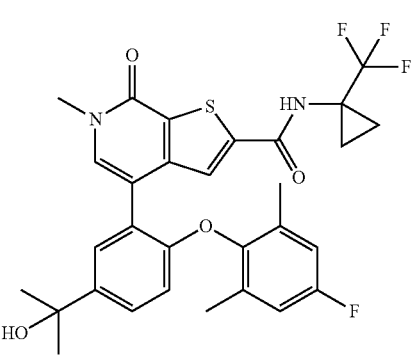 [SMILES: Cc1cc(F)cc(C)c1Oc1ccc(C(C)(C)O)cc1-c1cn(C)c(=O)c2sc(C(=O)NC3(C(F)(F)F)CC3)cc12] |
| 17 | 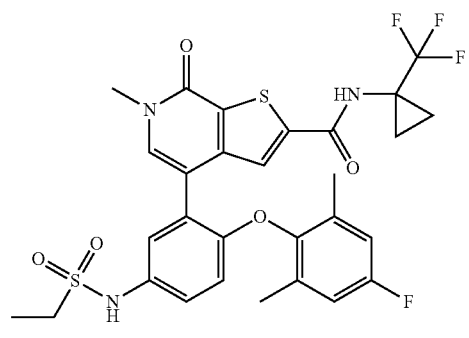 [SMILES: CCS(=O)(=O)Nc1ccc(Oc2c(C)cc(F)cc2C)c(-c2cn(C)c(=O)c3sc(C(=O)NC4(C(F)(F)F)CC4)cc23)c1] |
| 18 | 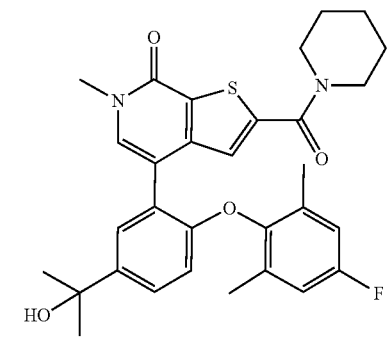 [SMILES: Cc1cc(F)cc(C)c1Oc1ccc(C(C)(C)O)cc1-c1cn(C)c(=O)c2sc(C(=O)N3CCCCC3)cc12] |
| 19 | 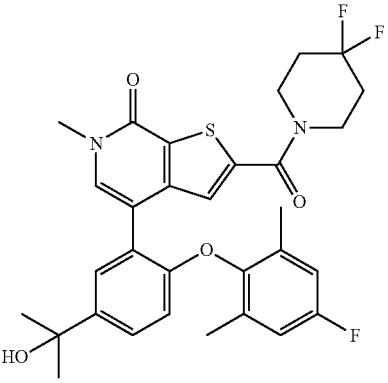 [SMILES: Cc1cc(F)cc(C)c1Oc1ccc(C(C)(C)O)cc1-c1cn(C)c(=O)c2sc(C(=O)N3CCC(F)(F)CC3)cc12] |
| 20 | 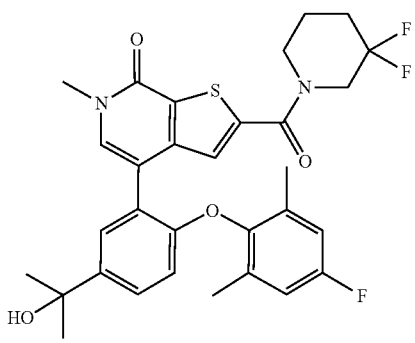 [SMILES: Cc1cc(F)cc(C)c1Oc1ccc(C(C)(C)O)cc1-c1cn(C)c(=O)c2sc(C(=O)N3CCCC(F)(F)C3)cc12] |
| 21 | 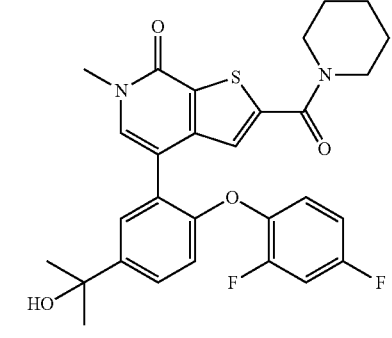 [SMILES: Cn1cc(-c2cc(C(C)(C)O)ccc2Oc2ccc(F)cc2F)c2cc(C(=O)N3CCCCC3)sc2c1=O] |
| 22 | 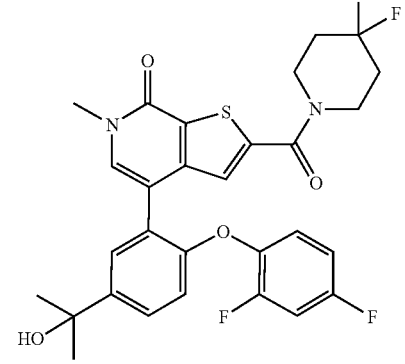 |

TABLE 1-continued
Representative Compounds
| Com. No. | Structure |
|---|---|
| 23 | 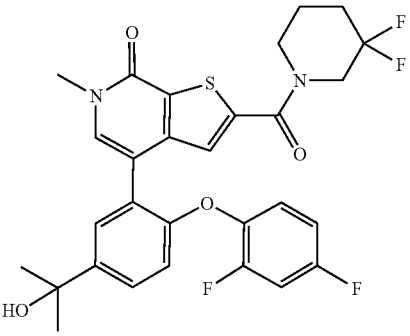 [SMILES: Cn1cc(-c2cc(C(C)(C)O)ccc2Oc2ccc(F)cc2F)c2cc(C(=O)N3CCCC(F)(F)C3)sc2c1=O] |
| 24 | 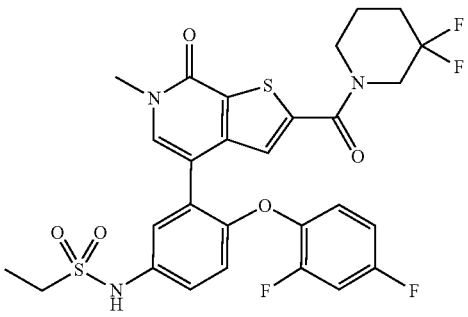 [SMILES: CCS(=O)(=O)Nc1ccc(Oc2ccc(F)cc2F)c(-c2cn(C)c(=O)c3sc(C(=O)N4CCCC(F)(F)C4)cc23)c1] |
| 25 | 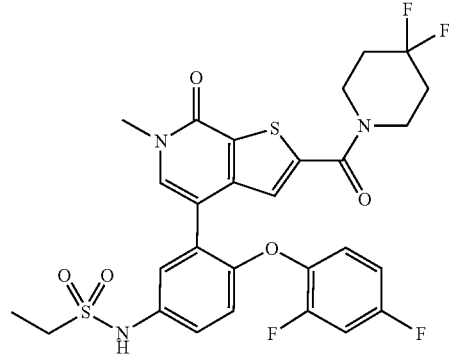 [SMILES: CCS(=O)(=O)Nc1ccc(Oc2ccc(F)cc2F)c(-c2cn(C)c(=O)c3sc(C(=O)N4CCC(F)(F)CC4)cc23)c1] |
| 26 | 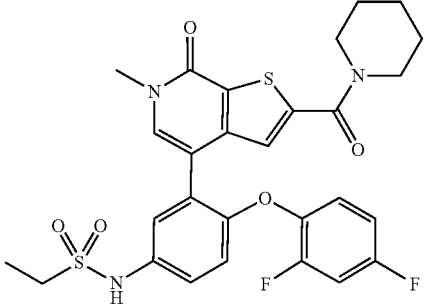 [SMILES: CCS(=O)(=O)Nc1ccc(Oc2ccc(F)cc2F)c(-c2cn(C)c(=O)c3sc(C(=O)N4CCCCC4)cc23)c1] |
| 27 | 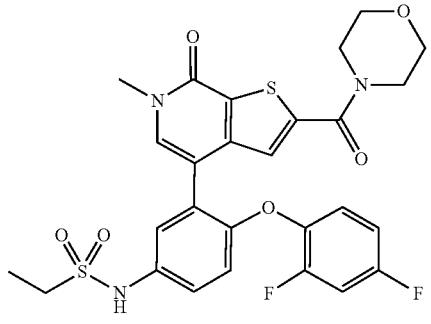 [SMILES: CCS(=O)(=O)Nc1ccc(Oc2ccc(F)cc2F)c(-c2cn(C)c(=O)c3sc(C(=O)N4CCOCC4)cc23)c1] |
| 28 | 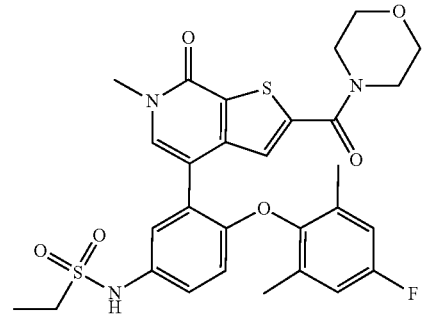 [SMILES: CCS(=O)(=O)Nc1ccc(Oc2c(C)cc(F)cc2C)c(-c2cn(C)c(=O)c3sc(C(=O)N4CCOCC4)cc23)c1] |
| 29 | 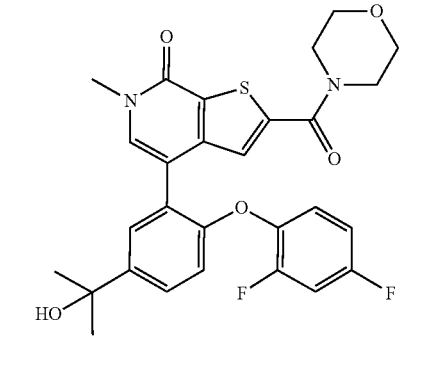 [SMILES: Cn1cc(-c2cc(C(C)(C)O)ccc2Oc2ccc(F)cc2F)c2cc(C(=O)N3CCOCC3)sc2c1=O] |
| 30 | 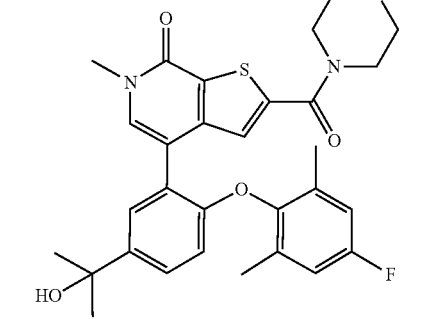 |

TABLE 1-continued

Representative Compounds

| Com. No. | Structure |
|---|---|
| 31 | |
| 32 | |
| 33 | |
| 34 | |
| 35 | 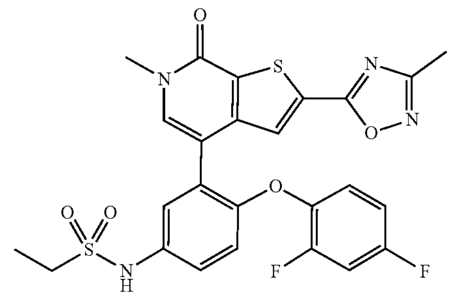 [SMILES: CCS(=O)(=O)Nc1ccc(Oc2ccc(F)cc2F)c(-c2cn(C)c(=O)c3sc(-c4nc(C)no4)cc23)c1] |
| 36 | 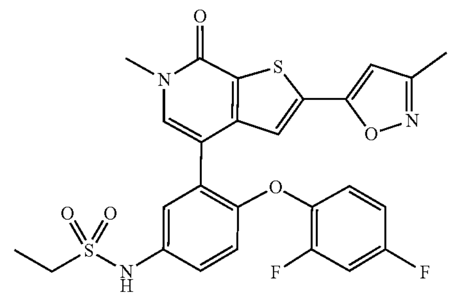 [SMILES: CCS(=O)(=O)Nc1ccc(Oc2ccc(F)cc2F)c(-c2cn(C)c(=O)c3sc(-c4cc(C)no4)cc23)c1] |
| 37 | 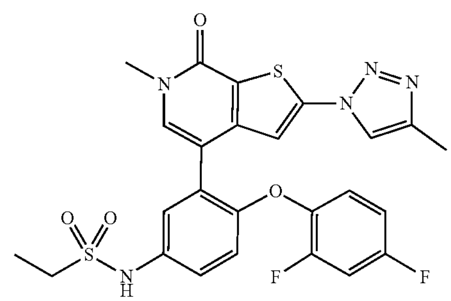 [SMILES: CCS(=O)(=O)Nc1ccc(Oc2ccc(F)cc2F)c(-c2cn(C)c(=O)c3sc(-n4cc(C)nn4)cc23)c1] |
| 38 | 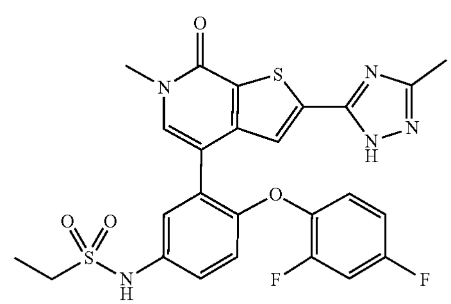 [SMILES: CCS(=O)(=O)Nc1ccc(Oc2ccc(F)cc2F)c(-c2cn(C)c(=O)c3sc(-c4nc(C)n[nH]4)cc23)c1] |
| 39 | 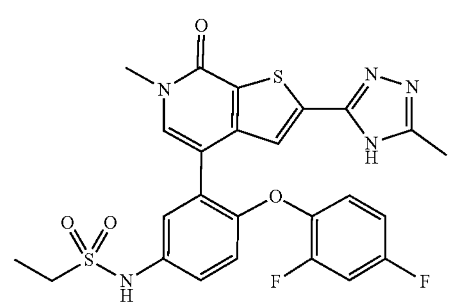 [SMILES: CCS(=O)(=O)Nc1ccc(Oc2ccc(F)cc2F)c(-c2cn(C)c(=O)c3sc(-c4nnc(C)[nH]4)cc23)c1] |

TABLE 1-continued

Representative Compounds

| Com. No. | Structure |
|---|---|
| 40 | (structure) |
| 41 | (structure) |
| 42 | (structure) |
| 43 | (structure) |
| 44 | (structure) |
| 45 | (structure) |
| 46 | (structure) |
| 47 | (structure) |
| 48 | (structure) |
| 49 | (structure) |

TABLE 1-continued

Representative Compounds

| Com. No. | Structure |
|---|---|
| 50 | (structure) |
| 51 | (structure) |
| 52 | (structure) |
| 53 | (structure) |
| 54 | (structure) |
| 55 | (structure) |
| 56 | (structure) |
| 57 | (structure) |
| 58 | (structure) |
| 59 | (structure) |

TABLE 1-continued

Representative Compounds

| Com. No. | Structure |
|---|---|
| 60 | |
| 61 | |
| 62 | |
| 63 | |
| 64 | 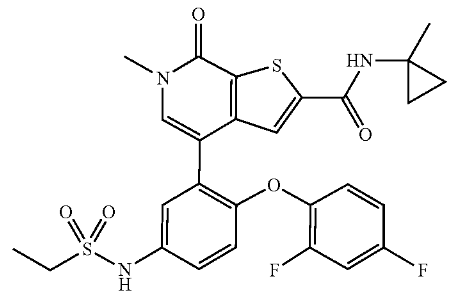 [SMILES: CCS(=O)(=O)Nc1ccc(Oc2ccc(F)cc2F)c(-c2cn(C)c(=O)c3sc(C(=O)NC4(C)CC4)cc23)c1] |
| 65 | 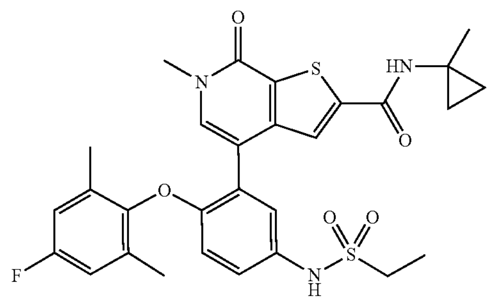 [SMILES: CCS(=O)(=O)Nc1ccc(Oc2c(C)cc(F)cc2C)c(-c2cn(C)c(=O)c3sc(C(=O)NC4(C)CC4)cc23)c1] |
| 66 | 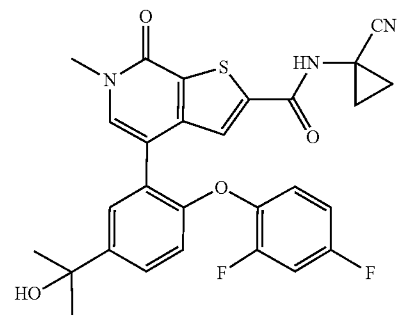 [SMILES: Cn1cc(-c2cc(C(C)(C)O)ccc2Oc2ccc(F)cc2F)c2cc(C(=O)NC3(C#N)CC3)sc2c1=O] |
| 67 | 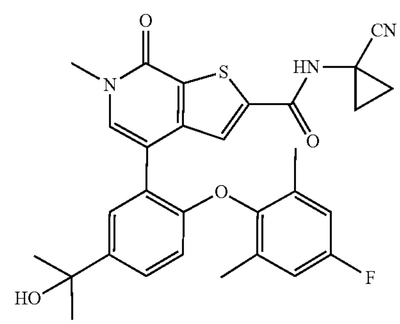 [SMILES: Cc1cc(F)cc(C)c1Oc1ccc(C(C)(C)O)cc1-c1cn(C)c(=O)c2sc(C(=O)NC3(C#N)CC3)cc12] |
| 68 | 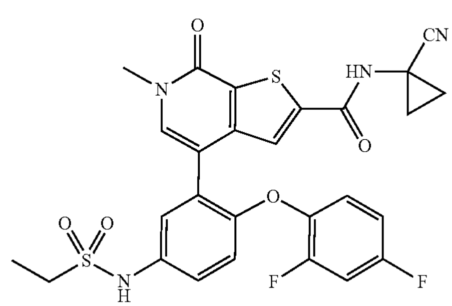 [SMILES: CCS(=O)(=O)Nc1ccc(Oc2ccc(F)cc2F)c(-c2cn(C)c(=O)c3sc(C(=O)NC4(C#N)CC4)cc23)c1] |

TABLE 1-continued
Representative Compounds
| Com. No. | Structure |
|---|---|
| 69 | 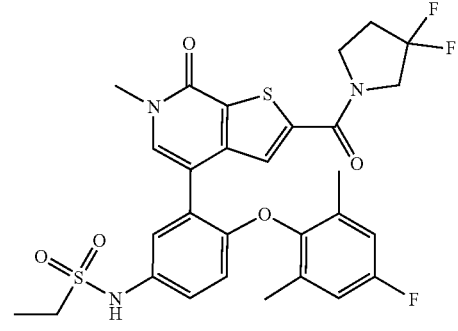 |
| 70 | 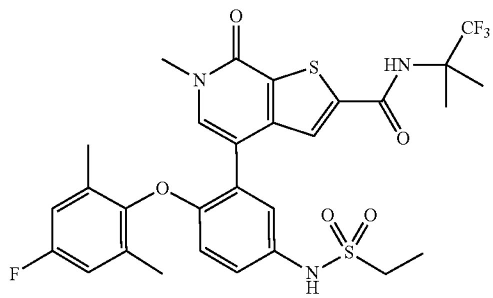 [SMILES: CCS(=O)(=O)Nc1ccc(Oc2c(C)cc(F)cc2C)c(-c2cn(C)c(=O)c3sc(C(=O)NC(C)(C)C(F)(F)F)cc23)c1] |
| 71 | 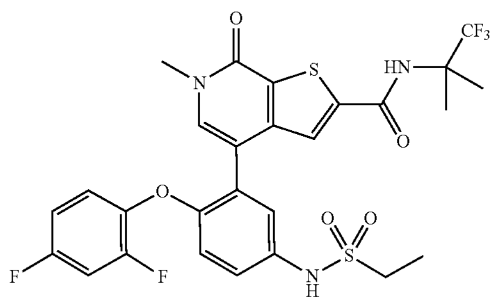 [SMILES: CCS(=O)(=O)Nc1ccc(Oc2ccc(F)cc2F)c(-c2cn(C)c(=O)c3sc(C(=O)NC(C)(C)C(F)(F)F)cc23)c1] |
| 72 | 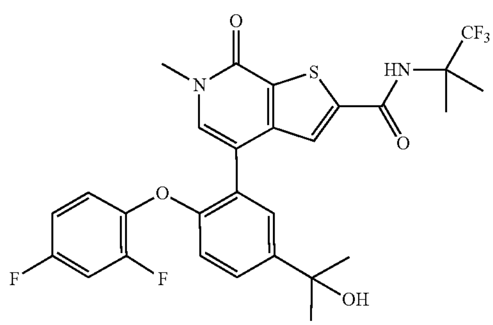 [SMILES: Cn1cc(-c2cc(C(C)(C)O)ccc2Oc2ccc(F)cc2F)c2cc(C(=O)NC(C)(C)C(F)(F)F)sc2c1=O] |
| 73 | 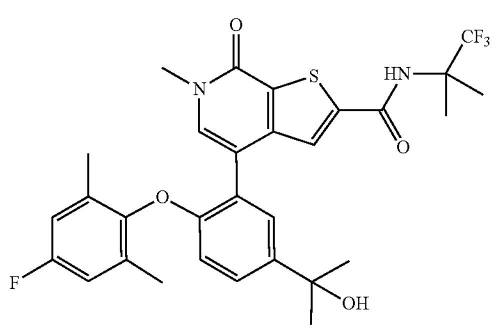 [SMILES: Cc1cc(F)cc(C)c1Oc1ccc(C(C)(C)O)cc1-c1cn(C)c(=O)c2sc(C(=O)NC(C)(C)C(F)(F)F)cc12] |
| 74 | 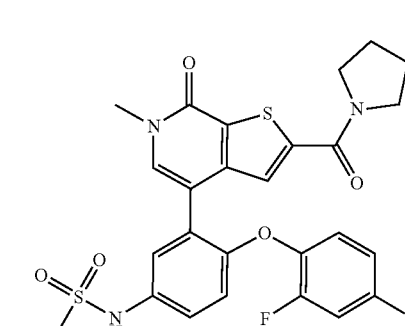 |
| 75 | |
| 76 | |
| 77 | |

TABLE 1-continued

Representative Compounds

| Com. No. | Structure |
|---|---|
| 78 | (structure) |
| 79 | (structure) |
| 80 | (structure) |
| 81 | (structure) |
| 82 | (structure) |
| 83 | (structure) |
| 84 | (structure) |
| 85 | (structure) |
| 86 | (structure) |

TABLE 1-continued

Representative Compounds

| Com. No. | Structure |
|---|---|
| 87 | (structure) |
| 88 | (structure) |
| 89 | (structure) |
| 90 | (structure) |
| 91 | (structure) |
| 92 | (structure) |
| 93 | (structure) |
| 94 | (structure) |

TABLE 1-continued
Representative Compounds
| Com. No. | Structure |
|---|---|
| 95 | 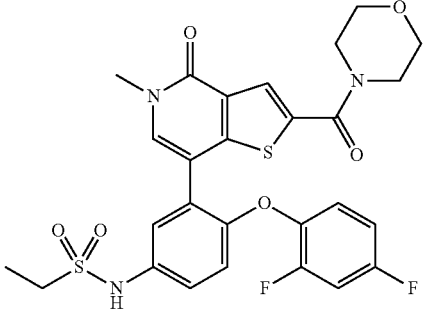 [SMILES: CCS(=O)(=O)Nc1ccc(Oc2ccc(F)cc2F)c(-c2cn(C)c(=O)c3cc(C(=O)N4CCOCC4)sc23)c1] |
| 96 | 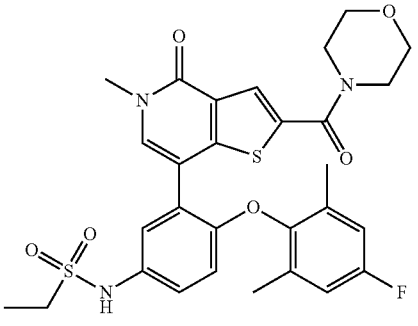 [SMILES: CCS(=O)(=O)Nc1ccc(Oc2c(C)cc(F)cc2C)c(-c2cn(C)c(=O)c3cc(C(=O)N4CCOCC4)sc23)c1] |
| 97 | 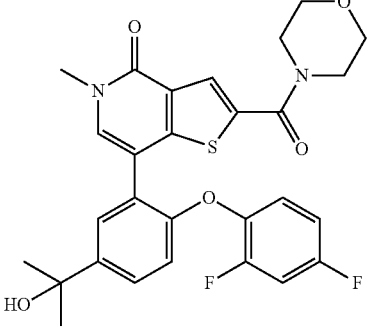 |
| 98 | 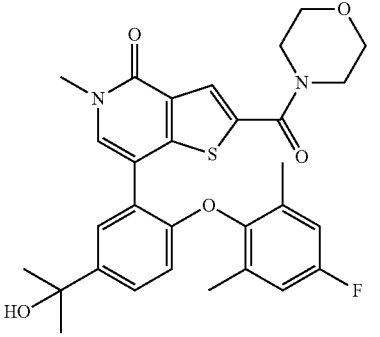 [SMILES: Cc1cc(F)cc(C)c1Oc1ccc(C(C)(C)O)cc1-c1cn(C)c(=O)c2cc(C(=O)N3CCOCC3)sc12] |
| 99 | 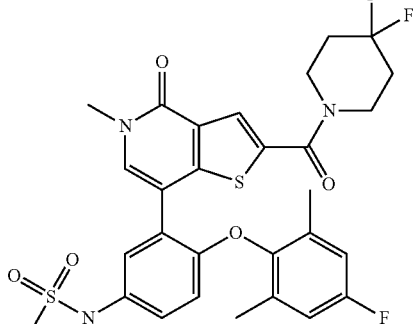 |
| 100 | 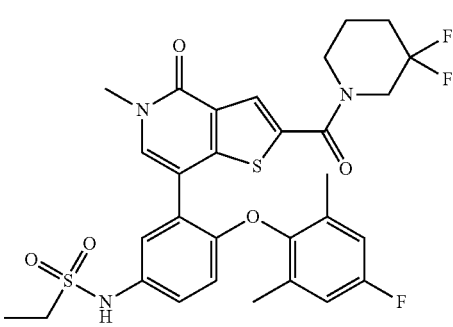 [SMILES: CCS(=O)(=O)Nc1ccc(Oc2c(C)cc(F)cc2C)c(-c2cn(C)c(=O)c3cc(C(=O)N4CCCC(F)(F)C4)sc23)c1] |
| 101 | 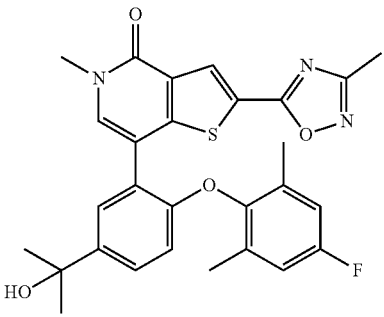 [SMILES: Cc1noc(-c2cc3c(=O)n(C)cc(-c4cc(C(C)(C)O)ccc4Oc4c(C)cc(F)cc4C)c3s2)n1] |
| 102 | 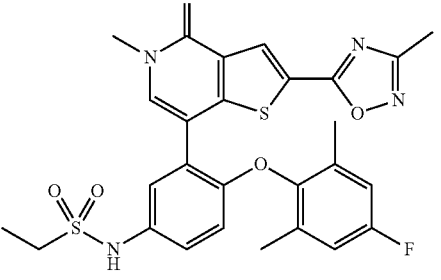 |

TABLE 1-continued

Representative Compounds

| Com. No. | Structure |
|---|---|
| 103 | 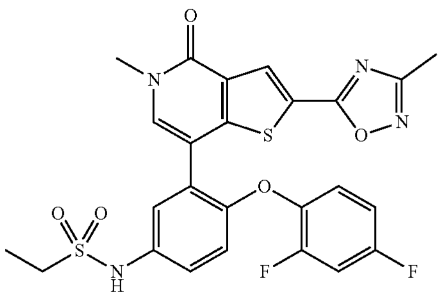 [SMILES: CCS(=O)(=O)Nc1ccc(Oc2ccc(F)cc2F)c(-c2cn(C)c(=O)c3cc(-c4nc(C)no4)sc23)c1] |
| 104 | 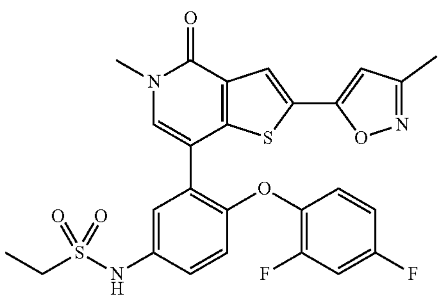 [SMILES: CCS(=O)(=O)Nc1ccc(Oc2ccc(F)cc2F)c(-c2cn(C)c(=O)c3cc(-c4cc(C)no4)sc23)c1] |
| 105 | 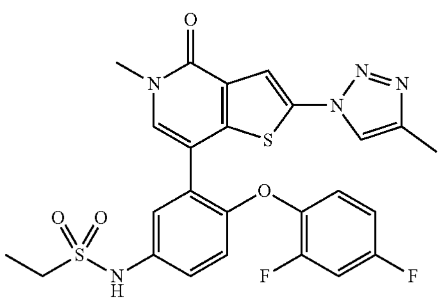 [SMILES: CCS(=O)(=O)Nc1ccc(Oc2ccc(F)cc2F)c(-c2cn(C)c(=O)c3cc(-n4cc(C)nn4)sc23)c1] |
| 106 | 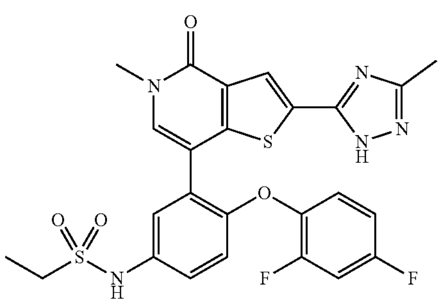 [SMILES: CCS(=O)(=O)Nc1ccc(Oc2ccc(F)cc2F)c(-c2cn(C)c(=O)c3cc(-c4nc(C)n[nH]4)sc23)c1] |
| 107 | 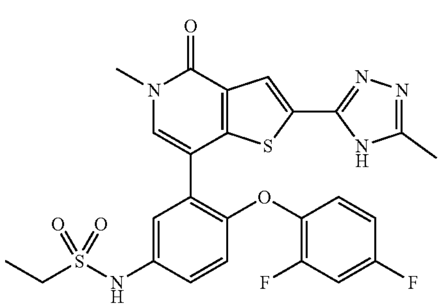 [SMILES: CCS(=O)(=O)Nc1ccc(Oc2ccc(F)cc2F)c(-c2cn(C)c(=O)c3cc(-c4nnc(C)[nH]4)sc23)c1] |
| 108 | 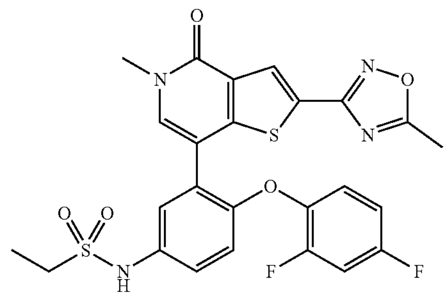 [SMILES: CCS(=O)(=O)Nc1ccc(Oc2ccc(F)cc2F)c(-c2cn(C)c(=O)c3cc(-c4noc(C)n4)sc23)c1] |
| 109 | 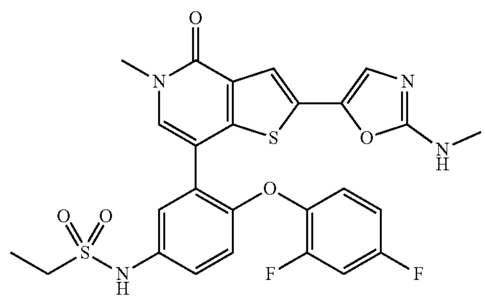 [SMILES: CCS(=O)(=O)Nc1ccc(Oc2ccc(F)cc2F)c(-c2cn(C)c(=O)c3cc(-c4cnc(NC)o4)sc23)c1] |
| 110 | 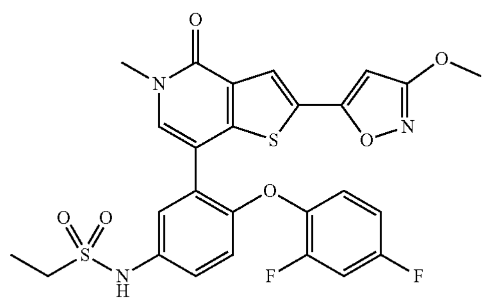 [SMILES: CCS(=O)(=O)Nc1ccc(Oc2ccc(F)cc2F)c(-c2cn(C)c(=O)c3cc(-c4cc(OC)no4)sc23)c1] |
| 111 | 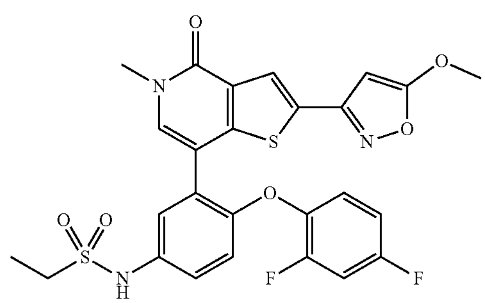 [SMILES: CCS(=O)(=O)Nc1ccc(Oc2ccc(F)cc2F)c(-c2cn(C)c(=O)c3cc(-c4cc(OC)on4)sc23)c1] |
| 112 | 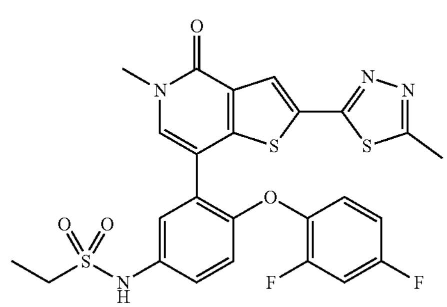 [SMILES: CCS(=O)(=O)Nc1ccc(Oc2ccc(F)cc2F)c(-c2cn(C)c(=O)c3cc(-c4nnc(C)s4)sc23)c1] |

TABLE 1-continued

Representative Compounds

| Com. No. | Structure |
|---|---|
| 113 | 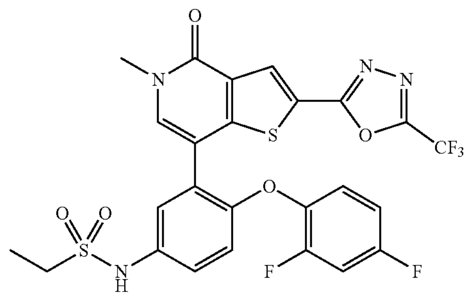 [SMILES: CCS(=O)(=O)Nc1ccc(Oc2ccc(F)cc2F)c(-c2cn(C)c(=O)c3cc(-c4nnc(C(F)(F)F)o4)sc23)c1] |
| 114 | 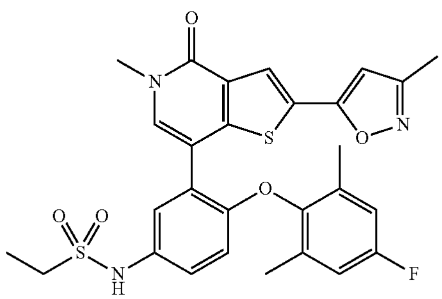 [SMILES: CCS(=O)(=O)Nc1ccc(Oc2c(C)cc(F)cc2C)c(-c2cn(C)c(=O)c3cc(-c4cc(C)no4)sc23)c1] |
| 115 | 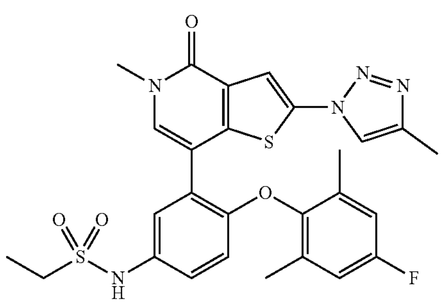 [SMILES: CCS(=O)(=O)Nc1ccc(Oc2c(C)cc(F)cc2C)c(-c2cn(C)c(=O)c3cc(-n4cc(C)nn4)sc23)c1] |
| 116 | 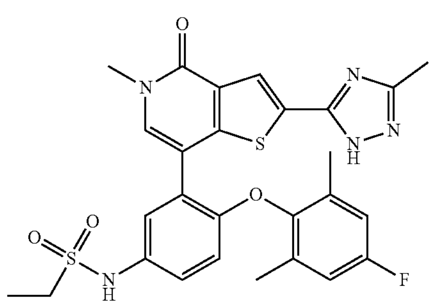 [SMILES: CCS(=O)(=O)Nc1ccc(Oc2c(C)cc(F)cc2C)c(-c2cn(C)c(=O)c3cc(-c4nc(C)n[nH]4)sc23)c1] |
| 117 | 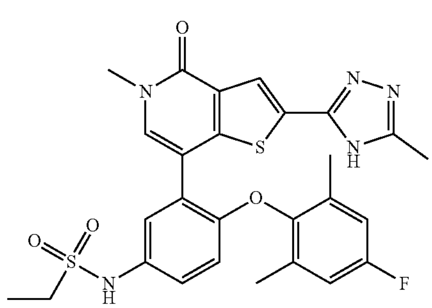 [SMILES: CCS(=O)(=O)Nc1ccc(Oc2c(C)cc(F)cc2C)c(-c2cn(C)c(=O)c3cc(-c4nnc(C)[nH]4)sc23)c1] |
| 118 | |
| 119 | |
| 120 | |
| 121 | |
| 122 | |

TABLE 1-continued

Representative Compounds

| Com. No. | Structure |
|---|---|
| 123 | 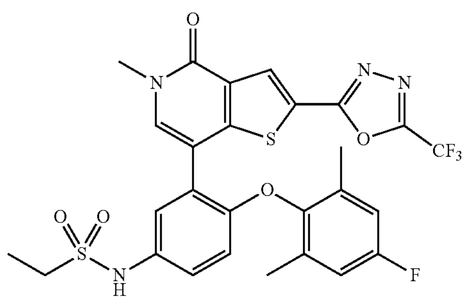 |
| 124 | 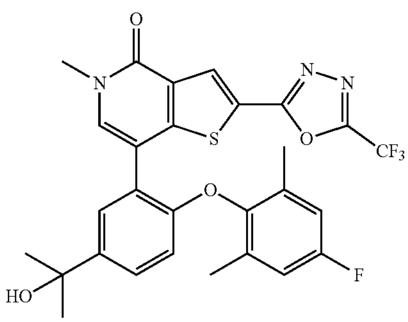 [SMILES: Cc1cc(F)cc(C)c1Oc1ccc(C(C)(C)O)cc1-c1cn(C)c(=O)c2cc(-c3nnc(C(F)(F)F)o3)sc12] |
| 125 | 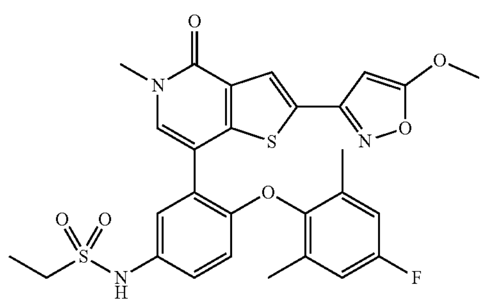 [SMILES: CCS(=O)(=O)Nc1ccc(Oc2c(C)cc(F)cc2C)c(-c2cn(C)c(=O)c3cc(-c4cc(OC)on4)sc23)c1] |
| 126 | 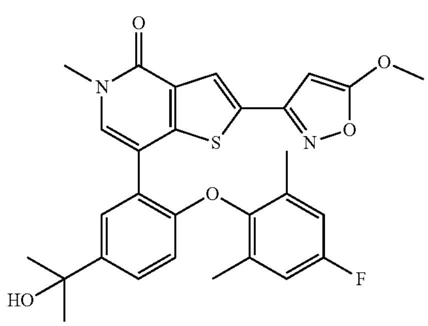 [SMILES: COc1cc(-c2cc3c(=O)n(C)cc(-c4cc(C(C)(C)O)ccc4Oc4c(C)cc(F)cc4C)c3s2)no1] |
| 127 | |
| 128 | |
| 129 | |
| 130 | |

TABLE 1-continued
Representative Compounds
| Com. No. | Structure |
|---|---|
| 131 | 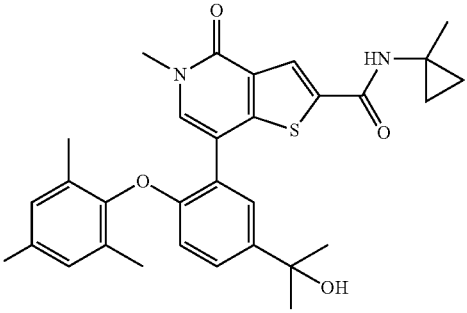 |
| 132 | 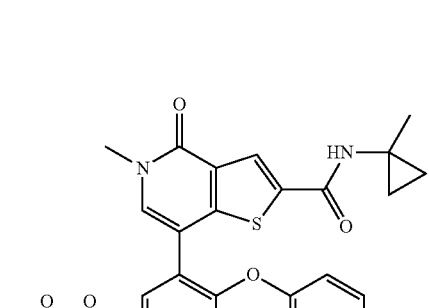 |
| 133 | 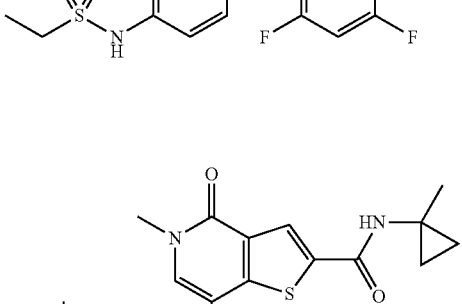 |
| 134 | 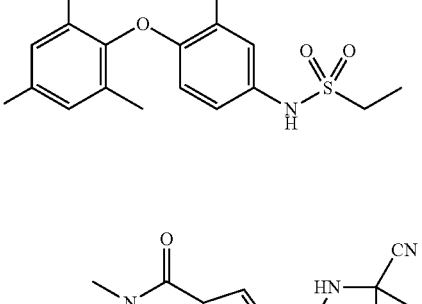 |
| 135 | 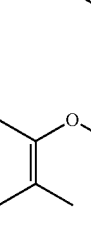 |
| 136 | 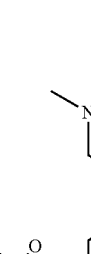 |
| 137 | 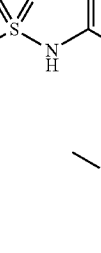 |
| 138 | 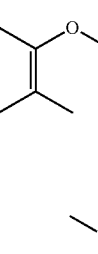 |
| 139 | 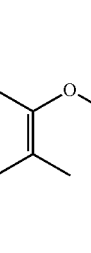 |

TABLE 1-continued
Representative Compounds
| Com. No. | Structure |
|---|---|
| 140 | 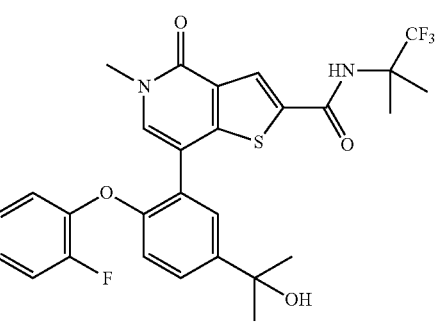 |
| 141 | 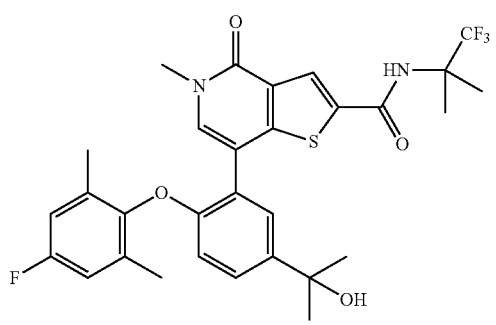 [SMILES: Cc1cc(F)cc(C)c1Oc1ccc(C(C)(C)O)cc1-c1cn(C)c(=O)c2cc(C(=O)NC(C)(C)C(F)(F)F)sc12] |
| 142 | 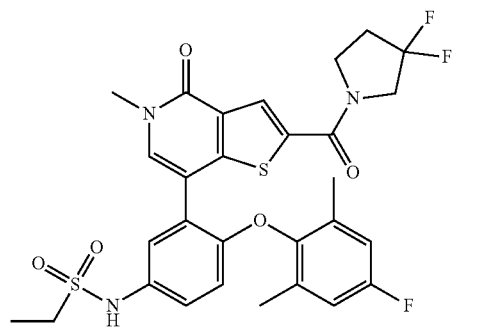 [SMILES: CCS(=O)(=O)Nc1ccc(Oc2c(C)cc(F)cc2C)c(-c2cn(C)c(=O)c3cc(C(=O)N4CCC(F)(F)C4)sc23)c1] |
| 143 | 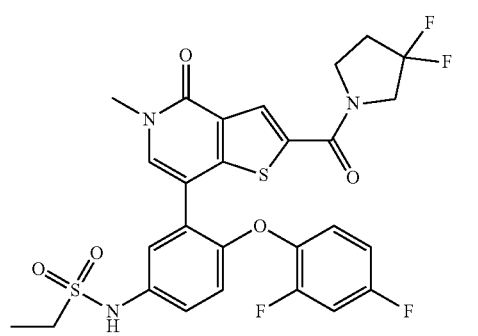 [SMILES: CCS(=O)(=O)Nc1ccc(Oc2ccc(F)cc2F)c(-c2cn(C)c(=O)c3cc(C(=O)N4CCC(F)(F)C4)sc23)c1] |
TABLE 1-continued
Representative Compounds
| Com. No. | Structure |
|---|---|
| 144 | 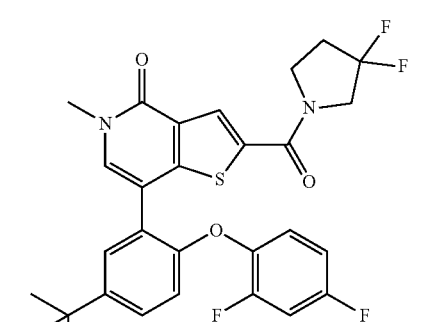 |
| 145 | 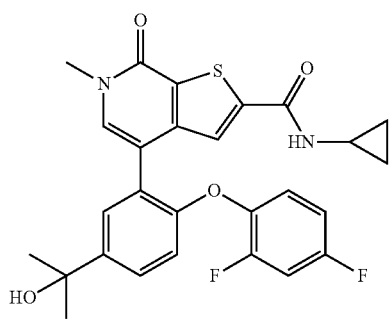 [SMILES: Cn1cc(-c2cc(C(C)(C)O)ccc2Oc2ccc(F)cc2F)c2cc(C(=O)NC3CC3)sc2c1=O] |
| 146 | 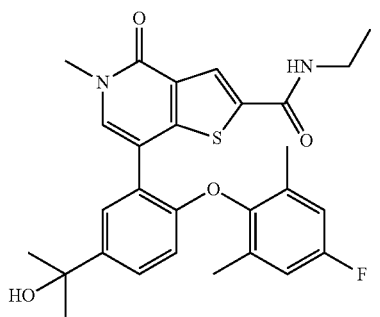 [SMILES: CCNC(=O)c1cc2c(=O)n(C)cc(-c3cc(C(C)(C)O)ccc3Oc3c(C)cc(F)cc3C)c2s1] |
| 147 | 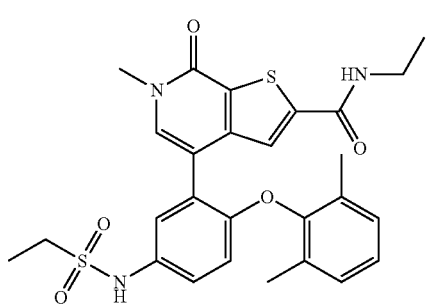 [SMILES: CCNC(=O)c1cc2c(-c3cc(NS(=O)(=O)CC)ccc3Oc3c(C)cccc3C)cn(C)c(=O)c2s1] |

TABLE 1-continued

Representative Compounds

| Com. No. | Structure |
|---|---|
| 148 | 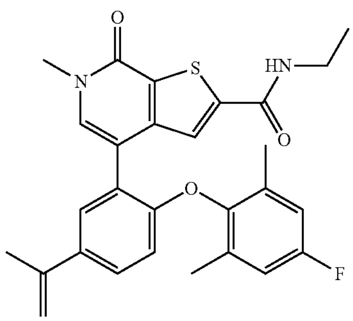 [SMILES: C=C(C)c1ccc(Oc2c(C)cc(F)cc2C)c(-c2cn(C)c(=O)c3sc(C(=O)NCC)cc23)c1] |
| 149 | 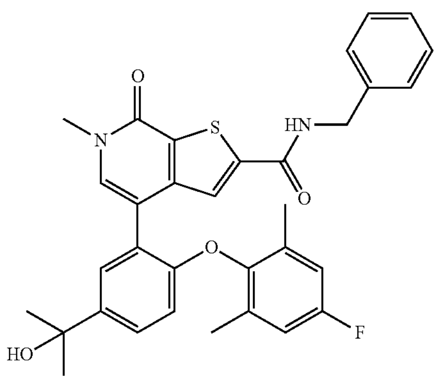 [SMILES: Cc1cc(F)cc(C)c1Oc1ccc(C(C)(C)O)cc1-c1cn(C)c(=O)c2sc(C(=O)NCc3ccccc3)cc12] |
| 150 | 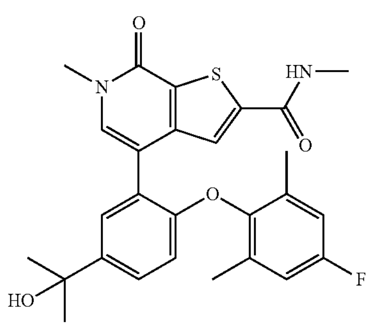 [SMILES: CNC(=O)c1cc2c(-c3cc(C(C)(C)O)ccc3Oc3c(C)cc(F)cc3C)cn(C)c(=O)c2s1] |
| 151 | 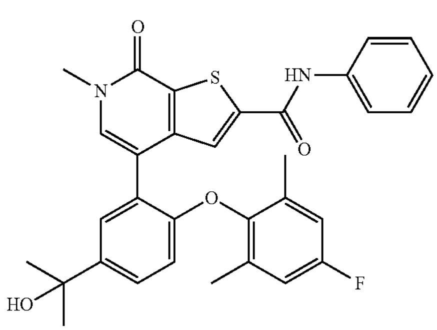 [SMILES: Cc1cc(F)cc(C)c1Oc1ccc(C(C)(C)O)cc1-c1cn(C)c(=O)c2sc(C(=O)Nc3ccccc3)cc12] |
| 152 | |
| 153 | |
| 154 | |
| 155 | |

TABLE 1-continued
Representative Compounds
| Com. No. | Structure |
|---|---|
| 156 | 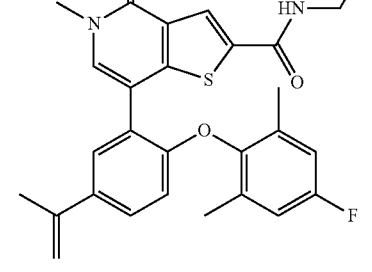 |
| 157 | 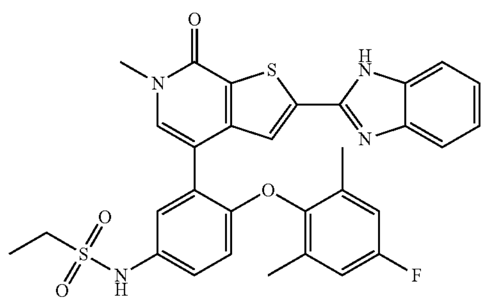 [SMILES: CCS(=O)(=O)Nc1ccc(Oc2c(C)cc(F)cc2C)c(-c2cn(C)c(=O)c3sc(-c4nc5ccccc5[nH]4)cc23)c1] |
| 158 | 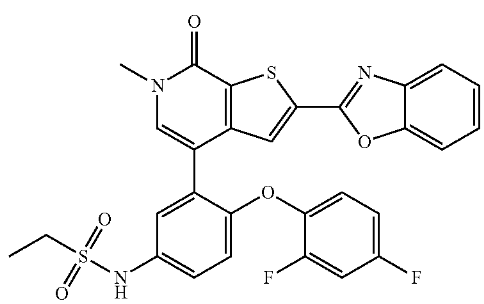 [SMILES: CCS(=O)(=O)Nc1ccc(Oc2ccc(F)cc2F)c(-c2cn(C)c(=O)c3sc(-c4nc5ccccc5o4)cc23)c1] |
| 159 | 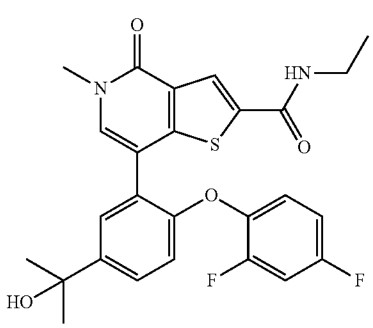 [SMILES: CCNC(=O)c1cc2c(=O)n(C)cc(-c3cc(C(C)(C)O)ccc3Oc3ccc(F)cc3F)c2s1] |
TABLE 1-continued
Representative Compounds
| Com. No. | Structure |
|---|---|
| 160 | 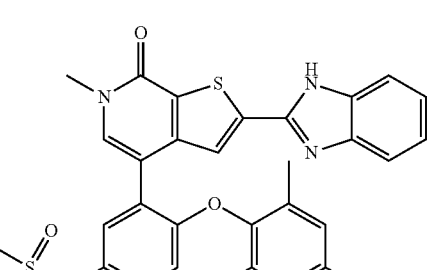 |
TABLE 2
Representative Compounds
| Compound No. | Structure |
|---|---|
| 2.1 | 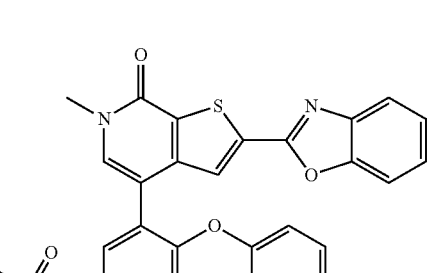 |
| 2.2 | 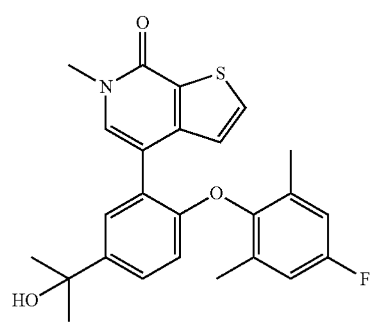 |
| 2.3 | 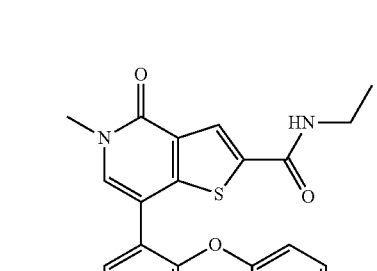 |

TABLE 2-continued

Representative Compounds

| Compound No. | Structure |
|---|---|
| 2.4 | 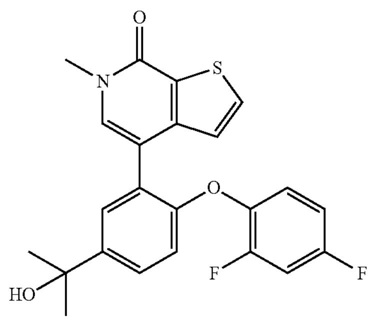 |
| 2.5 | 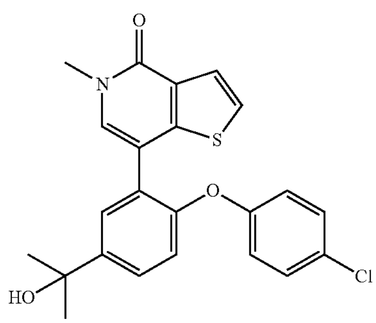 |
| 2.6 | 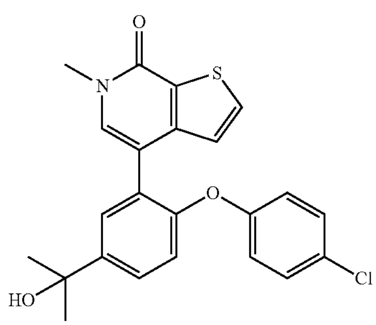 |
| 2.7 | 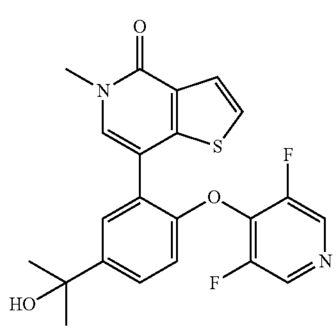 |
| 2.8 | |
| 2.9 | |
| 2.10 | |
| 2.11 | |

TABLE 2-continued

Representative Compounds

| Compound No. | Structure |
|---|---|
| 2.12 | 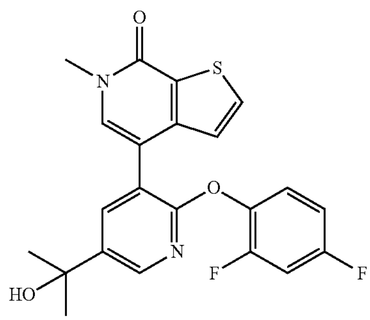 |
| 2.13 | 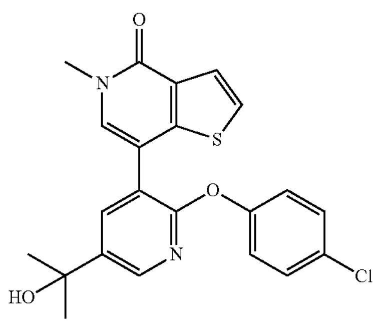 |
| 2.14 | 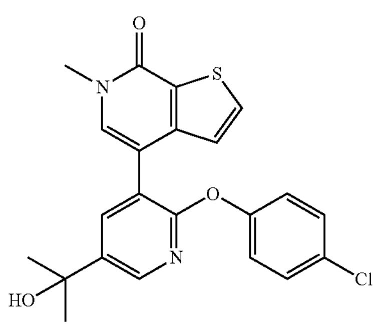 |
| 2.15 | 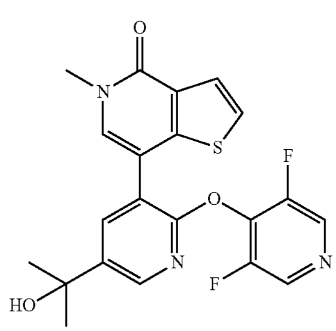 [SMILES: Cn1cc(-c2cc(C(C)(C)O)cnc2Oc2c(F)cncc2F)c2sccc2c1=O] |
| 2.16 | |
| 2.17 | |
| 2.18 | |
| 2.19 | |

TABLE 2-continued

Representative Compounds

| Compound No. | Structure |
|---|---|
| 2.20 | 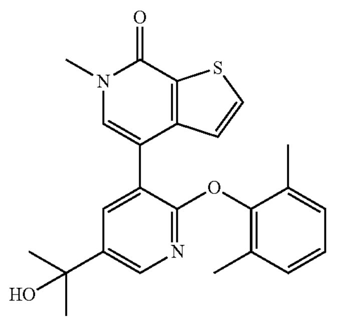 [SMILES: Cc1cccc(C)c1Oc1ncc(C(C)(C)O)cc1-c1cn(C)c(=O)c2sccc12] |
| 2.21 | 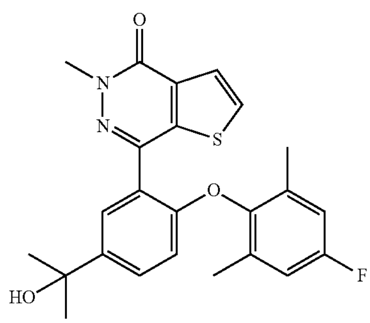 |
| 2.22 | 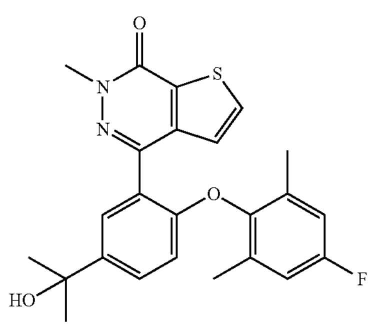 |
| 2.23 | 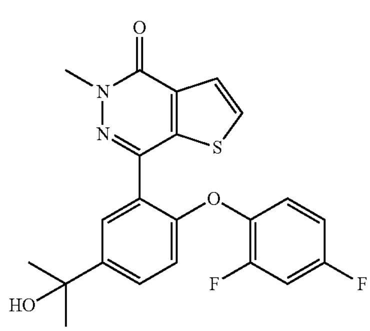 |
| 2.24 | |
| 2.25 | |
| 2.26 | |
| 2.27 | |

TABLE 2-continued

Representative Compounds

| Compound No. | Structure |
|---|---|
| 2.28 | 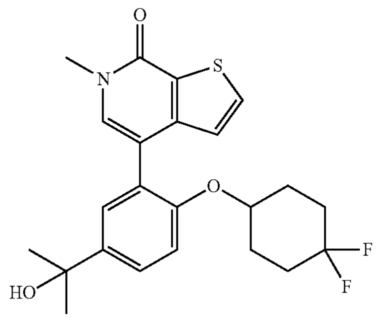 [SMILES: Cn1cc(-c2cc(C(C)(C)O)ccc2OC2CCC(F)(F)CC2)c2ccsc2c1=O] |
| 2.29 | 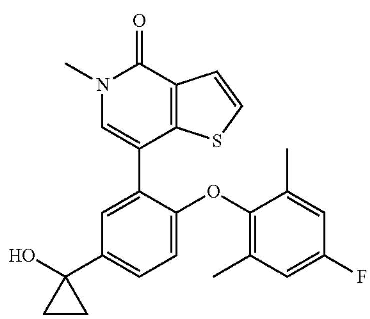 [SMILES: Cc1cc(F)cc(C)c1Oc1ccc(C2(C#N)CC2)cc1-c1cn(C)c(=O)c2ccsc12] |
| 2.30 | 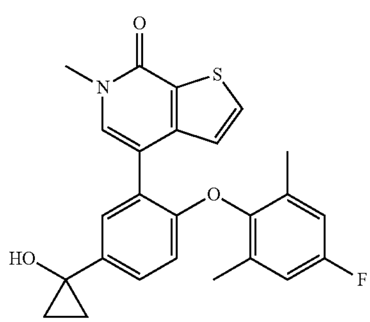 [SMILES: Cc1cc(F)cc(C)c1Oc1ccc(C2(C#N)CC2)cc1-c1cn(C)c(=O)c2sccc12] |
| 2.31 | 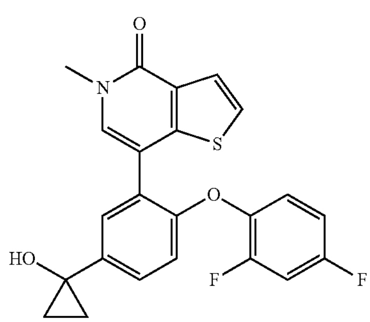 [SMILES: Cn1cc(-c2cc(C3(C#N)CC3)ccc2Oc2ccc(F)cc2F)c2sccc2c1=O] |
| 2.32 | |
| 2.33 | |
| 2.34 | |
| 2.35 | |

TABLE 2-continued

Representative Compounds

| Compound No. | Structure |
|---|---|
| 2.36 | (structure) |
| 2.37 | (structure) |
| 2.38 | (structure) |
| 2.39 | (structure) |
| 2.40 | (structure) |
| 2.41 | (structure) |
| 2.42 | (structure) |
| 2.43 | (structure) |

TABLE 2-continued

Representative Compounds

| Compound No. | Structure |
|---|---|
| 2.44 | 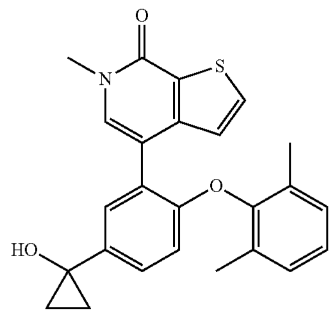 |
| 2.45 | 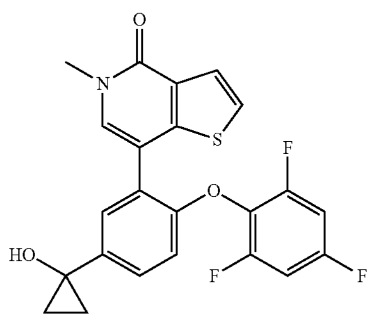 |
| 2.46 | 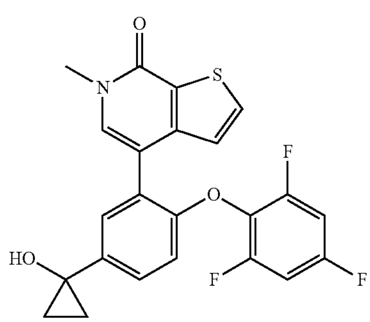 |
| 2.47 | 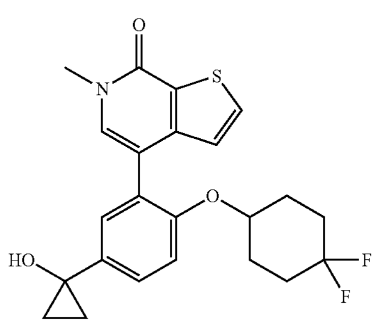 |
| 2.48 | |
| 2.49 | |
| 2.50 | |
| 2.51 | |

TABLE 2-continued

Representative Compounds

| Compound No. | Structure |
|---|---|
| 2.52 | 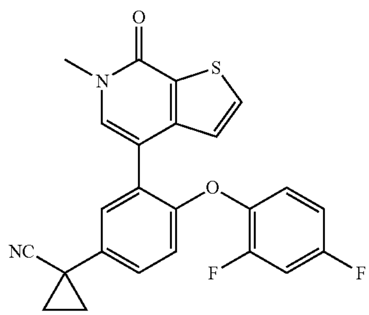 [SMILES: Cn1cc(-c2cc(C3(C#N)CC3)ccc2Oc2ccc(F)cc2F)c2ccsc2c1=O] |
| 2.53 | 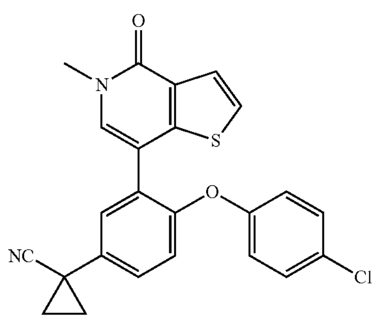 [SMILES: Cn1cc(-c2cc(C3(C#N)CC3)ccc2Oc2ccc(Cl)cc2)c2sccc2c1=O] |
| 2.54 | 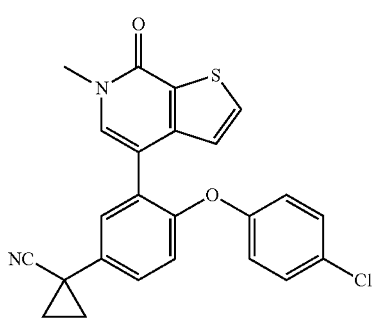 [SMILES: Cn1cc(-c2cc(C3(C#N)CC3)ccc2Oc2ccc(Cl)cc2)c2ccsc2c1=O] |
| 2.55 | 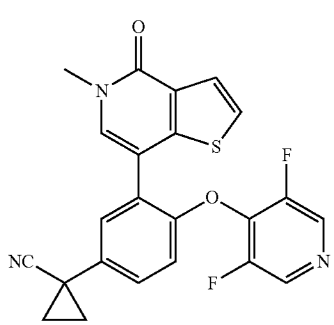 [SMILES: Cn1cc(-c2cc(C3(C#N)CC3)ccc2Oc2c(F)cncc2F)c2sccc2c1=O] |
| 2.56 | 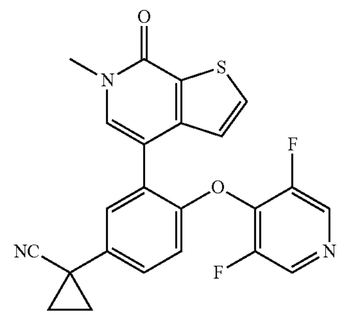 [SMILES: Cn1cc(-c2cc(C3(C#N)CC3)ccc2Oc2c(F)cncc2F)c2ccsc2c1=O] |
| 2.57 | 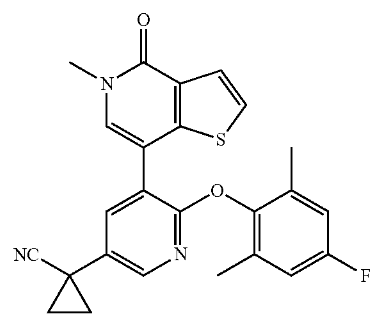 [SMILES: Cc1cc(F)cc(C)c1Oc1ncc(C2(C#N)CC2)cc1-c1cn(C)c(=O)c2ccsc12] |
| 2.58 | 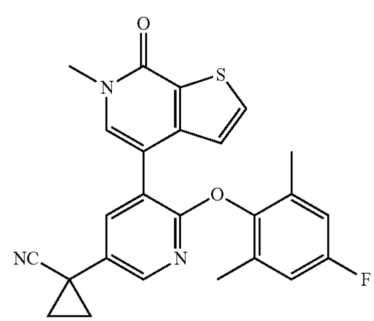 [SMILES: Cc1cc(F)cc(C)c1Oc1ncc(C2(C#N)CC2)cc1-c1cn(C)c(=O)c2sccc12] |
| 2.59 | 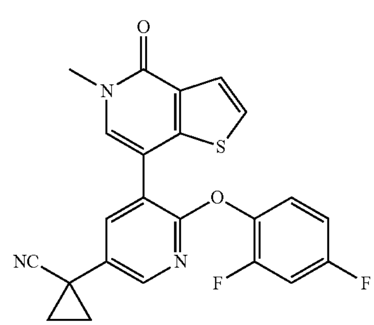 [SMILES: Cn1cc(-c2cc(C3(C#N)CC3)cnc2Oc2ccc(F)cc2F)c2sccc2c1=O] |

TABLE 2-continued

Representative Compounds

| Compound No. | Structure |
|---|---|
| 2.60 | 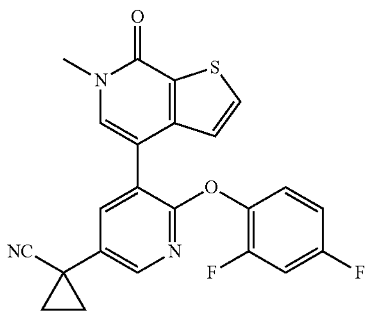 [SMILES: Cn1cc(-c2cc(C3(C#N)CC3)cnc2Oc2ccc(F)cc2F)c2ccsc2c1=O] |
| 2.61 | 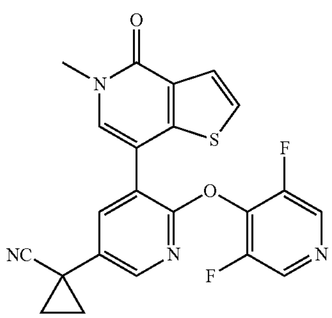 |
| 2.62 | 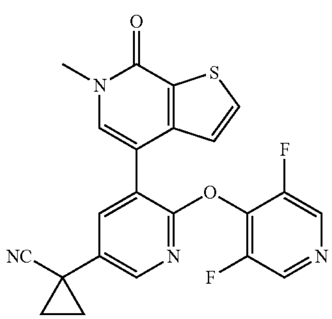 |
| 2.63 | 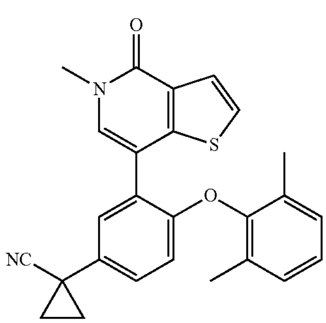 [SMILES: Cc1cccc(C)c1Oc1ccc(C2(C#N)CC2)cc1-c1cn(C)c(=O)c2ccsc12] |
| 2.64 | |
| 2.65 | |
| 2.66 | |
| 2.67 | |

TABLE 2-continued
Representative Compounds
| Compound No. | Structure |
|---|---|
| 2.68 | 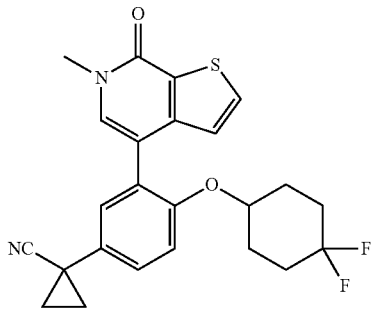 [SMILES: Cn1cc(-c2cc(C3(C#N)CC3)ccc2OC2CCC(F)(F)CC2)c2ccsc2c1=O] |
| 2.69 | 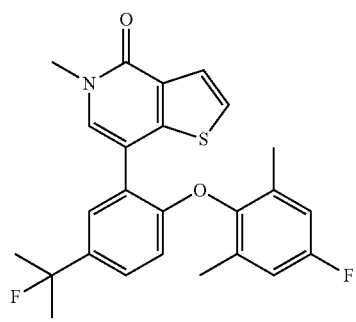 [SMILES: Cc1cc(F)cc(C)c1Oc1ccc(C(C)(C)F)cc1-c1cn(C)c(=O)c2ccsc12] |
| 2.70 | 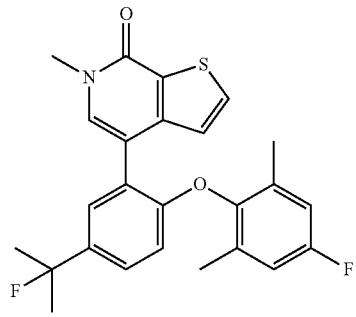 [SMILES: Cc1cc(F)cc(C)c1Oc1ccc(C(C)(C)F)cc1-c1cn(C)c(=O)c2sccc12] |
| 2.71 | 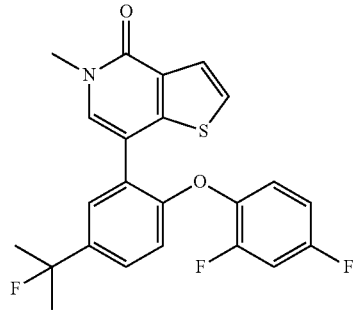 [SMILES: Cn1cc(-c2cc(C(C)(C)F)ccc2Oc2ccc(F)cc2F)c2sccc2c1=O] |
| 2.72 | 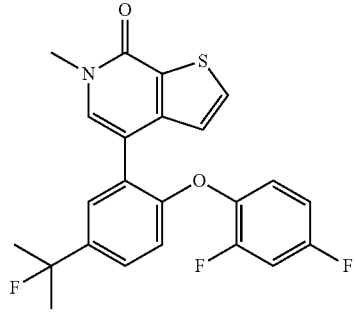 [SMILES: Cn1cc(-c2cc(C(C)(C)F)ccc2Oc2ccc(F)cc2F)c2ccsc2c1=O] |
| 2.73 | 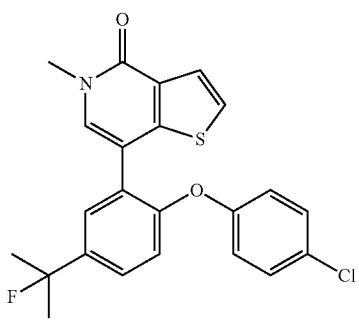 [SMILES: Cn1cc(-c2cc(C(C)(C)F)ccc2Oc2ccc(Cl)cc2)c2sccc2c1=O] |
| 2.74 | 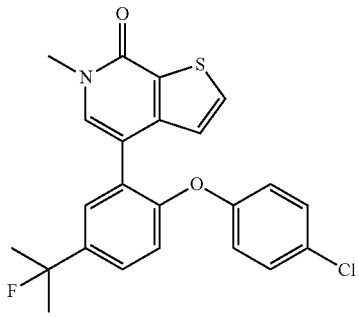 [SMILES: Cn1cc(-c2cc(C(C)(C)F)ccc2Oc2ccc(Cl)cc2)c2ccsc2c1=O] |
| 2.75 | 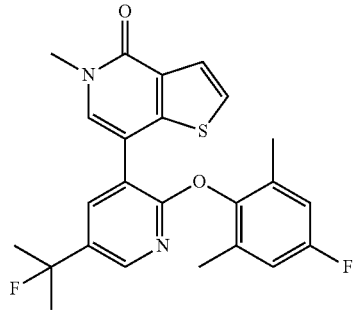 [SMILES: Cc1cc(F)cc(C)c1Oc1ncc(C(C)(C)F)cc1-c1cn(C)c(=O)c2ccsc12] |

TABLE 2-continued

Representative Compounds

| Compound No. | Structure |
|---|---|
| 2.76 | 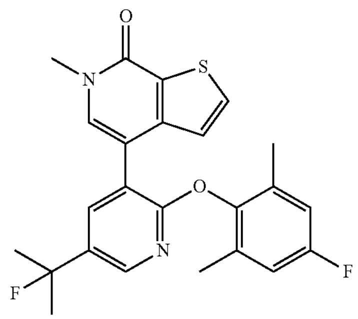 [SMILES: Cc1cc(F)cc(C)c1Oc1ncc(C(C)(C)F)cc1-c1cn(C)c(=O)c2sccc12] |
| 2.77 | 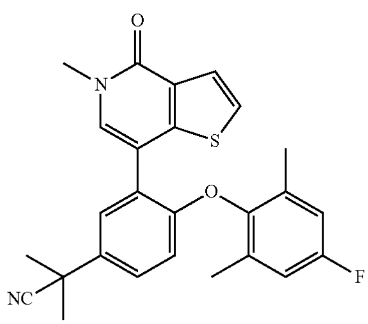 [SMILES: Cc1cc(F)cc(C)c1Oc1ccc(C(C)(C)C#N)cc1-c1cn(C)c(=O)c2ccsc12] |
| 2.78 | 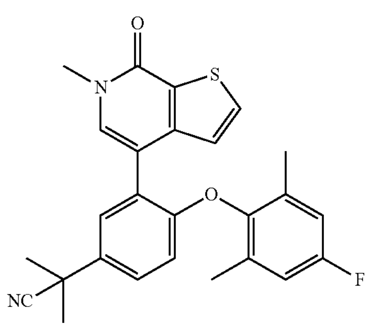 [SMILES: Cc1cc(F)cc(C)c1Oc1ccc(C(C)(C)C#N)cc1-c1cn(C)c(=O)c2sccc12] |
| 2.79 | 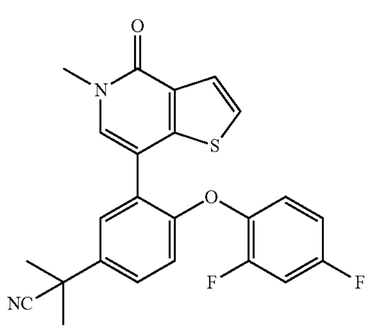 [SMILES: Cn1cc(-c2cc(C(C)(C)C#N)ccc2Oc2ccc(F)cc2F)c2sccc2c1=O] |
| 2.80 | |
| 2.81 | |
| 2.82 | |
| 2.83 | |

TABLE 2-continued

Representative Compounds

| Compound No. | Structure |
|---|---|
| 2.84 | (structure) |
| 2.85 | (structure) |
| 2.86 | (structure) |
| 2.87 | (structure) |
| 2.88 | (structure) |
| 2.89 | (structure) |
| 2.90 | (structure) |
| 2.91 | (structure) |
| 2.92 | (structure) |
| 2.93 | (structure) |

TABLE 2-continued

Representative Compounds

| Compound No. | Structure |
|---|---|
| 2.94 | (structure) |
| 2.95 | (structure) |
| 2.96 | (structure) |
| 2.97 | (structure) |
| 2.98 | (structure) |
| 2.99 | (structure) |
| 2.100 | (structure) |
| 2.101 | (structure) |
| 2.102 | (structure) |
| 2.103 | (structure) |

TABLE 2-continued

Representative Compounds

| Compound No. | Structure |
|---|---|
| 2.104 | 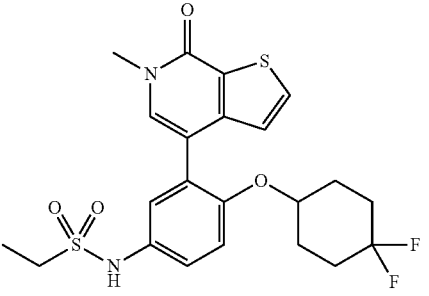 [SMILES: CCS(=O)(=O)Nc1ccc(OC2CCC(F)(F)CC2)c(-c2cn(C)c(=O)c3sccc23)c1] |

In some embodiments, provided herein are compounds described in Table 1, including or a pharmaceutic ally acceptable salt, hydrate, solvate, isotope, individual isomer, or mixtures of isomers thereof, and uses thereof. In some embodiments, provided herein are compounds 1-147, including or a pharmaceutically acceptable salt, hydrate, solvate, isotope, individual isomer, or mixtures of isomers thereof, and uses thereof. In some embodiments, provided herein are compounds 2.1-2.104, including or a pharmaceutically acceptable salt, hydrate, solvate, isotope, individual isomer, or mixtures of isomers thereof, and uses thereof.

The embodiments and variations described herein are suitable for compounds of any formulae detailed herein, where applicable.

Representative examples of compounds detailed herein, including intermediates and final compounds according to the present disclosure are depicted herein. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein.

The present disclosure also includes any or all of the stereochemical forms, including any enantiomeric or diastereomeric forms of the compounds described. The structure or name is intended to embrace all possible stereoisomers of a compound depicted, and each unique stereoisomer has a compound number bearing a suffix "a", "b", etc. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of the Formula (I) or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^2$H, $^3$H, $^{11}$C, $^{13}$C, $^{14}$C, $^{13}$N, $^{15}$O, $^{17}$O, $^{35}$S, $^{18}$F, $^{36}$Cl. Certain isotope labeled compounds (e.g. $^3$H and $^{14}$C) are useful in compound or substrate tissue distribution study. Incorporation of heavier isotopes such as deuterium ($^2$H) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound, such as would be generated in vivo following administration to a human.

Articles of manufacture comprising a compound described herein, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., for the treatment of cancer.

General Synthetic Methods

The compounds of the invention may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol.

Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

Abbreviations used in the descriptions of the schemes and the specific examples have the following meanings: EtOH for ethyl alcohol, $B_2Pin_2$ for Bis(pinacolato)diboron, KOAc for potassium acetate, DMSO for dimethyl sulfoxide, Pd(dppf)Cl$_2$ for [1,1'-Bis(diphenylphosphino)ferrocene]dichloropalladium(II); EtOAc for ethyl acetate; Et$_3$N for triethylamine; DCM for dichloromethane, DIPEA for N,N-Diisopropylethylamine, THE for tetrahydrofuran, T$_3$P for Propylphosphonic Anhydride, DMAP for 4-Dimethylaminopyridine and HPLC for high performance liquid chromatography.

The compounds described herein, including compounds of general Formula (I), (II), (IIa-1) to (IIa-7), (III) or (IIIa-1) to (IIIa-7), and specific examples, may be prepared, for example, through the reaction routes depicted in the Scheme. The variables $R^1$, $R^2$, $R^4$, $R^{c1}$, Cu, $G_2$, $Z_2$, $Z_3$, $W_1$ and m used in the scheme have the meanings as set forth in the summary and detailed description sections unless otherwise noted.

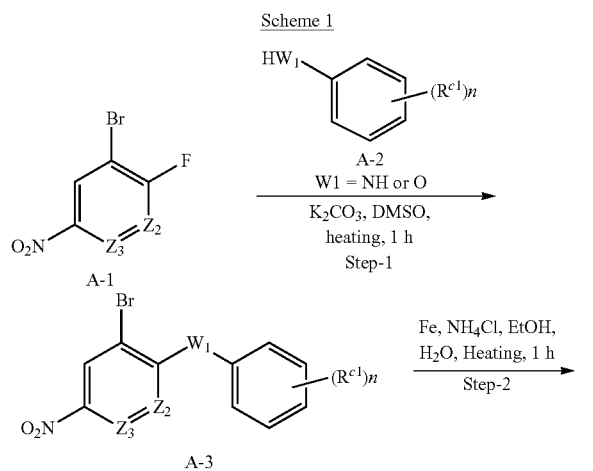

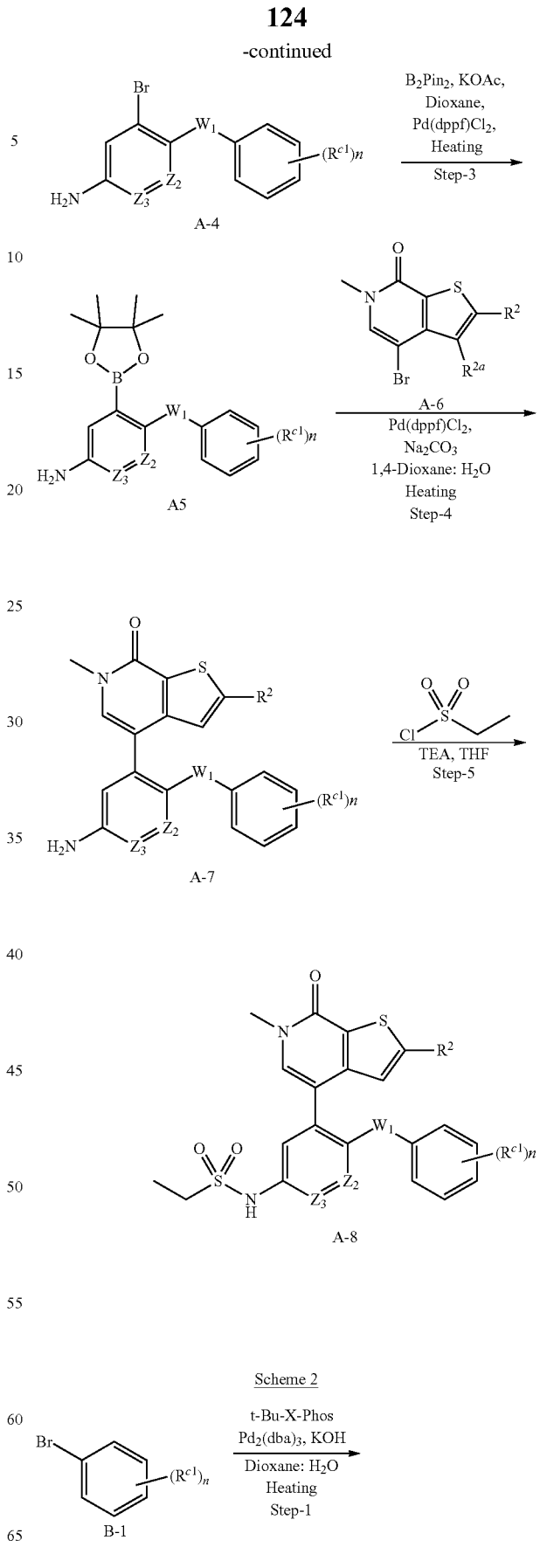

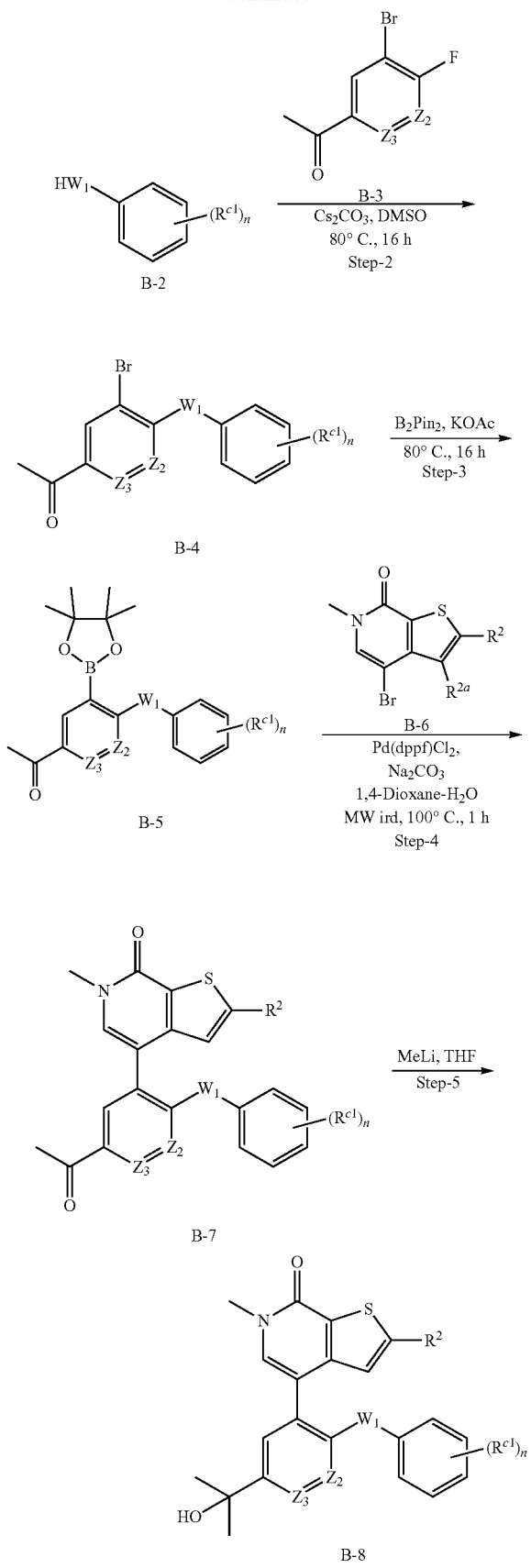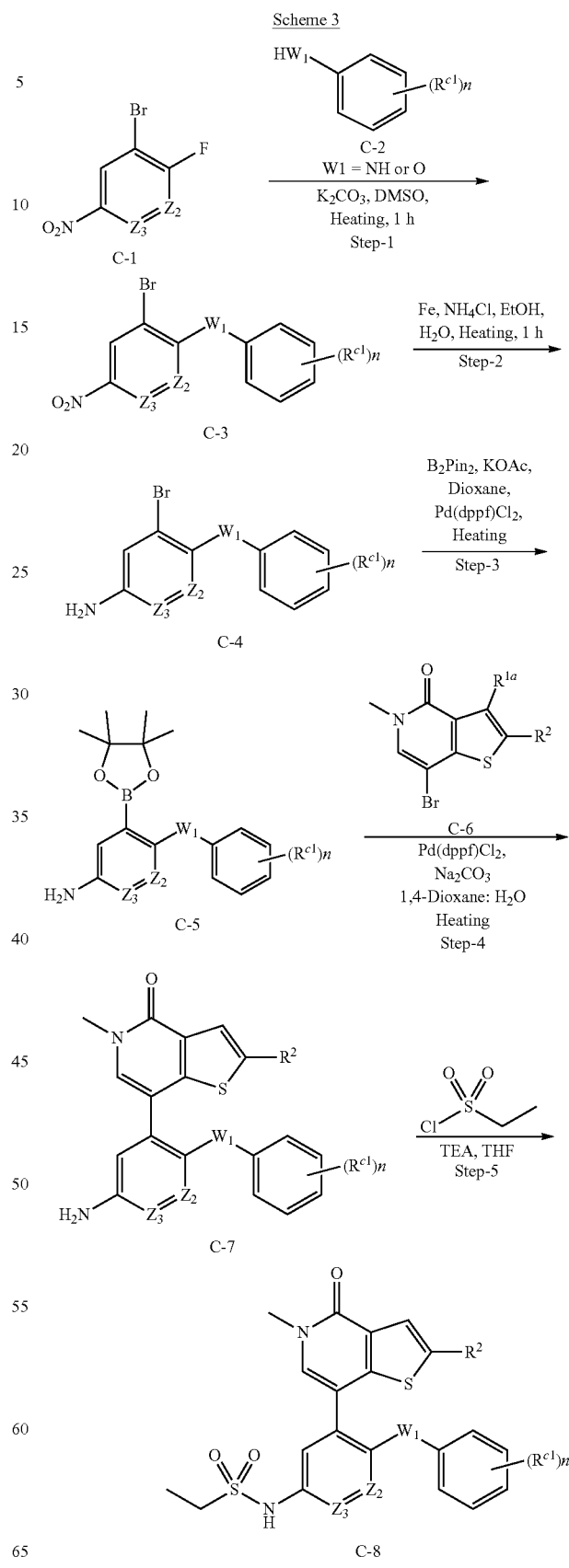
Scheme 3

US 11,584,756 B2
127 128
Scheme 4
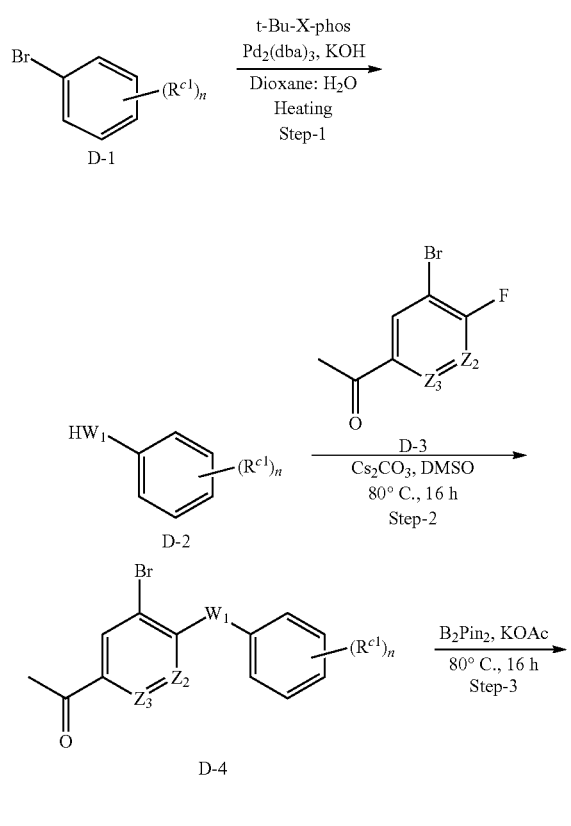
-continued
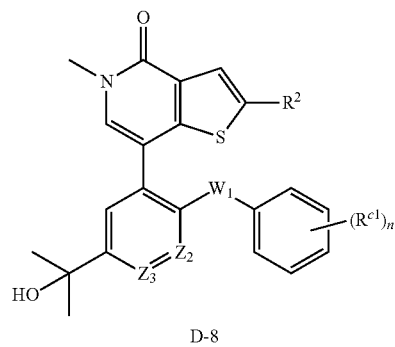
D-8
Scheme 5
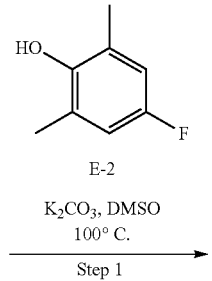
E-1
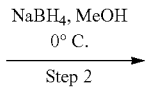
E-3
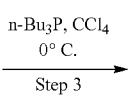
E-4
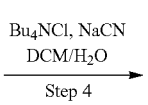
E-5

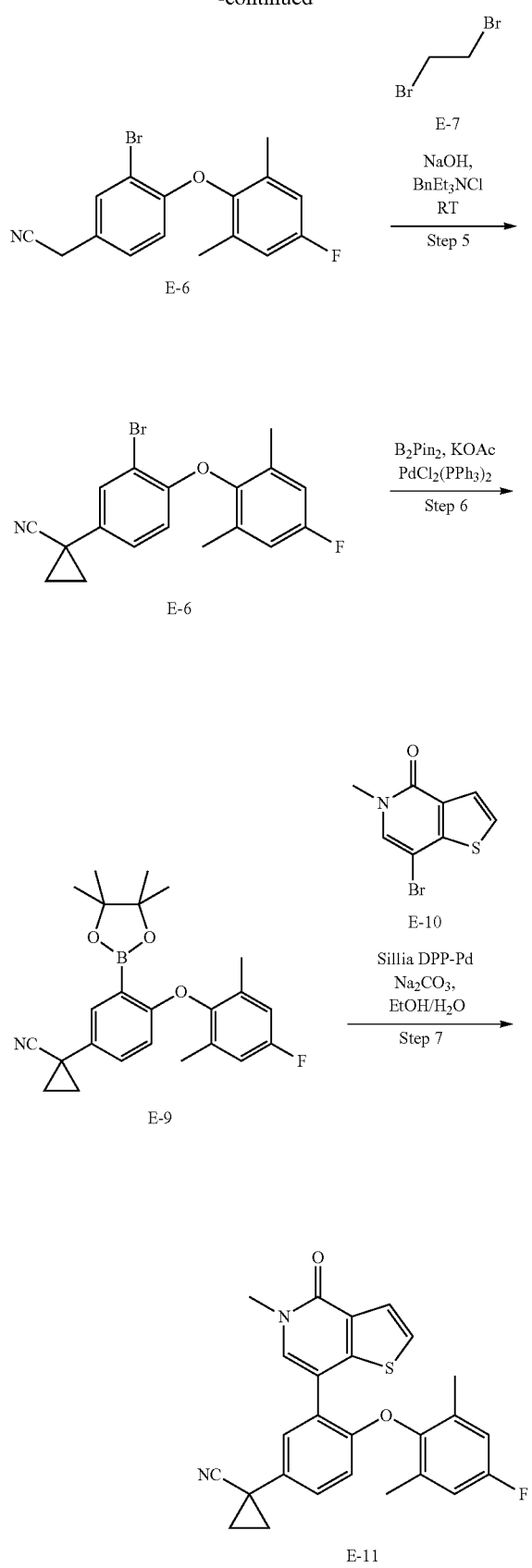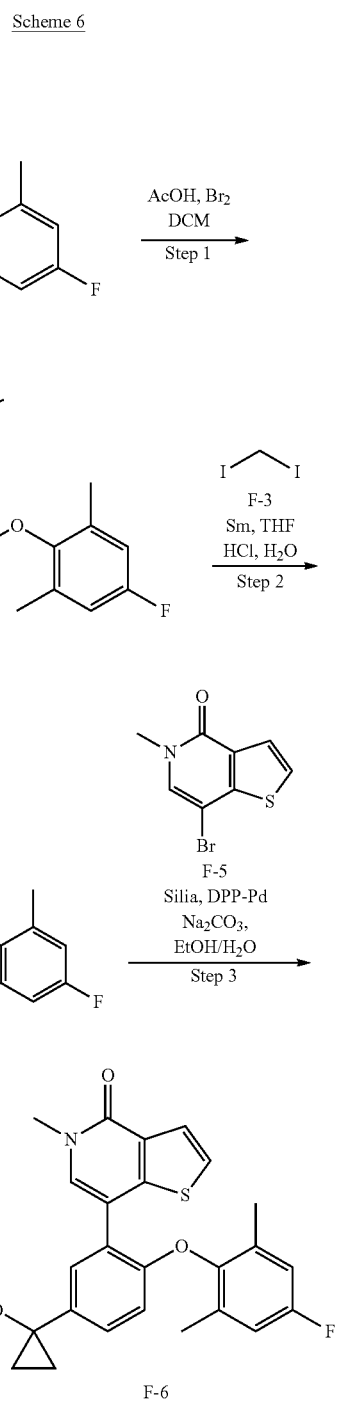

Scheme 6

It is understood that General Synthetic Schemes 1 to Schemes 4 and present synthetic routes involving steps clearly familiar to those skilled in the art, wherein the substituents described in compounds of the Formula (I), (II), (IIa-1) to (IIa-8), (III) or (IIIa-1) to (IIIa-8) herein can be varied with a choice of appropriate starting materials and reagents utilized in the steps presented.

It is understood that General Synthetic Schemes 1 to 6 and present synthetic routes involving steps clearly familiar to those skilled in the art, wherein the substituents described in compounds of the Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11) herein can be varied with a choice of appropriate starting materials and reagents utilized in the steps presented.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be further processed in the conventional manner, e.g. by eliminating the solvent from the residue and further purified according to methodologies generally known in the art such as, but not limited to, crystallization, distillation, extraction, trituration and chromatography.

Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Pharmaceutical Compositions and Formulations

Pharmaceutical compositions of any of the compounds detailed herein are embraced by this disclosure. Thus, the present disclosure includes pharmaceutical compositions comprising a compound as detailed herein or a pharmaceutically acceptable salt thereof and a pharmaceutically acceptable carrier or excipient. In one aspect, the pharmaceutically acceptable salt is an acid addition salt, such as a salt formed with an inorganic or organic acid.

Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oilin-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., $20^{th}$ ed. (2000), which is incorporated herein by reference Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc.

Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

Compositions comprising a compound provided herein are also described. In one variation, the composition comprises a compound or salt thereof and a pharmaceutically acceptable carrier or excipient. In another variation, a composition of substantially pure compound is provided.

Methods of Use

Compounds and compositions detailed herein, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation. In an embodiment, use of a compound having the structure of Formula (I), (II), (IIa-1) to (IIa-7), (III) or (IIIa-1) to (IIIa-7), or a pharmaceutically acceptable isomer, racemate, hydrate, solvate, isotope, or salt thereof, for the manufacture of a medicament is provided.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation. In an embodiment, use of a compound having the structure of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable isomer, racemate, hydrate, solvate, isotope, or salt thereof, for the manufacture of a medicament is provided.

Provided herein is a method of treating a disease in an individual comprising administering an effective amount of a compound of Formula (I) or any embodiment, variation or aspect thereof (collectively, a compound of Formula (I) or the present compounds or the compounds detailed or described herein) or a pharmaceutically acceptable salt thereof, to the individual. In some embodiments, provided herein is a method of treating a disease mediated by inhibition of the BET family of proteins in an individual comprising administering an effective amount of a compound of Formula (I), or a pharmaceutically acceptable salt thereof, to the individual. In an embodiment, the present invention provides for methods for treating or preventing disorders that are ameliorated by inhibition of BET.

Provided herein is a method of treating a disease in an individual comprising administering an effective amount of a compound of Formula (J) or any embodiment, variation or aspect thereof (collectively, a compound of Formula (J) or the present compounds or the compounds detailed or described herein) or a pharmaceutically acceptable salt thereof, to the individual. In some embodiments, provided herein is a method of treating a disease mediated by inhibition of the BET family of proteins in an individual comprising administering an effective amount of a compound of Formula (J), or a pharmaceutically acceptable salt thereof, to the individual. In an embodiment, the present invention provides for methods for treating or preventing disorders that are ameliorated by inhibition of BET.

The present compounds or salts thereof are believed to be effective for treating a variety of diseases and disorders. For example, in some embodiments, the present compositions may be used to treat an inflammatory disease, a proliferative disease, such as cancer, or AIDS.

In another aspect, the present invention relates to methods of treating cancer in a subject comprising administering a therapeutically effective amount of a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof, to a subject in need thereof. In some embodiments, the present invention relates to methods of treating cancer in a subject comprising administering a therapeutically effective amount of a compound of Formula (I), (II), (IIa-1) to (IIa-8), (III) or (IIIa-1) to (IIIa-8) or a pharmaceutically acceptable salt thereof, to a subject in need thereof. In certain embodiments, the cancer is selected from the group consisting of: acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone sensitive and insensitive prostate cancer, enzalutamide (XTANDI) and abiraterone resistant prostate cancer in the pre- and post-chemo stages, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor. In certain embodiments, the methods further comprise administering a therapeutically effective amount of at least one additional therapeutic agent. In certain embodiments, the additional therapeutic agent is an anti-cancer agent. In particular embodiments, the additional therapeutic agents are selected from the group consisting of cytarabine, bortezomib, and 5-azacitidine.

In some embodiments, the cancer is a solid tumor. In some embodiments the cancer is any of adult and pediatric oncology, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer, including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including melanoma, tumor progression of human skin keratinocytes, squamous cell cancer, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

In some embodiments, the cancer in the individual has one or more mutations or amplification or overexpression of the genes encoding BET proteins. In some embodiments, the cancer in the individual has mutation or amplification or overexpression of BRD4. In some embodiments, the cancer in the individual has mutation or amplification or overexpression of c-MYC. In some embodiments, the cancer in the individual has mutation or amplification or overexpression of MYCN. In some embodiments, the cancer in the individual is characterized by Androgen Receptor (AR) expression.

In some embodiments, there is provided a method of treating a cancer in an individual, comprising (a) selecting the individual for treatment based on (i) the mutation or amplification or overexpression of BRD4 or other BET family members, or (ii) presence of mutation or amplification or overexpression of c-MYC in the cancer, and administering an effective amount of the compound of Formula (I), (II), (IIa-1) to (IIa-8), (III) or (IIIa-1) to (IIIa-8) or a pharmaceutically acceptable salt thereof, to the individual. In some embodiments, the cancer is sequenced to detect the one or more mutations or amplifications. In some embodiments, the gene is sequenced from the biopsied cancer. In some embodiments, the gene is sequenced by sequencing circulating-tumor DNA (ctDNA) from the individual. In some embodiments, there is provided a method of treating a cancer in an individual, comprising (a) selecting the individual for treatment based on (i) the mutation or amplification or overexpression of BRD4 or other BET family members, or (ii) presence of mutation or amplification or overexpression of c-MYC in the cancer, and administering an effective amount of the compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof, to the individual. In some embodiments, the cancer is sequenced to detect the one or more mutations or amplifications. In some embodiments, the gene is sequenced from the biopsied cancer. In some embodiments, the gene is sequenced by sequencing circulating-tumor DNA (ctDNA) from the individual.

In another aspect, the present invention relates to methods of treating a disease or condition in a subject comprising administering a therapeutically effective amount of a compound of Formula (I), (II), (IIa-1) to (IIa-8), (III) or (IIIa-1) to (IIIa-8), or a pharmaceutically acceptable salt thereof, to a subject in need thereof, wherein said disease or condition is selected from the group consisting of: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In certain embodiments, the methods further comprise administering a therapeutically effective amount of at least one additional therapeutic agent. In certain embodiments, the methods further comprise administering a therapeutically effective amount of at least one additional therapeutic agent. In another aspect, the present invention relates to methods of treating a disease or condition in a subject comprising administering a therapeutically effective amount of a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof, to a subject in need thereof, wherein said disease or condition is selected from the group consisting of: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis. In certain embodiments, the methods further comprise administering a therapeutically effective amount of at least one additional therapeutic agent. In certain embodiments, the methods further comprise administering a therapeutically effective amount of at least one additional therapeutic agent. In another aspect, the present invention relates to methods of treating a chronic kidney disease or condition in a subject comprising administering a therapeutically effective amount of a compound of Formula (I), (II), (IIa-1) to (IIa-8), (III) or (IIIa-1) to (IIIa-8)) or a pharmaceutically acceptable salt thereof, to a subject in need thereof, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis. In certain embodiments, the methods further comprise administering a therapeutically effective amount of at least one additional therapeutic agent. In certain embodiments, the methods further comprise administering a therapeutically effective amount of at least one additional therapeutic agent. In another aspect, the present invention relates to methods of treating a chronic kidney disease or condition in a subject comprising administering a therapeutically effective amount of a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof, to a subject in need thereof, wherein said disease or condition is selected from the group consisting of: diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis. In certain embodiments, the methods further comprise administering a therapeutically effective amount of at least one additional therapeutic agent. In certain embodiments, the methods further comprise administering a therapeutically effective amount of at least one additional therapeutic agent.

In another aspect, the present invention relates to methods of treating an acute kidney injury or disease or condition in a subject comprising administering a therapeutically effective amount of a compound of Formula (I), (II), (IIa-1) to (IIa-8), (III) or (IIIa-1) to (IIIa-8), or a pharmaceutically acceptable salt thereof, to a subject in need thereof, wherein said acute kidney injury or disease or condition is selected from the group consisting of: ischemia-reperfusion induced, cardiac and major surgery induced, percutaneous coronary intervention induced, radio-contrast agent induced, sepsis induced, pneumonia induced, and drug toxicity induced. In certain embodiments, the methods further comprise administering a therapeutically effective amount of at least one additional therapeutic agent. In certain embodiments, the methods further comprise administering a therapeutically effective amount of at least one additional therapeutic agent. In another aspect, the present invention relates to methods of treating an acute kidney injury or disease or condition in a subject comprising administering a therapeutically effective amount of a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof, to a subject in need thereof, wherein said acute kidney injury or disease or condition is selected from the group consisting of: ischemia-reperfusion induced, cardiac and major surgery induced, percutaneous coronary intervention induced, radio-contrast agent induced, sepsis induced, pneumonia induced, and drug toxicity induced. In certain embodiments, the methods further comprise administering a therapeutically effective amount of at least one additional therapeutic agent. In certain embodiments, the methods further comprise administering a therapeutically effective amount of at least one additional therapeutic agent.

In another aspect, the present invention relates to methods of treating AIDS in a subject comprising administering a therapeutically effective amount of a compound of Formula (I), (II), (IIa-1) to (IIa-8), (III) or (IIIa-1) to (IIIa-8), or a pharmaceutically acceptable salt thereof, to a subject in need thereof. In certain embodiments, the methods further comprise administering a therapeutically effective amount of at least one additional therapeutic agent. In another aspect, the present invention relates to methods of treating AIDS in a subject comprising administering a therapeutically effective amount of a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof, to a subject in need thereof. In certain embodiments, the methods further comprise administering a therapeutically effective amount of at least one additional therapeutic agent.

In another aspect, the present invention relates to methods of treating obesity, dyslipidemia, hypercholesterolemia, Alzheimer's disease, metabolic syndrome, hepatic steatosis, type II diabetes, insulin resistance, diabetic retinopathy or diabetic neuropathy in a subject comprising administering a therapeutically effective amount of a compound of Formula (I), (II), (IIa-1) to (IIa-8), (III) or (IIIa-1) to (IIIa-8), or a pharmaceutically acceptable salt thereof, to a subject in need thereof. In certain embodiments, the methods further comprise administering a therapeutically effective amount of at least one additional therapeutic agent. In another aspect, the present invention relates to methods of treating obesity, dyslipidemia, hypercholesterolemia, Alzheimer's disease, metabolic syndrome, hepatic steatosis, type II diabetes, insulin resistance, diabetic retinopathy or diabetic neuropathy in a subject comprising administering a therapeutically effective amount of a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof, to a subject in need thereof. In certain embodiments, the methods further comprise administering a therapeutically effective amount of at least one additional therapeutic agent.

In another aspect, the present invention relates to methods of preventing conception by inhibiting spermatogenesis in a subject comprising administering a therapeutically effective amount of a compound of Formula (I), (II), (IIa-1) to (IIa-8), (III) or (IIIa-1) to (IIIa-8), or a pharmaceutically acceptable salt thereof, to a subject in need thereof. In certain embodiments, the methods further comprise administering a therapeutically effective amount of at least one additional therapeutic agent. In another aspect, the present invention relates to methods of preventing conception by inhibiting spermatogenesis in a subject comprising administering a therapeutically effective amount of a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof, to a subject in need thereof. In certain embodiments, the methods further comprise administering a therapeutically effective amount of at least one additional therapeutic agent.

Combination Therapy

As provided herein, the presently disclosed compounds or a salt thereof may be combined with an additional therapeutic agent. In some embodiments, a method of treating a disease in an individual is provided, the method comprising administering an effective amount of a compound of Formula (I), (II), (IIa-1) to (IIa-8), (III) or (IIIa-1) to (IIIa-8), or any embodiment, variation or aspect thereof (collectively, a compound of formula Formula (I), (II), (IIa-1) to (IIa-8), (III) or (IIIa-1) to (IIIa-8)), or the present compounds or the compounds detailed or described herein) or a pharmaceutically acceptable salt thereof, and an additional therapeutic agent to the individual. In some embodiments, the disease is a proliferative disease such as cancer. In another aspect, the present invention relates to methods of preventing conception by inhibiting spermatogenesis in a subject comprising administering a therapeutically effective amount of a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof, to a subject in need thereof. In certain embodiments, the methods further comprise administering a therapeutically effective amount of at least one additional therapeutic agent.

In some embodiments, the additional therapeutic agent is a cancer immunotherapy agent. In some embodiments, the additional therapeutic agent is an immunostimulatory agent. In some embodiments, the additional therapeutic agent targets a checkpoint protein (for example an immune checkpoint inhibitor). In some embodiments, the additional therapeutic agent is effective to stimulate, enhance or improve an immune response against a tumor.

In some embodiments, a method of treating a disease in an individual is provided, the method comprising administering an effective amount of Formula (I), (II), (IIa-1) to (IIa-8), (III) or (IIIa-1) to (IIIa-8), or any embodiment, variation or aspect thereof (collectively, a compound of Formula (I), (II), (IIa-1) to (IIa-8), (III) or (IIIa-1) to (IIIa-8)), or the present compounds or the compounds detailed or described herein) or a pharmaceutically acceptable salt thereof, in combination with radiation therapy. In some embodiments, a method of treating a disease in an individual is provided, the method comprising administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, a compound of (I), (II), (IIa-1) to (IIa-8), (III), (IIIa-1) to (IIIa-8), (IV), (V), (Va-1) to (Va-11), (VI), (VIa-1) to (VIa-11)), or the present compounds or the compounds detailed or described herein) or a pharmaceutically acceptable salt thereof, in combination with radiation therapy.

In some embodiments, a method of treating a disease in an individual is provided, the method comprising (a) administering an effective amount of Formula (I), (II), (IIa-1) to (IIa-8), (III) or (IIIa-1) to (IIIa-8), or any embodiment, variation or aspect thereof (collectively, Formula (I), (II), (IIa-1) to (IIa-8), (III) or (IIIa-1) to (IIIa-8)) or a pharmaceutically acceptable salt thereof, and (b) administering an effective amount of a chemotherapeutic agent. In some embodiments, Formula (I), (II), (IIa-1) to (IIa-8), (III) or (IIIa-1) to (IIIa-8), 7 or a pharmaceutically acceptable salt thereof is administered prior to, after, or simultaneously co-administered with the chemotherapeutic agent. In some embodiments, Formula (I), (II), (IIa-1) to (IIa-8), (III) or (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the chemotherapeutic agent. In some embodiments, a method of treating a disease in an individual is provided, the method comprising (a) administering an effective amount of Formula (I), (II), (IIa-1) to (IIa-8), (III), (IIIa-1) to (IIIa-8), (IV), (V), (Va-1) to (Va-11), (VI), (VIa-1) to (VIa-11), or any embodiment, variation or aspect thereof (collectively, Formula (I), (II), (IIa-1) to (IIa-8), (III), (IIIa-1) to (IIIa-8), (IV), (V), (Va-1) to (Va-11), (VI), (VIa-1) to (VIa-11)) or a pharmaceutically acceptable salt thereof, and (b) administering an effective amount of a chemotherapeutic agent. In some embodiments, Formula (I), (II), (IIa-1) to (IIa-8), (III), (IIIa-1) to (IIIa-8), (IV), (V), (Va-1) to (Va-11), (VI), (VIa-1) to (VIa-11), or a pharmaceutically acceptable salt thereof is administered prior to, after, or simultaneously co-administered with the chemotherapeutic agent. In some embodiments, Formula (I), (II), (IIa-1) to (IIa-8), (III), (IIIa-1) to (IIIa-8), (IV), (V), (Va-1) to (Va-11), (VI), (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the chemotherapeutic agent.

Examples of chemotherapeutic agents that can be used in combination with Formula (I), (II), (IIa-1) to (IIa-8), (III) or (IIIa-1) to (IIIa-8), or a pharmaceutically acceptable salt thereof include a DNA alkylating agent (such as cyclophosphamide, mechlorethamine, chlorambucil, melphalan, dacarbazine, or nitrosoureas), a topoisomerase inhibitor (such as a Topoisomerase I inhibitor (e.g., irinotecan or topotecan) or a Topoisomerase II inhibitor (e.g., etoposide or tempo side), an anthracycline (such as daunorubicin, doxorubicin, epirubicin, idarubicin, mitoxantrone, or valrubicin), a histone deacetylase inhibitor (such as vorinostat or romidepsin), another bromodomain inhibitor, other epigenetic inhibitors, a taxane (such as paclitaxel or docetaxel), a kinase inhibitor (such as bortezomib, erlotinib, gefitinib, imatinib, vemurafenib, vismodegib, ibrutinib), a mTOR inhibitor, a DNA Damage Repair (DDR) pathway inhibitor, such as a PARP inhibitor, ATM inhibitor, ATR inhibitor, a Wee1 inhibitor, a proteasome inhibitor (such as bortezomib), an anti-angiogenic inhibitor, endocrine therapy, anti-estrogen therapy, anti-androgen therapy, glucocorticoid receptor inhibitor, a nucleotide analog or precursor analog (such as azacitidine, azathioprine, capecitabine, cytarabine, doxifluridine, 5-fluorouracil, gemcitabine, hydroxyurea, mercaptopurine, methotrexate, or tioguanine), or a platinum-based chemotherapeutic agent (such as cisplatin, carboplatin, or oxaliplatin), pemetrexed, or a combination thereof. Examples of chemotherapeutic agents that can be used in combination with Formula (I), (II), (IIa-1) to (IIa-8), (III), (IIIa-1) to (IIIa-8), (IV), (V), (Va-1) to (Va-11), (VI), (VIa-1) to (VIa-11), or a pharmaceutically acceptable salt thereof include a DNA alkylating agent (such as cyclophosphamide, mechlorethamine, chlorambucil, melphalan, dacarbazine, or nitrosoureas), a topoisomerase inhibitor (such as a Topoisomerase I inhibitor (e.g., irinotecan or topotecan) or a Topoisomerase II inhibitor (e.g., etoposide or tempo side), an anthracycline (such as daunorubicin, doxorubicin, epirubicin, idarubicin, mitoxantrone, or valrubicin), a histone deacetylase inhibitor (such as vorinostat or romidepsin), another bromodomain inhibitor, other epigenetic inhibitors, a taxane (such as paclitaxel or docetaxel), a kinase inhibitor (such as bortezomib, erlotinib, gefitinib, imatinib, vemurafenib, vismodegib, ibrutinib), a mTOR inhibitor, a DNA Damage Repair (DDR) pathway inhibitor, such as a PARP inhibitor, ATM inhibitor, ATR inhibitor, a Weel inhibitor, a proteasome inhibitor (such as bortezomib), an anti-angiogenic inhibitor, endocrine therapy, anti-estrogen therapy, anti-androgen therapy, glucocorticoid receptor inhibitor, a nucleotide analog or precursor analog (such as azacitidine, azathioprine, capecitabine, cytarabine, doxifluridine, 5-fluorouracil, gemcitabine, hydroxyurea, mercaptopurine, methotrexate, or tioguanine), or a platinum-based chemotherapeutic agent (such as cisplatin, carboplatin, or oxaliplatin), pemetrexed, or a combination thereof.

In some embodiments, a method of treating a disease in an individual is provided, the method comprising (a) administering an effective amount of Formula (I), (II), (IIa-1) to (IIa-8), (III) or (IIIa-1) to (IIIa-8), or any embodiment, variation or aspect thereof (collectively, Formula (I), (II), (IIa-1) to (IIa-8), (III) or (IIIa-1) to (IIIa-8)) or a pharmaceutically acceptable salt thereof, and (b) administering an effective amount of a DNA damaging agent. In some embodiments, Formula (I), (II), (IIa-1) to (IIa-8), (III) or (IIIa-1) to (IIIa-8), or a pharmaceutically acceptable salt thereof is administered prior to, after, or simultaneously co-administered with the DNA damaging agent. In some embodiments, Formula (I), (II), (IIa-1) to (IIa-8), (III) or (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the DNA damaging agent. In some embodiments, a method of treating a disease in an individual is provided, the method comprising (a) administering an effective amount of Formula (I), (II), (IIa-1) to (IIa-8), (III), (IIIa-1) to (IIIa-8), (IV), (V), (Va-1) to (Va-11), (VI), (VIa-1) to (VIa-11), or any embodiment, variation or aspect thereof (collectively, Formula (I), (II), (IIa-1) to (IIa-8), (III), (IIIa-1) to (IIIa-8), (IV), (V), (Va-1) to (Va-11), (VI), (VIa-1) to (VIa-11)) or a pharmaceutically acceptable salt thereof, and (b) administering an effective amount of a DNA damaging agent. In some embodiments, Formula (I), (II), (IIa-1) to (IIa-8), (III), (IIIa-1) to (IIIa-8), (IV), (V), (Va-1) to (Va-11), (VI), (VIa-1) to (VIa-11), or a pharmaceutically acceptable salt thereof is administered prior to, after, or simultaneously co-administered with the DNA damaging agent. In some embodiments, Formula ((I), (II), (IIa-1) to (IIa-8), (III), (IIIa-1) to (IIIa-8), (IV), (V), (Va-1) to (Va-11), (VI), (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the DNA damaging agent.

In some embodiments, a method of treating a disease in an individual is provided, the method comprising (a) administering an effective amount of Formula (I), (II), (IIa-1) to (IIa-8), (III) or (IIIa-1) to (IIIa-8), or any embodiment, variation or aspect thereof (collectively, Formula (I), (II), (IIa-1) to (IIa-8), (III) or (IIIa-1) to (IIIa-8)) or a pharmaceutically acceptable salt thereof, and (b) administering an effective amount of a DNA alkylating agent (such as cyclophosphamide, mechlorethamine, chlorambucil, melphalan, dacarbazine, or nitrosoureas). In some embodiments, Formula (I), (II), (IIa-1) to (IIa-8), (III) or (IIIa-1) to (IIIa-8), or a pharmaceutically acceptable salt thereof is administered prior to, after, or simultaneously co-administered with the DNA alkylating agent. In some embodiments, Formula (I), (II), (IIa-1) to (IIa-8), (III) or (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the DNA alkylating agent. In some embodiments, a method of treating a disease in an individual is provided, the method comprising (a) administering an effective amount of Formula (I), (II), (IIa-1) to (IIa-8), (III), (IIIa-1) to (IIIa-8), (IV), (V), (Va-1) to (Va-11), (VI), (VIa-1) to (VIa-11), or any embodiment, variation or aspect thereof (collectively, Formula (I), (II), (IIa-1) to (IIa-8), (III), (IIIa-1) to (IIIa-8), (IV), (V), (Va-1) to (Va-11), (VI), (VIa-1) to (VIa-11)) or a pharmaceutically acceptable salt thereof, and (b) administering an effective amount of a DNA alkylating agent (such as cyclophosphamide, mechlorethamine, chlorambucil, melphalan, dacarbazine, or nitrosoureas). In some embodiments, Formula (I), (II), (IIa-1) to (IIa-8), (III), (IIIa-1) to (IIIa-8), (IV), (V), (Va-1) to (Va-11), (VI), (VIa-1) to (VIa-11), or a pharmaceutically acceptable salt thereof is administered prior to, after, or simultaneously co-administered with the DNA alkylating agent. In some embodiments, Formula (I), (II), (IIa-1) to (IIa-8), (III), (IIIa-1) to (IIIa-8), (IV), (V), (Va-1) to (Va-11), (VI), (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the DNA alkylating agent.

In some embodiments, a method of treating a disease in an individual is provided, the method comprising (a) administering an effective amount of Formula (I), (II), (IIa-1) to (IIa-8), (III) or (IIIa-1) to (IIIa-8), or any embodiment, variation or aspect thereof (collectively, Formula (I), (II), (IIa-1) to (IIa-8), (III) or (IIIa-1) to (IIIa-8)) or a pharmaceutically acceptable salt thereof, and (b) administering an effective amount of a topoisomerase inhibitor (such as a Topoisomerase I inhibitor (e.g., irinotecan or topotecan) or a Topoisomerase II inhibitor (e.g., etoposide or tempo side)). In some embodiments, Formula (I), (II), (IIa-1) to (IIa-8), (III) or (IIIa-1) to (IIIa-8), or a pharmaceutic ally acceptable salt thereof is administered prior to, after, or simultaneously co-administered with the topoisomerase inhibitor. In some embodiments, Formula (I), (II), (IIa-1) to (IIa-8), (III) or (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the topoisomerase inhibitor. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (I), (II), (IIa-1) to (IIa-8), (III), (IIIa-1) to (IIIa-8), (IV), (V), (Va-1) to (Va-11), (VI), (VIa-1) to (VIa-11)) or a pharmaceutically acceptable salt thereof, and (b) administering an effective amount of a topoisomerase inhibitor (such as a Topoisomerase I inhibitor (e.g., irinotecan or topotecan) or a Topoisomerase II inhibitor (e.g., etoposide or teniposide)). In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the topoisomerase inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the topoisomerase inhibitor.

In some embodiments, a method of treating a disease in an individual is provided, the method comprising (a) administering an effective amount of Formula (I), (II), (IIa-1) to (IIa-8), (III) or (IIIa-1) to (IIIa-8), or any embodiment, variation or aspect thereof (collectively, Formula (I), (II), (IIa-1) to (IIa-8), (III) or (IIIa-1) to (IIIa-8)) or a pharmaceutically acceptable salt thereof, and (b) administering an effective amount of an anthracycline (such as daunorubicin, doxorubicin, epirubicin, idarubicin, mitoxantrone, or valrubicin). In some embodiments, Formula (I), (II), (IIa-1) to (IIa-8), (III) or (IIIa-1) to (IIIa-8), or a pharmaceutically acceptable salt thereof is administered prior to, after, or simultaneously co-administered with the anthracycline. In some embodiments, Formula (I), (II), (IIa-1) to (IIa-8), (III) or (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the anthracycline. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (I), (II), (IIa-1) to (IIa-8), (III), (IIIa-1) to (IIIa-8), (IV), (V), (Va-1) to (Va-11), (VI), (VIa-1) to (VIa-11)) or a pharmaceutically acceptable salt thereof, and (b) administering an effective amount of an anthracycline (such as daunorubicin, doxorubicin, epirubicin, idarubicin, mitoxantrone, or valrubicin). In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the anthracycline. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the anthracycline.

In some embodiments, a method of treating a disease in an individual is provided, the method comprising (a) administering an effective amount of Formula (I), (II), (IIa-1) to (IIa-8), (III) or (IIIa-1) to (IIIa-8), or any embodiment, variation or aspect thereof (collectively, Formula (I), (II), (IIa-1) to (IIa-8), (III) or (IIIa-1) to (IIIa-8)) or a pharmaceutically acceptable salt thereof, and (b) administering an effective amount of a histone deacetylase inhibitor (such as vorinostat or romidepsin). In some embodiments, Formula (I), (II), (IIa-1) to (IIa-8), (III) or (IIIa-1) to (IIIa-8), or a pharmaceutic ally acceptable salt thereof is administered prior to, after, or simultaneously co-administered with the histone deacetylase inhibitor. In some embodiments, Formula (I), (II), (IIa-1) to (IIa-8), (III) or (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the histone deacetylase inhibitor. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11)) or a pharmaceutically acceptable salt thereof, and (b) administering an effective amount of a histone deacetylase inhibitor (such as vorinostat or romidepsin). In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the histone deacetylase inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the histone deacetylase inhibitor.

In some embodiments, a method of treating a disease in an individual is provided, the method comprising (a) administering an effective amount of Formula (I), (II), (IIa-1) to (IIa-8), (III) or (IIIa-1) to (IIIa-8), or any embodiment, variation or aspect thereof (collectively, Formula (I), (II), (IIa-1) to (IIa-8), (III) or (IIIa-1) to (IIIa-8)) or a pharmaceutically acceptable salt thereof, and (b) administering an effective amount of a taxane (such as paclitaxel or docetaxel). In some embodiments, Formula (I), (II), (IIa-1) to (IIa-8), (III) or (IIIa-1) to (IIIa-8), or a pharmaceutically acceptable salt thereof is administered prior to, after, or simultaneously co-administered with the taxane. In some embodiments, Formula (I), (II), (IIa-1) to (IIa-8), (III) and (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the taxane. In some embodiments, a method of treating a disease in an individual is provided, the method comprising (a) administering an effective amount of Formula (J) or any related formulae where applicable, such as Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11)) or a pharmaceutically acceptable salt thereof, and (b) administering an effective amount of a taxane (such as paclitaxel or docetaxel). In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the taxane. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the taxane.

In some embodiments, a method of treating a disease in an individual is provided, the method comprising (a) administering an effective amount of Formula (I), (II), (IIa-1) to (IIa-8), (III) and (IIIa-1) to (IIIa-8), or any embodiment, variation or aspect thereof (collectively, Formula (I), (II), (IIa-1) to (IIa-8), (III) and (IIIa-1) to (IIIa-8)) or a pharmaceutically acceptable salt thereof, and (b) administering an effective amount of a nucleotide analog or precursor analog (such as azacitidine, azathioprine, capecitabine, cytarabine, doxifluridine, 5-fluorouracil, gemcitabine, hydroxyurea, mercaptopurine, methotrexate, or tioguanine). In some embodiments, Formula (I), (II), (IIa-1) to (IIa-8), (III) and (IIIa-1) to (IIIa-8), or a pharmaceutic ally acceptable salt thereof is administered prior to, after, or simultaneously co-administered with the nucleotide analog or precursor analog. In some embodiments, Formula (I), (II), (IIa-1) to (IIa-8), (III) and (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the nucleotide analog or precursor analog. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11)) or a pharmaceutically acceptable salt thereof, and (b) administering an effective amount of a nucleotide analog or precursor analog (such as azacitidine, azathioprine, capecitabine, cytarabine, doxifluridine, 5-fluorouracil, gemcitabine, hydroxyurea, mercaptopurine, methotrexate, or tioguanine). In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the nucleotide analog or precursor analog. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the nucleotide analog or precursor analog.

In some embodiments, a method of treating a disease in an individual is provided, the method comprising (a) administering an effective amount of Formula (I), (II), (IIa-1) to (IIa-8), (III) and (IIIa-1) to (IIIa-8), or any embodiment, variation or aspect thereof (collectively, Formula (I), (II), (IIa-1) to (IIa-8), (III) and (IIIa-1) to (IIIa-8)) or a pharmaceutically acceptable salt thereof, and (b) administering an effective amount of a platinum-based chemotherapeutic agent (such as cisplatin, carboplatin, or oxaliplatin). In some embodiments, Formula (I), (II), (IIa-1) to (IIa-8), (III) and (IIIa-1) to (IIIa-8), or a pharmaceutically acceptable salt thereof is administered prior to, after, or simultaneously co-administered with the platinum-based chemotherapeutic agent. In some embodiments, Formula (I), (II), (IIa-1) to (IIa-8), (III) and (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the platinum-based chemotherapeutic agent. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11)) or a pharmaceutically acceptable salt thereof, and (b) administering an effective amount of a platinum-based chemotherapeutic agent (such as cisplatin, carboplatin, or oxaliplatin). In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the platinum-based chemotherapeutic agent. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the platinum-based chemotherapeutic agent.

In some embodiments, a method of treating a disease in an individual is provided, the method comprising (a) administering an effective amount of Formula (I), (II), (IIa-1) to (IIa-8), (III) and (IIIa-1) to (IIIa-8), or any embodiment, variation or aspect thereof (collectively, Formula (I), (II), (IIa-1) to (IIa-8), (III) and (IIIa-1) to (IIIa-8)) or a pharmaceutically acceptable salt thereof, and (b) administering an effective amount of pemetrexed. In some embodiments, Formula (I), (II), (IIa-1) to (IIa-8), (III) and (IIIa-1) to (IIIa-8), or a pharmaceutically acceptable salt thereof is administered prior to, after, or simultaneously co-administered with the pemetrexed. In some embodiments, Formula (I), (II), (IIa-1) to (IIa-8), (III) and (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the pemetrexed. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11)) or a pharmaceutically acceptable salt thereof, and (b) administering an effective amount of pemetrexed. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the pemetrexed. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the pemetrexed.

In some embodiments, a method of treating a disease in an individual is provided, the method comprising (a) administering an effective amount of Formula (I), (II), (IIa-1) to (IIa-8), (III) and (IIIa-1) to (IIIa-8), or any embodiment, variation or aspect thereof (collectively, Formula (I), (II), (IIa-1) to (IIa-8), (III) and (IIIa-1) to (IIIa-8)) or a pharmaceutically acceptable salt thereof, and (b) administering an effective amount of a kinase inhibitor (such as bortezomib, erlotinib, gefitinib, imatinib, vemurafenib, vismodegib, or ibrutinib). In some embodiments, Formula I or a pharmaceutically acceptable salt thereof is administered prior to, after, or simultaneously co-administered with the kinase inhibitor. In some embodiments, Formula I or a pharmaceutically acceptable salt thereof is administered 1 or more hours (such as 2 or more hours, 4 or more hours, 8 or more hours, 12 or more hours, 24 or more hours, or 48 or more hours) prior to or after the kinase inhibitor. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11)) or a pharmaceutically acceptable salt thereof, and (b) administering an effective amount of a kinase inhibitor (such as bortezomib, erlotinib, gefitinib, imatinib, vemurafenib, vismodegib, or ibrutinib). In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11) or a pharmaceutically acceptable salt thereof is administered prior to, after, or simultaneously co-administered with the kinase inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11) or a pharmaceutically acceptable salt thereof is administered 1 or more hours (such as 2 or more hours, 4 or more hours, 8 or more hours, 12 or more hours, 24 or more hours, or 48 or more hours) prior to or after the kinase inhibitor.

In some embodiments, a method of treating a disease in an individual is provided, the method comprising (a) administering an effective amount of Formula (I), (II), (IIa-1) to (IIa-8), (III) and (IIIa-1) to (IIIa-8), or any embodiment, variation or aspect thereof (collectively, Formula (I), (II), (IIa-1) to (IIa-8), (III) and (IIIa-1) to (IIIa-8)) or a pharmaceutically acceptable salt thereof, and (b) administering an effective amount of a mTOR inhibitor (such as everolimus). In some embodiments, Formula (I), (II), (IIa-1) to (IIa-8), (III) and (IIIa-1) to (IIIa-8), or a pharmaceutically acceptable salt thereof is administered prior to, after, or simultaneously co-administered with the mTOR inhibitor. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11)) or a pharmaceutically acceptable salt thereof, and (b) administering an effective amount of a mTOR inhibitor (such as everolimus). In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the mTOR inhibitor.

In some embodiments, a method of treating a disease in an individual is provided, the method comprising (a) administering an effective amount of Formula (I), (II), (IIa-1) to (IIa-8), (III) and (IIIa-1) to (IIIa-8), or any embodiment, variation or aspect thereof (collectively, Formula (I), (II), (IIa-1) to (IIa-8), (III) and (IIIa-1) to (IIIa-8)) or a pharmaceutically acceptable salt thereof, and (b) administering an effective amount of a PI3K or Akt inhibitor. In some embodiments, Formula (I), (II), (IIa-1) to (IIa-8), (III) and (IIIa-1) to (IIIa-8), or a pharmaceutically acceptable salt thereof is administered prior to, after, or simultaneously co-administered with the PI3K or Akt inhibitor. In some embodiments, Formula (I), (II), (IIa-1) to (IIa-8), (III) and (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the PI3K or Akt inhibitor. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11)) or a pharmaceutically acceptable salt thereof, and (b) administering an effective amount of a PI3K or Akt inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the PI3K or Akt inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the PI3K or Akt inhibitor.

In some embodiments, a method of treating a disease in an individual is provided, the method comprising (a) administering an effective amount of Formula (I), (II), (IIa-1) to (IIa-8), (III) and (IIIa-1) to (IIIa-8), or any embodiment, variation or aspect thereof (collectively, Formula (I), (II), (IIa-1) to (IIa-8), (III) and (IIIa-1) to (IIIa-8),) or a pharmaceutically acceptable salt thereof, and (b) administering an effective amount of a Bruton's tyrosine kinase (BTK) inhibitor. In some embodiments, Formula (I), (II), (IIa-1) to (IIa-8), (III) and (IIIa-1) to (IIIa-8), or a pharmaceutically acceptable salt thereof is administered prior to, after, or simultaneously co-administered with the BTK inhibitor. In some embodiments, Formula (I), (II), (IIa-1) to (IIa-8), (III) and (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the BTK inhibitor. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11)) or a pharmaceutically acceptable salt thereof, and (b) administering an effective amount of a Bruton's tyrosine kinase (BTK) inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the BTK inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the BTK inhibitor.

In some embodiments, a method of treating a disease in an individual is provided, the method comprising (a) administering an effective amount of Formula (I), (II), (IIa-1) to (IIa-8), (III) and (IIIa-1) to (IIIa-8)), or any embodiment, variation or aspect thereof (collectively, Formula (I), (II), (IIa-1) to (IIa-8), (III) and (IIIa-1) to (IIIa-8)) or a pharmaceutically acceptable salt thereof, and (b) administering an effective amount of a Cyclin-dependent kinase (CDK) inhibitor, such as inhibitor of CDK1, CDK2, CDK4, CDK5, CDK6, CDK7, or CDK9, or any combination thereof. In some embodiments, Formula (I), (II), (IIa-1) to (IIa-8), (III) and (IIIa-1) to (IIIa-8), or a pharmaceutically acceptable salt thereof is administered prior to, after, or simultaneously co-administered with the CDK inhibitor. In some embodiments, Formula (I), (II), (IIa-1) to (IIa-8), (III) and (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the CDK inhibitor. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11)) or a pharmaceutically acceptable salt thereof, and (b) administering an effective amount of a Cyclin-dependent kinase (CDK) inhibitor, such as inhibitor of CDK1, CDK2, CDK4, CDK5, CDK6, CDK7, or CDK9, or any combination thereof. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the CDK inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the CDK inhibitor.

In some embodiments, a method of treating a disease in an individual is provided, the method comprising (a) administering an effective amount of Formula (I), (II), (IIa-1) to (IIa-8), (III) and (IIIa-1) to (IIIa-8), or any embodiment, variation or aspect thereof (collectively, Formula (I), (II), (IIa-1) to (IIa-8), (III) and (IIIa-1) to (IIIa-8)) or a pharmaceutically acceptable salt thereof, and (b) administering an effective amount of a DNA damage repair (DDR) pathway inhibitor. In some embodiments, Formula (I), (II), (IIa-1) to (IIa-8), (III) and (IIIa-1) to (IIIa-8), or a pharmaceutically acceptable salt thereof is administered prior to, after, or simultaneously co-administered with the DDR pathway inhibitor. In some embodiments, Formula (I), (II), (IIa-1) to (IIa-8), (III) and (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the DDR pathway inhibitor. Examples of inhibitors of the DDR pathway include poly(ADP-ribose) polymerase (PARP) inhibitors (such as olaparib, rucaparib, niraparib, or talazoparib), ataxia telangiectasia mutated (ATM) protein inhibitors, ataxia telangiectasia and Rad3-related (ATR) protein inhibitors, checkpoint kinase 1 (Chk1) inhibitors, or combinations thereof. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11)) or a pharmaceutically acceptable salt thereof, and (b) administering an effective amount of a DNA damage repair (DDR) pathway inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the DDR pathway inhibitor. In some embodiments, Formula (J) or any related formulae where applicable, such as Formula (I), (II), (IIa-1) to (IIa-8), (IIIa-1) to (IIIa-8), (IV), (V), (Va-1) to (Va-11), (VI), or (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the DDR pathway inhibitor. Examples of inhibitors of the DDR pathway include poly(ADP-ribose) polymerase (PARP) inhibitors (such as olaparib, rucaparib, niraparib, or talazoparib), ataxia telangiectasia mutated (ATM) protein inhibitors, ataxia telangiectasia and Rad3-related (ATR) protein inhibitors, checkpoint kinase 1 (Chk1) inhibitors, or combinations thereof.

In some embodiments, a method of treating a disease in an individual is provided, the method comprising (a) administering an effective amount of Formula (I), (II), (IIa-1) to (IIa-8), (III) and (IIIa-1) to (IIIa-8), or any embodiment, variation or aspect thereof (collectively, Formula (I), (II), (IIa-1) to (IIa-8), (III) and (IIIa-1) to (IIIa-8),) or a pharmaceutically acceptable salt thereof, and (b) administering an effective amount of a PARP inhibitor (such as olaparib, rucaparib, niraparib, or talazoparib). In some embodiments, Formula (I), (II), (IIa-1) to (IIa-8), (III) and (IIIa-1) to (IIIa-8), or a pharmaceutically acceptable salt thereof is administered prior to, after, or simultaneously co-administered with the PARP inhibitor. In some embodiments, Formula (I), (II), (IIa-1) to (IIa-8), (III) and (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the PARP inhibitor. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11)) or a pharmaceutically acceptable salt thereof, and (b) administering an effective amount of a PARP inhibitor (such as olaparib, rucaparib, niraparib, or talazoparib). In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the PARP inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the PARP inhibitor.

In some embodiments, a method of treating a disease in an individual is provided, the method comprising (a) administering an effective amount of Formula (I), (II), (IIa-1) to (IIa-8), (III) and (IIIa-1) to (IIIa-8), or any embodiment, variation or aspect thereof (collectively, Formula (I), (II), (IIa-1) to (IIa-8), (III) and (IIIa-1) to (IIIa-8)) or a pharmaceutically acceptable salt thereof, and (b) administering an effective amount of an ATM protein inhibitor. In some embodiments, Formula (I), (II), (IIa-1) to (IIa-8), (III) and (IIIa-1) to (IIIa-8), or a pharmaceutically acceptable salt thereof is administered prior to, after, or simultaneously co-administered with the ATM protein inhibitor. In some embodiments, Formula (I), (II), (IIa-1) to (IIa-8), (III) and (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the ATM protein inhibitor. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11)) or a pharmaceutically acceptable salt thereof, and (b) administering an effective amount of an ATM protein inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the ATM protein inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the ATM protein inhibitor.

In some embodiments, a method of treating a disease in an individual is provided, the method comprising (a) administering an effective amount of Formula (I), (II), (IIa-1) to (IIa-8), (III) and (IIIa-1) to (IIIa-8)), or any embodiment, variation or aspect thereof (collectively, Formula (I), (II), (IIa-1) to (IIa-8), (III) and (IIIa-1) to (IIIa-8)) or a pharmaceutically acceptable salt thereof, and (b) administering an effective amount of an ATR protein inhibitor. In some embodiments, Formula (I), (II), (IIa-1) to (IIa-8), (III) and (IIIa-1) to (IIIa-8), or a pharmaceutically acceptable salt thereof is administered prior to, after, or simultaneously co-administered with the ATR protein inhibitor. In some embodiments, Formula (I), (II), (IIa-1) to (IIa-8), (III) and (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the ATR protein inhibitor. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11)) or a pharmaceutically acceptable salt thereof, and (b) administering an effective amount of an ATR protein inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the ATR protein inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the ATR protein inhibitor.

In some embodiments, a method of treating a disease in an individual is provided, the method comprising (a) administering an effective amount of Formula (I), (II), (IIa-1) to (IIa-8), (III) and (IIIa-1) to (IIIa-8), or any embodiment, variation or aspect thereof (collectively, Formula (I), (II), (IIa-1) to (IIa-8), (III) and (IIIa-1) to (IIIa-8)) or a pharmaceutically acceptable salt thereof, and (b) administering an effective amount of a Chk1 inhibitor. In some embodiments, Formula (I), (II), (IIa-1) to (IIa-8), (III) and (IIIa-1) to (IIIa-8), or a pharmaceutic ally acceptable salt thereof is administered prior to, after, or simultaneously co-administered with the Chk1 inhibitor. In some embodiments, Formula (I), (II), (IIa-1) to (IIa-8), (III) and (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the Chk1 inhibitor. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11)) or a pharmaceutically acceptable salt thereof, and (b) administering an effective amount of a Chk1 inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the Chk1 inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the Chk1 inhibitor.

In some embodiments, a method of treating a disease in an individual is provided, the method comprising (a) administering an effective amount of Formula (I), (II), (IIa-1) to (IIa-8), (III) and (IIIa-1) to (IIIa-8), or any embodiment, variation or aspect thereof (collectively, Formula (I), (II), (IIa-1) to (IIa-8), (III) and (IIIa-1) to (IIIa-8)) or a pharmaceutically acceptable salt thereof, and (b) administering an effective amount of a Weel inhibitor. In some embodiments, Formula (I), (II), (IIa-1) to (IIa-8), (III) and (IIIa-1) to (IIIa-8), or a pharmaceutic ally acceptable salt thereof is administered prior to, after, or simultaneously co-administered with the Weel inhibitor. In some embodiments, Formula (I), (II), (IIa-1) to (IIa-8), (III) and (IIIa-1) to (IIIa-8), or a pharmaceutically acceptable salt thereof is administered 1 or more hours (such as 2 or more hours, 4 or more hours, 8 or more hours, 12 or more hours, 24 or more hours, or 48 or more hours) prior to or after the Weel inhibitor. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11)) or a pharmaceutically acceptable salt thereof, and (b) administering an effective amount of a Weel inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the Weel inhibitor. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the Weel inhibitor.

In some embodiments, a method of treating a disease in an individual is provided, the method comprising (a) administering an effective amount of Formula (I), (II), (IIa-1) to (IIa-8), (III) and (IIIa-1) to (IIIa-8), or any embodiment, variation or aspect thereof (collectively, Formula (I), (II), (IIa-1) to (IIa-8), (III) and (IIIa-1) to (IIIa-8)) or a pharmaceutically acceptable salt thereof, and (b) administering an effective amount of an endocrine therapy agent. In some embodiments, the endocrine therapy is antiestrogen therapy. In some embodiments, the endocrine therapy is a selective estrogen receptor degrader (SERD, such as fulvestrant). In some embodiments, the endocrine therapy is an aromatase inhibitor (such as letrozole). In some embodiments, the endocrine therapy is an anti-androgen therapy (such as enzalutamide or apalutamide). In some embodiments, the endocrine therapy is a CYP17 inhibitor (such as abiraterone). In some embodiments, Formula (I), (II), (IIa-1) to (IIa-8), (III) and (IIIa-1) to (IIIa-8), or a pharmaceutically acceptable salt thereof is administered prior to, after, or simultaneously co-administered with the endocrine therapy agent. In some embodiments, Formula (I), (II), (IIa-1) to (IIa-8), (III) and (IIIa-1) to (IIIa-8), or a pharmaceutic ally acceptable salt thereof is administered 1 or more hours (such as 2 or more hours, 4 or more hours, 8 or more hours, 12 or more hours, 24 or more hours, or 48 or more hours) prior to or after the endocrine therapy agent. In some embodiments, a method of treating a disease in an individual is provided, the method comprising (a) administering an effective amount of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or any embodiment, variation or aspect thereof (collectively, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11)) or a pharmaceutically acceptable salt thereof, and (b) administering an effective amount of an endocrine therapy agent. In some embodiments, the endocrine therapy is antiestrogen therapy. In some embodiments, the endocrine therapy is a selective estrogen receptor degrader (SERD, such as fulvestrant). In some embodiments, the endocrine therapy is an aromatase inhibitor (such as letrozole). In some embodiments, the endocrine therapy is an anti-androgen therapy (such as enzalutamide or apalutamide). In some embodiments, the endocrine therapy is a CYP17 inhibitor (such as abiraterone). In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered prior to, after, or simultaneously co-administered with the endocrine therapy agent. In some embodiments, Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a pharmaceutically acceptable salt thereof is administered 1 or more hours (such as 2 or more hours, 4 or more hours, 8 or more hours, 12 or more hours, 24 or more hours, or 48 or more hours) prior to or after the endocrine therapy agent.

In another aspect, provided herein is a combination therapy in which a compound of Formula (I), (II), (IIa-1) to (IIa-8), (III) and (IIIa-1) to (IIIa-8), or a salt thereof is coadministered (which may be separately or simultaneously) with one or more additional agents that are effective in stimulating immune responses to thereby further enhance, stimulate or upregulate immune responses in a subject. For example, provided is a method for stimulating an immune response in a subject comprising administering to the subject a compound of Formula (I), (II), (IIa-1) to (IIa-8), (III) and (IIIa-1) to (IIIa-8), or a salt thereof and one or more immunostimulatory antibodies, such as an anti-PD-1 antibody, an anti-PD-L1 antibody and/or an anti-CTLA-4 antibody, such that an immune response is stimulated in the subject, for example to inhibit tumor growth. In one embodiment, the subject is administered a compound of Formula (I), (II), (IIa-1) to (IIa-8), (III) and (IIIa-1) to (IIIa-8), or a salt thereof and an anti-PD-1 antibody. In another embodiment, the subject is administered a compound of Formula (I), (II), (IIa-1) to (IIa-8), (III) and (IIIa-1) to (IIIa-8), or a salt thereof and an anti-PD-L1 antibody. In yet another embodiment, the subject is administered a compound of Formula (I), (II), (IIa-1) to (IIa-8), (III) and (IIIa-1) to (IIIa-8), or a salt thereof and an anti-CTLA-4 antibody. In another embodiment, the immunostimulatory antibody (e.g., anti-PD-1, anti-PD-L1 and/or anti-CTLA-4 antibody) is a human antibody. Alternatively, the immunostimulatory antibody can be, for example, a chimeric or humanized antibody (e.g., prepared from a mouse anti-PD-1, anti-PD-L1 and/or anti-CTLA-4 antibody). In another aspect, provided herein is a combination therapy in which a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof is coadministered (which may be separately or simultaneously) with one or more additional agents that are effective in stimulating immune responses to thereby further enhance, stimulate or upregulate immune responses in a subject. For example, provided is a method for stimulating an immune response in a subject comprising administering to the subject a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof and one or more immunostimulatory antibodies, such as an anti-PD-1 antibody, an anti-PD-L1 antibody and/or an anti-CTLA-4 antibody, such that an immune response is stimulated in the subject, for example to inhibit tumor growth. In one embodiment, the subject is administered a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof and an anti-PD-1 antibody. In another embodiment, the subject is administered a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof and an anti-PD-L1 antibody. In yet another embodiment, the subject is administered a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof and an anti-CTLA-4 antibody. In another embodiment, the immunostimulatory antibody (e.g., anti-PD-1, anti-PD-L1 and/or anti-CTLA-4 antibody) is a human antibody. Alternatively, the immunostimulatory antibody can be, for example, a chimeric or humanized antibody (e.g., prepared from a mouse anti-PD-1, anti-PD-L1 and/or anti-CTLA-4 antibody).

In one embodiment, the present disclosure provides a method for treating a proliferative disease (e.g., cancer), comprising administering a compound of Formula (I), (II), (IIa-1) to (IIa-8), (III) and (IIIa-1) to (IIIa-8), or a salt thereof and an anti-PD-1 antibody or to a subject. In further embodiments, a compound of Formula (I), (II), (IIa-1) to (IIa-8), (III) and (IIIa-1) to (IIIa-8), or a salt thereof is administered at a subtherapeutic dose, the anti-PD-1 antibody is administered at a subtherapeutic dose, or both are administered at a subtherapeutic dose. In another embodiment, the present disclosure provides a method for altering an adverse event associated with treatment of a hyperproliferative disease with an immuno stimulatory agent, comprising administering a compound of Formula (I), (II), (IIa-1) to (IIa-8), (III) and (IIIa-1) to (IIIa-8), or a salt thereof and a subtherapeutic dose of anti-PD-1 antibody to a subject. In certain embodiments, the subject is human. In certain embodiments, the anti-PD-1 antibody is a human sequence monoclonal antibody. In one embodiment, the present disclosure provides a method for treating a proliferative disease (e.g., cancer), comprising administering a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof and an anti-PD-1 antibody or to a subject. In further embodiments, a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof is administered at a subtherapeutic dose, the anti-PD-1 antibody is administered at a subtherapeutic dose, or both are administered at a subtherapeutic dose. In another embodiment, the present disclosure provides a method for altering an adverse event associated with treatment of a hyperproliferative disease with an immunostimulatory agent, comprising administering a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof and a subtherapeutic dose of anti-PD-1 antibody to a subject. In certain embodiments, the subject is human. In certain embodiments, the anti-PD-1 antibody is a human sequence monoclonal antibody.

In one embodiment, the present invention provides a method for treating a hyperproliferative disease (e.g., cancer), comprising administering a compound of Formula (I), (II), (IIa-1) to (IIa-8), (III) and (IIIa-1) to (IIIa-8), or a salt thereof and an anti-PD-L1 antibody to a subject. In further embodiments, a compound of Formula (I), (II), (IIa-1) to (IIa-8), (III) and (IIIa-1) to (IIIa-8), or a salt thereof is administered at a subtherapeutic dose, the anti-PD-L1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering a compound of Formula (I), (II), (IIa-1) to (IIa-8), (III) and (IIIa-1) to (IIIa-8), or a salt thereof and a subtherapeutic dose of anti-PD-L1 antibody to a subject. In certain embodiments, the subject is human. In certain embodiments, the anti-PD-L1 antibody is a human sequence monoclonal antibody. In one embodiment, the present invention provides a method for treating a hyperproliferative disease (e.g., cancer), comprising administering a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof and an anti-PD-L1 antibody to a subject. In further embodiments, a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof is administered at a subtherapeutic dose, the anti-PD-L1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof and a subtherapeutic dose of anti-PD-L1 antibody to a subject. In certain embodiments, the subject is human. In certain embodiments, the anti-PD-L1 antibody is a human sequence monoclonal antibody.

In certain embodiments, the combination of therapeutic agents discussed herein can be administered concurrently as a single composition in a pharmaceutically acceptable carrier, or concurrently as separate compositions each in a pharmaceutically acceptable carrier. In another embodiment, the combination of therapeutic agents can be administered sequentially. For example, an anti-CTLA-4 antibody and a compound of Formula (I), (II), (IIa-1) to (IIa-8), (III) and (IIIa-1) to (IIIa-8), or a salt thereof can be administered sequentially, such as anti-CTLA-4 antibody being administered first and a compound of Formula (I), (II), (IIa-1) to (IIa-8), (III) and (IIIa-1) to (IIIa-8), or a salt thereof second, or a compound of Formula (I), (II), (IIa-1) to (IIa-8), (III) and (IIIa-1) to (IIIa-8), or a salt thereof being administered first and anti-CTLA-4 antibody second. Additionally or alternatively, an anti-PD-1 antibody and a compound of Formula (I), (II), (IIa-1) to (IIa-8), (III) and (IIIa-1) to (IIIa-8), or a salt thereof can be administered sequentially, such as anti-PD-1 antibody being administered first and a compound of Formula (I), (II), (IIa-1) to (IIa-8), (III) and (IIIa-1) to (IIIa-8), or a salt thereof second, or a compound of Formula (I), (II), (IIa-1) to (IIa-8), (III) and (IIIa-1) to (IIIa-8), or a salt thereof being administered first and anti-PD-1 antibody second. Additionally or alternatively, an anti-PD-L1 antibody and a compound of Formula (I), (II), (IIa-1) to (IIa-8), (III) and (IIIa-1) to (IIIa-8), or a salt thereof can be administered sequentially, such as anti-PD-L1 antibody being administered first and a compound of Formula (I), (II), (IIa-1) to (IIa-8), (III) and (IIIa-1) to (IIIa-8), or a salt thereof second, or a compound of Formula (I), (II), (IIa-1) to (IIa-8), (III) and (IIIa-1) to (IIIa-8), or a salt thereof being administered first and anti-PD-L1 antibody second. In certain embodiments, the combination of therapeutic agents discussed herein can be administered concurrently as a single composition in a pharmaceutic ally acceptable carrier, or concurrently as separate compositions each in a pharmaceutically acceptable carrier. In another embodiment, the combination of therapeutic agents can be administered sequentially. For example, an anti-CTLA-4 antibody and a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof can be administered sequentially, such as anti-CTLA-4 antibody being administered first and a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof second, or a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof being administered first and anti-CTLA-4 antibody second. Additionally or alternatively, an anti-PD-1 antibody and a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof can be administered sequentially, such as anti-PD-1 antibody being administered first and a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof second, or a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof being administered first and anti-PD-1 antibody second. Additionally or alternatively, an anti-PD-L1 antibody and a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof can be administered sequentially, such as anti-PD-L1 antibody being administered first and a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof second, or a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof being administered first and anti-PD-L1 antibody second.

Furthermore, if more than one dose of the combination therapy is administered sequentially, the order of the sequential administration can be reversed or kept in the same order at each time point of administration, sequential administrations can be combined with concurrent administrations, or any combination thereof.

Optionally, the combination of a compound of Formula (I), (II), (IIa-1) to (IIa-8), (III) and (IIIa-1) to (IIIa-8), or a salt thereof can be further combined with an immunogenic agent, such as cancerous cells, purified tumor antigens (including recombinant proteins, peptides, and carbohydrate molecules), cells, and cells transfected with genes encoding immune stimulating cytokines. Optionally, the combination of a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof can be further combined with an immunogenic agent, such as cancerous cells, purified tumor antigens (including recombinant proteins, peptides, and carbohydrate molecules), cells, and cells transfected with genes encoding immune stimulating cytokines.

A compound of Formula (I), (II), (IIa-1) to (IIa-8), (III) and (IIIa-1) to (IIIa-8), or a salt thereof can also be further combined with standard cancer treatments. For example, a compound of Formula (I), (II), (IIa-1) to (IIa-8), (III) and (IIIa-1) to (IIIa-8), or a salt thereof can be effectively combined with chemotherapeutic regimens. In these instances, it is possible to reduce the dose of other chemotherapeutic reagent administered with the combination of the instant disclosure. Other combination therapies with a compound of Formula (I), (II), (IIa-1) to (IIa-8), (III) and (IIIa-1) to (IIIa-8), or a salt thereof include radiation, surgery, or hormone deprivation. Angiogenesis inhibitors can also be combined with a compound of Formula (I), (II), (IIa-1) to (IIa-8), (III) and (IIIa-1) to (IIIa-8), or a salt thereof. Inhibition of angiogenesis leads to tumor cell death, which can be a source of tumor antigen fed into host antigen presentation pathways. A compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof can also be further combined with standard cancer treatments. For example, a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof can be effectively combined with chemotherapeutic regimens. In these instances, it is possible to reduce the dose of other chemotherapeutic reagent administered with the combination of the instant disclosure. Other combination therapies with a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof include radiation, surgery, or hormone deprivation. Angiogenesis inhibitors can also be combined with a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof. Inhibition of angiogenesis leads to tumor cell death, which can be a source of tumor antigen fed into host antigen presentation pathways.

In another example, a compound of Formula (I), (II), (IIa-1) to (IIa-8), (III) and (IIIa-1) to (IIIa-8), or a salt thereof can be used in conjunction with anti-neoplastic antibodies. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4, PD-1, PD-L1 or a compound of Formula (I), (II), (IIa-1) to (IIa-8), (III) and (IIIa-1) to (IIIa-8), or a salt thereof. In an exemplary embodiment, a treatment of a hyperproliferative disease (e.g., a cancer tumor) can include an anti-cancer antibody in combination with a compound of Formula (I), (II), (IIa-1) to (IIa-8), (III) and (IIIa-1) to (IIIa-8), or a salt thereof and anti-CTLA-4 and/or anti-PD-1 and/or anti-PD-L1 antibodies, concurrently or sequentially or any combination thereof, which can potentiate anti-tumor immune responses by the host. Other antibodies that can be used to activate host immune responsiveness can be further used in combination with a compound of Formula (I), (II), (IIa-1) to (IIa-8), (III) and (IIIa-1) to (IIIa-8), or a salt thereof. In another example, a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof can be used in conjunction with anti-neoplastic antibodies. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4, PD-1, PD-L1 or a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof. In an exemplary embodiment, a treatment of a hyperproliferative disease (e.g., a cancer tumor) can include an anti-cancer antibody in combination with a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof and anti-CTLA-4 and/or anti-PD-1 and/or anti-PD-L1 antibodies, concurrently or sequentially or any combination thereof, which can potentiate anti-tumor immune responses by the host. Other antibodies that can be used to activate host immune responsiveness can be further used in combination with a compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof.

In yet further embodiments, the compound of Formula (I), (II), (IIa-1) to (IIa-8), (III) and (IIIa-1) to (IIIa-8), or a salt thereof is administered in combination with another BET inhibitor. In yet further embodiments, the compound of Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), or a salt thereof is administered in combination with another BET inhibitor.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein or a salt thereof and a pharmaceutically acceptable excipient.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral and transdermal. A compound provided herein can be administered frequently at low doses, known as "metronomic therapy," or as part of a maintenance therapy using compound alone or in combination with one or more additional drugs. Metronomic therapy or maintenance therapy can comprise administration of a compound provided herein in cycles. Metronomic therapy or maintenance therapy can comprise intra-tumoral administration of a compound provided herein.

In one aspect, the invention provides a method of treating cancer in an individual by parenterally administering to the individual (e.g., a human) an effective amount of a compound or salt thereof. In some embodiments, the route of administration is intravenous, intra-arterial, intramuscular, or subcutaneous. In some embodiments, the route of administration is oral. In still other embodiments, the route of administration is transdermal.

The invention also provides compositions (including pharmaceutical compositions) as described herein for the use in treating, preventing, and/or delaying the onset and/or development of cancer and other methods described herein. In certain embodiments, the composition comprises a pharmaceutical formulation which is present in a unit dosage form.

Also provided are articles of manufacture comprising a compound of the disclosure or a salt thereof, composition, and unit dosages described herein in suitable packaging for use in the methods described herein. Suitable packaging is known in the art and includes, for example, vials, vessels, ampules, bottles, jars, flexible packaging and the like. An article of manufacture may further be sterilized and/or sealed kits.

The present disclosure further provides kits for carrying out the methods of the invention, which comprises one or more compounds described herein or a composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or subunit doses. For example, kits may be provided that contain sufficient dosages of a compound as disclosed herein and/or a second pharmaceutically active compound useful for a disease detailed herein (e.g., hypertension) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention can be further understood by reference to the following examples, which are provided by way of illustration and are not meant to be limiting.

General Information

NMR spectra and $^{13}$C NMR spectra were recorded on a Bruker Avance 400 MHz spectrometer. Spectra are referenced to residual chloroform ($\delta$ 7.26, $^1$H), DMSO ($\delta$ 2.54, $^1$H) or methanol ($\delta$ 3.34, $^1$H) unless otherwise noted. Chemical shifts are reported in ppm ($\delta$); multiplicities are indicated by s (singlet), d (doublet), t (triplet), q (quartet), quint (quintet), sext (sextet), m (multiplet) and hr (broad). Coupling constants, J, are reported in Hertz. Analytical HPLC was performed on an Agilent 1200 HPLC with an Agilent G1365D diode array detector using an Agilent Eclipse XDB-C18 (4.6×150 mm, 5 µm) column. Analytical LCMS was performed on an Agilent 6410 triple quadrupole LCMS. Commercially available reagents and solvents were used as received unless otherwise indicated.

SELECTED EMBODIMENTS

Embodiment 1. A compound of Formula (I):

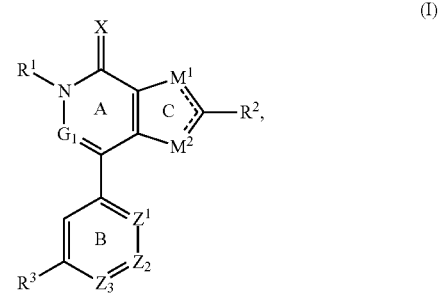

(I)

or a tautomer or isomer thereof, or a pharmaceutically acceptable salt of any of the foregoing, wherein:

each ==== is independently a single bond or double bond;

X is O or S;

$R^1$ is hydrogen, $C_1$-$C_3$ alkyl, —($C_1$-$C_3$ alkylene)OH, $C_1$-$C_3$ haloalkyl, or $C_3$-$C_4$ cycloalkyl;

$G_1$ is $CR^a$ or N, wherein:
  $R^a$ is hydrogen, halogen, or $C_1$-$C_4$ alkyl;

$Z_1$ is C—$W_1$—$R^c$; wherein:
  each $W_1$ is independently —O— or —$NR^{w1}$—, wherein:
    $R^{w1}$ is hydrogen, $C_3$-$C_6$ cycloalkyl, or $C_1$-$C_4$ alkyl optionally substituted by oxo, —OH, or halogen, and
  $R^c$ is independently 4- to 6-membered heterocyclyl, $C_6$-$C_{14}$ aryl, or 5- or 6-membered heteroaryl, each of which is independently optionally substituted by $R^{c1}$, wherein each $R^{c1}$ is independently halogen, $C_1$-$C_4$ alkyl, $C_3$-$C_6$ cycloalkyl, 3- to 6-membered heterocyclyl, cyano, oxo, $C_1$-$C_4$ alkoxy, $C_1$-$C_4$ haloalkoxy, $C_1$-$C_4$ haloalkyl, —$OR^{10}$, —$NR^{10}R^{11}$, —$C(O)NR^{10}R^{11}$, —$NR^{10}C(O)R^{11}$, —$S(O)_2R^{10}$, —$NR^{10}S(O)_2R^{11}$, or —$S(O)_2NR^{10}R^{11}$;

$Z_2$ is C—$W_2$—$R^d$ or N, wherein:
  $W_2$ is —O—, —$NR^{w2}$—, or a bond, wherein:
    $R^{w2}$ is hydrogen, $C_3$-$C_6$ cycloalkyl, or $C_1$-$C_4$ alkyl optionally substituted by oxo, —OH, or halogen, and
  $R^d$ is independently hydrogen, halogen, cyano, 3- to 6-membered heterocyclyl, or $C_1$-$C_4$ alkyl;

$Z_3$ is C—$R^e$ or N, wherein:
  $R^e$ is independently hydrogen, halogen, cyano, 3- to 6-membered heterocyclyl, or $C_1$-$C_4$ alkyl;

$M^1$ is S or $CR^{1a}$;

$M^2$ is S or $CR^{2a}$, provided that
(1) when $M^1$ is S, then the ==== adjacent to $M^1$ is a single bond and the ==== adjacent to $M^2$ is a double bond,
(2) when $M^2$ is S, then the ==== adjacent to $M^2$ is a single bond and the ==== adjacent to $M^1$ is a double bond, and
(3) at least one of $M^1$ and $M^2$ is not S;

$R^{1a}$ and $R^{2a}$ are each independently hydrogen, halogen, $C_1$-$C_4$ alkyl, $C_3$-$C_6$ cycloalkyl, 3- to 6-membered heterocyclyl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{11}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is independently optionally substituted by $R^{12}$;

$R^2$ is halogen, $C_1$-$C_4$ alkyl, $C_3$-$C_6$ cycloalkyl, 3- to 6-membered heterocyclyl, —($C_1$-$C_3$ alkylene)3- to 6-membered heterocyclyl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{11}$, —$C(O)NR^{10}R^{11}$, —$NR^{10}C(O)R^{11}$, —$S(O)_2R^{10}$, —$NR^{10}S(O)_2R^{11}$, or —$S(O)_2NR^{10}R^{11}$, each of which is independently optionally substituted by $R^{12}$;

$R^3$ is —$(CH_2)_mNR^{13}S(O)_2R^{14}$, $C_3$-$C_6$ cycloalkyl, or $C_1$-$C_4$ alkyl substituted by halogen, oxo, —CN, or —OH, wherein m is 0, 1, 2 or 3;

$R^{10}$ and $R^{11}$ are each independently hydrogen, $C_1$-$C_4$ alkyl, $C_1$-$C_4$ alkoxy, $C_1$-$C_4$ alkenyl, $C_3$-$C_6$ cycloalkyl, 3- to 6-membered heterocyclyl, —($C_1$-$C_3$ alkylene)$C_3$-$C_6$ cycloalkyl, —($C_1$-$C_3$ alkylene) 3- to 6-membered heterocyclyl, —$NR^{15}R^{16}$, or —$C(O)R^{12}$, wherein each of $R^{10}$ and $R^{11}$ is independently optionally substituted by halogen, oxo, —CN, —$CF_3$, —OH, —$NR^{13}R^{14}$, —$C(O)NR^{13}R^{14}$, or $C_1$-$C_4$ alkyl optionally substituted by halogen, oxo, —CN, —$CF_3$, or —OH, or $R^{10}$ and $R^{11}$ are taken together with the atom or atoms to which they are attached to form a 3- to 6-membered heterocyclyl ring optionally substituted by halogen, oxo, —CN, —$CF_3$, —OH, or $C_1$-$C_4$ alkyl optionally substituted by halogen, oxo, —CN, or —OH;

each $R^{12}$ is independently halogen, cyano, $C_1$-$C_4$ haloalkyl, $C_1$-$C_4$ alkoxy, $C_1$-$C_4$ haloalkoxy, —$OR^{15}$, —$NR^{15}R^{16}$, —$C(O)NR^{15}R^{16}$, —$NR^{15}C(O)R^{16}$, —$S(O)_2R^{15}$, —$NR^{15}S(O)_2R^{16}$, —$S(O)_2NR^{15}R^{16}$, $C_3$-$C_6$ cycloalkyl, 3- to 6-membered heterocyclyl, or $C_1$-$C_4$ alkyl, each of which is independently optionally substituted by halogen, oxo, —$CF_3$, —CN, —OH, —$NR^{13}R^{14}$, or —$NR^{13}C(O)R^{14}$;

$R^{13}$ and $R^{14}$ are independently hydrogen, $C_1$-$C_4$ alkyl $C_3$-$C_6$ cycloalkyl, or 3- to 6-membered heterocyclyl, each of which is independently optionally substituted by halogen, oxo, —CN, or —OH, or $R^{13}$ and $R^{14}$ are taken together with the atom or atoms to which they are attached to form a 3- to 6-membered heterocyclyl ring optionally substituted by halogen, oxo, —CN, —OH, or $C_1$-$C_4$ alkyl optionally substituted by halogen, oxo, —CN, or —OH; and each $R^{15}$ and $R^{16}$ are independently hydrogen, $C_1$-$C_4$ alkyl, $C_3$-$C_6$ cycloalkyl, or 3- to 6-membered heterocyclyl, each of which is independently optionally substituted by halogen, oxo, —CN, or —OH, or $R^{15}$ and $R^{16}$ are taken together with the atoms to which they are attached to form a 3- to 6-membered heterocyclyl ring optionally substituted by halogen, oxo, —CN, —OH, or $C_1$-$C_4$ alkyl optionally substituted by halogen, oxo, —CN, or —OH.

Embodiment 2. The compound of embodiment 1, or a tautomer or isomer thereof, or a pharmaceutically acceptable salt of any of the foregoing, wherein the compound is of Formula (II),

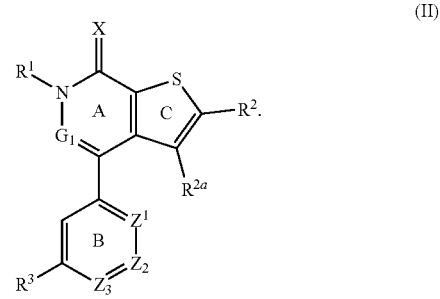

(II)

Embodiment 3. The compound of embodiment 1, or a tautomer or isomer thereof, or a pharmaceutically acceptable salt of any of the foregoing, wherein the compound is of Formula (III),

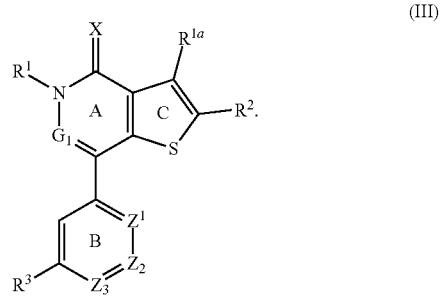

(III)

Embodiment 4. The compound of any one of embodiments 1-3, or a tautomer or isomer thereof, or a pharmaceutically acceptable salt of any of the foregoing, wherein X is O.

Embodiment 5. The compound of any one of embodiments 1-4, or a tautomer or isomer thereof, or a pharmaceutically acceptable salt of any of the foregoing, wherein $G_1$ is CH.

Embodiment 6. The compound of any one of embodiments 1-5, or a tautomer or isomer thereof, or a pharmaceutically acceptable salt of any of the foregoing, wherein $Z^1$ is $C—W_1—R^c$ and $R^c$ is $C_6$-$C_{14}$ aryl optionally substituted by $R^{c1}$.

Embodiment 7. The compound of embodiment 6, or a tautomer or isomer thereof, or a pharmaceutically acceptable salt of any of the foregoing, wherein $R^c$ is phenyl optionally substituted by halogen or $C_1$-$C_4$ alkyl.

Embodiment 8. The compound of any one of embodiments 1-7, or a tautomer or isomer thereof, or a pharmaceutically acceptable salt of any of the foregoing, wherein $Z_2$ is CH.

Embodiment 9. The compound of any one of embodiments 1-8, or a tautomer or isomer thereof, or a pharmaceutically acceptable salt of any of the foregoing, wherein $Z_3$ is CH.

Embodiment 10. The compound of any one of embodiments 1-9, or a tautomer or isomer thereof, or a pharmaceutically acceptable salt of any of the foregoing, wherein $R^1$ is $C_1$-$C_3$ alkyl.

Embodiment 11. The compound of any one of embodiments 1-10, or a tautomer or isomer thereof, or a pharmaceutically acceptable salt of any of the foregoing, wherein $R^2$ is —C(O)NR$^{10}$R$^{11}$, 5- to 10-membered heteroaryl, —($C_1$-$C_3$ alkylene)3- to 6-membered heterocyclyl, or $C_1$-$C_4$ alkyl, each of which is independently optionally substituted by $R^{12}$.

Embodiment 12. The compound of embodiment 11, or a tautomer or isomer thereof, or a pharmaceutically acceptable salt of any of the foregoing, wherein $R^2$ is —C(O)NR$^{10}$R$^{11}$ which is optionally substituted by $R^{12}$, wherein $R^{10}$ and $R^{11}$ are each independently hydrogen, $C_1$-$C_4$ alkyl, or $C_3$-$C_6$ cycloalkyl, or $R^{10}$ and $R^{11}$ are taken together with the atom or atoms to which they are attached to form a 3- to 6-membered heterocyclyl ring optionally substituted by halogen.

Embodiment 13. The compound of embodiment 11, or a tautomer or isomer thereof, or a pharmaceutically acceptable salt of any of the foregoing, wherein $R^2$ is 5- to 10-membered heteroaryl optionally substituted by $R^{12}$.

Embodiment 14. The compound of any one of embodiments 1-13, or a tautomer or isomer thereof, or a pharmaceutically acceptable salt of any of the foregoing, wherein $R^3$ is —(CH$_2$)$_m$NR$^{13}$S(O)$_2$R$^{14}$ or $C_1$-$C_4$ alkyl substituted by halogen, oxo, —CN, or —OH.

Embodiment 15. The compound of any one of embodiments 1-14, or a tautomer or isomer thereof, or a pharmaceutically acceptable salt of any of the foregoing, wherein $R^3$ is —(CH$_2$)$_m$NR$^{13}$S(O)$_2$R$^{14}$.

Embodiment 16. The compound of any one of embodiments 1-15, or a tautomer or isomer thereof, or a pharmaceutically acceptable salt of any of the foregoing, wherein $R^3$ is

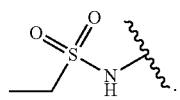

Embodiment 17. The compound of any one of embodiments 1-14, or a tautomer or isomer thereof, or a pharmaceutically acceptable salt of any of the foregoing, wherein $R^3$ is $C_1$-$C_4$ alkyl substituted by —OH.

Embodiment 18. The compound of embodiment 17, or a tautomer or isomer thereof, or a pharmaceutically acceptable salt of any of the foregoing, wherein $R^3$ is

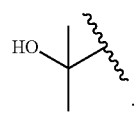

Embodiment 19. The compound of any one of embodiments 1 and 3-18, or a tautomer or isomer thereof, or a pharmaceutically acceptable salt of any of the foregoing, wherein $R^{1a}$ is hydrogen.

Embodiment 20. The compound of any one of embodiments 1, 2, and 4-18, or a tautomer or isomer thereof, or a pharmaceutically acceptable salt of any of the foregoing, wherein $R^{2a}$ is hydrogen.

Embodiment 21. The compound of embodiment 1, or a pharmaceutically acceptable salt thereof, wherein the compound is selected from the group consisting of the compounds in Table 1.

Embodiment 22. A pharmaceutical composition comprising the compound of any one of embodiments 1-21, or a tautomer or isomer thereof, or a pharmaceutically acceptable salt of any of the foregoing, and a pharmaceutically acceptable carrier.

Embodiment 23. A method of treating disease mediated by bromodomain and extraterminal domain (BET) in an individual in need thereof comprising administering to the individual a therapeutically effective amount of the compound of any one of embodiments 1-21, or a tautomer or isomer thereof, or a pharmaceutically acceptable salt of any of the foregoing.

Embodiment 24. A method of treating cancer in an individual in need thereof comprising administering to the individual a therapeutically effective amount of the compound of any one of embodiments 1-21, or a tautomer or isomer thereof, or a pharmaceutically acceptable salt of any of the foregoing.

Embodiment 25. A method of inhibiting bromodomain and extraterminal domain (BET) in a cell, comprising administering the compound of any one of embodiments 1-21, or a tautomer or isomer thereof, or a pharmaceutically acceptable salt of any of the foregoing, to the cells.

Embodiment 26. Use of the compound of any one of embodiments 1-21, or a tautomer or isomer thereof, or a pharmaceutically acceptable salt of any of the foregoing, in the manufacture of a medicament for treatment of a disease mediated by bromodomain and extraterminal domain (BET).

Embodiment 27. A kit comprising the compound of any one of embodiments 1-21, or a tautomer or isomer thereof, or a pharmaceutically acceptable salt of any of the foregoing.

Embodiment 2.1. A compound of Formula (IV):

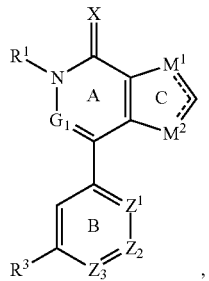

(IV)

or a tautomer or isomer thereof, or a pharmaceutically acceptable salt of any of the foregoing, wherein:
each ---- is independently a single bond or double bond;
X is O or S;
$R^1$ is hydrogen, $C_1$-$C_3$ alkyl, —($C_1$-$C_3$ alkylene)OH, $C_1$-$C_3$ haloalkyl, or $C_3$-$C_4$ cycloalkyl;
$G_1$ is $CR^a$ or N, wherein:
$R^a$ is hydrogen, halogen, $C_1$-$C_6$ alkyl, or $C_1$-$C_6$ haloalkyl;
$Z_1$ is C—$W_1$—$R^c$, wherein:
each $W_1$ is independently —O— or —$NR^{w1}$—, wherein:
$R^{w1}$ is hydrogen, $C_3$-$C_6$ cycloalkyl, or $C_1$-$C_4$ alkyl optionally substituted by oxo, —OH, or halogen, and
$R^c$ is independently $C_3$-$C_6$ cycloalkyl, 4- to 6-membered heterocyclyl, $C_6$-$C_{14}$ aryl, or 5- or 6-membered heteroaryl, each of which is independently optionally substituted by $R^{c1}$, wherein each $R^{c1}$ is independently halogen, $C_1$-$C_4$ alkyl, $C_3$-$C_6$ cycloalkyl, 3- to 6-membered heterocyclyl, cyano, oxo, $C_1$-$C_4$ alkoxy, $C_1$-$C_4$ haloalkoxy, $C_1$-$C_4$ haloalkyl, —$OR^{10}$, —$NR^{10}R^{11}$, —$C(O)NR^{10}R^{11}$, —$NR^{10}C(O)R^{11}$, —$S(O)_2R^{10}$, —$NR^{10}S(O)_2R^{11}$, or —$S(O)_2NR^{10}R^{11}$;
$Z_2$ is C—$W_2$—$R^d$ or N, wherein:
$W_2$ is —O—, —$NR^{w2}$—, or a bond, wherein:
$R^{w2}$ is hydrogen, $C_3$-$C_6$ cycloalkyl, or $C_1$-$C_4$ alkyl optionally substituted by oxo, —OH, or halogen, and
$R^d$ is independently hydrogen, halogen, cyano, 3- to 6-membered heterocyclyl, or $C_1$-$C_4$ alkyl;
$Z_3$ is C—$R^e$ or N, wherein:
$R^e$ is independently hydrogen, halogen, cyano, 3- to 6-membered heterocyclyl, or $C_1$-$C_4$ alkyl;
$M^1$ is S or $CR^{1a}$;
$M^2$ is S or $CR^{2a}$, provided that
(1) when $M^1$ is S, then the ---- adjacent to $M^1$ is a single bond and the ---- adjacent to $M^2$ is a double bond,
(2) when $M^2$ is S, then the ---- adjacent to $M^2$ is a single bond and the ---- adjacent to $M^1$ is a double bond, and
(3) at least one of $M^1$ and $M^2$ is S;
$R^{1a}$ and $R^{2a}$ are each independently hydrogen, halogen, $C_1$-$C_4$ alkyl, $C_3$-$C_6$ cycloalkyl, 3- to 6-membered heterocyclyl, 5- to 10-membered heteroaryl, cyano, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{11}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is independently optionally substituted by $R^{12}$;
$R^3$ is —$(CH_2)_mNR^{13}S(O)_2R^{14}$, wherein m is 0, 1, 2 or 3; $C_3$-$C_6$ cycloalkyl optionally substituted by halogen, oxo, —CN, or —OH; or $C_1$-$C_4$ alkyl substituted by halogen, oxo, —CN, or —OH;
$R^{10}$ and $R^{11}$ are each independently hydrogen, $C_1$-$C_4$ alkyl, $C_1$-$C_4$ alkoxy, $C_1$-$C_4$ alkenyl, $C_3$-$C_6$ cycloalkyl, 3- to 6-membered heterocyclyl, —($C_1$-$C_3$ alkylene) $C_3$-$C_6$ cycloalkyl, —($C_1$-$C_3$ alkylene) 3- to 6-membered heterocyclyl, —$NR^{15}R^{16}$, or —$C(O)R^{12}$, wherein each of $R^{10}$ and $R^{11}$ is independently optionally substituted by halogen, oxo, —CN, —$CF_3$, —OH, —$NR^{13}R^{14}$, —$C(O)NR^{13}R^{14}$, or $C_1$-$C_4$ alkyl optionally substituted by halogen, oxo, —CN, —$CF_3$, or —OH,
or $R^{10}$ and $R^{11}$ are taken together with the atom or atoms to which they are attached to form a 3- to 6-membered heterocyclyl ring optionally substituted by halogen, oxo, —CN, —$CF_3$, —OH, or $C_1$-$C_4$ alkyl optionally substituted by halogen, oxo, —CN, or —OH;
each $R^{12}$ is independently halogen, cyano, $C_1$-$C_4$ haloalkyl, $C_1$-$C_4$ alkoxy, $C_1$-$C_4$ haloalkoxy, —$OR^{15}$, —$NR^{15}R^{16}$, —$C(O)NR^{15}R^{16}$, —$NR^{15}C(O)R^{16}$, —$S(O)_2R^{15}$, —$NR^{15}S(O)_2R^{16}$, —$S(O)_2NR^{15}R^{16}$, $C_3$-$C_6$ cycloalkyl, 3- to 6-membered heterocyclyl, or $C_1$-$C_4$ alkyl, each of which is independently optionally substituted by halogen, oxo, —$CF_3$, —CN, —OH, —$NR^{13}R^{14}$, or —$NR^{13}C(O)R^{14}$;
$R^{13}$ and $R^{14}$ are independently hydrogen, $C_1$-$C_4$ alkyl $C_3$-$C_6$ cycloalkyl, or 3- to 6-membered heterocyclyl, each of which is independently optionally substituted by halogen, oxo, —CN, or —OH,
or $R^{13}$ and $R^{14}$ are taken together with the atom or atoms to which they are attached to form a 3- to 6-membered heterocyclyl ring optionally substituted by halogen, oxo, —CN, —OH, or $C_1$-$C_4$ alkyl optionally substituted by halogen, oxo, —CN, or —OH; and
each $R^{15}$ and $R^{16}$ are independently hydrogen, $C_1$-$C_4$ alkyl, $C_3$-$C_6$ cycloalkyl, or 3- to 6-membered heterocyclyl, each of which is independently optionally substituted by halogen, oxo, —CN, or —OH,
or $R^{15}$ and $R^{16}$ are taken together with the atoms to which they are attached to form a 3- to 6-membered heterocyclyl ring optionally substituted by halogen, oxo, —CN, —OH, or $C_1$-$C_4$ alkyl optionally substituted by halogen, oxo, —CN, or —OH.

Embodiment 2.2. The compound of embodiment 2.1, or a tautomer or isomer thereof, or a pharmaceutically acceptable salt of any of the foregoing, wherein $M^1$ is S.

Embodiment 2.3. The compound of embodiment 2.1, or a tautomer or isomer thereof, or a pharmaceutically acceptable salt of any of the foregoing, wherein $M^2$ is S.

Embodiment 2.4. The compound of any one of embodiments 2.1-2.3, or a tautomer or isomer thereof, or a pharmaceutically acceptable salt of any of the foregoing, wherein X is O.

Embodiment 2.5. The compound of any one of embodiments 2.1-2.4, or a tautomer or isomer thereof, or a pharmaceutically acceptable salt of any of the foregoing, wherein $Z_1$ is C—O—$R^c$.

Embodiment 2.6. The compound of embodiment 2.5, or a tautomer or isomer thereof, or a pharmaceutically acceptable salt of any of the foregoing, wherein $R^c$ is phenyl, pyridinyl, or cyclohexyl, each of which is independently optionally substituted by $R^{c1}$.

Embodiment 2.7. The compound of embodiment 2.5 or 2.6, or a tautomer or isomer thereof, or a pharmaceutically acceptable salt of any of the foregoing, wherein $R^c$ is

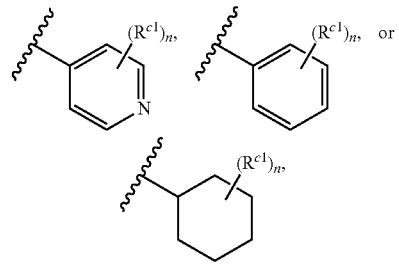

wherein n is 0, 1, 2, 3, or 4.

Embodiment 2.8. The compound of embodiment 2.6 or 2.7, or a tautomer or isomer thereof, or a pharmaceutically acceptable salt of any of the foregoing, wherein each $R^{c1}$ is independently halogen or $C_1$-$C_4$ alkyl.

Embodiment 2.9. The compound of embodiment 2.8, or a tautomer or isomer thereof, or a pharmaceutically acceptable salt of any of the foregoing, wherein $R^c$ is

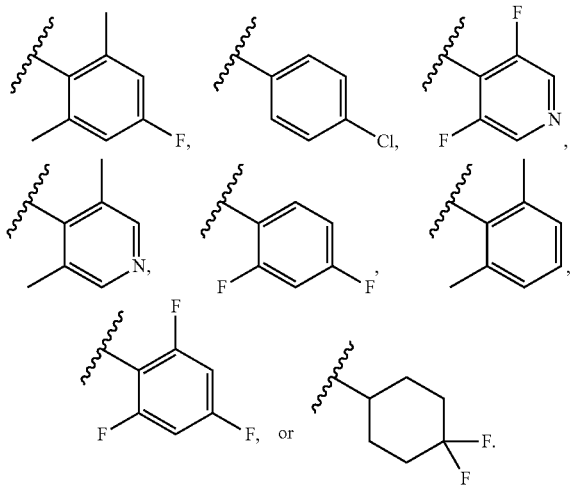

Embodiment 2.10. The compound of any one of embodiments 2.1-2.9, or a tautomer or isomer thereof, or a pharmaceutically acceptable salt of any of the foregoing, wherein $Z_2$ is CH.

Embodiment 2.11. The compound of any one of embodiments 2.1-2.9, or a tautomer or isomer thereof, or a pharmaceutically acceptable salt of any of the foregoing, wherein $Z_2$ is N.

Embodiment 2.12. The compound of any one of embodiments 2.1-2.11, or a tautomer or isomer thereof, or a pharmaceutically acceptable salt of any of the foregoing, wherein $Z_3$ is CH.

Embodiment 2.13. The compound of any one of embodiment 2.1-2.12, or a tautomer or isomer thereof, or a pharmaceutically acceptable salt of any of the foregoing, wherein $R^1$ is $C_1$-$C_3$ alkyl.

Embodiment 2.14. The compound of embodiment 2.13, or a tautomer or isomer thereof, or a pharmaceutically acceptable salt of any of the foregoing, wherein $R^1$ is methyl.

Embodiment 2.15. The compound of any one of embodiment 2.1-2.14, or a tautomer or isomer thereof, or a pharmaceutically acceptable salt of any of the foregoing, wherein $G_1$ is $CR^a$, wherein $R^a$ is hydrogen.

Embodiment 2.16. The compound of any one of embodiment 2.1-2.15, or a tautomer or isomer thereof, or a pharmaceutically acceptable salt of any of the foregoing, wherein $G_1$ is N.

Embodiment 2.17. The compound of embodiment 2.1, or a tautomer or isomer thereof, or a pharmaceutically acceptable salt of any of the foregoing, wherein the compound is selected from the compounds in Table 1.

Embodiment 2.18. A pharmaceutical composition comprising the compound of any one of embodiments 2.1-2.17, or a tautomer or isomer thereof, or a pharmaceutically acceptable salt of any of the foregoing, and a pharmaceutically acceptable carrier.

Embodiment 2.19. A method of treating disease mediated by bromodomain and extraterminal domain (BET) in an individual in need thereof comprising administering to the individual a therapeutically effective amount of the compound of any one of embodiments 2.1-2.17, or a tautomer or isomer thereof, or a pharmaceutically acceptable salt of any of the foregoing.

Embodiment 2.20. A method of treating cancer in an individual in need thereof comprising administering to the individual a therapeutically effective amount of the compound of any one of embodiments 2.1-2.17, or a tautomer or isomer thereof, or a pharmaceutically acceptable salt of any of the foregoing.

Embodiment 2.21. A method of inhibiting bromodomain and extraterminal domain (BET) in a cell, comprising administering the compound of any one of embodiments 2.1-2.17, or a tautomer or isomer thereof, or a pharmaceutically acceptable salt of any of the foregoing, to the cells.

Embodiment 2.22. Use of the compound of any one of embodiments 2.1-2.17, or a tautomer or isomer thereof, or a pharmaceutically acceptable salt of any of the foregoing, in the manufacture of a medicament for treatment of a disease mediated by bromodomain and extraterminal domain (BET).

Embodiment 2.23. A kit comprising the compound of any one of embodiment 2.1-2.17, or a tautomer or isomer thereof, or a pharmaceutically acceptable salt of any of the foregoing.

SYNTHETIC EXAMPLES

Example S-1: Synthesis of N-ethyl-4-(2-(4-fluoro-2,6-dimethylphenoxy)-5-(2-hydroxypropan-2-yl)phenyl)-6-methyl-7-oxo-6,7-dihydrothieno[2,3-c]pyridine-2-carboxamide (General Procedure 1) (Compound 1)

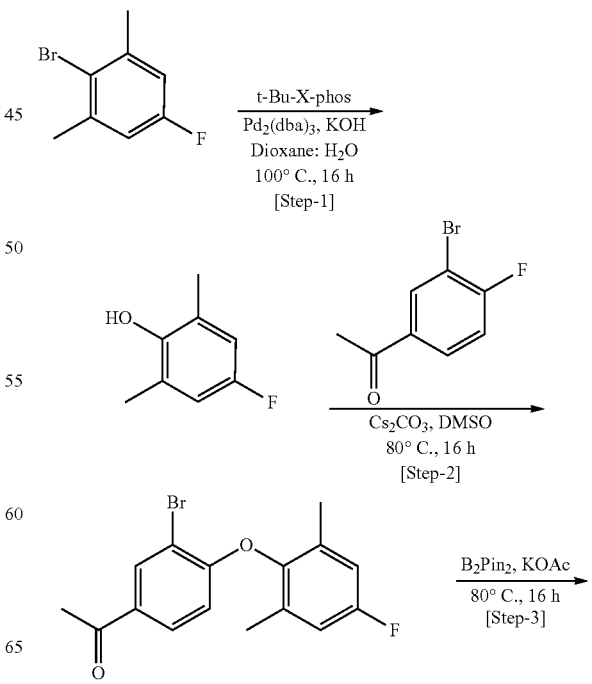

-continued

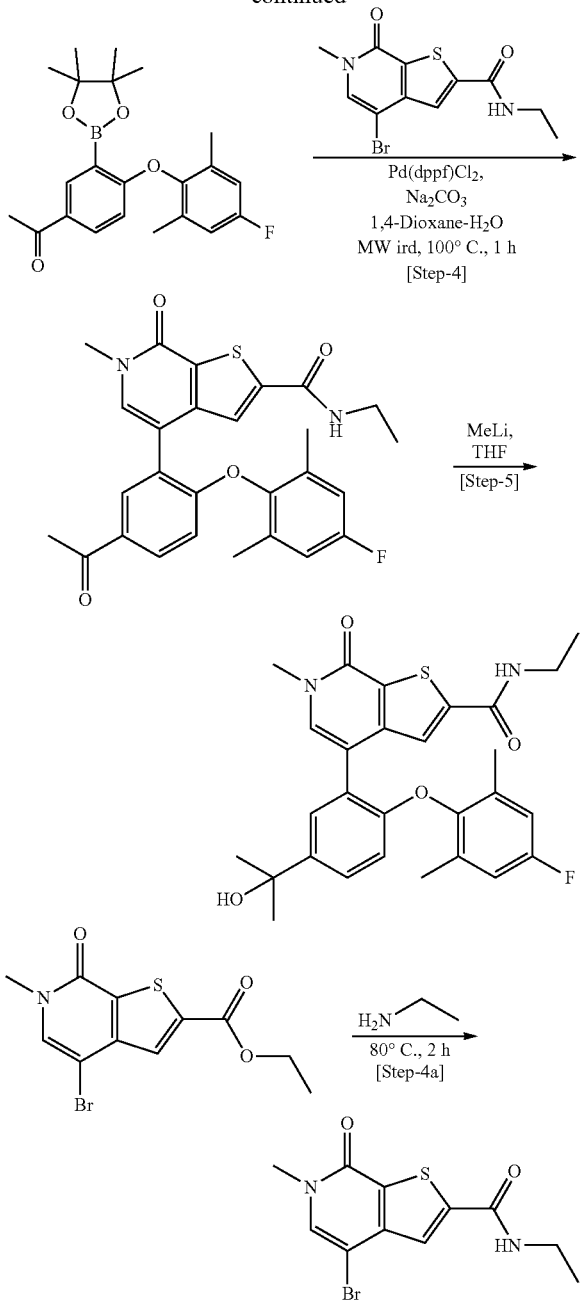

Step 1. Synthesis of 4-fluoro-2,6-dimethylphenol: Step 1: Synthesis of 4-fluoro-2,6-dimethylphenol: A solution of 2-bromo-5-fluoro-1,3-dimethylbenzene (5.0 g, 24.7 mmol, 1 eq) in 1,4-Dioxane:water (25 mL:25 mL) was added KOH (4.15 g, 74.2 mmol, 3 eq) and the mixture was degassed under nitrogen for 15 min. In another set-up, t-Bu-X-phos (839 mg, 7.98 mmol 0.08 eq) and Pd$_2$(dba)$_3$ (452 mg, 0.49 mmol, 0.08 eq) in 1,4-dioxane:water (10 mL:10 mL) was degassed under nitrogen for 15 min. The contents of the first degassed mixture was transferred into the degassed solution of the second and the mixture was heated at 100° C. and monitored by TLC and LC-MS. The reaction was complete after 16 h and the mixture was acidified with 6N—HCl (pH 2-3) and extracted with EtOAc (700 mL). The organic layer was washed with water (300 mL), brine (200 mL), dried over anhydrous Na$_2$SO$_4$, filtered and concentrated under reduced pressure to obtain a crude residue which was purified by CombiFlash chromatography to afford 4-fluoro-2,6-dimethylphenol (2.2 g, 64%) as a viscous brown solid. LCMS: 141 [M+1]$^+$ Step 2. Synthesis of 1-(3-bromo-4-(4-fluoro-2,6-dimethylphenoxy)phenyl)ethanone: To a solution of 4-fluoro-2,6-dimethylphenol (0.50 g, 3.57 mmol) in DMSO (20 mL) was added Cs$_2$CO$_3$ (8.9 g, 27.2 mmol) at RT and the mixture was stirred for 15 min. 1-(3-bromo-4-fluorophenyl)ethanone (0.93 g, 4.28 mmol, 1.2 eq) was then added to the mixture and the resultant mixture was heated 80° C. for 16 h. The reaction was complete after 16 h and the mixture was diluted with water (200 mL) and extracted with EtOAc (200 mL×2). The combined organic layers were washed with brine (100 mL), dried over anhydrous Na$_2$SO$_4$, filtered and concentrated under reduced pressure to obtain a crude which was purified by CombiFlash Chromatography to afford 1-(3-bromo-4-(4-fluoro-2,6-dimethyl phenoxy) phenyl)ethanone (0.30 g, 25%) as an off-white solid. LCMS: 337 [M+H]$^+$, 339 [M+H+2]$^+$ Step 3. Synthesis of 1-(4-(4-fluoro-2,6-dimethylphenoxy)-3-(4,4,5,5-tetramethyl-1,3,2-dioxaborolan-2-yl)phenyl)ethanone: To a solution of 1-(3-bromo-4-(4-fluoro-2,6-dimethylphenoxy)phenyl)ethanone (0.55 g, 1.63 mmol, 1 eq) in dioxane (5 mL), was added B$_2$Pin$_2$ (0.50 g, 1.96 mmol), KOAc (0.48 g, 4.89 mmol), and Pd(dppf)Cl$_2$ (0.12 g, 0.16 mmol). The reaction mixture was degassed and purged with N$_2$. Then the mixture was stirred at overnight at 80° C. TLC analysis indicated the reaction was complete. The mixture was concentrated under reduced pressure. The residue was purified by column chromatography on silica gel to give 1-(4-(4-fluoro-2,6-dimethylphenoxy)-3-(4,4,5,5-tetra methyl-1,3,2-dioxaborolan-2-yl)phenyl)ethanone as black viscous liquid (0.35 g, 56%). NMR (400 MHz, CDCl$_3$): δ 8.35 (d, J=2.4 Hz, 1H), 7.86 (s, 1H), 6.81 (d, J=8.8 Hz, 2H), 6.35 (d, J=8.8 Hz, 1H), 2.57 (s, 3H), 1.37 (s, 6H), 1.25 (d, 7=7.3 Hz, 12H)

Step 4a. Synthesis of 4-bromo-N-ethyl-6-methyl-7-oxo-6,7-dihydrothieno[2,3-c]pyridine-2-carboxamide: To ethyl 4-bromo-6-methyl-7-oxo-6,7-dihydrothieno[2,3-c]pyridine-2-carboxylate (1.5 g, 4.3 mmol, 1 eq), was added ethyl amine (17 mL; 70% solution in H$_2$O) and the mixture was heated at 80° C. and monitored by TLC. The reaction was complete after 2 h and to it was added ice-cold water (50 mL) to obtain a precipitate which was filtered over Büchner funnel; dried under vacuum to afford 4-bromo-N-ethyl-6-methyl-7-oxo-6,7-dihydrothieno[2,3-c]pyridine-2-carboxamide (1.23 g, 95%) as a white solid. LCMS: 315 [M+H]$^+$, 317 [M+H+2]$^+$ Step 4. Synthesis of 4-(5-acetyl-2-(4-fluoro-2,6-dimethylphenoxy)phenyl)-N-ethyl-6-methyl-7-oxo-6,7-dihydrothieno[2,3-c]pyridine-2-carboxamide: To a stirred solution of 4-bromo-A-ethyl-6-methyl-7-oxo-6,7-dihydrothieno[2,3-c]pyridine-2-carboxamide (0.27 g, 0.86 mmol, 1 eq) in 1,4-dioxane (1 mL) was added 1-(4-(4-fluoro-2,6-dimethylphenoxy)-3-(4,4,5,5-tetra methyl-1,3,2-dioxaborolan-2-yl) phenyl)ethanone (0.49 g, 1.28 mmol, 1.5 eq) and Na$_2$CO$_3$ (0.27 g, 2.57 mmol, 3 eq) dissolved in water (0.3 mL) followed by addition of Pd(dppf)Cl$_2$ (63 mg, 0.085 mmol, 0.1 eq) at RT. The reaction mixture was heated by microwave irradiation at 100° C. and monitored by TLC. The reaction was complete after 45 min and the mixture was diluted with water (200 mL) and extracted with EtOAc (300 mL). The organic layer was washed with water (100 mL), brine (150 mL) dried over anhydrous Na$_2$SO$_4$, filtered and concentrated under reduced pressure to afford a crude material which was purified by CombiFlash chromatography-to afford 4-(5-acetyl-2-(4-fluoro-2,6-dimethylphenoxy)phenyl)-A-ethyl-6-methyl-7-oxo-6,7-dihydrothieno[2,3-c]pyridine-2-carboxamide (0.16 g, 38%) as brown viscous liquid. LCMS: 493 [M+H]$^+$ Step 5. Synthesis of A-ethyl-4-(2-(4-fluoro-2,6-dimethylphenoxy)-5-(2-hydroxypropan-2-yl)phenyl)-6-methyl-7-oxo-6,7-dihydrothieno[2,3-c]pyridine-2-carboxamide: To a stirred solution of 4-(5-acetyl-2-(4-fluoro-2,6-dimethylphenoxy)phenyl)-N-ethyl-6-methyl-7-oxo-6,7-dihydrothieno[2,3-c]pyridine-2-carboxamide (0.050 g, 0.10 mmol) in anhydrous THF (3 mF) was added methyl lithium (0.2 mF, 0.33 mmol, 6 eq) at 0° C. dropwise and the mixture was stirred at same temperature for 10 min. The reaction was complete after 10 min and the mixture was quenched with saturated NH$_4$Cl solution (10 mF) slowly. The aqueous layer was then extracted with EtOAc (100 mF×2). The combined organic layers were washed with water (50 mF), brine (50 mF), dried over anhydrous Na$_2$SO$_4$, filtered and concentrated under reduced pressure to obtain a crude which was purified by reversed phase HPLC to afford A-ethyl-4-(2-(4-fluoro-2,6-dimethylphenoxy)-5-(2-hydroxypropan-2-yl)phenyl)-6-methyl-7-oxo-6,7-dihydrothieno[2,3-c]pyridine-2-carboxamide (3.5 mg, 7%) as an off white solid. LCMS: 509 [M+1]$^+$. $^1$H NMR (400 MHz, DMSO-d$_6$): δ 8.86 (t, J=5.6 Hz, 1H), 7.85 (s, 1H), 7.69 (s, 1H), 7.51 (d, J=2.4 Hz, 1H), 7.40 (dd, J=8.4, 2.5 Hz, 1H), 6.97 (d, J=9.0 Hz, 2H), 6.35 (d, J=8.6 Hz, 1H), 5.02 (s, 1H), 3.63 (s, 3H), 3.24 (q, J=7.2 Hz, 2H), 2.00 (s, 6H), 1.45 (s, 6H), 1.09 (t, J=7.2 Hz, 3H).

Example S-2: Synthesis of 4-(2-(2,4-dichlorophenoxy)-5-(2-hydroxypropan-2-yl)phenyl)-N-ethyl-6-methyl-7-oxo-6,7-dihydrothieno[2,3-c]pyridine-2-carboxamide (Compound 2)

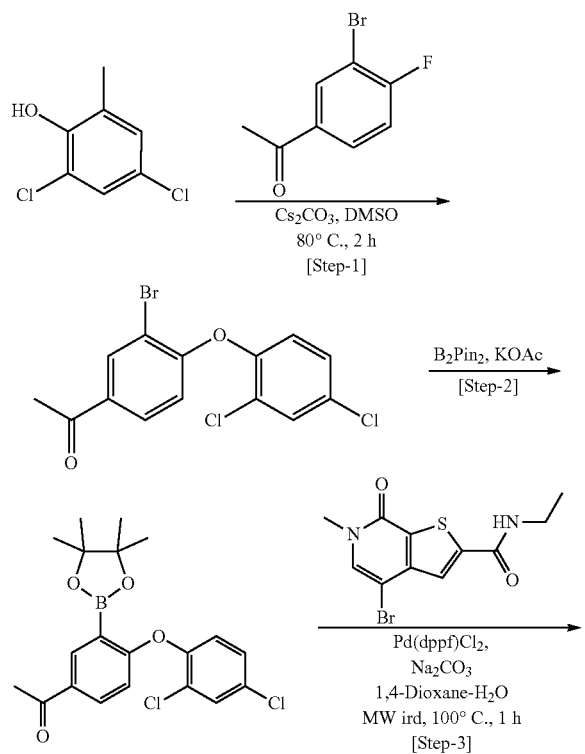

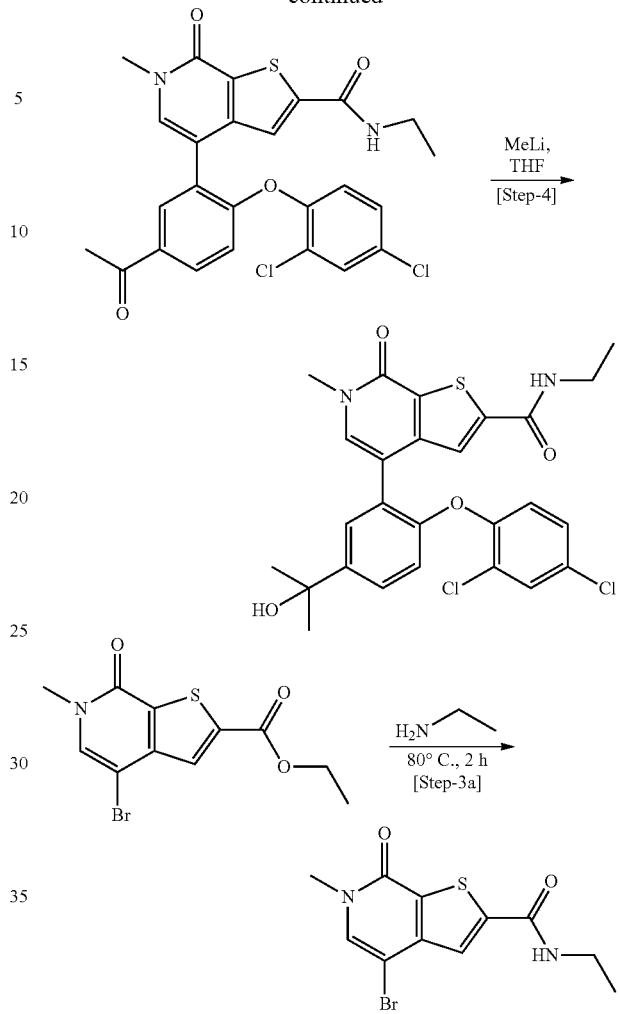

Step 1. Synthesis of 1-(3-bromo-4-(2,4-dichlorophenoxy)phenyl)ethanone: 1-(3-bromo-4-(2,4-dichlorophenoxy)phenyl)ethanone (1.56 g, 71%, white solid) was prepared following General Procedure 1, Step 2 using 2,4-dichlorophenol (1 g, 6.1 mmol, 1 eq). LCMS: 359 [M+H]$^+$, 361 [M+H+2]$^+$ Step 2: Synthesis of 1-(4-(2,4-dichlorophenoxy)-3-(4,4,5,5-tetramethyl-1,3,2-dioxaborolan-2-yl)phenyl)ethanone: 1-(4-(2,4-dichlorophenoxy)-3-(4,4,5,5-tetramethyl-1,3,2-dioxaborolan-2-yl)phenyl)ethanone (0.19 g, 17%, white solid) was prepared following General Procedure 1, Step 3 using 1-(3-bromo-4-(2,4-dichlorophenoxy)phenyl)ethanone (1 g, 2.77 mmol, 1 eq). LCMS: 407 [M+H]$^+$ Step 3a. Synthesis of 4-Bromo-N-ethyl-6-methyl-7-oxo-6,7-dihydrothieno[2,3-c]pyridine-2-carboxamide: 4-Bromo-N-ethyl-6-methyl-7-oxo-6,7-dihydrothieno[2,3-c]pyridine-2-carboxamide (1.23 g, 95%, white solid) was prepared following General Procedure 1, Step 4a using ethyl 4-bromo-6-methyl-7-oxo-6,7-dihydrothieno[2,3-c]pyridine-2-carboxylate (1.5 g, 4.3 mmol, 1 eq). LCMS: 315 [M+H]$^+$, 317[M+H+2]$^+$ Step 3: Synthesis of 4-(5-acetyl-2-(2,4-dichlorophenoxy)phenyl)-N-ethyl-6-methyl-7-oxo-6,7-dihydrothieno[2,3-c]pyridine-2-carboxamide: 4-(5-acetyl-2-(2,4-dichlorophenoxy) phenyl)-N-ethyl-6-methyl-7-oxo-6,7-dihydrothieno[2,3-c]pyridine-2-carboxamide (0.10 g, 61%, black viscous liquid) was prepared following General Procedure 1, Step 4 using 1-(4-(2,4-dichlorophenoxy)-3-(4,4,5,5-tetramethyl-1,3,2-dioxaborolan-2-yl)phenyl)ethanone (0.1 g, 0.31 mmol, 1.0 eq). LCMS: 515 [M+H]⁺

Step 4: Synthesis of 4-(2-(2,4-dichlorophenoxy)-5-(2-hydroxypropan-2-yl)phenyl)-N-ethyl-6-methyl-7-oxo-6,7-dihydrothieno[2,3-c]pyridine-2-carboxamide: 4-(2-(2,4-dichloro phenoxy)-5-(2-hydroxypropan-2-yl)phenyl)-N-ethyl-6-methyl-7-oxo-6,7-dihydrothieno[2,3-c]pyridine-2-carboxamide (0.012 mg, 11.5%, off-white solid)) was prepared following General Procedure 1, Step 5 using 4-(5-acetyl-2-(2,4-dichlorophenoxy)phenyl)-N-ethyl-6-methyl-7-oxo-6,7-dihydrothieno[2,3-c]pyridine-2-carboxamide (1.0 g, 0.19 mmol, 1.0 eq). LCMS: 531 [M+H]⁺, NMR (400 MHz, MeOH-d₄): δ 7.68 (s, 1H), 7.65-7.57 (m, 2H), 7.50 (s, 1H), 7.33 (d, J=2.6 Hz, 1H), 7.13-7.06 (m, 2H), 6.74 (d, J=8.8 Hz, 1H), 3.65 (s, 3H), 3.40-3.35 (m, 2H), 1.59 (s, 6H), 1.20 (t, J=7.3 Hz, 3H).

Example S-3: Synthesis of 4-(2-(2,4-difluorophenoxy)-5-(2-hydroxypropan-2-yl)phenyl)-N-ethyl-6-methyl-7-oxo-6,7-dihydrothieno[2,3-c]pyridine-2-carboxamide (Compound 3)

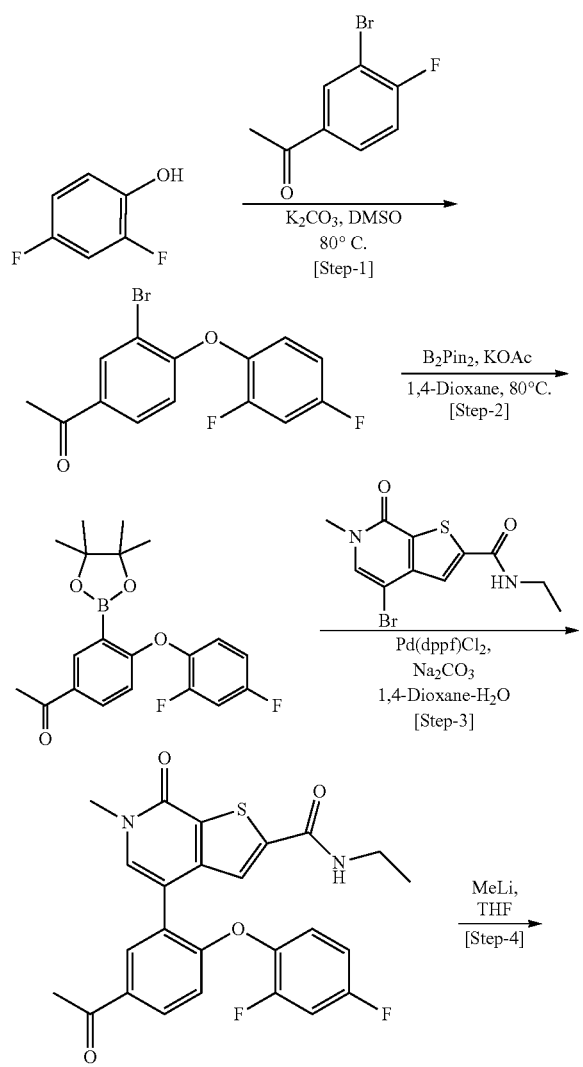

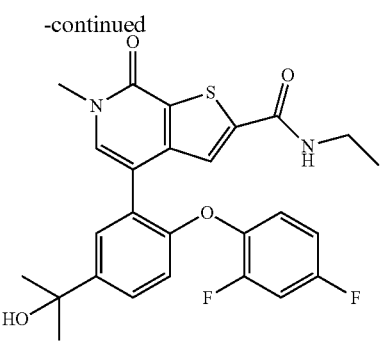

Step 1: Synthesis of 1-(3-bromo-4-(2,4-difluorophenoxy)phenyl)ethan-1-one: 1-(3-bromo-4-(2,4-difluorophenoxy)phenyl)ethan-1-one (1.0 g, 40%, white solid) was prepared following General Procedure 1, Step 2 using 2,4-difluorophenol (0.98 g, 8.46 mmol, 1.1 eq). LCMS: 327[M+H]⁺, 329 [M+H+2]⁺

Step 2: Synthesis of 1-(4-(2,4-difluorophenoxy)-3-(4,4,5,5-tetramethyl-1,3,2-dioxaborolan-2-yl)phenyl)ethanone: 1-(4-(2,4-difluorophenoxy)-3-(4,4,5,5-tetramethyl-1,3,2-dioxaborolan-2-yl)phenyl)ethanone (1.0 g, 87%, white solid) was prepared following General Procedure 1, Step 3 using 1-(3-bromo-4-(2,4-difluorophenoxy)phenyl)ethan-1-one (1.0 g, 3.06 mmol, 1.0 eq). LCMS: 375 [M+H]⁺

Step 3: Synthesis of 4-(5-acetyl-2-(2,4-difluorophenoxy)phenyl)-N-ethyl-6-methyl-7-oxo-6,7-dihydrothieno[2,3-c]pyridine-2-carboxamide: 4-(5-acetyl-2-(2,4-difluorophenoxy) phenyl)-N-ethyl-6-methyl-7-oxo-6,7-dihydrothieno[2,3-c]pyridine-2-carboxamide (0.2 g, 65%, white solid) was prepared following General Procedure 1, Step 4 using 1-(4-(2,4-difluorophenoxy)-3-(4,4,5,5-tetramethyl-1,3,2-dioxaborolan-2-yl)phenyl)ethanone (0.28 g, 0.76 mmol, 1.2 eq). LCMS: 483 [M+H]⁺

Step 4: Synthesis of 4-(2-(2,4-difluorophenoxy)-5-(2-hydroxypropan-2-yl)phenyl)-N-ethyl-6-methyl-7-oxo-6,7-dihydrothieno[2,3-c]pyridine-2-carboxamide: 4-(2-(2,4-difluoro phenoxy)-5-(2-hydroxypropan-2-yl)phenyl)-N-ethyl-6-methyl-7-oxo-6,7-dihydrothieno[2,3-c]pyridine-2-carboxamide (0.006 g, 7%, off-white solid) was prepared following General Procedure 1, Step 5 using 4-(5-acetyl-2-(2,4-difluorophenoxy)phenyl)-N-ethyl-6-methyl-7-oxo-6,7-dihydrothieno[2,3-c]pyridine-2-carboxamide (0.08 g, 0.16 mmol, 1 eq). LCMS: 499 [M+1]⁺, NMR (400 MHz, MeOH-d₄): δ 7.69 (s, 1H), 7.58 (d, J=2.4 Hz, 1H), 7.54 (d, J=9.2 Hz, 2H), 7.04-6.91 (m, 3H), 6.88-6.78 (m, 1H), 3.68 (s, 3H), 3.38 (q, J=7.2 Hz, 2H), 1.58 (s, 6H).

Example S-4: Synthesis of N-(4-(2,6-dimethylphenoxy)-3-(6-methyl-2-(5-methyl-1,3,4-oxadiazol-2-yl)-7-oxo-6,7-dihydrothieno[2,3-c]pyridin-4-yl)phenyl)ethanesulfonamide (General Procedure 2) (Compound 4)

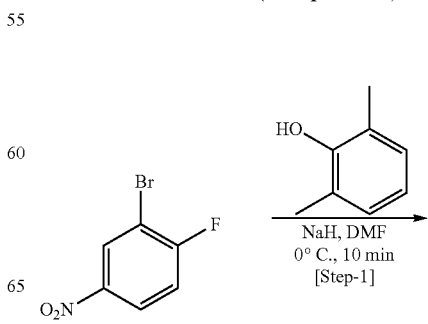

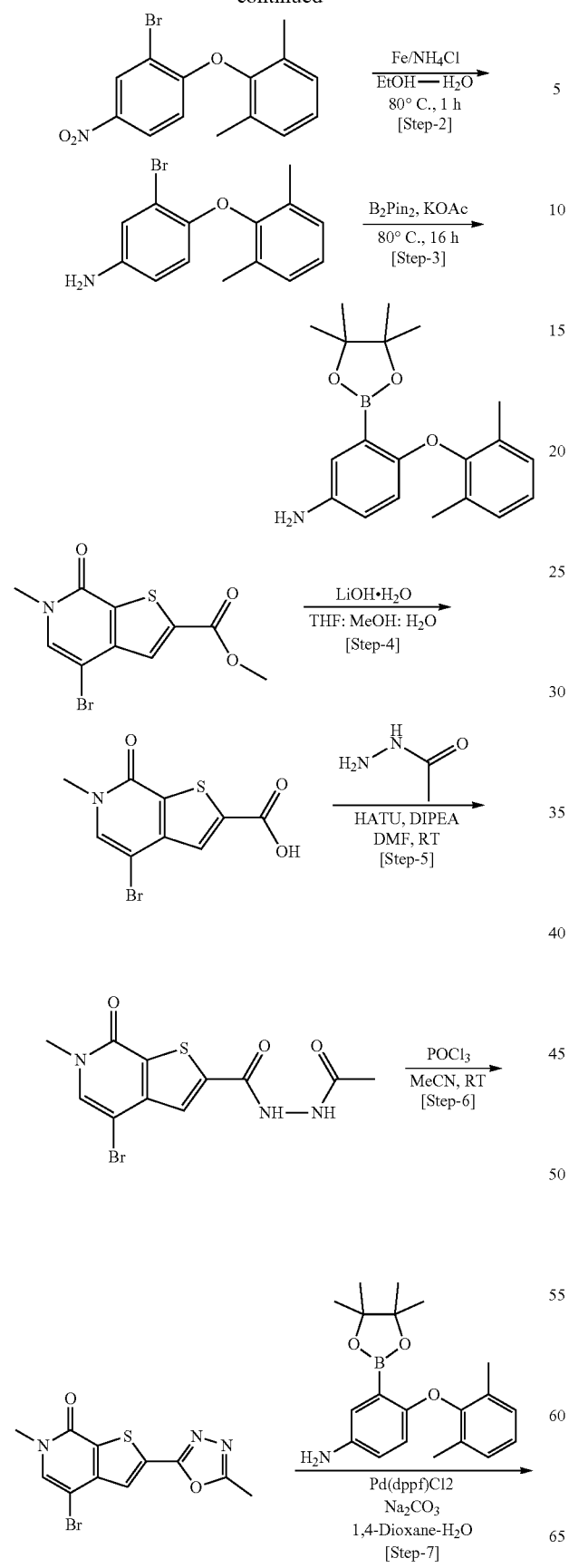

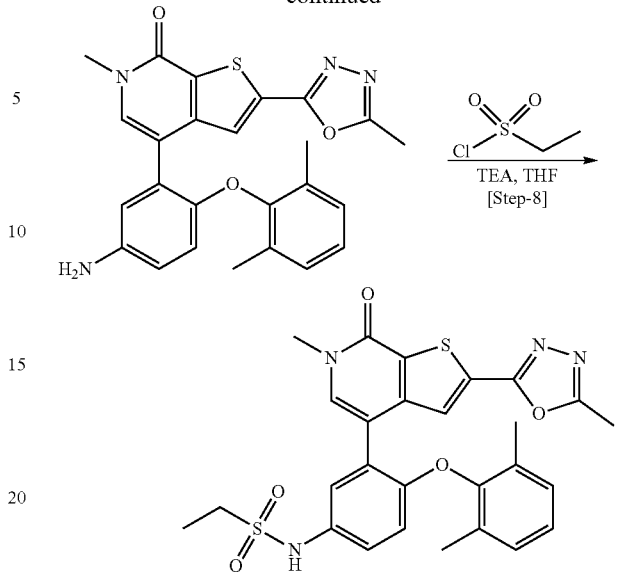

Step 1: Synthesis of 2-(2-bromo-4-nitrophenoxy)-1,3-dimethylbenzene: To a stirred solution of 2,6-dimethylphenol (2.0 g, 16.03 mmol, 1.0 eq) in DMF (10 mL) was added NaH (0.721 g, 18.00 mmol, 1.1 eq) at 0° C. followed by an addition of 2-bromo-1-fluoro-4-nitrobenzene (3.49 g, 18.0 mmol, 1.1 eq) and monitored by TLC and LC-MS. The reaction was complete after 10 min and to the the mixture was added ice-cold water (50 mL) to obtain a precipitate which was filtered over Büchner funnel; dried under vacuum to afford 2-(2-bromo-4-nitrophenoxy)-1,3-dimethylbenzene (4.5 g, 68%) as a yellow solid. LCMS: 322 [M+H]$^+$, 324 [M+H+2]$^+$ Step 2: Synthesis of 3-bromo-4-(2,6-dimethylphenoxy) aniline: To a solution of 2-(2-bromo-4-nitrophenoxy)-1,3-dimethylbenzene (4.0 g, 12.42 mmol, 1.0 eq) in ethanol (20 mL), a solution of NH$_4$Cl (6.6 g, 124.16 mmol) in water (22 mL) was added followed by addition of iron powder (5.5 g, 99.3 mmol). The reaction mixture was stirred at 90° C. for 1 h. TLC analysis indicated the reaction was complete. The reaction mixture was filtered through a pad of Celite. The filtrate was diluted with water and extracted with EtOAc. The combined organic layers were washed with brine, dried over anhydrous Na$_2$SO$_4$, filtered and concentrated under reduced pressure to give 3-bromo-4-(2,6-dimethylphenoxy) aniline (3.5 g, 97%) as a black viscous liquid. LCMS: 292 [M+H]$^+$, 294 [M+H+2]$^+$ Step 3: Synthesis of 4-(2,6-dimethylphenoxy)-3-(4,4,5,5-tetramethyl-1,3,2-dioxaborolan-2-yl)aniline: 4-(2,6-dimethylphenoxy)-3-(4,4,5,5-tetramethyl-1,3,2-dioxaborolan-2-yl) aniline (0.700 g, 66%, black viscous liquid) was prepared following General Procedure 1, Step 3 using 3-bromo-4-(2,6-dimethylphenoxy)aniline (1.0 g, 45.6 mmol, 1.0 eq) and Pd(dppf)Cl$_2$ (0.16 g, 0.228 mmol, 0.05 eq). NMR: (400 MHz, CDCl$_3$) δ 6.97-7.11 (m, 3H), 6.58 (d, J=3.95 Hz, 1H), 6.14 (d, J=8.77 Hz, 1H), 2.05-2.18 (m, 6H), 1.23-1.28 (m, 12H).

Step 4: Synthesis of 4-bromo-6-methyl-7-oxo-6,7-dihydrothieno[2,3-c]pyridine-2-carboxylic acid: To a stirred solution of methyl 4-bromo-6-methyl-7-oxo-6,7-dihydrothieno[2,3-c]pyridine-2-carboxylate (0.50 g, 1.66 mmol, 1 eq) in THF:MeOH:H$_2$O (6:3:1) (10 mL) was added LiOH.H$_2$O (0.7 g, 16.6 mmol, 10 eq) and the mixture was stirred at RT for 1 h. The reaction was complete after 1 h and the mixture was concentrated under reduced pressure. The residue obtained was then diluted with ice-cold water (20 mL) and acidified using 2N—HCl (pH2) to obtain a precipitate which was filtered over Büchner funnel to afford 4-bromo-6-methyl-7-oxo-6,7-dihydrothieno[2,3-c]pyridine-2-carboxylic acid (430 mg, 90%) as an off-white solid. LCMS: 288 [M+1]$^+$, 290 [M+H+2]$^+$ Step 5: Synthesis of N'-acetyl-4-bromo-6-methyl-7-oxo-6,7-dihydrothieno[2,3-c]pyridine-2-carbohydrazide: To a stirred solution of 4-bromo-6-methyl-7-oxo-6,7-dihydrothieno[2,3-c]pyridine-2-carboxylic acid (0.43 g, 1.49 mmol) in DML (7 mL) were successively added HATU (1.10 g, 3.0 mmol, 2.0 eq) and DIPEA (1.6 mL, 8.84 mmol, 6 eq) at 0° C. and the mixture was stirred at same temperature 10 min. Acetohydrazide (0.33 g, 4.47 mmol, 3.0 eq) was then added to the mixture and the resultant mixture was stirred at RT for 1 h. The reaction was complete after 1 h, the mixture was diluted with water (20 mL) and extracted with EtOAc (30 mL×2). The combined organic layers were washed with water (25 mL), brine (25 mL) dried over anhydrous Na$_2$SO$_4$, filtered and concentrated under reduced pressure to obtain a crude which was purified by CombiFlash Chromatography to afford N'-acetyl-4-bromo-6-methyl-7-oxo-6,7-dihydrothieno[2,3-c]pyridine-2-carbohydrazide (350 mg, 68%) as a yellow solid. LCMS: 344 [M+1]$^+$, 346 [M+H+2]$^+$ Step 6: Synthesis of 4-bromo-6-methyl-2-(5-methyl-1,3,4-oxadiazol-2-yl)thieno[2,3-c]pyridin-7(6H)-one: To a stirred solution of N'-acetyl-4-bromo-6-methyl-7-oxo-6,7-dihydrothieno[2,3-c]pyridine-2-carbohydrazide (0.2 g, 0.58 mmol) in acetonitrile (10 mL) was added POCl$_3$ (0.35 g, 2.38 mmol, 5.0 eq) at 0° C. and the mixture was heated at 50° C. for 1 h. The reaction was complete after 1 h and the mixture was quenched slowly with saturated NaHCO$_3$ solution at ice-cold condition and then extracted with EtOAc (100 mL×3). The combined organic layers were washed with water (100 mL), brine (100 mL) dried over anhydrous Na$_2$SO$_4$, filtered and concentrated under reduced pressure to obtain a crude which was purified by CombiFlash Chromatography to afford 4-bromo-6-methyl-2-(5-methyl-1,3,4-oxadiazol-2-yl)thieno[2,3-c]pyridin-7(6H)-one (110 mg, 58%) as a yellow sticky solid. LCMS: 326 [M+1]$^+$, 328 [M+H+2]$^+$ Step 7: Synthesis of 4-(5-amino-2-(2,6-dimethylphenoxy)phenyl)-6-methyl-2-(5-methyl-1,3,4-oxadiazol-2-yl)thieno[2,3-c]pyridin-7(6H)-one: 4-(5-amino-2-(2,6-dimethylphenoxy) phenyl)-6-methyl-2-(5-methyl-1,3,4-oxadiazol-2-yl)thieno[2,3-c]pyridin-7(6H)-one (0.085 g, 56%, off-white solid) was prepared following General Procedure 1, Step 3 using 4-bromo-6-methyl-2-(5-methyl-1,3,4-oxadiazol-2-yl)thieno[2,3-c]pyridin-7(6H)-one (0.11 g, 0.33 mmol, 1 eq). LCMS: 459 [M+1]

Step 8: Synthesis of N-(4-(2,6-dimethylphenoxy)-3-(6-methyl-2-(5-methyl-1,3,4-oxadiazol-2-yl)-7-oxo-6,7-dihydrothieno[2,3-c]pyridin-4-yl)phenyl)ethanesulfonamide: To a stirred solution of 4-(5-amino-2-(2,6-dimethylphenoxy) phenyl)-6-methyl-2-(5-methyl-1,3,4-oxadiazol-2-yl)thieno [2,3-c]pyridin-7(6H)-one (0.085 g, 0.185 mmol) in THF (8 mL) was added triethylamine (0.056 g, 0.55 mmol, 3 eq) followed by the addition of ethanesulfonyl chloride (0.095 g, 0.74 mmol, 4.0 eq) at 0° C. and the resultant mixture was stirred at RT for 16 h. The reaction was complete after 16 h and to the mixture was added water (30 mL) and extracted with EtOAc (30 ml×2). The combined organic layers was washed with saturated NaHCO$_3$ solution (30 mL), brine (30 mL), dried over anhydrous Na$_2$SO$_4$, filtered and concentrated under reduced pressure to obtain a crude which was purified by reversed-phase HPLC to afford N-(4-(2,6-dim-ethylphenoxy)-3-(6-methyl-2-(5-methyl-1,3,4-oxadiazol-2-yl)-7-oxo-6,7-dihydrothieno[2,3-c]pyridin-4-yl)phenyl)ethanesulfonamide (4.2 mg, 4.1%) as an off-white solid. LCMS: 551 [M+1]$^+$, $^1$H NMR (400 MHz, MeOH-d$_4$): δ 7.88 (s, 1H), 7.74 (s, 1H), 7.38 (d, J=2.7 Hz, 1H), 7.18 (dd, J=8.8, 2.7 Hz, 1H), 7.12-6.99 (m, 3H), 6.45 (d, J=8.8 Hz, 1H), 3.77 (s, 3H), 3.21-315 (m, 2H), 2.62 (s, 3H), 2.07 (s, 6H), 1.34 (t, J=7.4 Hz, 3H).

Example S-5: Synthesis of 4-(2-(2,4-difluorophenoxy)-5-(2-hydroxypropan-2-yl)phenyl)-6-methyl-7-oxo-N-(2,2,2-trifluoroethyl)-6,7-dihydrothieno[2,3-c]pyridine-2-carboxamide (Compound 5)

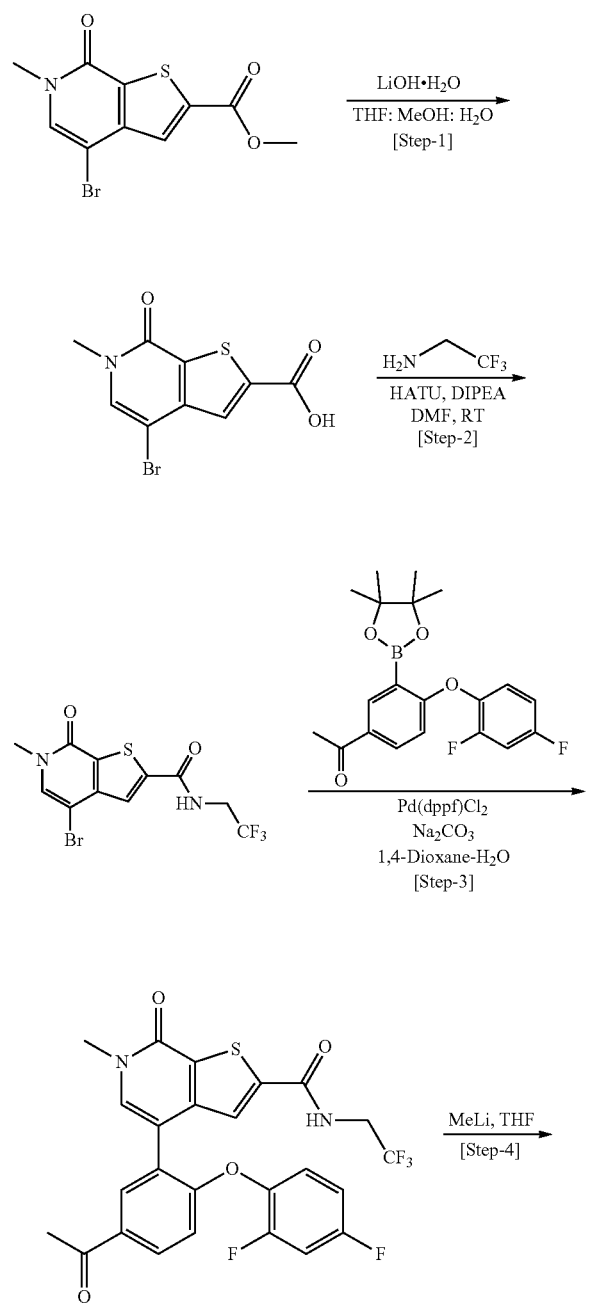

-continued

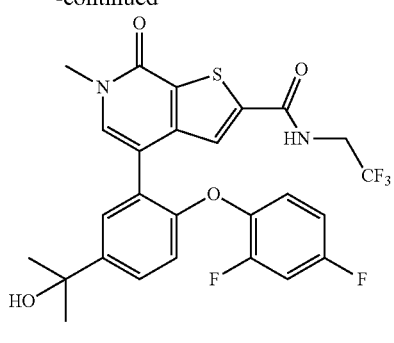

Step 1: Synthesis of 4-bromo-6-methyl-7-oxo-6,7-dihydrothieno[2,3-c]pyridine-2-carboxylic acid: 4-bromo-6-methyl-7-oxo-6,7-dihydrothieno[2,3-c]pyridine-2-carboxylic acid (0.43 g, 90%, off-white solid) was prepared following General Procedure 2, Step 4 using Methyl-4-bromo-6-methyl-7-oxo-6,7-dihydrothieno[2,3-c]pyridine-2-carboxylate (0.50 g, 1.66 mmol, 1 eq). LCMS: 288 [M+1]$^+$, 290 [M+H+2]$^+$ Step 2: Synthesis of 4-bromo-6-methyl-7-oxo-N-(2,2,2-trifluoroethyl)-6,7-dihydrothieno[2,3-c]pyridine-2-carboxamide: 4-bromo-6-methyl-7-oxo-N-(2,2,2-trifluoroethyl)-6,7-dihydro thieno[2,3-c]pyridine-2-carboxamide (0.2 g, 78%, off-white solid) was prepared following General Procedure 2, Step 5 using 4-bromo-6-methyl-7-oxo-6,7-dihydrothieno[2,3-c]pyridine-2-carboxylic acid (0.2 g, 0.69 mmol, 1 eq) and 2,2,2-trifluoroethanamine (0.04 g, 0.26 mmol, 2.0 eq). LCMS: 369 [M+1]$^+$, 371 [M+H+2]$^+$ Step 3: Synthesis of 4-(5-acetyl-2-(2,4-difluorophenoxy) phenyl)-6-methyl-7-oxo-N-(2,2,2-trifluoroethyl)-6,7-dihydrothieno[2,3-c]pyridine-2-carboxamide: 4-(5-acetyl-2-(2,4-difluoro phenoxy)phenyl)-6-methyl-7-oxo-N-(2,2,2-trifluoroethyl)-6,7-dihydrothieno[2,3-c]pyridine-2-carboxamide (70 mg, 24%, white solid) was prepared following General Procedure 1, Step 4 using 4-bromo-6-methyl-7-oxo-N-(2,2,2-trifluoroethyl)-6,7-dihydrothieno[2,3-c]pyridine-2-carboxamide (0.2 g, 0.54 mmol, 1.0 eq). LCMS: 537 [M+1]$^+$ Step 4: Synthesis of 4-(2-(2,4-difluorophenoxy)-5-(2-hydroxypropan-2-yl)phenyl)-6-methyl-7-oxo-N-(2,2,2-trifluoroethyl)-6,7-dihydrothieno[2,3-c]pyridine-2-carboxamide: 4-(2-(2,4-difluorophenoxy)-5-(2-hydroxypropan-2-yl)phenyl)-6-methyl-7-oxo-N-(2,2,2-trifluoroethyl)-6,7-dihydrothieno[2,3-c]pyridine-2-carboxamide (0.006 g, 12.5%, off-white solid) was prepared following General Procedure 1, Step 5 using 4-(5-acetyl-2-(2,4-difluorophenoxy)phenyl)-6-methyl-7-oxo-N-(2,2,2-trifluoroethyl)-6,7-dihydrothieno[2,3-c]pyridine-2-carboxamide (0.095 g, 0.18 mmol, 1.0 eq). LCMS: 553 [M+1]$^+$, NMR (400 MHz, MeOD-d$_4$): δ 7.79 (s, 1H), 7.62-7.50 (m, 3H), 7.03-6.90 (m, 3H), 6.82 (ddd, J=12.8, 6.9, 2.3 Hz, 1H), 4.05 (q, J=9.3 Hz, 2H), 3.69 (s, 3H), 1.58 (s, 6H).

Example S-6: Synthesis of 4-(2-(2,4-difluorophenoxy)-5-(2-hydroxypropan-2-yl)phenyl)-6-methyl-2-(piperidine-1-carbonyl)thieno[2,3-c]pyridin-7(6H)-one (Compound 6)

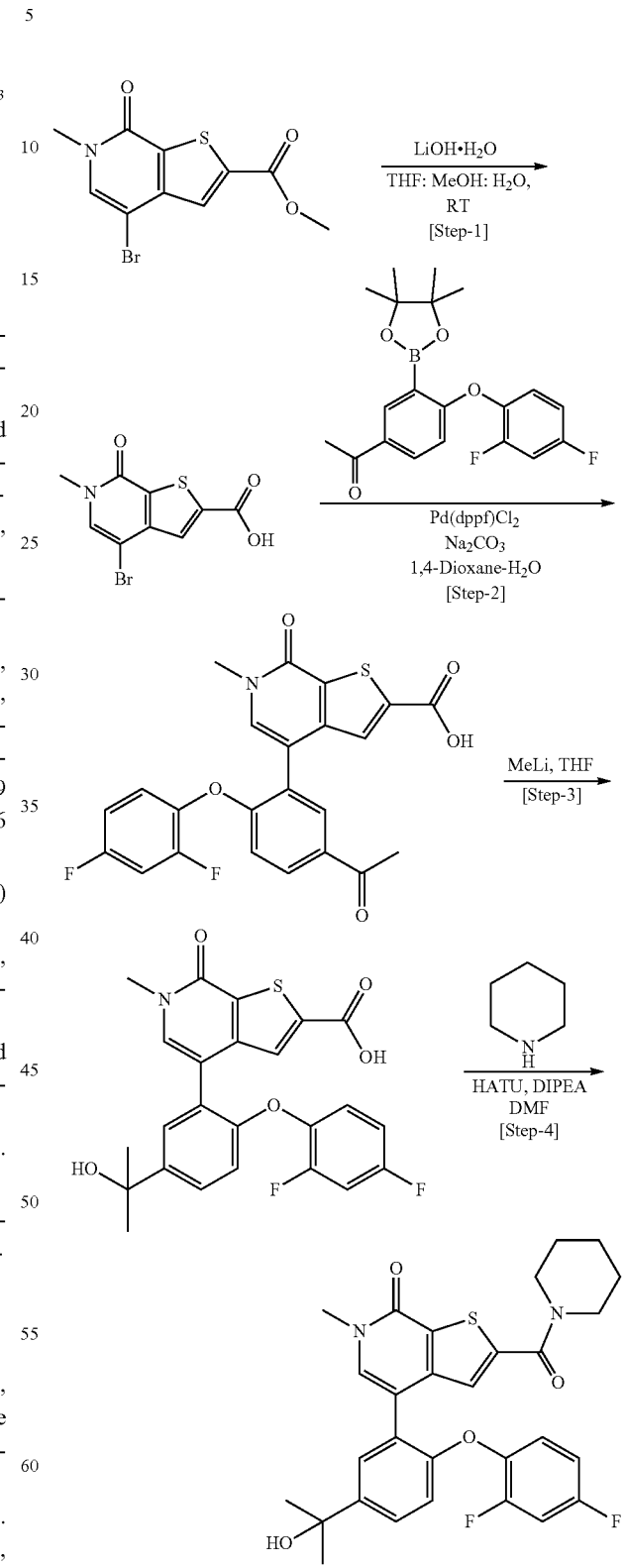

Step 1: Synthesis of 4-bromo-6-methyl-7-oxo-6,7-dihydrothieno[2,3-c]pyridine-2-carboxylic acid: To a stirred solution of methyl 4-bromo-6-methyl-7-oxo-6,7-dihydrothieno[2,3-c]pyridine-2-carboxylate (1.0 g, 3.3 mmol) in THF:MeOH:H₂O [6:3:1; (10 mL)] was LiOH.H₂O (1.39 mg, 33.3 mmol, 10 eq) and the mixture was stirred at RT for 1 h. The reaction was complete after 1 h and the mixture was concentrated under reduced pressure. The residue obtained was diluted with water (30 mL) and acidified using 1N—HCl (pH ~2) to obtain a precipitate solid which was filtered over Büchner funnel to afford 4-bromo-6-methyl-7-oxo-6,7-dihydrothieno[2,3-c]pyridine-2-carboxylic acid (380 mg, 39%) as an off-white solid. LCMS: 287 [M+1]⁺, 290 [M+H+2]⁺

Step 2: Synthesis of 4-(5-acetyl-2-(2,4-difluorophenoxy)phenyl)-6-methyl-7-oxo-6,7-dihydrothieno[2,3-c]pyridine-2-carboxylic acid: 4-(5-acetyl-2-(2,4-difluorophenoxy)phenyl)-6-methyl-7-oxo-6,7-dihydrothieno[2,3-c]pyridine-2-carboxylic acid (0.1 g, 79%, white solid) was prepared following General Procedure 1, Step 4 using 4-bromo-6-methyl-7-oxo-6,7-dihydrothieno[2,3-c]pyridine-2-carboxylic acid (0.08 g, 0.28 mmol, 1 eq). LCMS: 456 [M+1]⁺

Step 3: Synthesis of 4-(2-(2,4-difluorophenoxy)-5-(2-hydroxypropan-2-yl)phenyl)-6-methyl-7-oxo-6,7-dihydrothieno[2,3-c]pyridine-2-carboxylic acid: 4-(2-(2,4-difluorophenoxy)-5-(2-hydroxypropan-2-yl)phenyl)-6-methyl-7-oxo-6,7-dihydrothieno[2,3-c]pyridine-2-carboxylic acid (0.10 g, 97%, off-white solid) was prepared following General Procedure 1, Step 5 using 4-(5-acetyl-2-(2,4-difluorophenoxy)phenyl)-6-methyl-7-oxo-6,7-dihydrothieno[2,3-c]pyridine-2-carboxylic acid (0.10 g, 0.22 mmol, 1 eq). LCMS: 472 [M+1]⁺

Step 4: Synthesis of 4-(2-(2,4-difluorophenoxy)-5-(2-hydroxypropan-2-yl)phenyl)-6-methyl-2-(piperidine-1-carbonyl)thieno[2,3-c]pyridin-7(6H)-one: To a stirred solution of 4-(2-(2,4-difluorophenoxy)-5-(2-hydroxypropan-2-yl)phenyl)-6-methyl-7-oxo-6,7-dihydrothieno[2,3-c]pyridine-2-carboxylic acid (0.1 g, 0.22 mmol, 1 eq)) in DMF (4 mL) were successively added HATU (0.13 g, 0.33 mmol, 1.5 eq) and DIPEA (0.153 mL, 0.88 mmol, 4 eq) at 0° C. and the mixture was stirred at same temperature for 10 min. Piperidine (37 mg, 0.44 mmol, 2.0 eq) was then added to the mixture and the resultant mixture was stirred at RT for 2 h. The reaction was complete after 2 h and the mixture was diluted with water (100 mL) and extracted with EtOAc (100 mL×2). The combined organic layers were washed with water (100 mL), brine (150 mL) dried over anhydrous Na₂SO₄, filtered and concentrated under reduced pressure to afford a crude which was purified by reversed phase HPLC to afford 4-(2-(2,4-difluorophenoxy)-5-(2-hydroxypropan-2-yl)phenyl)-6-methyl-2-(piperidine-1-carbonyl)thieno[2,3-c]pyridin-7(6H)-one (0.004 g, 4%) as an off-white solid. LCMS: 539 [M+1]⁺, NMR (400 MHz, DMSO-d₆): δ 7.69 (s, 1H), 7.54 (d, J=2.3 Hz, 1H), 7.49 (dd, J=8.5, 2.4 Hz, 1H), 7.38 (ddd, J=11.3, 8.7, 3.0 Hz, 1H), 7.20 (s, 1H), 7.11 (td, J=9.3, 5.6 Hz, 1H), 7.02 (t, J=8.6 Hz, 1H), 6.85 (d, J=8.5 Hz, 1H), 5.08 (s, 1H), 3.60 (s, 3H), 3.52 (m, 4H), 2.08 (m, 4H), 1.60 (m, 2H), 1.46 (s, 6H).

Example S-7: Synthesis of 4-(2-(2,4-difluorophenoxy)-5-(2-hydroxypropan-2-yl)phenyl)-6-methyl-2-(piperidin-1-ylmethyl)thieno[2,3-c]pyridin-7(6H)-one (Compound 7)

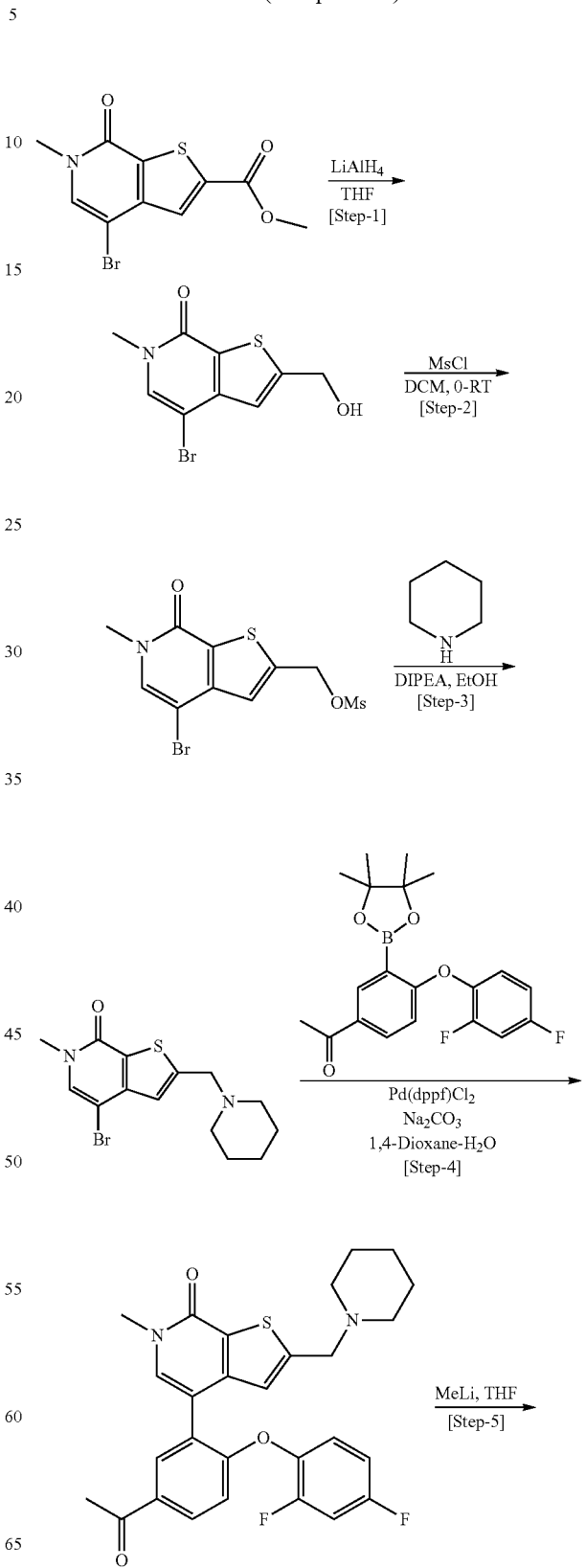

-continued

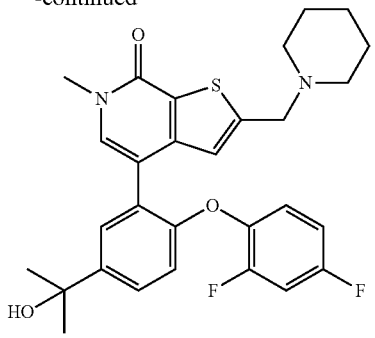

Step 1: Synthesis of 4-bromo-2-(hydroxymethyl)-6-methylthieno[2,3-c]pyridin-7(6H)-one: To LiAlH$_4$ (113 mg, 2.9 mmol, 1.8 eq) in THF (10 mL) was added methyl 4-bromo-6-methyl-7-oxo-6,7-dihydrothieno[2,3-c]pyridine-2-carboxylate (500 mg, 1.60 mmol in THF) at −10° C. slowly and the mixture was stirred at same temperature for 10 min. The reaction was complete after 10 min and the mixture was slowly quenched with saturated sodium sulphate solution (30 mL). The crude mixture was filtered through celite bed washing with EtOAc (500 mL). The organic layer was then washed with water (200 mL), brine (150 mL) dried over anhydrous Na$_2$SO$_4$, filtered and concentrated under reduced pressure to afford a crude material which was purified by CombiFlash Chromatography to afford 4-bromo-2-(hydroxymethyl)-6-methylthieno[2,3-c]pyridin-7(6H)-one (305 mg, 67%) as a sticky solid. LCMS: 274 [M+1]$^+$, 276 [M+H+2]$^+$ Step 2: Synthesis of (4-bromo-6-methyl-7-oxo-6,7-dihydrothieno[2,3-c]pyridin-2-yl)methyl methanesulfonate: To a stirred solution of 4-bromo-2-(hydroxymethyl)-6-methylthieno[2,3-c]pyridin-7(6H)-one (300 mg, 1.1. mmol, 1 eq) in DCM (10 mL) were successively added triethylamine (0.75 mL, 5.5. mmol, 5 eq) and methane sulphonyl chloride (0.18 mL, 2.2 mmol, 3 eq) at 0° C. slowly and the mixture was stirred at RT for 1 h. The reaction was complete after 1 h and to the mixture was added ice-cold water (100 mL) and extracted with DCM (100 mL×2). The combined organic layers was washed with water (100 mL×2), brine (150 mL) dried over anhydrous Na$_2$SO$_4$, filtered and concentrated under reduced pressure to afford (4-bromo-6-methyl-7-oxo-6,7-dihydrothieno[2,3-c]pyridin-2-yl)methyl methanesulfonate (300 mg, 77%) as a brown sticky liquid which was taken to next step without further purification. $^1$H NMR (400 MHz, DMSO-d$_6$): δ 8.02 (s, 1H), 7.49 (s, 1H), 5.61 (s, 2H), 3.50-3.56 (m, 3H).

Step 3: Synthesis of 4-bromo-6-methyl-2-(piperidin-1-ylmethyl)thieno[2,3-c]pyridin-7(6H)-one: To a stirred solution of piperidine (0.114 mg, 1.7 mmol, 2 eq) in ethanol (8 mL) was added DIPEA (0.5 mL, 3.4 mmol, 4 eq) and the mixture was stirred at RT for 15 min. (4-bromo-6-methyl-7-oxo-6,7-dihydrothieno[2,3-c]pyridin-2-yl)methyl methanesulfonate (300 mg, 0.85 mmol) dissolved in EtOH (2 mL) was then added to the mixture and the mixture was heated at 100° C. for 1 h. The reaction was complete after 1 h and the mixture was concentrated under reduced pressure to obtain a crude which was purified by CombiFlash Chromatograph to afford 4-bromo-6-methyl-2-(piperidin-1-ylmethyl)thieno[2,3-c]pyridin-7(6H)-one (120 mg, 41%) as an off-white solid. LCMS: 341 [M+1]$^+$, 343 [M+H+2]$^+$ Step 4: Synthesis of 4-(5-acetyl-2-(2,4-difluorophenoxy)phenyl)-6-methyl-2-(piperidin-1-ylmethyl)thieno[2,3-c]pyridin-7(6H)-one: 4-(5-acetyl-2-(2,4-difluorophenoxy)phenyl)-6-methyl-2-(piperidin-1-ylmethyl)thieno[2,3-c]pyridin-7(6H)-one (140 mg, 78%, off-white solid) was prepared following General Procedure 1, Step 4 using 4-bromo-6-methyl-2-(piperidin-1-ylmethyl)thieno[2,3-c]pyridin-7(6H)-one (120 mg, 0.35 mmol, 1 eq). LCMS: 509 [M+1]$^+$ Step 5: Synthesis of 4-(2-(2,4-difluorophenoxy)-5-(2-hydroxypropan-2-yl)phenyl)-6-methyl-2-(piperidin-1-ylmethyl)thieno[2,3-c]pyridin-7(6H)-one: 4-(2-(2,4-difluorophenoxy)-5-(2-hydroxypropan-2-yl)phenyl)-6-methyl-2-(piperidin-1-ylmethyl) thieno[2,3-c]pyridin-7(6H)-one (28 mg, 40%, off-white solid) was prepared following General Procedure 1, Step 5 using 4-(5-acetyl-2-(2,4-difluorophenoxy)phenyl)-6-methyl-2-(piperidin-1-ylmethyl) thieno[2,3-c]pyridin-7(6H)-one (0.070 g, 0.13 mmol, 1 eq). LCMS: 525 [M+1]$^+$, NMR (400 MHz, MeOH-d$_4$): δ 7.56 (d, J=2.4 Hz, 1H), 7.52 (dd, J=8.5, 2.4 Hz, 1H), 7.48 (s, 1H), 7.04-6.88 (m, 4H), 6.87-6.77 (m, 1H), 3.75 (s, 2H), 3.68 (s, 3H), 2.46 (s, 4H), 1.93 (d, J=2.5 Hz, 2H), 1.58 (d, J=6.2 Hz, 10H).

Example S-8: Synthesis of 4-(2-(2,4-difluorophenoxy)-5-(2-hydroxypropan-2-yl)phenyl)-6-methyl-2-(3-methyl-1,2,4-oxadiazol-5-yl)thieno[2,3-c]pyridin-7(6H)-one (Compound 8)

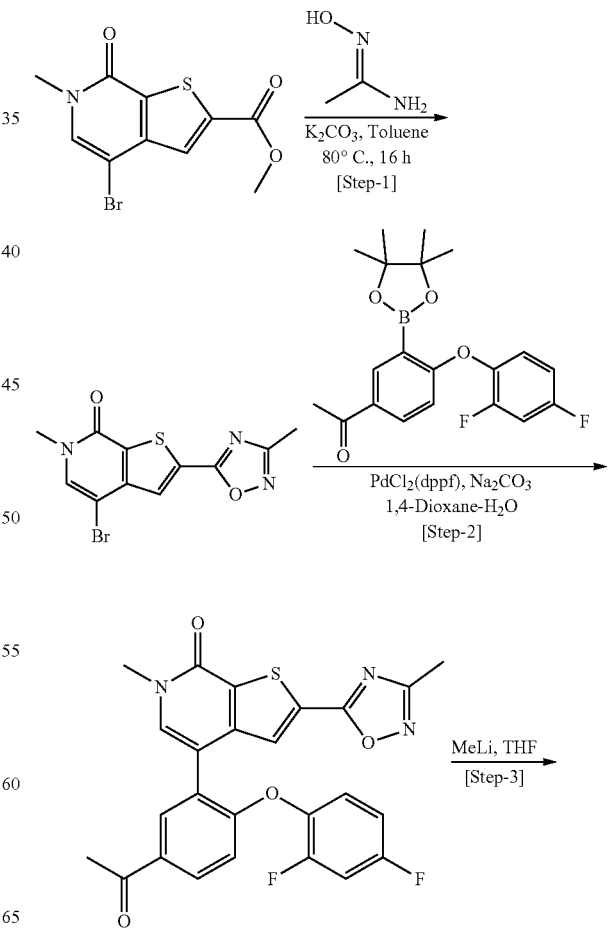

-continued

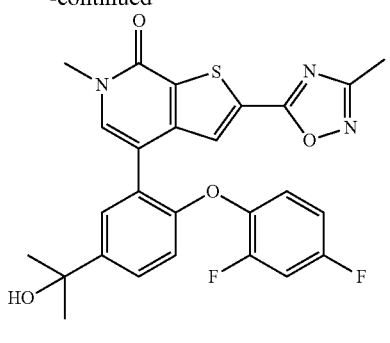

Step 1: Synthesis of 4-bromo-6-methyl-2-(3-methyl-1,2,4-oxadiazol-5-yl)thieno[2,3-c]pyridin-7(6H)-one: To a stirred solution of methyl 4-bromo-6-methyl-7-oxo-6,7-dihydrothieno[2,3-c]pyridine-2-carboxylate (0.4 g, 1.32 mmol) in toluene (6 mL) were successively added $K_2CO_3$ (0.27 g, 1.99 mmol, 3 eq) and (E)-N'-hydroxyacetimidamide (0.15 g, 1.99 mmol, 1.5 eq) at RT and the mixture was heated at 120° C. for 16 h. The reaction was complete after 16 h and to the mixture was added water (20 mL). The aqueous layer was then extracted with EtOAc (30 mL×2). The combined organic layers were washed with water (10 mL), brine (15 mL) dried over anhydrous $Na_2SO_4$, filtered and concentrated under reduced pressure to obtain a crude which was purified by CombiFlash Chromatograph to afford 4-bromo-6-methyl-2-(3-methyl-1,2,4-oxadiazol-5-yl)thieno[2,3-c]pyridin-7(6H)-one (0.4 g, 92%) an off-white solid. LCMS: 326 [M+1]$^+$, 328 [M+H+2]$^+$ Step 2: Synthesis of 4-(5-acetyl-2-(2,4-difluorophenoxy)phenyl)-6-methyl-2-(3-methyl-1,2,4-oxadiazol-5-yl)thieno[2,3-c]pyridin-7(6H)-one: 4-(5-acetyl-2-(2,4-difluorophenoxy) phenyl)-6-methyl-2-(3-methyl-1,2,4-oxadiazol-5-yl)thieno[2,3-c]pyridin-7(6H)-one (0.15 g, 33%, off-white solid) was prepared following General Procedure 1, Step 4 using 4-bromo-6-methyl-2-(3-methyl-1,2,4-oxadiazol-5-yl)thieno[2,3-c]pyridin-7(6H)-one (0.3 g, 0.92 mmol, 1 eq). LCMS: 494 [M+1]$^+$ Step 3: Synthesis of 4-(2-(2,4-difluorophenoxy)-5-(2-hydroxypropan-2-yl)phenyl)-6-methyl-2-(3-methyl-1,2,4-oxadiazol-5-yl)thieno[2,3-c]pyridin-7(6H)-one: 4-(2-(2,4-difluoro phenoxy)-5-(2-hydroxypropan-2-yl)phenyl)-6-methyl-2-(3-methyl-1,2,4-oxadiazol-5-yl)thieno [2,3-c] pyridin-7(6H)-one (2 mg, 2.7%, off-white solid) was prepared following General Procedure 1, Step 5 using 4-(5-acetyl-2-(2,4-difluorophenoxy)phenyl)-6-methyl-2-(3-methyl-1,2,4-oxadiazol-5-yl)thieno[2,3-c]pyridin-7(6H)-one (0.070 g, 0.14 mmol, 1 eq). LCMS: 510 [M+1]$^+$, NMR (400 MHz, MeOH-$d_4$): δ 7.89 (s, 1H), 7.65-7.59 (m, 2H), 7.56 (dd, J=8.6, 2.4 Hz, 1H), 7.07-6.96 (m, 2H), 6.92 (d, J=8.5 Hz, 1H), 6.85 (t, J=8.7 Hz, 1H), 3.72 (s, 3H), 2.44 (s, 3H), 1.59 (s, 6H).

Example S-9: Synthesis of 4-(2-(2,4-difluorophenoxy)-5-(2-hydroxypropan-2-yl)phenyl)-6-methyl-7-oxo-N-(1-(trifluoromethyl)cyclopropyl)-6,7-dihydrothieno[2,3-c]pyridine-2-carboxamide (Compound 14)

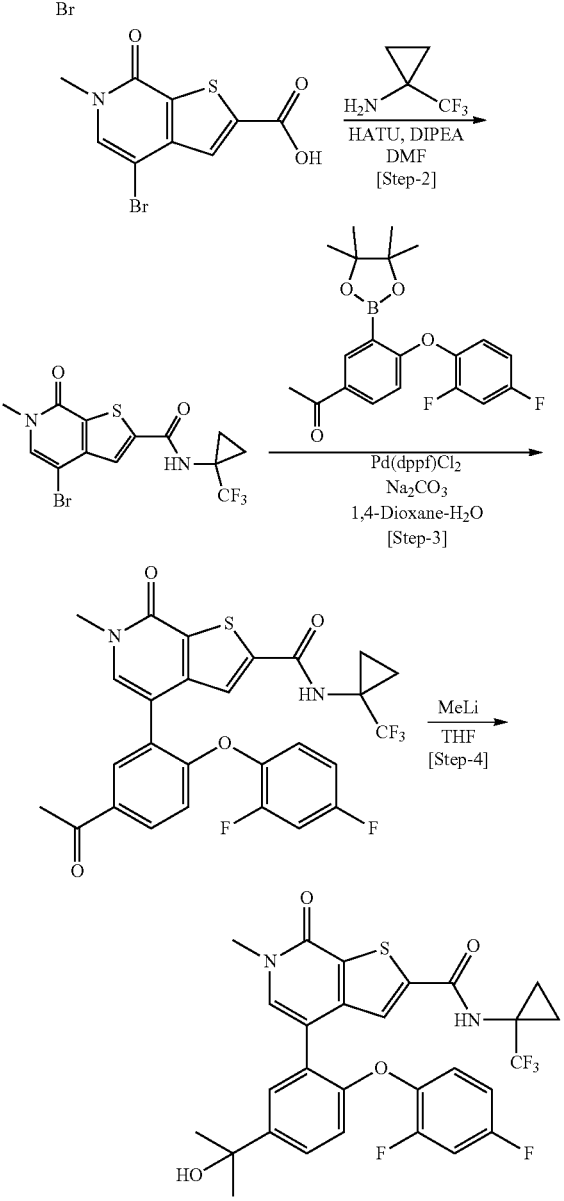

Step 1: Synthesis of 4-bromo-6-methyl-7-oxo-6,7-dihydrothieno[2,3-c]pyridine-2-carboxylic acid: 4-bromo-6-methyl-7-oxo-6,7-dihydrothieno[2,3-c]pyridine-2-carboxylic acid (430 mg, 90%, off-white solid) was prepared following General Procedure 2, Step 4 using methyl 4-bromo-6-methyl-7-oxo-6,7-dihydrothieno[2,3-c]pyridine-2-carboxylate (0.50 g, 1.66 mmol, 1 eq). LCMS: 288 [M+1]+, 290 [M+H+2]+

Step 2: Synthesis of 4-bromo-6-methyl-7-oxo-N-(1-(trifluoromethyl)cyclopropyl)-6,7-dihydrothieno[2,3-c]pyridine-2-carboxamide: 4-bromo-6-methyl-7-oxo-N-(1-(trifluoro methyl)cyclopropyl)-6,7-dihydrothieno[2,3-c]pyridine-2-carboxamide (0.14 g, 59%, off-white solid) was prepared following General Procedure 2, Step 5 using 4-bromo-6-methyl-7-oxo-6,7-dihydrothieno[2,3-c]pyridine-2-carboxylic acid (0.18 g, 0.63 mmol, 1 eq) and 1-(trifluoromethyl)cyclopropanamine (0.30 g, 1.8 mmol, 3.0 eq). LCMS: 395 [M+1]+, 397 [M+H+2]+

Step 3: Synthesis of 4-(5-acetyl-2-(2,4-difluorophenoxy)phenyl)-6-methyl-7-oxo-N-(1-(trifluoromethyl)cyclopropyl)-6,7-dihydrothieno[2,3-c]pyridine-2-carboxamide: 4-(5-acetyl-2-(2,4-difluorophenoxy)phenyl)-6-methyl-7-oxo-N-(1-(trifluoromethyl)cyclopropyl)-6,7-dihydrothieno[2,3-c]pyridine-2-carboxamide (0.16 g, 80%, off-white solid) was prepared following General Procedure 1, Step 4 using 4-bromo-6-methyl-7-oxo-N-(1-(trifluoromethyl)cyclopropyl)-6,7-dihydrothieno[2,3-c]pyridine-2-carboxamide (0.14 g, 0.36 mmol, 1 eq) and 1-(4-(2,4-difluorophenoxy)-3-(4,4,5,5-tetramethyl-1,3,2-dioxaborolan-2-yl)phenyl)ethanone (0.19 g, 0.55 mmol, 1.5 eq). LCMS: 563 [M+1]+

Step 4: Synthesis of 4-(2-(2,4-difluorophenoxy)-5-(2-hydroxypropan-2-yl)phenyl)-6-methyl-7-oxo-N-(1-(trifluoromethyl)cyclopropyl)-6,7-dihydrothieno[2,3-c]pyridine-2-carboxamide: 4-(2-(2,4-difluorophenoxy)-5-(2-hydroxypropan-2-yl)phenyl)-6-methyl-7-oxo-N-(1-(trifluoromethyl)cyclopropyl)-6,7-dihydrothieno[2,3-c]pyridine-2-carboxamide (5 mg, 6%, off-white solid) was prepared following General Procedure 20, Step 5 using 4-(5-acetyl-2-(2,4-difluorophenoxy)phenyl)-6-methyl-7-oxo-N-(1-(trifluoromethyl)cyclopropyl)-6,7-dihydrothieno[2,3-c]pyridine-2-carboxamide (0.080 g, 0.14 mmol, 1 eq). LCMS: 579 [M+1]+, 1H NMR (400 MHz, MeOH-d4): δ 7.77 (s, 1H), 7.61-7.50 (m, 3H), 6.97 (dt, J=15.5, 9.4 Hz, 3H), 6.83 (t, J=8.2 Hz, 1H), 3.68 (s, 3H), 1.57 (s, 6H), 1.43-1.31 (m, 2H), 1.18 (s, 2H).

Example S-10: Synthesis of N-cyclopropyl-4-(2-(2,4-difluorophenoxy)-5-(2-hydroxypropan-2-yl)phenyl)-6-methyl-7-oxo-6,7-dihydrothieno[2,3-c]pyridine-2-carboxamide (Compound 145)

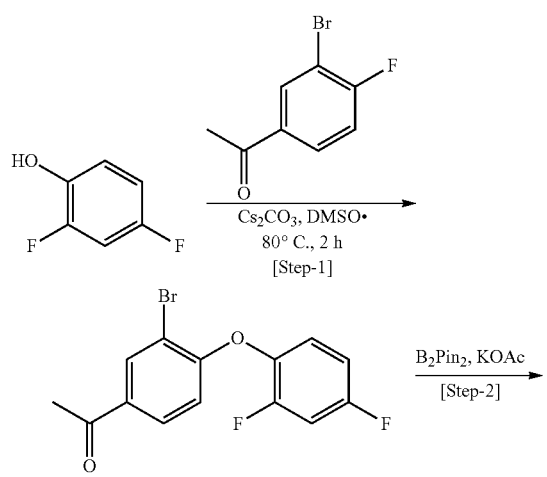

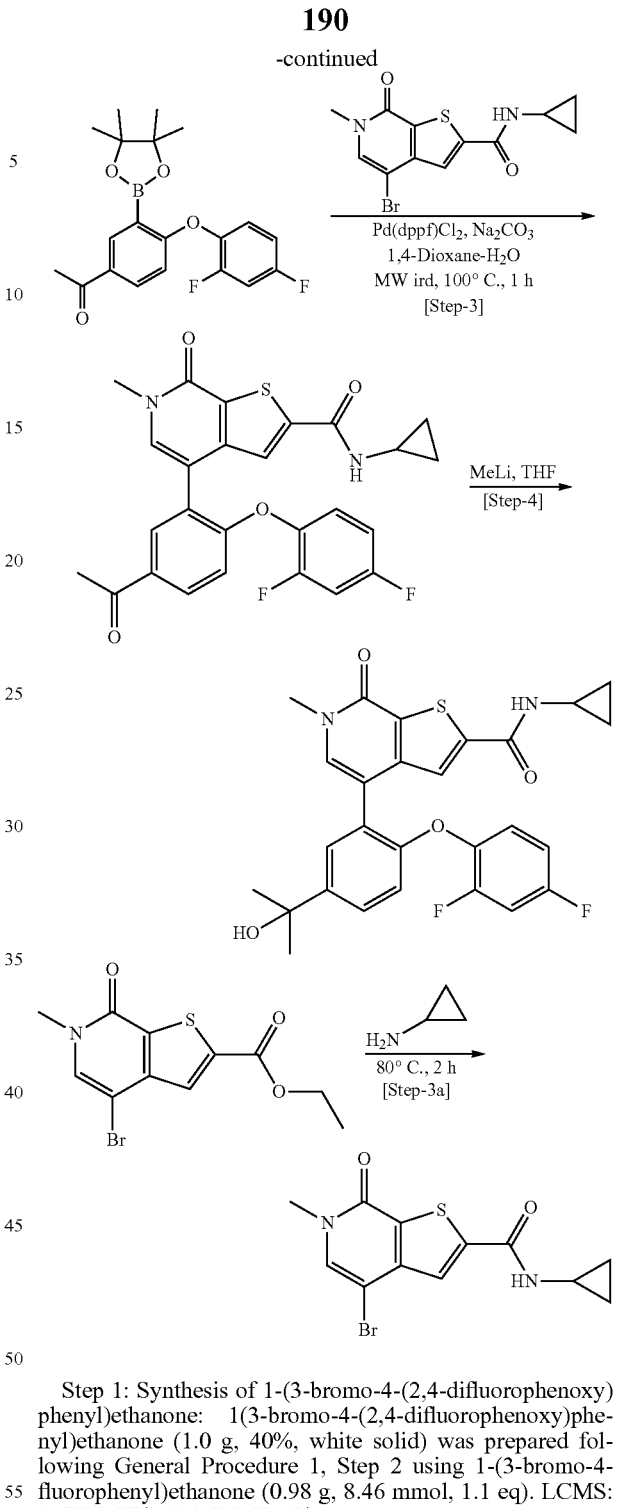

Step 1: Synthesis of 1-(3-bromo-4-(2,4-difluorophenoxy)phenyl)ethanone: 1(3-bromo-4-(2,4-difluorophenoxy)phenyl)ethanone (1.0 g, 40%, white solid) was prepared following General Procedure 1, Step 2 using 1-(3-bromo-4-fluorophenyl)ethanone (0.98 g, 8.46 mmol, 1.1 eq). LCMS: 327[M+H]+, 329 [M+H+2]+

Step 2: Synthesis of 1-(4-(2,4-difluorophenoxy)-3-(4,4,5,5-tetramethyl-1,3,2-dioxaborolan-2-yl)phenyl)ethanone: 1-(4-(2,4-difluorophenoxy)-3-(4,4,5,5-tetramethyl-1,3,2-dioxaborolan-2-yl)phenyl)ethanone (1.0 g, 87%, white solid) was prepared following General Procedure 1, Step 3 using 4-(2-(2,4-difluorophenoxy)-5-(2-hydroxypropan-2-yl)phenyl)-N-ethyl-6-methyl-7-oxo-6,7-dihydrothieno[2,3-c]pyridine-2-carboxamide (1.0 g, 3.06 mmol, 1.0 eq). LCMS: 375 [M+H]+

Step 3a: Synthesis of 4-bromo-N-cyclopropyl-6-methyl-7-oxo-6,7-dihydrothieno[2,3-c]pyridine-2-carboxamide:

4-bromo-N-cyclopropyl-6-methyl-7-oxo-6,7-dihydrothieno [2,3-c]pyridine-2-carboxamide (0.20 g, 93%, white solid) was prepared following General Procedure 1, Step 4a using ethyl 4-bromo-6-methyl-7-oxo-6,7-dihydrothieno[2,3-c] pyridine-2-carboxylate (0.2 g, 0.664 mmol, 1 eq). LCMS: 327 [M+H]$^+$, 329 [M+H+2]$^+$ Step 3: Synthesis of 4-(5-acetyl-2-(2,4-difluorophenoxy) phenyl)-N-cyclopropyl-6-methyl-7-oxo-6,7-dihydrothieno [2,3-c]pyridine-2-carboxamide: 4-(5-acetyl-2-(2,4-difluorophenoxy) phenyl)-N-cyclopropyl-6-methyl-7-oxo-6,7-dihydrothieno[2,3-c]pyridine-2-carboxamide e (0.07 g, 41%, brown solid) was prepared following General Procedure 1, Step 4 using 1-(4-(2,4-difluorophenoxy)-3-(4,4,5,5-tetramethyl-1,3,2-dioxaborolan-2-yl)phenyl)ethanone (0.13 g, 0.97 mmol, 1.2 eq). LCMS: 495 [M+H]$^+$ Step 4: Synthesis N-cyclopropyl-4-(2-(2,4-difluorophenoxy)-5-(2-hydroxypropan-2-yl)phenyl)-6-methyl-7-oxo-6,7-dihydrothieno[2,3-c]pyridine-2-carboxamide: N-cyclopropyl-4-(2-(2,4-difluorophenoxy)-5-(2-hydroxypropan-2-yl)phenyl)-6-methyl-7-oxo-6,7-dihydrothieno[2,3-c] pyridine-2-carboxamide (0.009 g, 12%, off-white solid) was prepared following General Procedure 1, Step 5 using 4-(5-acetyl-2-(2,4-difluorophenoxy)phenyl)-N-cyclopropyl-6-methyl-7-oxo-6,7-dihydrothieno[2,3-c]pyridine-2-carboxamide (0.070 g, 0.141 mmol, 1.0 eq). LCMS: 511 [M+H]$^+$, NMR (400 MHz, MeOH-d$_4$): δ 7.68 (s, 1H), 7.60-7.49 (m, 3H), 7.04-6.90 (m, 3H), 6.83 (t, J=8.5 Hz, 1H), 3.68 (s, 3H), 2.83 (tt, J=7.4, 3.8 Hz, 1H), 1.57 (s, 6H), 0.79 (td, J=7.1, 5.0 Hz, 2H), 0.62 (p, J=4.7 Hz, 2H).

Example S-11: Synthesis of N-ethyl-7-(2-(4-fluoro-2,6-dimethylphenoxy)-5-(2-hydroxypropan-2-yl) phenyl)-5-methyl-4-oxo-4,5-dihydrothieno[3,2-c] pyridine-2-carboxamide (Compound 146)

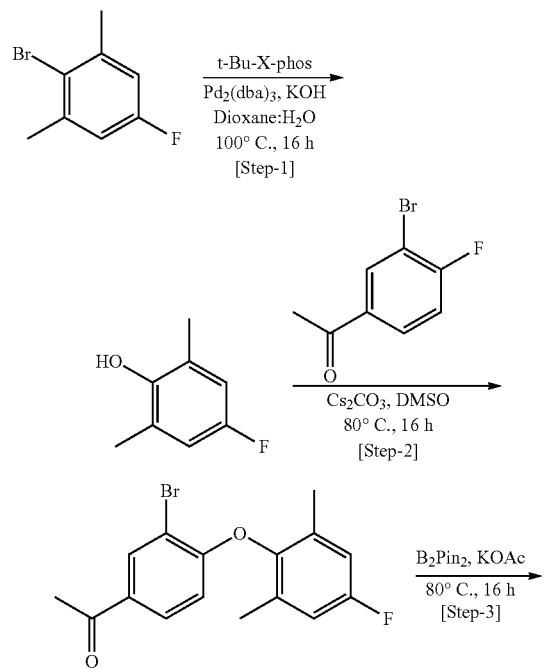

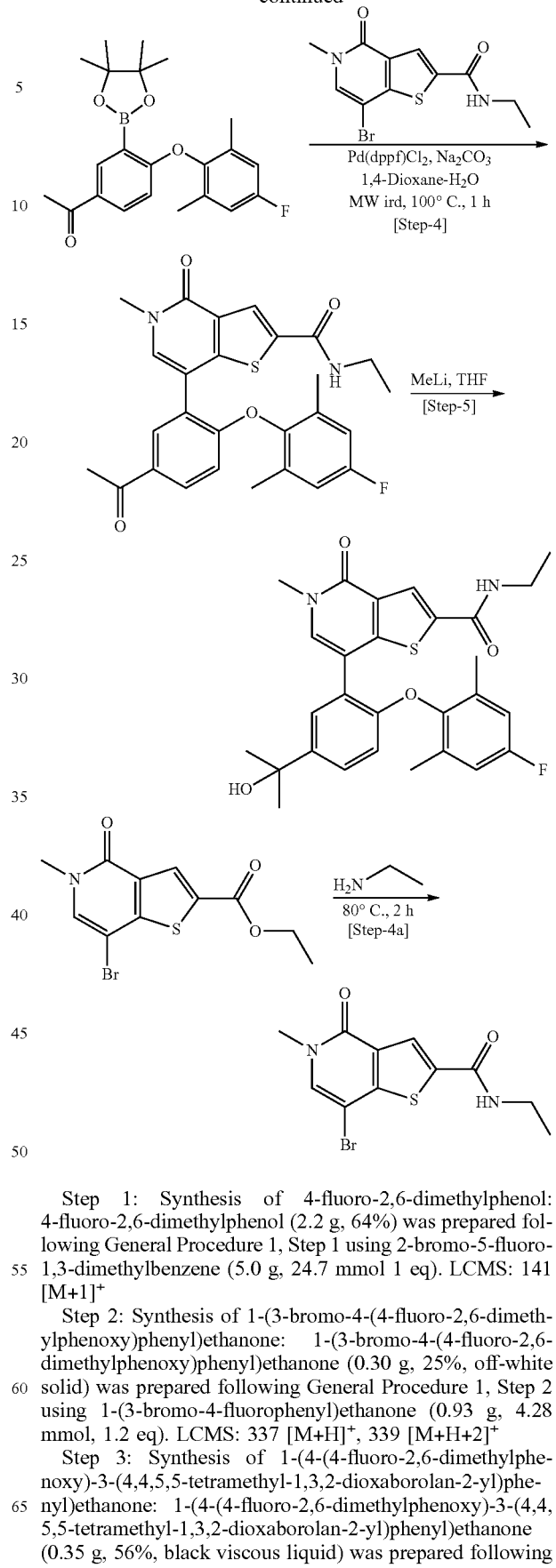

Step 1: Synthesis of 4-fluoro-2,6-dimethylphenol: 4-fluoro-2,6-dimethylphenol (2.2 g, 64%) was prepared following General Procedure 1, Step 1 using 2-bromo-5-fluoro-1,3-dimethylbenzene (5.0 g, 24.7 mmol 1 eq). LCMS: 141 [M+1]$^+$ Step 2: Synthesis of 1-(3-bromo-4-(4-fluoro-2,6-dimethylphenoxy)phenyl)ethanone: 1-(3-bromo-4-(4-fluoro-2,6-dimethylphenoxy)phenyl)ethanone (0.30 g, 25%, off-white solid) was prepared following General Procedure 1, Step 2 using 1-(3-bromo-4-fluorophenyl)ethanone (0.93 g, 4.28 mmol, 1.2 eq). LCMS: 337 [M+H]$^+$, 339 [M+H+2]$^+$ Step 3: Synthesis of 1-(4-(4-fluoro-2,6-dimethylphenoxy)-3-(4,4,5,5-tetramethyl-1,3,2-dioxaborolan-2-yl)phenyl)ethanone: 1-(4-(4-fluoro-2,6-dimethylphenoxy)-3-(4,4,5,5-tetramethyl-1,3,2-dioxaborolan-2-yl)phenyl)ethanone (0.35 g, 56%, black viscous liquid) was prepared following General Procedure 1, Step 3 using 1-(3-bromo-4-(4-fluoro-2,6-dimethylphenoxy)phenyl)ethanone (0.55 g, 1.63 mmol, 1 eq). $^1$H NMR (400 MHz, CDCl$_3$): δ 8.35 (d, J=2.4 Hz, 1H), 7.86 (s, 1H), 6.81 (d, J=8.8 Hz, 2H), 6.35 (d, J=8.8 Hz, 1H), 2.57 (s, 3H), 1.37 (s, 6H), 1.25 (d, J=7.3 Hz, 12H).

Step 4a: Synthesis of 7-bromo-N-ethyl-5-methyl-4-oxo-4,5-dihydrothieno[3,2-c]pyridine-2-carboxamide: 7-bromo-N-ethyl-5-methyl-4-oxo-4,5-dihydrothieno[3,2-c]pyridine-2-carboxamide (1.23 g, 95%, white solid) was prepared following General Procedure 1, Step 4a using ethyl 7-bromo-5-methyl-4-oxo-4,5-dihydrothieno[3,2-c]pyridine-2-carboxylate (1.5 g, 4.3 mmol, 1 eq). LCMS: 315 [M+H]$^+$, 317 [M+H+2]$^+$ Step 4: Synthesis of 7-(5-acetyl-2-(4-fluoro-2,6-dimethylphenoxy)phenyl)-N-ethyl-5-methyl-4-oxo-4,5-dihydrothieno[3,2-c]pyridine-2-carboxamide: 7-(5-acetyl-2-(4-fluoro-2,6-dimethylphenoxy)phenyl)-N-ethyl-5-methyl-4-oxo-4,5-dihydrothieno[3,2-c]pyridine-2-carboxamide (0.13 g, 52%, brown solid) was prepared following General Procedure 1, Step 4 using 1-(4-(4-fluoro-2,6-dimethylphenoxy)-3-(4,4,5,5-tetramethyl-1,3,2-dioxaborolan-2-yl)phenyl)ethanone (0.25 g, 0.66 mmol, 1.3 eq) and 7-bromo-N-ethyl-5-methyl-4-oxo-4,5-dihydrothieno[3,2-c]pyridine-2-carboxamide (0.16 g, 0.80 mmol, 1 eq). LCMS: 493 [M+H]$^+$ Step 5: Synthesis of N-ethyl-7-(2-(4-fluoro-2,6-dimethylphenoxy)-5-(2-hydroxypropan-2-yl)phenyl)-5-methyl-4-oxo-4,5-dihydrothieno[3,2-c]pyridine-2-carboxamide: N-ethyl-7-(2-(4-fluoro-2,6-dimethylphenoxy)-5-(2-hydroxypropan-2-yl)phenyl)-5-methyl-4-oxo-4,5-dihydrothieno[3,2-c]pyridine-2-carboxamide (35 mg, 25%, off-white solid) was prepared following General Procedure 1, Step 5 using 7-(5-acetyl-2-(4-fluoro-2,6-dimethylphenoxy)phenyl)-N-ethyl-5-methyl-4-oxo-4,5-dihydrothieno[3,2-c]pyridine-2-carboxamide (0.13 g, 0.263 mmol, 1.0 eq). LCMS: 509 [M+1]$^+$, NMR (400 MHz, MeOH-d$_4$): δ 8.14 (s, 1H), 7.67 (s, 1H), 7.62 (d, J=2.5 Hz, 1H), 7.43 (dd, J=8.7, 2.5 Hz, 1H), 6.85 (d, J=8.9 Hz, 2H), 6.42 (d, J=8.7 Hz, 1H), 3.72 (s, 3H), 3.45-3.32 (m, 2H), 2.07 (s, 6H), 1.55 (s, 6H), 1.23 (t, J=7.2 Hz, 3H).

Example S-12: Synthesis of 4-(2-(4-fluoro-2,6-dimethylphenoxy)-5-(2-hydroxypropan-2-yl)phenyl)-6-methyl-2-(5-methyl-1,3,4-oxadiazol-2-yl)thieno[2,3-c]pyridin-7(6H)-one (Compound 13)

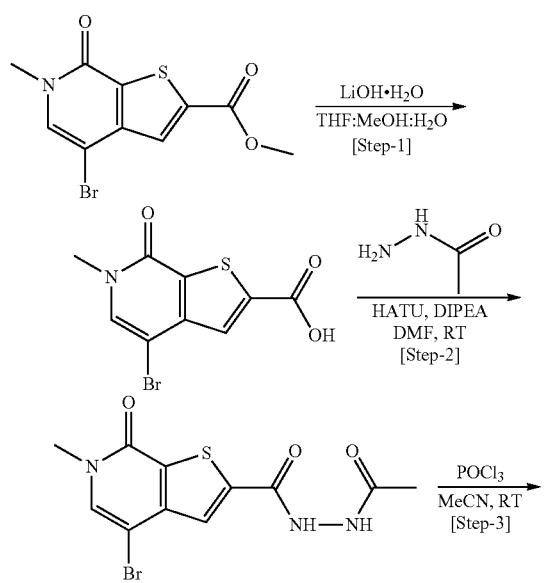

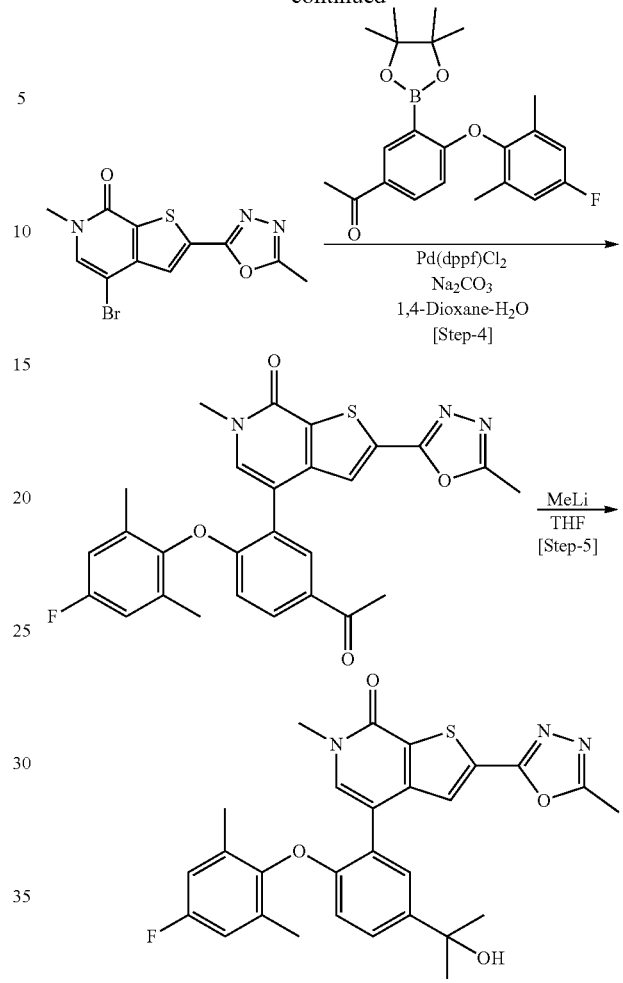

Step 1: Synthesis of 4-bromo-6-methyl-7-oxo-6,7-dihydrothieno[2,3-c]pyridine-2-carboxylic acid: 4-bromo-6-methyl-7-oxo-6,7-dihydrothieno[2,3-c]pyridine-2-carboxylic acid (0.43 g, 90%, off-white solid) was prepared following General Procedure 2, Step 4 using methyl 4-bromo-6-methyl-7-oxo-6,7-dihydrothieno[2,3-c]pyridine-2-carboxylate (0.50 g, 1.66 mmol, 1 eq). LCMS: 288 [M+1]$^+$, 290 [M+H+2]$^+$ Step 2: Synthesis of N'-acetyl-4-bromo-6-methyl-7-oxo-6,7-dihydrothieno[2,3-c]pyridine-2-carbohydrazide: N'-acetyl-4-bromo-6-methyl-7-oxo-6,7-dihydrothieno[2,3-c]pyridine-2-carbohydrazide (350 mg, 68%, yellow solid) was prepared following General Procedure 2, Step 5 using 4-bromo-6-methyl-7-oxo-6,7-dihydrothieno[2,3-c]pyridine-2-carboxylic acid (0.43 g, 1.49 mmol, 1 eq). LCMS: 344 [M+1]$^+$, 346 [M+H+2]$^+$ Step 3: Synthesis of 4-bromo-6-methyl-2-(5-methyl-1,3,4-oxadiazol-2-yl)thieno[2,3-c]pyridin-7(6H)-one: 4-bromo-6-methyl-2-(5-methyl-1,3,4-oxadiazol-2-yl)thieno[2,3-c]pyridin-7(6H)-one (110 mg, 58%, yellow solid) was prepared following General Procedure 2, Step 6 using N'-acetyl-4-bromo-6-methyl-7-oxo-6,7-dihydrothieno[2,3-c]pyridine-2-carbohydrazide (0.20 g, 0.58 mmol, 1 eq). LCMS: 326 [M+1]$^+$, 328 [M+H+2]$^+$ Step 4: Synthesis of 4-(5-acetyl-2-(4-fluoro-2,6-dimethylphenoxy)phenyl)-6-methyl-2-(5-methyl-1,3,4-oxadiazol-2-yl)thieno[2,3-c]pyridin-7(6H)-one: 4-(5-acetyl-2-(4- fluoro-2,6-dimethylphenoxy)phenyl)-6-methyl-2-(5-methyl-1,3,4-oxadiazol-2-yl)thieno[2,3-c]pyridin-7(6H)-one (0.1 g, 32%, off-white solid) was prepared following General Procedure 2, Step 7 using 4-bromo-6-methyl-2-(5-methyl-1,3,4-oxadiazol-2-yl)thieno[2,3-c]pyridin-7(6H)-one (0.2 g, 0.306 mmol, 1 eq) and 1-(4-(4-fluoro-2,6-dimethylphenoxy)-3-(4,4,5,5-tetramethyl-1,3,2-dioxaborolan-2-yl)phenyl)ethanone (0.306 g, 0.797 mmol, 1.3 eq). LCMS: 504 [M+1]$^+$ Step 5: Synthesis of 4-(2-(4-fluoro-2,6-dimethylphenoxy)-5-(2-hydroxypropan-2-yl)phenyl)-6-methyl-2-(5-methyl-1,3,4-oxadiazol-2-yl)thieno[2,3-c]pyridin-7(6H)-one: 4-(2-(4-fluoro-2,6-dimethylphenoxy)-5-(2-hydroxypropan-2-yl)phenyl)-6-methyl-2-(5-methyl-1,3,4-oxadiazol-2-yl)thieno[2,3-c]pyridin-7(6H)-one (13 mg, 25%, off-white solid) was prepared following General Procedure 1, Step 5 using 4-(5-acetyl-2-(4-fluoro-2,6-dimethylphenoxy)phenyl)-6-methyl-2-(5-methyl-1,3,4-oxadiazol-2-yl)thieno[2,3-c]pyridin-7(6H)-one (0.05 g, 0.099 mmol, 1 eq). LCMS: 520 [M+1]$^+$, NMR (400 MHz, DMSO-d$_6$): δ 7.82 (s, 1H), 7.66 (s, 1H), 7.53 (d, J=2.4 Hz, 1H), 7.41 (dd, J=8.6, 2.4 Hz, 1H), 6.99 (d, J=9.1 Hz, 2H), 6.37 (d, J=8.6 Hz, 1H), 5.04 (s, 1H), 3.67 (s, 3H), 2.57 (s, 3H), 2.02 (s, 6H), 1.45 (s, 6H)

Example S-13: Synthesis of 4-(2-(2,4-difluorophenoxy)-5-(2-hydroxypropan-2-yl)phenyl)-2-(3,3-difluoropiperidine-1-carbonyl)-6-methylthieno[2,3-c]pyridin-7(6H)-one (Compound 23)

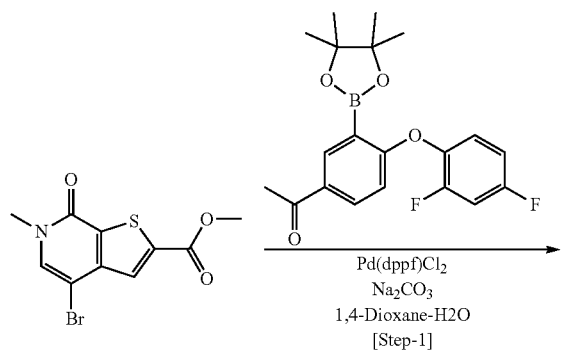

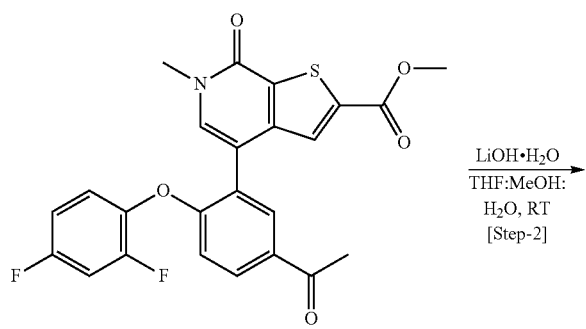

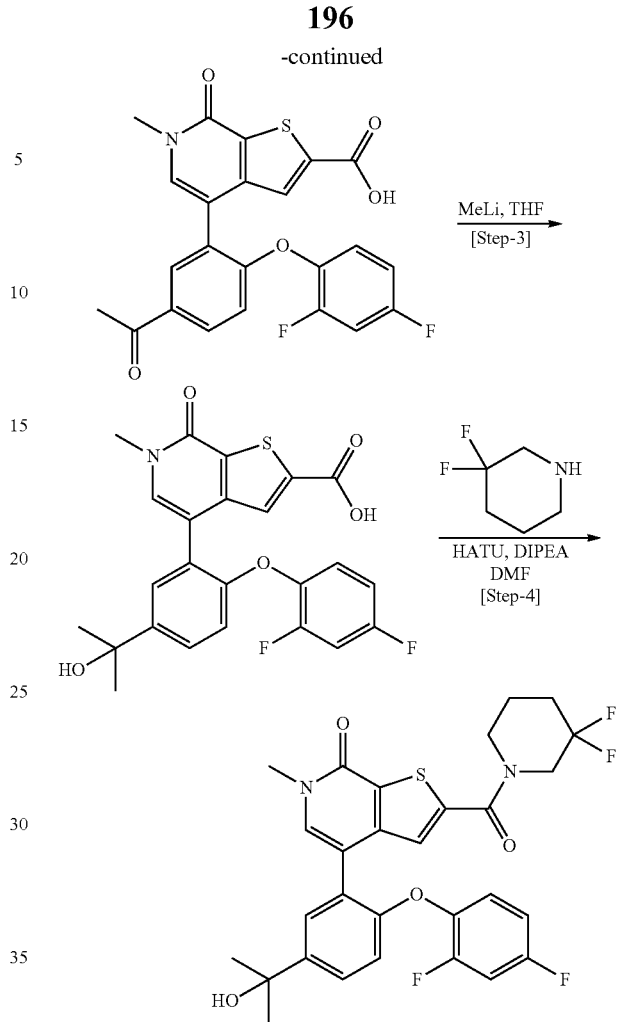

Step 1: Synthesis of methyl 4-(5-acetyl-2-(2,4-difluorophenoxy)phenyl)-6-methyl-7-oxo-6,7-dihydrothieno[2,3-c]pyridine-2-carboxylate: Methyl 4-(5-acetyl-2-(2,4-difluorophenoxy) phenyl)-6-methyl-7-oxo-6,7-dihydrothieno[2,3-c] pyridine-2-carboxylate (0.85 mg, 65%, white solid) was prepared following General Procedure 1, Step 4 using methyl 4-bromo-6-methyl-7-oxo-6,7-dihydrothieno[2,3-c]pyridine-2-carboxylate (0.9 g, 3.3 mmol, 1 eq). LCMS: 470 [M+1]$^+$ Step 2: Synthesis of 4-(5-acetyl-2-(2,4-difluorophenoxy)phenyl)-6-methyl-7-oxo-6,7-dihydrothieno[2,3-c]pyridine-2-carboxylic acid: 4-(5-acetyl-2-(2,4-difluorophenoxy)phenyl)-6-methyl-7-oxo-6,7-dihydrothieno[2,3-c]pyridine-2-carboxylic acid (450 mg, 92%, off-white solid) was prepared following General Procedure 2, Step 4 using 4-(5-acetyl-2-(2,4-difluorophenoxy)phenyl)-6-methyl-7-oxo-6,7-dihydrothieno[2,3-c]pyridine-2-carboxylate (0.50 g, 1.06 mmol, 1 eq). LCMS: 456 [M+1]$^+$ Step 3: Synthesis of 4-(2-(2,4-difluorophenoxy)-5-(2-hydroxypropan-2-yl)phenyl)-6-methyl-7-oxo-6,7-dihydrothieno[2,3-c]pyridine-2-carboxylic acid: 4-(2-(2,4-difluorophenoxy)-5-(2-hydroxypropan-2-yl)phenyl)-6-methyl-7-oxo-6,7-dihydrothieno[2,3-c]pyridine-2-carboxylic acid (200 mg, 72%, off-white solid) was prepared following General Procedure 1, Step 5 using 4-(5-acetyl-2-(2,4-difluorophenoxy)phenyl)-6-methyl-7-oxo-6,7-dihydrothieno[2,3-c]pyridine-2-carboxylic acid (0.20 g, 0.44 mmol, 1 eq). LCMS: 472 [M+1]$^+$ Step 4: Synthesis of 4-(2-(2,4-difluorophenoxy)-5-(2-hydroxypropan-2-yl)phenyl)-2-(3,3-difluoro piperidine-1-carbonyl)-6-methylthieno[2,3-c]pyridin-7(6H)-one: 4-(2-(2,4-difluorophenoxy)-5-(2-hydroxypropan-2-yl)phenyl)-2-(3,3-difluoro piperidine-1-carbonyl)-6-methylthieno[2,3-c] pyridin-7(6H)-one (0.018 g, 10%, off-white solid) was prepared following General Procedure 2, Step 5 using 4-(2-(2,4-difluorophenoxy)-5-(2-hydroxypropan-2-yl)phenyl)-6-methyl-7-oxo-6,7-dihydrothieno[2,3-c]pyridine-2-carboxylic acid (0.15 g, 0.33 mmol, 1 eq) and 3,3-difluoropiperidine (0.150 g, 0.95 mmol, 3.0 eq). LCMS: 575 [M+1]$^+$, $^1$H NMR (400 MHz, DMSO-d$_6$): δ 7.70 (s, 1H), 7.54 (d, J=2.4 Hz, 1H), 7.50 (dd, J=8.7, 2.5 Hz, 1H), 7.35 (ddd, J=11.4, 8.7, 3.0 Hz, 1H), 7.27 (s, 1H), 7.09 (td, J=9.1, 5.4 Hz, 1H), 7.04-6.95 (m, 1H), 6.86 (d, J=8.5 Hz, 1H), 5.09 (s, 1H), 3.91 (t, J=11.8 Hz, 2H), 3.60 (s, 5H), 2.10 (ddt, J=14.5, 10.4, 6.3 Hz, 2H), 1.67 (s, 2H), 1.46 (s, 6H).

Example S-14: Synthesis of N-(4-(4-fluoro-2,6-dimethylphenoxy)-3-(6-methyl-2-(5-methyl-1,3,4-oxadiazol-2-yl)-7-oxo-6,7-dihydrothieno[2,3-c]pyridin-4-yl)phenyl)ethanesulfonamide (Compound 10)

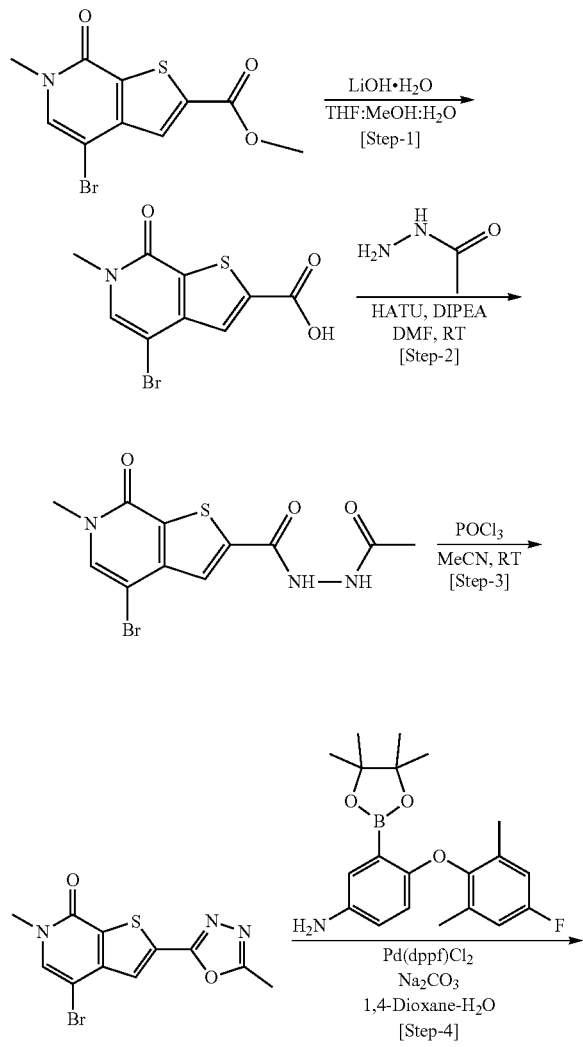

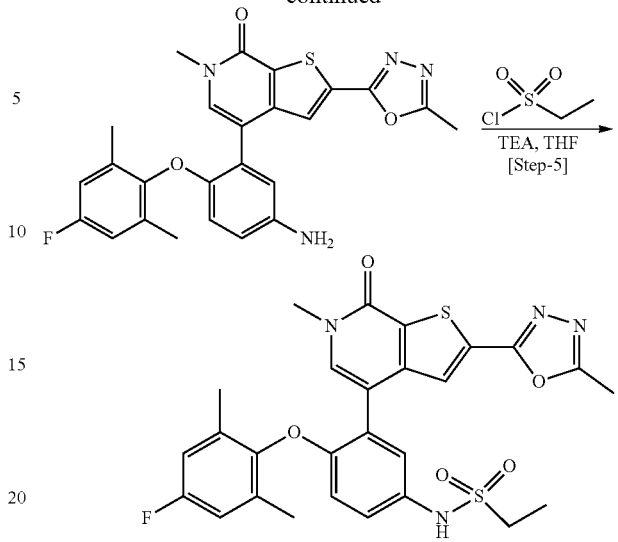

Step 1: Synthesis of 4-bromo-6-methyl-7-oxo-6,7-dihydrothieno[2,3-c]pyridine-2-carboxylic acid: 4-bromo-6-methyl-7-oxo-6,7-dihydrothieno[2,3-c]pyridine-2-carboxylic acid (0.43 mg, 90%, off-white solid) was prepared following General Procedure 2, Step 4 using methyl 4-bromo-6-methyl-7-oxo-6,7-dihydrothieno[2,3-c]pyridine-2-carboxylate (0.5 g, 1.66 mmol, 1 eq). LCMS: 288 [M+1]$^+$, 290 [M+H+2]$^+$ Step 2: Synthesis of N'-acetyl-4-bromo-6-methyl-7-oxo-6,7-dihydrothieno[2,3-c]pyridine-2-carbohydrazide: N'-acetyl-4-bromo-6-methyl-7-oxo-6,7-dihydrothieno[2,3-c]pyridine-2-carbohydrazide (450 mg, 87%, yellow solid) was prepared following General Procedure 2, Step 5 using 4-bromo-6-methyl-7-oxo-6,7-dihydrothieno[2,3-c]pyridine-2-carboxylic acid (0.43 g, 1.5 mmol, 1 eq). LCMS: 344 [M+1]$^+$, 346 [M+H+2]$^+$ Step 3: Synthesis of 4-bromo-6-methyl-2-(5-methyl-1,3,4-oxadiazol-2-yl)thieno[2,3-c]pyridin-7(6H)-one: 4-bromo-6-methyl-2-(5-methyl-1,3,4-oxadiazol-2-yl)thieno[2,3-c]pyridin-7(6H)-one (240 mg, 50%, yellow solid) was prepared following General Procedure 2, Step 6 using N'-acetyl-4-bromo-6-methyl-7-oxo-6,7-dihydrothieno[2,3-c]pyridine-2-carbohydrazide (0.45 g, 1.35 mmol, 1 eq). LCMS: 326 [M+1]$^+$, 328 [M+H+2]$^+$ Step 4: Synthesis of 4-(5-amino-2-(4-fluoro-2,6-dimethylphenoxy)phenyl)-6-methyl-2-(5-methyl-1,3,4-oxadiazol-2-yl)thieno[2,3-c]pyridin-7(6H)-one: 4-(5-amino-2-(4-fluoro-2,6-dimethylphenoxy)phenyl)-6-methyl-2-(5-methyl-1,3,4-oxadiazol-2-yl)thieno[2,3-c]pyridin-7(6H)-one (0.018 g, 10%, off-white solid) was prepared following General Procedure 2, Step 7 using 4-bromo-6-methyl-2-(5-methyl-1,3,4-oxadiazol-2-yl)thieno[2,3-c]pyridin-7(6H)-one (0.24 g, 0.73 mmol, 1 eq). LCMS: 477 [M+1]$^+$ Step 5: Synthesis of N-(4-(4-fluoro-2,6-dimethylphenoxy)-3-(6-methyl-2-(5-methyl-1,3,4-oxadiazol-2-yl)-7-oxo-6,7-dihydrothieno[2,3-c]pyridin-4-yl)phenyl)ethanesulfonamide: N-(4-(4-fluoro-2,6-dimethylphenoxy)-3-(6-methyl-2-(5-methyl-1,3,4-oxadiazol-2-yl)-7-oxo-6,7-dihydrothieno[2,3-c]pyridin-4-yl)phenyl)ethanesulfonamide (0.018 g, 16%, off-white solid) was prepared following General Procedure 2, Step 8 using 4-(5-amino-2-(4-fluoro-2,6-dimethylphenoxy)phenyl)-6-methyl-2-(5-methyl-1,3,4-oxadiazol-2-yl)thieno[2,3-c]pyridin-7(6H)-one (0.11 g, 0.23 mmol, 1 eq). LCMS: 569 [M+1]$^+$, NMR (400 MHz, DMSO-d$_6$): δ 7.85 (s, 1H), 7.71 (s, 1H), 7.26 (d, J=2.6 Hz, 1H), 7.14 (d, J=8.8 Hz, 1H), 6.98 (d, J=8.8 Hz, 2H), 6.40 (d, J=8.8 Hz, 1H), 3.66 (s, 3H), 3.06 (d, J=7.5 Hz, 2H), 2.57 (s, 3H), 2.02 (s, 6H), 1.21 (t, J=7.5 Hz, 3H).

Example S-15: Synthesis of 4-(2-(2,6-dimethylphenoxy)-5-(ethylsulfonamido)phenyl)-N-ethyl-6-methyl-7-oxo-6,7-dihydrothieno[2,3-c]pyridine-2-carboxamide (Compound 147)

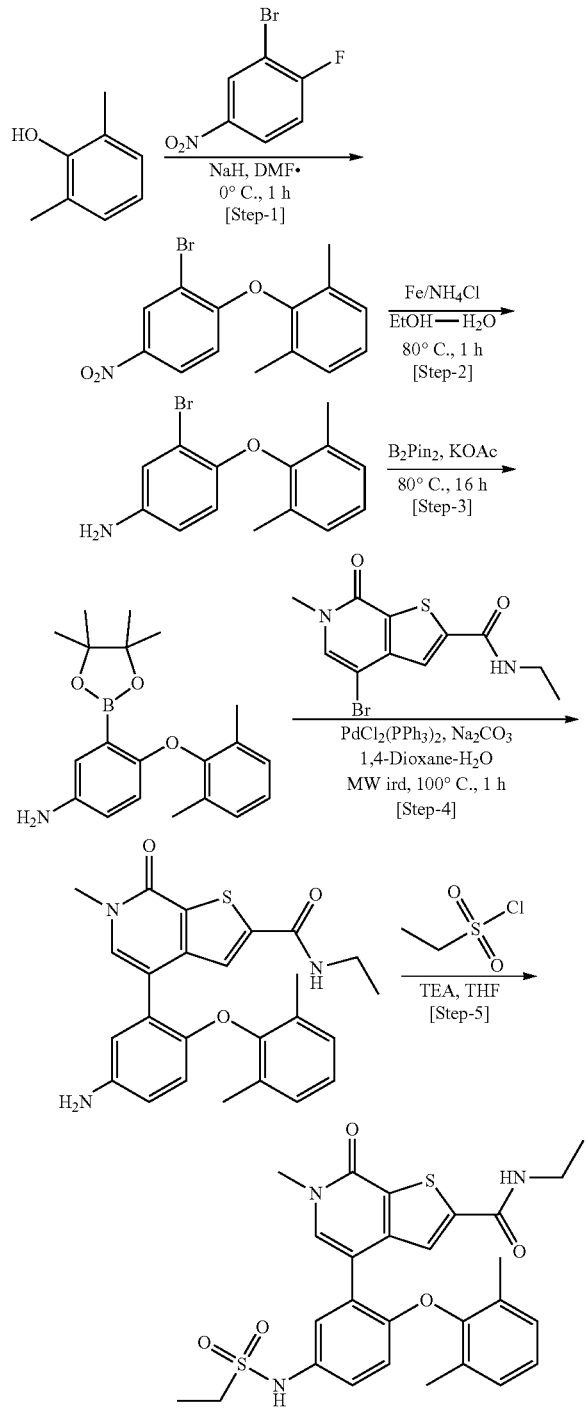

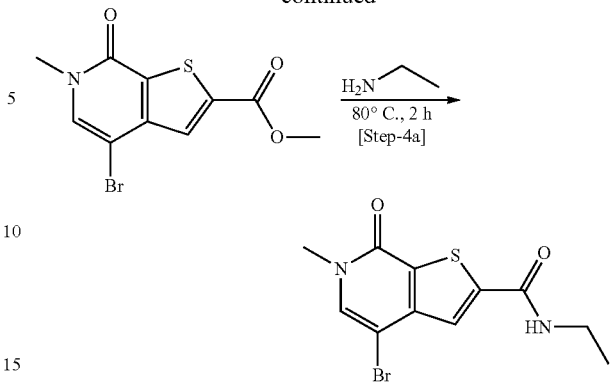

Step 1: Synthesis of 2-(2-bromo-4-nitrophenoxy)-1,3-dimethylbenzene: 2-(2-bromo-4-nitrophenoxy)-1,3-dimethylbenzene (4.5 g, 68%, yellow solid) was prepared following General Procedure 2, Step 1 using 2,6-dimethylphenol (2.0 g, 16.03 mmol, 1.0 eq). LCMS: 322 [M+H]$^+$, 324 [M+H+2]$^+$ Step 2: Synthesis of 3-bromo-4-(2,6-dimethylphenoxy)aniline: 3-bromo-4-(2,6-dimethylphenoxy)aniline (3.5 g, 97%, black viscous liquid) was prepared following General Procedure 2, Step 2 using 2-(2-bromo-4-nitrophenoxy)-1,3-dimethylbenzene (4.0 g, 12.46 mmol, 1.0 eq). LCMS: 292 [M+H]$^+$, 294 [M+H+2]$^+$ Step 3: Synthesis of 4-(2,6-dimethylphenoxy)-3-(4,4,5,5-tetramethyl-1,3,2-dioxaborolan-2-yl)aniline: 4-(2,6-dimethylphenoxy)-3-(4,4,5,5-tetramethyl-1,3,2-dioxaborolan-2-yl)aniline (0.700 g, 66%, black viscous liquid) was prepared following General Procedure 2, Step 3 using 3-bromo-4-(2,6-dimethylphenoxy)aniline (1.0 g, 45.6 mmol, 1.0 eq). $^1$H NMR: (400 MHz, CDCl$_3$) δ 6.97-7.11 (m, 3H), 6.58 (d, J=3.95 Hz, 1H), 6.14 (d, J=8.77 Hz, 1H), 2.05-2.18 (m, 6H), 1.23-1.28 (m, 12H).

Step 4a: Synthesis of 7-bromo-N-ethyl-5-methyl-4-oxo-4,5-dihydrothieno[3,2-c]pyridine-2-carboxamide: 7-bromo-N-ethyl-5-methyl-4-oxo-4,5-dihydrothieno[3,2-c]pyridine-2-carboxamide (100 mg, 67%, brown solid)) was prepared following General Procedure 1, Step 4a using ethyl 7-bromo-5-methyl-4-oxo-4,5-dihydrothieno[3,2-c]pyridine-2-carboxylate (1.0 g, 45.6 mmol, 1.0 eq). LCMS: 315 [M+H]$^+$, 317 [M+H+2]$^+$ Step 4: Synthesis of 7-(5-amino-2-(2,6-dimethylphenoxy)phenyl)-N-ethyl-5-methyl-4-oxo-4,5-dihydrothieno[3,2-c]pyridine-2-carboxamide: 7-(5-amino-2-(2,6-dimethylphenoxy) phenyl)-N-ethyl-5-methyl-4-oxo-4,5-dihydrothieno[3,2-c]pyridine-2-carboxamide (0.23 g, 30%, brown viscous liquid) was prepared following General Procedure 2, Step 7 using 4-(2,6-dimethylphenoxy)-3-(4,4,5,5-tetramethyl-1,3,2-dioxaborolan-2-yl)aniline (0.807 g, 2.37 mmol, 1.5 eq) and 7-bromo-N-ethyl-5-methyl-4-oxo-4,5-dihydrothieno[3,2-c]pyridine-2-carboxamide (0.50 g, 1.58 mmol, 1 eq). LCMS: 448[M+H]$^+$ Step 5: Synthesis of 4-(2-(2,6-dimethylphenoxy)-5-(ethylsulfonamido)phenyl)-N-ethyl-6-methyl-7-oxo-6,7-dihydrothieno[2,3-c]pyridine-2-carboxamide: 4-(2-(2,6-dimethylphenoxy)-5-(ethylsulfonamido)phenyl)-N-ethyl-6-methyl-7-oxo-6,7-dihydrothieno[2,3-c]pyridine-2-carboxamide (30 mg, 16.5%) was prepared following General Procedure 2, Step-8 using 7-(5-amino-2-(2,6-dimethylphenoxy)phenyl)-N-ethyl-5-methyl-4-oxo-4,5-dihydrothieno[3,2-c]pyridine-2-carboxamide (0.15 g, 0.335 mmol, 1.0 eq). LCMS: 540 [M+H]$^+$, $^1$H NMR: (400 MHz, MeOH-d$_4$) δ 7.81 (s, 1H), 7.68 (s, 1H), 7.35 (d, J=2.6 Hz, 1H), 7.17 (d, J=8.8 Hz, 1H), 7.12-6.98 (m, 3H), 6.43 (d, J=8.8 Hz, 1H), 3.75 (s, 3H), 3.40-3.20 (m, 2H), 3.09 (d, J=7.5 Hz, 2H), 2.05 (s, 6H), 1.34 (t, J=7.2 Hz, 3H), 1.20 (t, J=7.2 Hz, 3H).

Example S-16: Synthesis of 4-(2-(2,4-difluorophenoxy)-5-(2-hydroxypropan-2-yl)phenyl)-2-(4,4-difluoropiperidine-1-carbonyl)-6-methylthieno[2,3-c]pyridin-7(6H)-one (Compound 22)

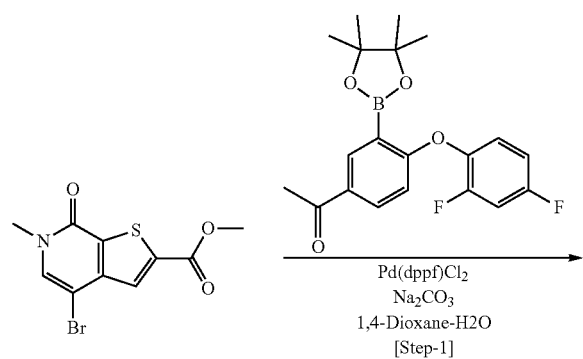

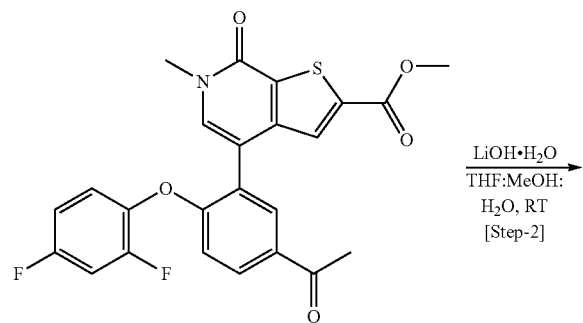

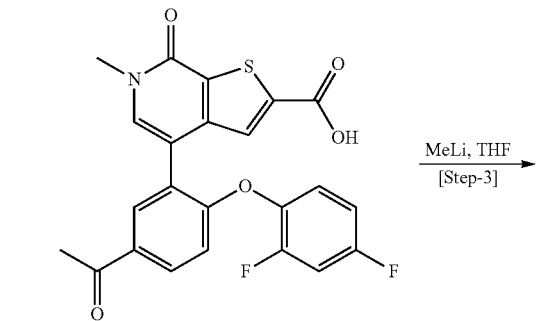

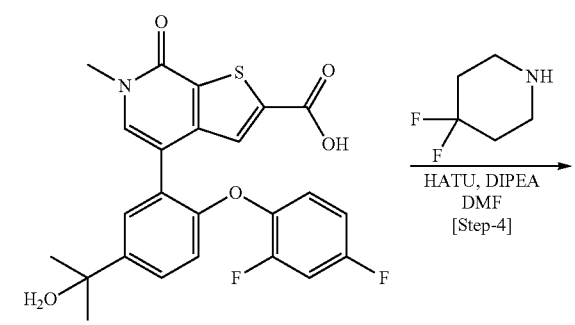

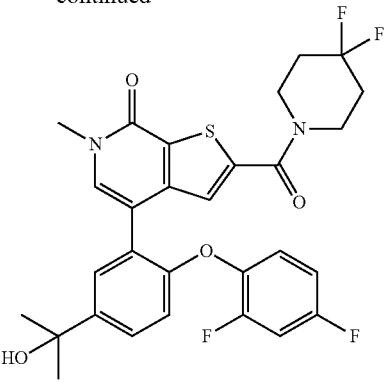

Step 1: Synthesis of methyl 4-(5-acetyl-2-(2,4-difluorophenoxy)phenyl)-6-methyl-7-oxo-6,7-dihydrothieno[2,3-c]pyridine-2-carboxylate: Methyl 4-(5-acetyl-2-(2,4-difluorophenoxy) phenyl)-6-methyl-7-oxo-6,7-dihydrothieno[2,3-c]pyridine-2-carboxylate (0.85 mg, 65%, white solid) was prepared following General Procedure 1, Step 4 using methyl 4-bromo-6-methyl-7-oxo-6,7-dihydrothieno[2,3-c]pyridine-2-carboxylate (0.9 g, 3.3 mmol, 1 eq). LCMS: 470 [M+1]+

Step 2: Synthesis of 4-(5-acetyl-2-(2,4-difluorophenoxy)phenyl)-6-methyl-7-oxo-6,7-dihydrothieno[2,3-c]pyridine-2-carboxylic acid: 4-(5-acetyl-2-(2,4-difluorophenoxy)phenyl)-6-methyl-7-oxo-6,7-dihydrothieno[2,3-c]pyridine-2-carboxylic acid (450 mg, 92%, off-white solid) was prepared following General Procedure 2, Step 4 using 4-(5-acetyl-2-(2,4-difluorophenoxy)phenyl)-6-methyl-7-oxo-6,7-dihydrothieno[2,3-c]pyridine-2-carboxylate (0.50 g, 1.06 mmol, 1 eq). LCMS: 456 [M+1]+

Step 3: Synthesis of 4-(2-(2,4-difluorophenoxy)-5-(2-hydroxypropan-2-yl)phenyl)-6-methyl-7-oxo-6,7-dihydrothieno[2,3-c]pyridine-2-carboxylic acid: 4-(2-(2,4-difluorophenoxy)-5-(2-hydroxypropan-2-yl)phenyl)-6-methyl-7-oxo-6,7-dihydrothieno[2,3-c]pyridine-2-carboxylic acid (200 mg, 72%, off-white solid) was prepared following General Procedure 1, Step 5 using 4-(5-acetyl-2-(2,4-difluorophenoxy)phenyl)-6-methyl-7-oxo-6,7-dihydrothieno[2,3-c]pyridine-2-carboxylic acid (0.20 g, 0.44 mmol, 1 eq). LCMS: 472 [M+1]+

Step 4: Synthesis of 4-(2-(2,4-difluorophenoxy)-5-(2-hydroxypropan-2-yl)phenyl)-2-(4,4-difluoropiperidine-1-carbonyl)-6-methylthieno[2,3-c]pyridin-7(6H)-one: 4-(2-(2,4-difluorophenoxy)-5-(2-hydroxypropan-2-yl)phenyl)-2-(4,4-difluoropiperidine-1-carbonyl)-6-methylthieno[2,3-c]pyridin-7(6H)-one (0.018 g, 10%, off-white solid) was prepared following General Procedure 2, Step 5 using 4-(2-(2,4-difluorophenoxy)-5-(2-hydroxypropan-2-yl)phenyl)-6-methyl-7-oxo-6,7-dihydrothieno[2,3-c]pyridine-2-carboxylic acid (0.09 g, 0.19 mmol, 1 eq) and 4,4-difluoropiperidine (0.90 g, 0.57 mmol, 3.0 eq). LCMS: 575 [M+1]+, 1H NMR (400 MHz, MeOH-d4): δ 7.64-7.49 (m, 3H), 7.36 (s, 1H), 7.02 (br. s., 1H), 6.99-6.88 (m, 2H), 6.86-6.8 (m, 1H), 3.8 (br. s., 4H), 3.69 (s, 3H), 2.04 (br. s., 4H), 1.58 (s, 6H).

Example S-17: Synthesis of 4-(2-(2,4-difluorophenoxy)-5-(2-hydroxypropan-2-yl)phenyl)-2-(3,3-difluoropyrrolidin-1-carbonyl)-6-methylthieno[2,3-c]pyridin-7(6H)-one (Compound 76)

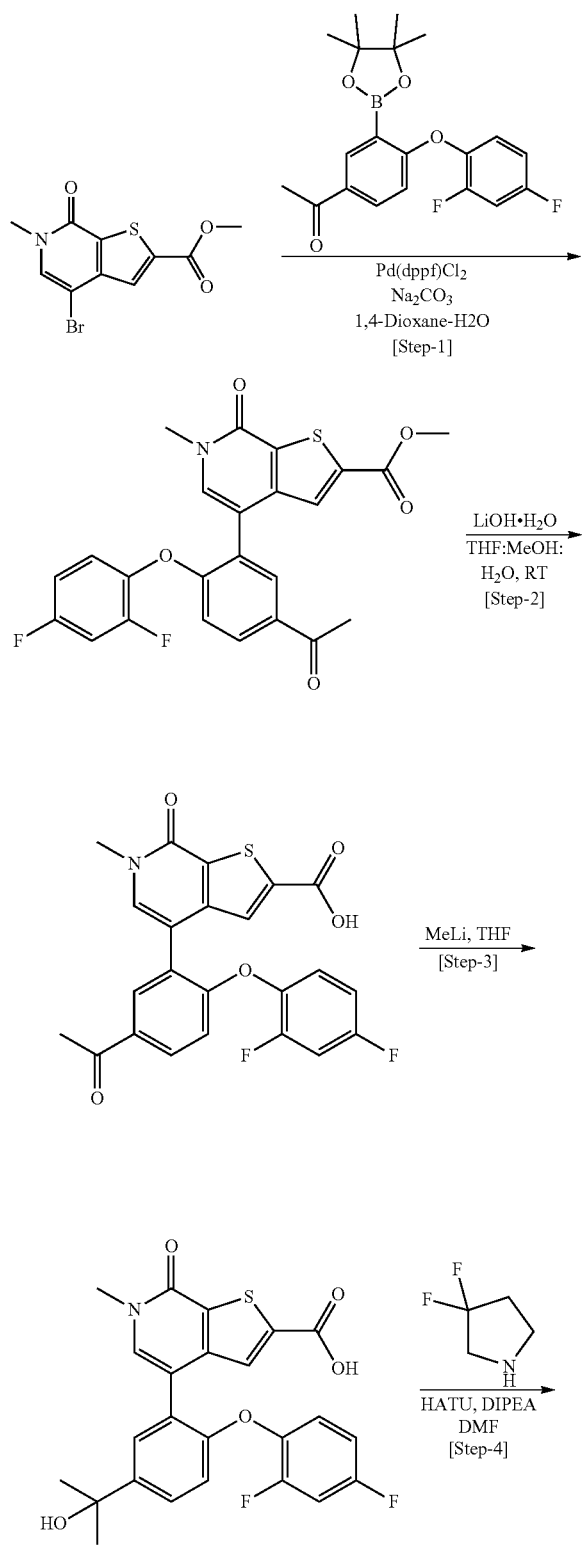

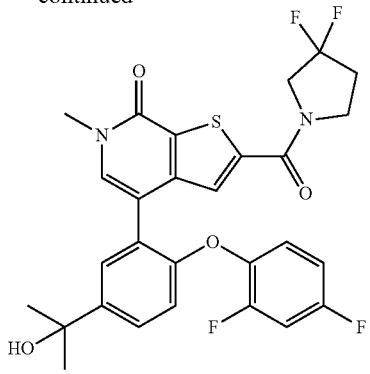

Step 1: Synthesis of methyl 4-(5-acetyl-2-(2,4-difluorophenoxy)phenyl)-6-methyl-7-oxo-6,7-dihydrothieno[2,3-c]pyridine-2-carboxylate: Methyl 4-(5-acetyl-2-(2,4-difluorophenoxy) phenyl)-6-methyl-7-oxo-6,7-dihydrothieno[2,3-c]pyridine-2-carboxylate (0.85 mg, 65%, white solid) was prepared following General Procedure 1, Step 4 using methyl 4-bromo-6-methyl-7-oxo-6,7-dihydrothieno[2,3-c]pyridine-2-carboxylate (0.9 g, 3.3 mmol, 1 eq). LCMS: 470 [M+1]$^+$ Step 2: Synthesis of 4-(5-acetyl-2-(2,4-difluorophenoxy)phenyl)-6-methyl-7-oxo-6,7-dihydrothieno[2,3-c]pyridine-2-carboxylic acid: 4-(5-acetyl-2-(2,4-difluorophenoxy)phenyl)-6-methyl-7-oxo-6,7-dihydrothieno[2,3-c]pyridine-2-carboxylic acid (450 mg, 92%, off-white solid) was prepared following General Procedure 2, Step 4 using 4-(5-acetyl-2-(2,4-difluorophenoxy)phenyl)-6-methyl-7-oxo-6,7-dihydrothieno[2,3-c]pyridine-2-carboxylate (0.50 g, 1.06 mmol, 1 eq). LCMS: 456 [M+1]$^+$ Step 3: Synthesis of 4-(2-(2,4-difluorophenoxy)-5-(2-hydroxypropan-2-yl)phenyl)-6-methyl-7-oxo-6,7-dihydrothieno[2,3-c]pyridine-2-carboxylic acid: 4-(2-(2,4-difluorophenoxy)-5-(2-hydroxypropan-2-yl)phenyl)-6-methyl-7-oxo-6,7-dihydrothieno[2,3-c]pyridine-2-carboxylic acid (200 mg, 72%, off-white solid) was prepared following General Procedure 1, Step 5 using 4-(5-acetyl-2-(2,4-difluorophenoxy)phenyl)-6-methyl-7-oxo-6,7-dihydrothieno[2,3-c]pyridine-2-carboxylic acid (0.20 g, 0.44 mmol, 1 eq). LCMS: 472 [M+1]$^+$ Step 4: Synthesis of 4-(2-(2,4-difluorophenoxy)-5-(2-hydroxypropan-2-yl)phenyl)-2-(3,3-difluoropyrrolidine-1-carbonyl)-6-methylthieno[2,3-c]pyridin-7(6H)-one: 4-(2-(2,4-difluorophenoxy)-5-(2-hydroxypropan-2-yl)phenyl)-2-(3,3-difluoropyrrolidine-1-carbonyl)-6-methylthieno[2,3-c]pyridin-7(6H)-one (0.006 g, 2.2%, off-white solid) was prepared following General Procedure 2, Step 5 using 4-(2-(2,4-difluorophenoxy)-5-(2-hydroxypropan-2-yl)phenyl)-6-methyl-7-oxo-6,7-dihydrothieno[2,3-c]pyridine-2-carboxylic acid (0.15 g, 0.3 mmol, 1 eq) and 3,3-difluoropyrrolidine (0.15 g, 0.95 mmol, 3.0 eq). LCMS: 561 [M+1]$^+$, $^1$H NMR (400 MHz, MeOH-d$_4$): δ 7.61 (s, 1H), 7.60-7.48 (m, 3H), 7.05-6.91 (m, 3H), 6.85 (d, J=6.6 Hz, 1H), 4.17 (hr. s., 1H), 4.01 (hr. s., 2H), 3.86 (hr. s., 1H), 3.70 (s, 3H), 2.49 (hr. s., 2H), 1.58 (s, 6H).

Example S-18: Synthesis of N-ethyl-4-(2-(4-fluoro-2,6-dimethylphenoxy)-5-(prop-1-en-2-yl)phenyl)-6-methyl-7-oxo-6,7-dihydrothieno[2,3-c]pyridine-2-carboxamide (Compound 148)

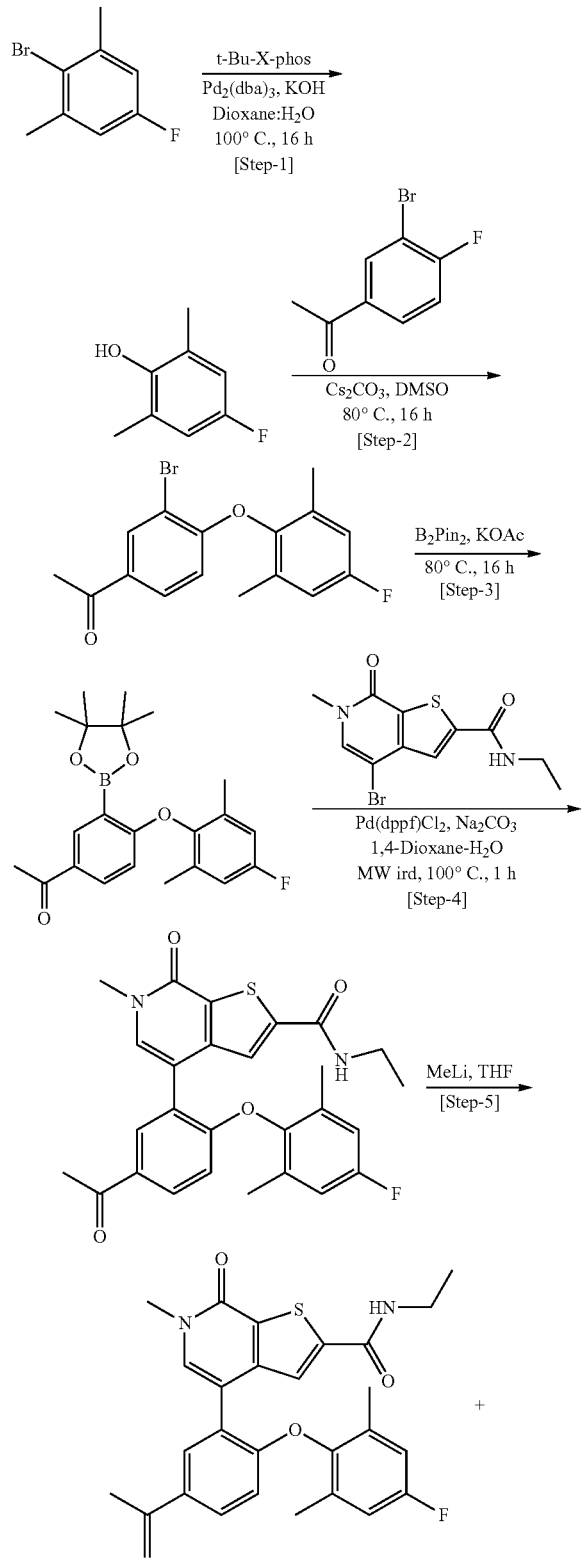

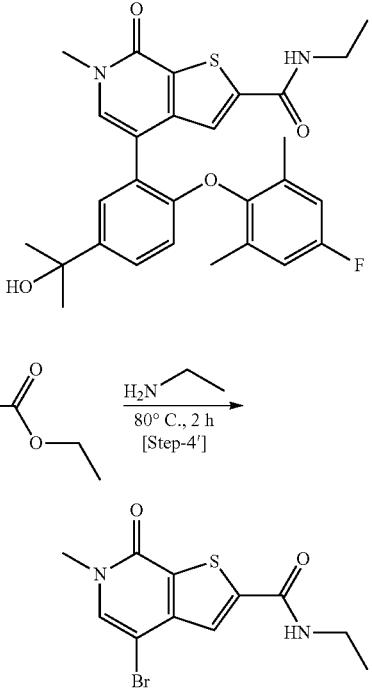

Step 1: Synthesis of 4-fluoro-2,6-dimethylphenol: 4-fluoro-2,6-dimethylphenol (2.2 g, 64%) was prepared following General Procedure 1, Step 1 using 2-bromo-5-fluoro-1,3-dimethylbenzene (5.0 g, 24.7 mmol, 1 eq). LCMS: 141 [M+1]$^+$ Step 2: Synthesis of 1-(3-bromo-4-(4-fluoro-2,6-dimethylphenoxy)phenyl)ethanone: 1-(3-bromo-4-(4-fluoro-2,6-dimethyl phenoxy) phenyl)ethanone (0.30 g, 25%) was prepared following General Procedure 1, Step 2 using 4-fluoro-2,6-dimethylphenol (0.50 g, 3.57 mmol) and 1-(3-bromo-4-fluorophenyl)ethanone (0.93 g, 4.28 mmol, 1.2 eq). LCMS: 337 [M+H]$^+$, 339 [M+H+2]$^+$ Step 3: Synthesis of 1-(4-(4-fluoro-2,6-dimethylphenoxy)-3-(4,4,5,5-tetramethyl-1,3,2-dioxaborolan-2-yl)phenyl)ethanone: 1-(4-(4-fluoro-2,6-dimethylphenoxy)-3-(4,4,5,5-tetra methyl-1,3,2-dioxaborolan-2-yl)phenyl)ethanone (0.35 g, 56%) was prepared following General Procedure 1, Step 3 using 1-(3-bromo-4-(4-fluoro-2,6-dimethylphenoxy) phenyl)ethanone (0.55 g, 1.63 mmol, 1 eq). NMR (400 MHz, CDCl$_3$): δ 8.35 (d, J=2.4 Hz, 1H), 7.86 (s, 1H), 6.81 (d, J=8.8 Hz, 2H), 6.35 (d, J=8.8 Hz, 1H), 2.57 (s, 3H), 1.37 (s, 6H), 1.25 (d, J=7.3 Hz, 12H)

Step 4a: Synthesis of 4-bromo-N-ethyl-6-methyl-7-oxo-6,7-dihydrothieno[2,3-c]pyridine-2-carboxamide: 4-bromo-N-ethyl-6-methyl-7-oxo-6,7-dihydrothieno[2,3-c]pyridine-2-carboxamide (1.23 g, 95%, white solid) was prepared following General Procedure 1, Step 4a using ethyl 4-bromo-6-methyl-7-oxo-6,7-dihydrothieno[2,3-c]pyridine-2-carboxylate (1.5 g, 4.3 mmol, 1 eq). LCMS: 315 [M+H]$^+$, 317 [M+H+2]$^+$ Step 4: Synthesis of 4-(5-acetyl-2-(4-fluoro-2,6-dimethylphenoxy)phenyl)-N-ethyl-6-methyl-7-oxo-6,7-dihydrothieno[2,3-c]pyridine-2-carboxamide: 4-(5-acetyl-2-(4-fluoro-2,6-dimethylphenoxy)phenyl)-N-ethyl-6-methyl-7-oxo-6,7-dihydrothieno[2,3-c]pyridine-2-carboxamide (0.16 g, 38%, off white solid) was prepared following General Procedure 1, Step 4 using 1-(4-(4-fluoro-2,6-dimethylphenoxy)-3-(4,4,5,5-tetra methyl-1,3,2-dioxaborolan-2-yl)phenyl)ethanone (0.46 g, 1.2 mmol, 1.5 eq) and 4-Bromo-N-ethyl-6-methyl-7-oxo-6,7-dihydrothieno[2,3-c]pyridine-2-carboxamide (0.27 g, 0.80 mmol, 1 eq). LCMS: 493 [M+H]$^+$ Step 5: Synthesis of N-ethyl-4-(2-(4-fluoro-2,6-dimethylphenoxy)-5-(prop-1-en-2-yl)phenyl)-6-methyl-7-oxo-6,7-dihydrothieno[2,3-c]pyridine-2-carboxamide: To a stirred solution of 4-(5-acetyl-2-(4-fluoro-2,6-dimethylphenoxy)phenyl)-N-ethyl-6-methyl-7-oxo-6,7-dihydrothieno [2,3-c]pyridine-2-carboxamide (0.60 g, 1.21 mmol) in anhydrous THF (10 mL) was added MeLi (3.0 mL, 4.86 mmol, 4 eq) at 0° C. dropwise and the mixture was stirred at same temperature for 10 min. The reaction was complete after 10 min and the mixture was quenched with saturated NH$_4$Cl solution (10 mL) slowly. The aqueous layer was then extracted with EtOAc (100 mL×2). The combined organic layers were washed with water (50 mL), brine (50 mL), dried over anhydrous Na$_2$SO$_4$, filtered and concentrated under reduced pressure to obtain a crude which was purified by CombiFlash Chromatography to afford A-ethyl-4-(2-(4-fluoro-2,6-dimethylphenoxy)-5-(2-hydroxypropan-2-yl)phenyl)-6-methyl-7-oxo-6,7-dihydrothieno[2,3-c]pyridine-2-carboxamide as a major product and N-ethyl-4-(2-(4-fluoro-2,6-dimethylphenoxy)-5-(prop-1-en-2-yl)phenyl)-6-methyl-7-oxo-6,7-dihydrothieno[2,3-c]pyridine-2-carboxamide as a minor product (46 mg, 7%). LCMS: 491 [M+1]$^+$; NMR (400 MHz, DMSO-d$_6$): δ 8.82 (s, 1H), 7.86 (s, 1H), 7.77 (s, 1H), 7.58 (d, J=2.2 Hz, 1H), 7.48 (dd, J=2.4, 8.6 Hz, 1H), 6.99 (d, J=9.2 Hz, 2H), 6.55 (s, 1H), 6.40 (d, J=8.8 Hz, 1H), 3.62 (s, 3H), 3.29-3.19 (m, 2H), 2.11 (s, 3H), 2.00 (br. s., 6H), 1.08 (t, J=7.2 Hz, 3H)

Example S-19: Synthesis of N-benzyl-4-(2-(4-fluoro-2,6-dimethylphenoxy)-5-(2-hydroxypropan-2-yl)phenyl)-6-methyl-7-oxo-6,7-dihydrothieno[2,3-c]pyridine-2-carboxamide (General Procedure 3) (Compound 149)

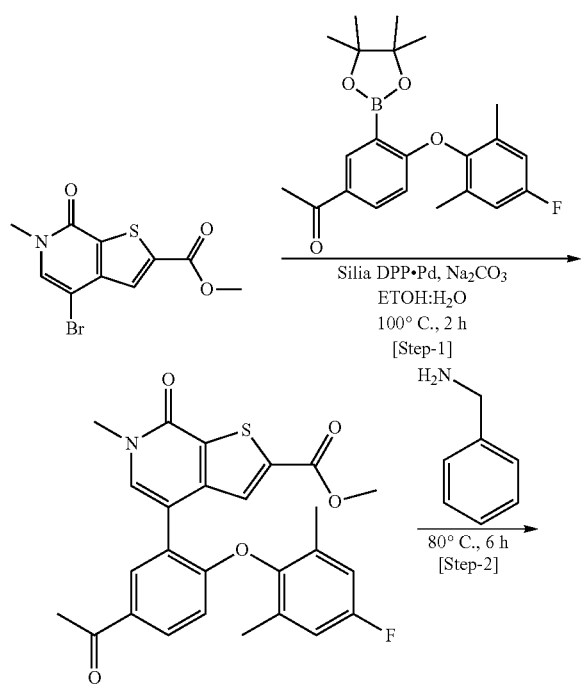

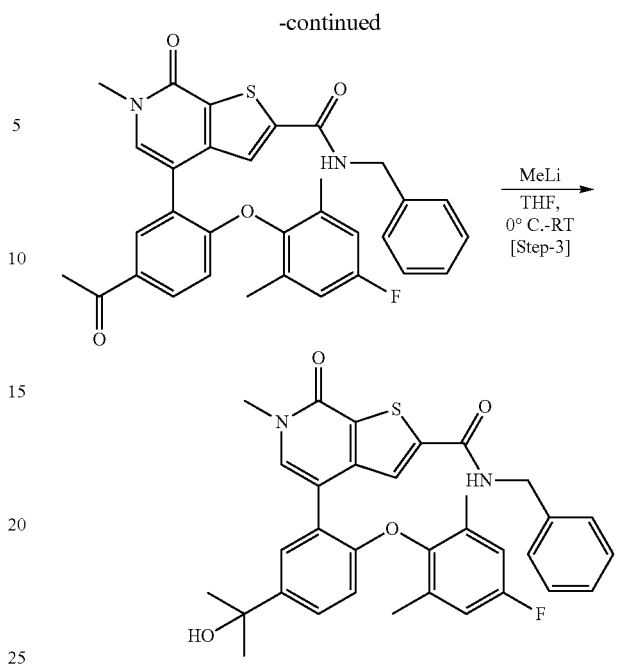

Step 1: Synthesis of methyl 4-(5-acetyl-2-(4-fluoro-2,6-dimethylphenoxy)phenyl)-6-methyl-7-oxo-6,7-dihydrothieno[2,3-c]pyridine-2-carboxylate: To a stirred solution of methyl 4-bromo-6-methyl-7-oxo-6,7-dihydrothieno[2,3-c]pyridine-2-carboxylate (5 g, 16.55 mmol, 1 eq) in ethanol (90 mL) were added 1-(4-(4-fluoro-2,6-dimethylphenoxy)-3-(4,4,5,5-tetra methyl-1,3,2-dioxaborolan-2-yl)phenyl)ethanone (7.62 g, 19.86 mmol, 1.2 eq) and Na$_2$CO$_3$ (3.50 g, 33.11 mmol, 2 eq) dissolved in water (10 mL). Silia DPP-Pd (0.30 mmol/g loading; 1.65 g, 0.496 mmol, 0.03 eq) was then added to the mixture and the resultant mixture was then heated at 100° C. for 2 h. The reaction was complete after 2 h and the mixture was filtered through the celite bed, washed with 5% MeOH in DCM (200 mL). The filtrate obtained was concentrated under reduced pressure to obtain a crude residue. The residue obtained (7.0 g) was stirred in MeOH (50 mL) for 30 min, filtered over Büchner funnel concentrated under reduced pressure to obtain a solid compound. Then solid obtained (6.0 g) was further stirred in diethyl ether (50 mL) for 30 min, filtered over Büchner funnel; dried under vacuum to afford title compound (5.0 g, 63%). LCMS: 480 [M+1]+

Step 2: Synthesis of 4-(5-acetyl-2-(4-fluoro-2,6-dimethylphenoxy)phenyl)-N-benzyl-6-methyl-7-oxo-6,7-dihydrothieno[2,3-c]pyridine-2-carboxamide: To methyl 4-(5-acetyl-2-(4-fluoro-2,6-dimethylphenoxy)phenyl)-6-methyl-7-oxo-6,7-dihydrothieno[2,3-c]pyridine-2-carboxylate (0.1 g, 0.208 mmol) was added benzylamine (2 mL) and the mixture was heated at 80° C. The reaction was complete after 6 h and the mixture was concentrated under reduced pressure to obtain a crude residue which was purified by CombiFlash Chromatography-to afford the title compound (0.1 g, 86%). LCMS: 555 [M+1]$^+$ Step 3: Synthesis of N-benzyl-4-(2-(4-fluoro-2,6-dimethylphenoxy)-5-(2-hydroxypropan-2-yl)phenyl)-6-methyl-7-oxo-6,7-dihydrothieno[2,3-c]pyridine-2-carboxamide: N-benzyl-4-(2-(4-fluoro-2,6-dimethylphenoxy)-5-(2-hydroxypropan-2-yl)phenyl)-6-methyl-7-oxo-6,7-dihydrothieno[2,3-c]pyridine-2-carboxamide (0.016 g, 15.6%) was prepared following General Procedure 1, Step 5 using 4-(5- acetyl-2-(4-fluoro-2,6-dimethylphenoxy)phenyl)-N-benzyl-6-methyl-7-oxo-6,7-dihydrothieno[2,3-c]pyridine-2-carboxamide (0.10 g, 0.18 mmol). LCMS: 571 [M+1]+; NMR (400 MHz, DMSO-d$_6$): δ 9.42 (s, 1H), 7.91 (s, 1H), 7.69 (s, 1H), 7.50 (d, J=2.2 Hz, 1H), 7.43-7.21 (m, 6H), 6.96 (d, J=8.8 Hz, 2H), 6.34 (d, J=8.3 Hz, 1H), 5.00 (s, 1H), 4.43 (d, J=5.3 Hz, 2H), 3.63 (s, 3H), 1.96 (hr. s., 6H), 1.44 (s, 6H).

Example S-20: Synthesis of 4-(2-(4-fluoro-2,6-dimethylphenoxy)-5-(2-hydroxypropan-2-yl)phenyl)-N,6-dimethyl-7-oxo-6,7-dihydrothieno[2,3-c]pyridine-2-carboxamide (Compound 150)

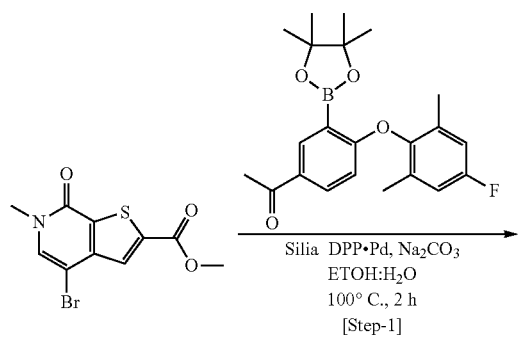

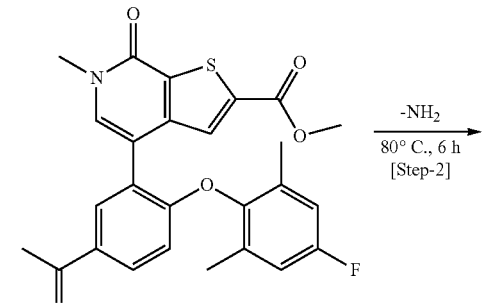

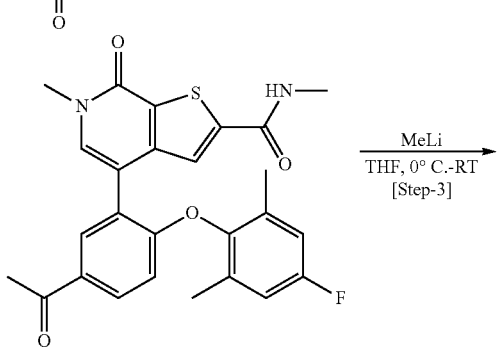

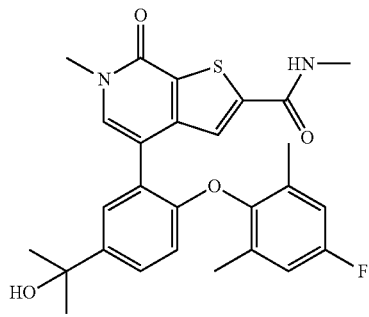

Step 1: Synthesis of methyl 4-(5-acetyl-2-(4-fluoro-2,6-dimethylphenoxy)phenyl)-6-methyl-7-oxo-6,7-dihydrothieno[2,3-c]pyridine-2-carboxylate: Methyl 4-(5-acetyl-2-(4-fluoro-2,6-dimethylphenoxy)phenyl)-6-methyl-7-oxo-6,7-dihydrothieno[2,3-c]pyridine-2-carboxylate (5.0 g, 63%) was prepared following General Procedure 3, Step 1 using methyl 4-bromo-6-methyl-7-oxo-6,7-dihydrothieno[2,3-c]pyridine-2-carboxylate (5 g, 16.55 mmol, 1 eq) and 1-(4-(4-fluoro-2,6-dimethylphenoxy)-3-(4,4,5,5-tetra methyl-1,3,2-dioxaborolan-2-yl)phenyl)ethanone (7.62 g, 19.86 mmol, 1.2 eq). LCMS: 480 [M+1]+

Step 2: Synthesis of 4-(5-acetyl-2-(4-fluoro-2,6-dimethylphenoxy)phenyl)-N,6-dimethyl-7-oxo-6,7-dihydrothieno[2,3-c]pyridine-2-carboxamide: 4-(5-acetyl-2-(4-fluoro-2,6-dimethyl phenoxy)phenyl)-N,6-dimethyl-7-oxo-6,7-dihydrothieno[2,3-c]pyridine-2-carboxamide (0.14 g, 73%) was prepared following General Procedure 3, Step 2 using methyl 4-(5-acetyl-2-(4-fluoro-2,6-dimethylphenoxy)phenyl)-6-methyl-7-oxo-6,7-dihydrothieno[2,3-c]pyridine-2-carboxylate (0.2 g, 0.42 mmol, 1 eq). LCMS: 479 [M+1]+

Step 3: Synthesis of 4-(2-(4-fluoro-2,6-dimethylphenoxy)-5-(2-hydroxypropan-2-yl)phenyl)-N,6-dimethyl-7-oxo-6,7-dihydrothieno[2,3-c]pyridine-2-carboxamide: 4-(2-(4-fluoro-2,6-dimethylphenoxy)-5-(2-hydroxypropan-2-yl)phenyl)-N,6-dimethyl-7-oxo-6,7-dihydrothieno[2,3-c]pyridine-2-carboxamide (0.009 g, 9%) was prepared following General Procedure 1, Step 5 using 4-(5-acetyl-2-(4-fluoro-2,6-dimethylphenoxy)phenyl)-N,6-dimethyl-7-oxo-6,7-dihydrothieno[2,3-c]pyridine-2-carboxamide (0.10 g, 0.209 mmol). LCMS: 495 [M+1]+; $^1$H NMR (400 MHz, DMSO-d$_6$): δ 8.81 (d, J=4.4 Hz, 1H), 7.78 (s, 1H), 7.69 (s, 1H), 7.50 (d, J=2.2 Hz, 1H), 7.40 (dd, J=2.2, 8.8 Hz, 1H), 6.97 (d, J=9.2 Hz, 2H), 6.35 (d, J=8.3 Hz, 1H), 5.01 (s, 1H), 3.63 (s, 3H), 2.74 (d, J=4.8 Hz, 3H), 1.99 (s, 6H), 1.45 (s, 6H).

Example S-21: Synthesis of 4-(2-(4-fluoro-2,6-dimethylphenoxy)-5-(2-hydroxypropan-2-yl)phenyl)-6-methyl-7-oxo-N-phenyl-6,7-dihydrothieno[2,3-c]pyridine-2-carboxamide (Compound 151)

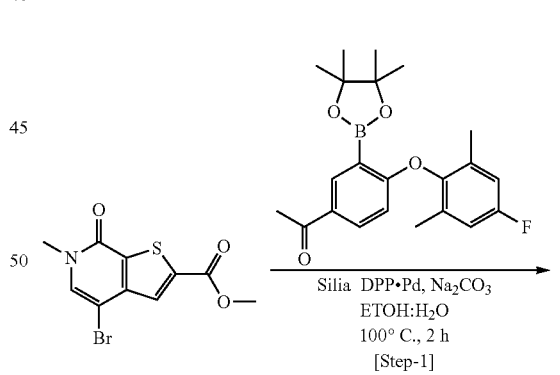

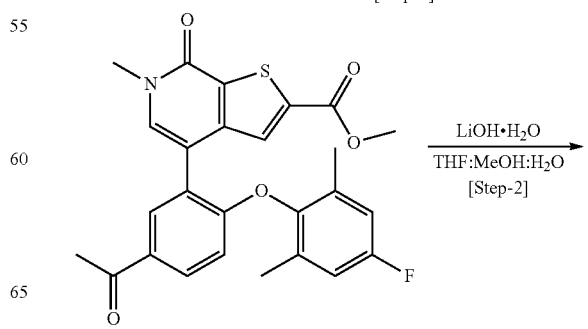

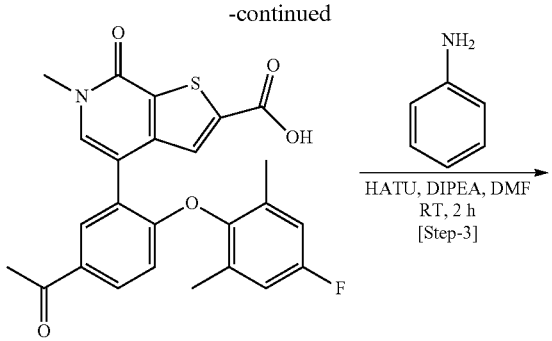

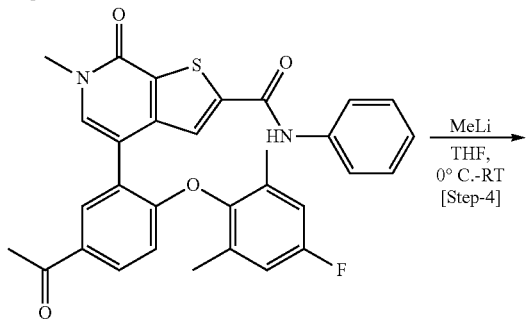

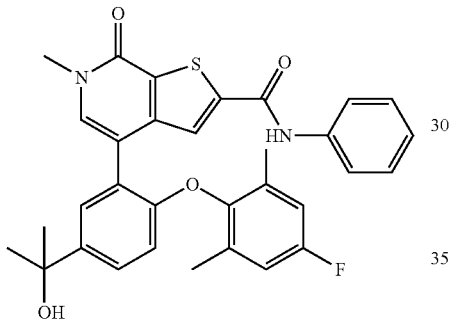

Step 1: Synthesis of methyl 4-(5-acetyl-2-(4-fluoro-2,6-dimethylphenoxy)phenyl)-6-methyl-7-oxo-6,7-dihydrothieno[2,3-c]pyridine-2-carboxylate: Methyl 4-(5-acetyl-2-(4-fluoro-2,6-dimethylphenoxy)phenyl)-6-methyl-7-oxo-6,7-dihydrothieno[2,3-c]pyridine-2-carboxylate (5.0 g, 63%) was prepared following General Procedure 3, Step 1 using methyl 4-bromo-6-methyl-7-oxo-6,7-dihydrothieno[2,3-c]pyridine-2-carboxylate (5 g, 16.55 mmol, 1 eq) and 1-(4-(4-fluoro-2,6-dimethylphenoxy)-3-(4,4,5,5-tetramethyl-1,3,2-dioxaborolan-2-yl)phenyl)ethanone (7.62 g, 19.86 mmol, 1.2 eq). LCMS: 480 [M+1]+

Step 2: Synthesis of 4-(5-acetyl-2-(4-fluoro-2,6-dimethylphenoxy)phenyl)-6-methyl-7-oxo-6,7-dihydrothieno[2,3-c]pyridine-2-carboxylic acid: 4-(5-acetyl-2-(4-fluoro-2,6-dimethylphenoxy)phenyl)-6-methyl-7-oxo-6,7-dihydrothieno[2,3-c]pyridine-2-carboxylic acid (0.35 g, 86%) was prepared following General Procedure 2, Step 4 using methyl 4-(5-acetyl-2-(4-fluoro-2,6-dimethylphenoxy)phenyl)-6-methyl-7-oxo-6,7-dihydrothieno[2,3-c]pyridine-2-carboxylate (0.30 g, 0.626 mmol). LCMS: 466 [M+1]+

Step 3: Synthesis of 4-(5-acetyl-2-(4-fluoro-2,6-dimethylphenoxy)phenyl)-6-methyl-7-oxo-N-phenyl-6,7-dihydrothieno[2,3-c]pyridine-2-carboxamide: To a stirred solution of 4-(5-acetyl-2-(4-fluoro-2,6-dimethylphenoxy)phenyl)-6-methyl-7-oxo-6,7-dihydrothieno[2,3-c]pyridine-2-carboxylic acid (0.1 g, 0.215 mmol) in DMF (5 mL) was added HATU (0.16 g, 0.43 mmol, 2.0 eq) at 0° C. and the mixture was stirred for 10 min. DIPEA (0.19 mL, 1.07 mmol, 4 eq) and aniline (0.3 g, 0.332 mmol, 1.5 eq) were then added to the mixture and the resultant mixture was stirred at RT for 16 h. The reaction was complete after 16 h and to the mixture was added water (200 mL) and extracted with EtOAc (300 mL). The organic layer was washed with water (100 mL), brine (150 mL) dried over anhydrous Na$_2$SO$_4$, filtered and concentrated under reduced pressure to afford a crude residue which was purified by combiFlash Chromatography to afford the title compound (0.1 g, 86%). LCMS: 541 [M+1]+

Step 4: Synthesis of 4-(2-(4-fluoro-2,6-dimethylphenoxy)-5-(2-hydroxypropan-2-yl)phenyl)-6-methyl-7-oxo-N-phenyl-6,7-dihydrothieno[2,3-c]pyridine-2-carboxamide: 4-(2-(4-fluoro-2,6-dimethylphenoxy)-5-(2-hydroxypropan-2-yl)phenyl)-6-methyl-7-oxo-N-phenyl-6,7-dihydrothieno[2,3-c]pyridine-2-carboxamide (0.007 g, 14%) was prepared following General Procedure 1, Step 5 using 4-(5-acetyl-2-(4-fluoro-2,6-dimethylphenoxy)phenyl)-6-methyl-7-oxo-N-phenyl-6,7-dihydrothieno[2,3-c]pyridine-2-carboxamide (0.050 g, 0.090 mmol). LCMS: 557 [M+1]+; NMR (400 MHz, DMSO-d$_6$): δ 10.59 (s, 1H), 8.20 (s, 1H), 7.77-7.66 (m, 2H), 7.56 (d, J=2.2 Hz, 1H), 7.45-7.39 (m, 1H), 7.38-7.32 (m, 1H), 7.13 (s, 1H), 6.96 (d, J=8.8 Hz, 2H), 6.38 (d, J=8.3 Hz, 1H), 5.03 (s, 1H), 3.66 (s, 3H), 2.02 (hr. s., 6H), 1.47 (s, 6H).

Example S-22: Synthesis of 4-(2-(4-fluoro-2,6-dimethylphenoxy)-5-(2-hydroxypropan-2-yl)phenyl)-6-methyl-2-(5-methyl-4H-1,2,4-triazol-3-yl)thieno[2,3-c]pyridin-7(6H)-one (General Procedure 4) (Compound 152)

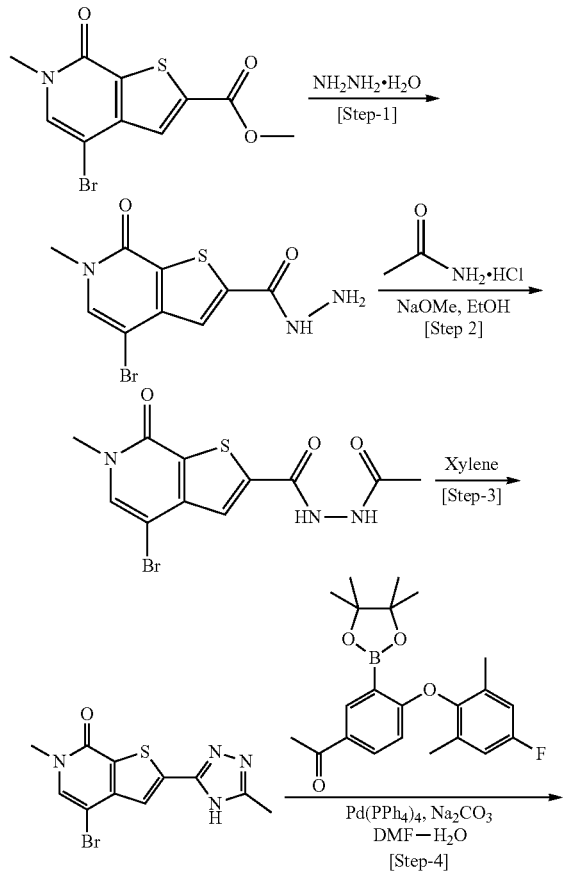

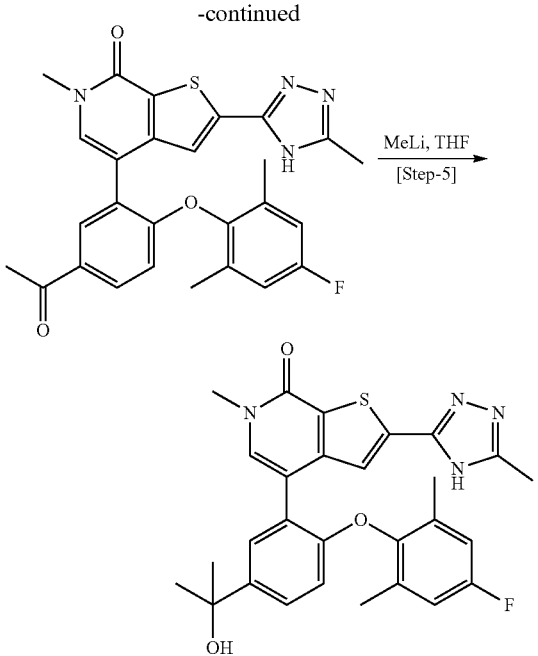

Step 1: Synthesis of 4-bromo-6-methyl-7-oxo-6,7-dihydrothieno[2,3-c]pyridine-2-carbohydrazide: To a stirred solution of methyl 4-bromo-6-methyl-7-oxo-6,7-dihydrothieno [2,3-c]pyridine-2-carboxylate (0.50 g, 1.66 mmol) in MeOH (10 mL) was added hydrazine hydrate (5.3 mL, 16.61 mmol, 10 eq) and the mixture was refluxed at 80° C. for 3 h. The reaction was complete after 3 h; water (100 mL) was added to it to obtain a precipitate which was filtered over Büchner funnel, washed with EtOAc (100 mL) to afford the title compound (400 mg, 80%). LCMS: 302 [M+H]+, 304 [M+H+2]+

Step 2: Synthesis of N'-acetyl-4-bromo-6-methyl-7-oxo-6,7-dihydrothieno[2,3-c]pyridine-2-carbohydrazide: To a stirred solution of acetamide hydrochloride (0.22 g, 2.31 mmol) in ethanol (5 mL) was added sodium methoxide (0.125 g, 2.13 mmol, 2.0 eq) and the mixture was heated at 70° C. for 3 h. After 3 h, the mixture was filtered by over Büchner funnel. To the filtrate obtained was added 4-bromo-6-methyl-7-oxo-6,7-dihydrothieno[2,3-c]pyridine-2-carbohydrazide (0.35 mg, 1.115 mmol) and the mixture was further heated at 70° C. for 16 h. The reaction was complete after 16 h and the mixture was poured in water (50 mL) to obtain a precipitate which was filtered over a Büchner funnel to afford the title compound (300 mg, 75%). LCMS: 343 [M]+, 344 [M+2H]+, 346 [M+H+2]+

Step 3: Synthesis of 4-bromo-6-methyl-2-(5-methyl-4H-1,2,4-triazol-3-yl)thieno[2,3-c]pyridin-7(6H)-one: N'-acetyl-4-bromo-6-methyl-7-oxo-6,7-dihydrothieno[2,3-c]pyridine-2-carbohydrazide (0.30 g, 0.87 mmol) in a mixture of xylene (5 mL) and EtOH (2 mL) was heated at 120° C. for 48 h. Upon completion, the mixture was filtrated through a Büchner funnel and filtrate was collected, concentrated under reduced pressure to obtain a crude which was purified by CombiFlash Chromatography to afford the title compound (100 mg, 35%). LCMS: 325 [M+H]+, 327 [M+H+2]+

Step 4: Synthesis of 4-(5-acetyl-2-(4-fluoro-2,6-dimethylphenoxy)phenyl)-6-methyl-2-(5-methyl-4H-1,2,4-triazol-3-yl)thieno[2,3-c]pyridin-7(6H)-one: To a stirred solution of 4-bromo-6-methyl-2-(5-methyl-4H-1,2,4-triazol-3-yl) thieno[2,3-c]pyridin-7(6H)-one (0.1 g, 0.307 mmol, 1 eq) in DMF (3 mL) were added 1-(4-(4-fluoro-2,6-dimethylphenoxy)-3-(4,4,5,5-tetramethyl-1,3,2-dioxaborolan-2-yl)phenyl)ethanone (0.15 g, 0.04 mmol, 1.3 eq) and Na$_2$CO$_3$ (0.08 g, 0.77 mmol, 2.5 eq) dissolved in water (0.5 mL) and the mixture was degassed under nitrogen for 40 min. Pd(PPh$_3$)$_4$ (0.017 g, 0.01 mmol, 0.03 eq) was then added to the mixture and the mixture was further degassed under nitrogen for 20 min. The resultant mixture was then heated at 120° C. for 16 h. Upon completion, the mixture was diluted with water (50 mL) and extracted with EtOAc (100 mL×2). The combined organic layers were washed with water (50 mL), brine (40 mL), dried over anhydrous Na$_2$SO$_4$, filtered and concentrated under reduced pressure to obtain a crude residue which was purified by CombiFlash Chromatography to afford the title compound (0.075 g, 50%). LCMS: 503 [M+1]+

Step 5: Synthesis of 4-(2-(4-fluoro-2,6-dimethylphenoxy)-5-(2-hydroxypropan-2-yl)phenyl)-6-methyl-2-(5-methyl-4H-1,2,4-triazol-3-yl)thieno[2,3-c]pyridin-7(6H)-one: 4-(2-(4-fluoro-2,6-dimethylphenoxy)-5-(2-hydroxypropan-2-yl)phenyl)-6-methyl-2-(5-methyl-4H-1,2,4-triazol-3-yl)thieno[2,3-c]pyridin-7(6H)-one (0.009 g, 17.6%) was prepared following General Procedure 1, Step 5 using 4-(5-acetyl-2-(4-fluoro-2,6-dimethylphenoxy)phenyl)-6-methyl-2-(5-methyl-4H-1,2,4-triazol-3-yl)thieno[2,3-c]pyridin-7(6H)-one (0.050 g, 0.099 mmol). LCMS: 519 [M+1]+; NMR (400 MHz, DMSO-d$_6$): δ 13.93 (hr. s., 1H), 7.71 (hr. s., 1H), 7.51 (hr. s., 2H), 7.39 (hr. s., 1H), 6.97 (d, J=8.8 Hz, 2H), 6.33 (hr. s., 1H), 5.02 (hr. s., 1H), 3.64 (hr. s., 3H), 2.39 (hr. s., 3H), 2.01 (hr. s., 6H), 1.45 (hr. s., 6H)

Example S-23: Synthesis of 2-(benzo[d]oxazol-2-yl)-4-(2-(4-fluoro-2,6-dimethylphenoxy)-5-(2-hydroxypropan-2-yl)phenyl)-6-methylthieno[2,3-c]pyridin-7(6H)-one (General Procedure 5) (Compound 153)

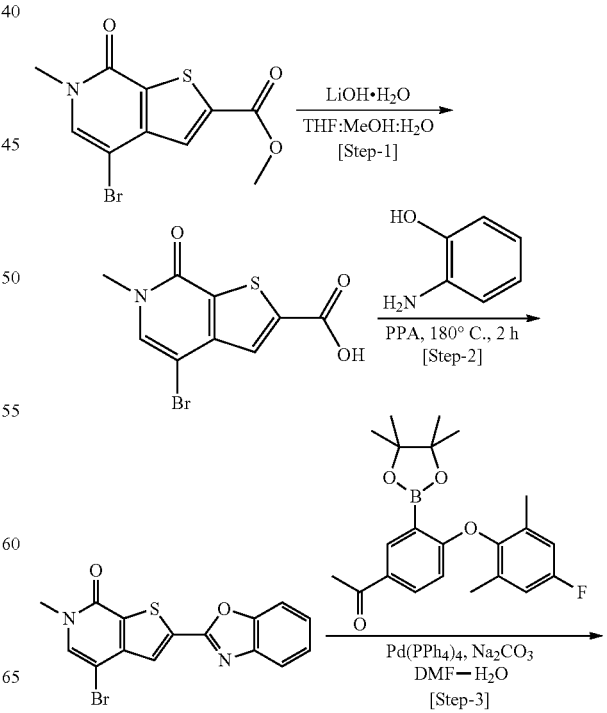

-continued

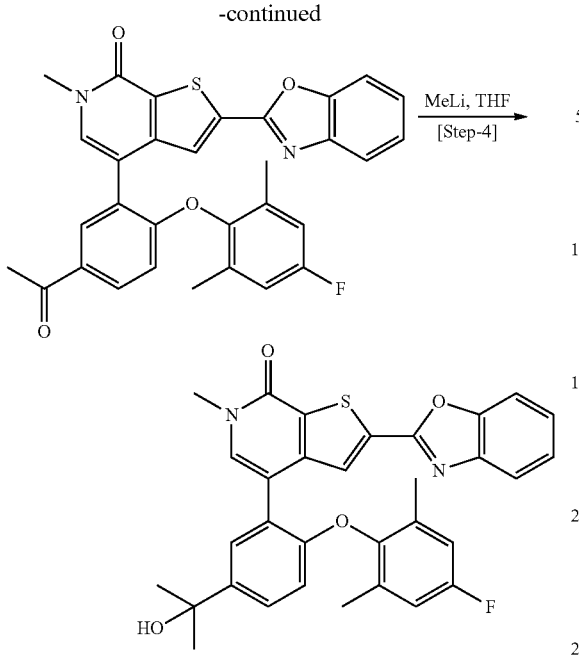

Step 1: Synthesis of 4-bromo-6-methyl-7-oxo-6,7-dihydrothieno[2,3-c]pyridine-2-carboxylic acid: 4-bromo-6-methyl-7-oxo-6,7-dihydrothieno[2,3-c]pyridine-2-carboxylic acid (4 g, 84%) was prepared following General Procedure 2, Step 4 using methyl 4-bromo-6-methyl-7-oxo-6,7-dihydrothieno[2,3-c]pyridine-2-carboxylate (5.0 g, 16.6 mmol). LCMS: 288 [M+H]+, 290 [M+H+2]+

Step 2: Synthesis of 2-(benzo[d]oxazol-2-yl)-4-bromo-6-methylthieno[2,3-c]pyridin-7(6H)-one: To a stirred solution of 4-bromo-6-methyl-7-oxo-6,7-dihydrothieno[2,3-c]pyridine-2-carboxylic acid (1.0 g, 3.47 mmol) in polyphosphoric acid (10 mL) was added 2-aminophenol (0.45 g, 4.10 mmol, 1.2 eq) and the mixture was heated at 180° C. The reaction was complete after 2 h and the mixture was quenched with 2N—NaOH (200 mL) to obtain a precipitate which was filtered over Büchner funnel to afford the title compound (0.5 g, 41%). LCMS: 361 [M+H]+, 363 [M+H+2]+

Step 3: Synthesis of 4-(5-acetyl-2-(4-fluoro-2,6-dimethylphenoxy)phenyl)-2-(benzo[d]oxazol-2-yl)-6-methylthieno[2,3-c]pyridin-7(6H)-one: 4-(5-acetyl-2-(4-fluoro-2,6-dimethylphenoxy)phenyl)-2-(benzo[d]oxazol-2-yl)-6-methylthieno[2,3-c]pyridin-7(6H)-one (0.15 g, 20%) was prepared following General Procedure 4, Step 4 using 2-(benzo[d]oxazol-2-yl)-4-bromo-6-methylthieno[2,3-c]pyridin-7(6H)-one (0.5 g, 1.392 mmol, 1 eq). LCMS: 539 [M+1]+

Step 4: Synthesis of 2-(benzo[d]oxazol-2-yl)-4-(2-(4-fluoro-2,6-dimethylphenoxy)-5-(2-hydroxypropan-2-yl)phenyl)-6-methylthieno[2,3-c]pyridin-7(6H)-one: 2-(benzo[d]oxazol-2-yl)-4-(2-(4-fluoro-2,6-dimethylphenoxy)-5-(2-hydroxypropan-2-yl)phenyl)-6-methylthieno [2,3-c]pyridin-7(6H)-one (0.022 g, 21%) was prepared following General Procedure 1, Step 5 using 4-(5-acetyl-2-(4-fluoro-2,6-dimethylphenoxy)phenyl)-2-(benzo[d]oxazol-2-yl)-6-methylthieno[2,3-c]pyridin-7(6H)-one (0.10 g, 0.185 mmol). LCMS: 555 [M+1]+; NMR (400 MHz, DMSO-d6): δ 7.84 (d, J=8.3 Hz, 3H), 7.78 (d, J=7.5 Hz, 1H), 7.56 (d, J=2.2 Hz, 1H), 7.52-7.37 (m, 3H), 6.98 (d, J=9.2 Hz, 2H), 6.40 (d, J=8.8 Hz, 1H), 5.06 (s, 1H), 3.68 (s, 3H), 2.05 (s, 6H), 1.46 (s, 6H).

Example S-24: Synthesis of 2-(1H-benzo[d]imidazol-2-yl)-4-(2-(4-fluoro-2,6-dimethylphenoxy)-5-(2-hydroxypropan-2-yl)phenyl)-6-methylthieno[2,3-c]pyridin-7(6H)-one (General Procedure 6) (Compound 154)

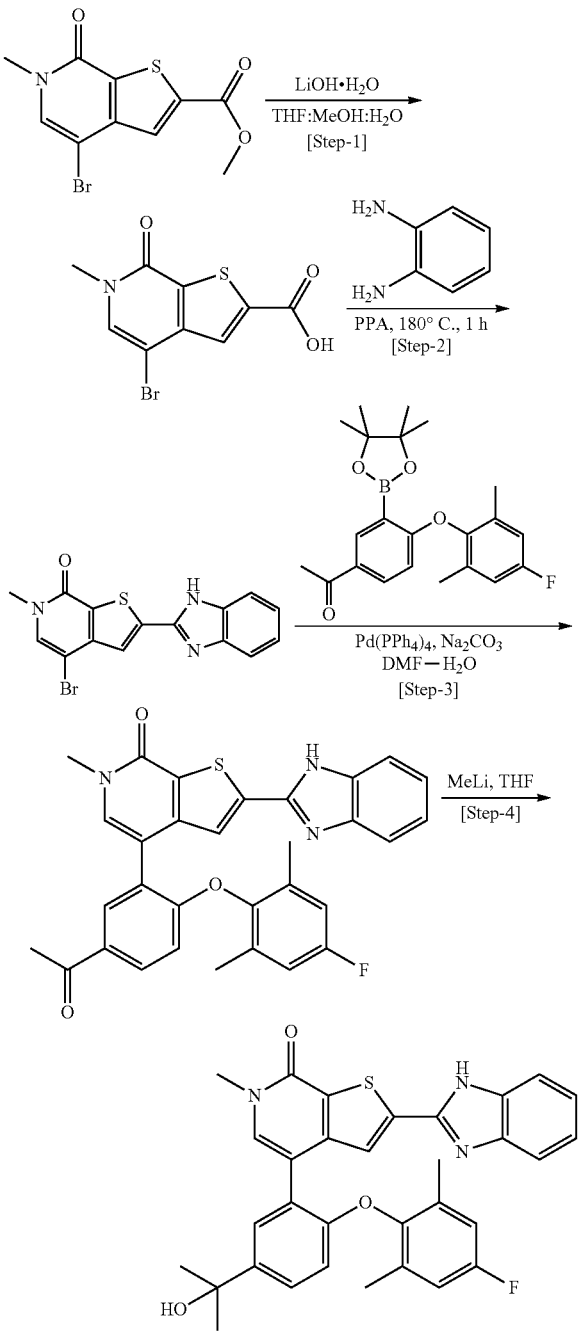

Step 1: Synthesis of 4-bromo-6-methyl-7-oxo-6,7-dihydrothieno[2,3-c]pyridine-2-carboxylic acid: 4-bromo-6-methyl-7-oxo-6,7-dihydrothieno[2,3-c]pyridine-2-carboxylic acid (4 g, 84%) was prepared following General Procedure 2, Step 4 using methyl 4-bromo-6-methyl-7-oxo-6,7-dihydrothieno[2,3-c]pyridine-2-carboxylate (5.0 g, 16.6 mmol). LCMS: 288 [M+H]+, 290 [M+H+2]+

Step 2: Synthesis of 2-(1H-benzo[d]imidazol-2-yl)-4-bromo-6-methylthieno[2,3-c]pyridin-7(6H)-one: To a stirred solution of 4-bromo-6-methyl-7-oxo-6,7-dihydrothieno[2,3-c]pyridine-2-carboxylic acid (1.0 g, 3.47 mmol) in polyphosphoric acid (10 mL) was added benzene-1,2-diamine (449 mg, 4.10 mmol, 1.2 eq) and the mixture was heated at 180° C. The reaction was complete after 1 h and the mixture was quenched with 2N—NaOH (200 mL) to obtain a precipitate which was filtered over Büchner funnel to afford the title compound (0.5 g, 41%). LCMS: 360 [M+H]⁺, 362 [M+H+2]⁺

Step 3: Synthesis of 4-(5-acetyl-2-(4-fluoro-2,6-dimethylphenoxy)phenyl)-2-(1H-benzo[d]imidazol-2-yl)-6-methylthieno[2,3-c]pyridin-7(6H)-one: 4-(5-acetyl-2-(4-fluoro-2,6-dimethylphenoxy)phenyl)-2-(1H-benzo[d]imidazol-2-yl)-6-methylthieno[2,3-c]pyridin-7(6H)-one (0.2 g, 26%) was prepared following General Procedure 4, Step 4 using 2-(1H-benzo[d]imidazol-2-yl)-4-bromo-6-methylthieno[2,3-c]pyridin-7(6H)-one (0.5 g, 1.39 mmol, 1 eq). LCMS: 538 [M+1]⁺

Step 4: Synthesis of 2-(1H-benzo[d]imidazol-2-yl)-4-(2-(4-fluoro-2,6-dimethylphenoxy)-5-(2-hydroxypropan-2-yl)phenyl)-6-methylthieno[2,3-c]pyridin-7(6H)-one: 2-(1H-benzo[d] imidazol-2-yl)-4-(2-(4-fluoro-2,6-dimethylphenoxy)-5-(2-hydroxypropan-2-yl)phenyl)-6-methylthieno[2,3-c]pyridin-7(6H)-one (0.007 g, 7%) was prepared following General Procedure 1, Step 5 using 4-(5-amino-2-(2,6-dimethylphenoxy)phenyl)-6-methyl-2-(5-methyl-1,3,4-oxadiazol-2-yl)thieno[2,3-c]pyridin-7(6H)-one (0.20 g, 0.186 mmol, 1 eq). LCMS: 554 [M+1]⁺; ¹H NMR (400 MHz, MeOH-d₄): δ 7.84 (s, 1H), 7.69-7.61 (m, 2H), 7.55-7.50 (m, 1H), 7.43 (dd, J=2.4, 8.6 Hz, 1H), 7.29 (d, J=3.5 Hz, 3H), 6.81 (d, J=8.8 Hz, 2H), 6.46 (d, J=8.3 Hz, 1H), 3.77 (s, 3H), 2.05 (s, 6H), 1.58 (s, 6H).

Example S-25: Synthesis of N,N-diethyl-4-(2-(4-fluoro-2,6-dimethylphenoxy)-5-(2-hydroxy propan-2-yl)phenyl)-6-methyl-7-oxo-6,7-dihydrothieno[2,3-c]pyridine-2-carboxamide (Compound 155)

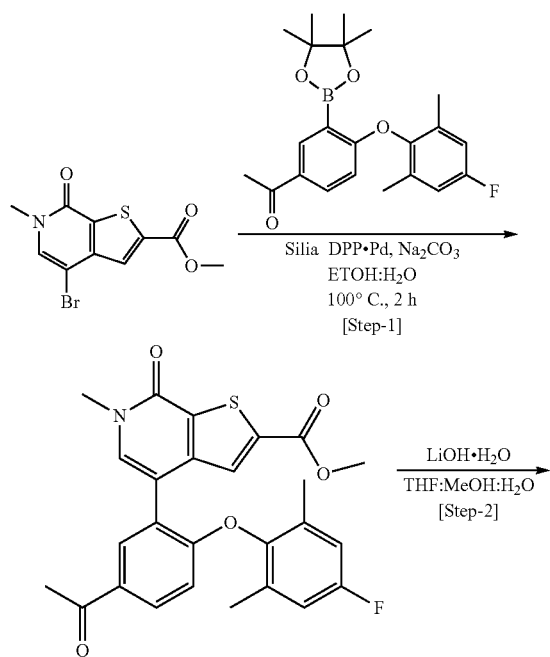

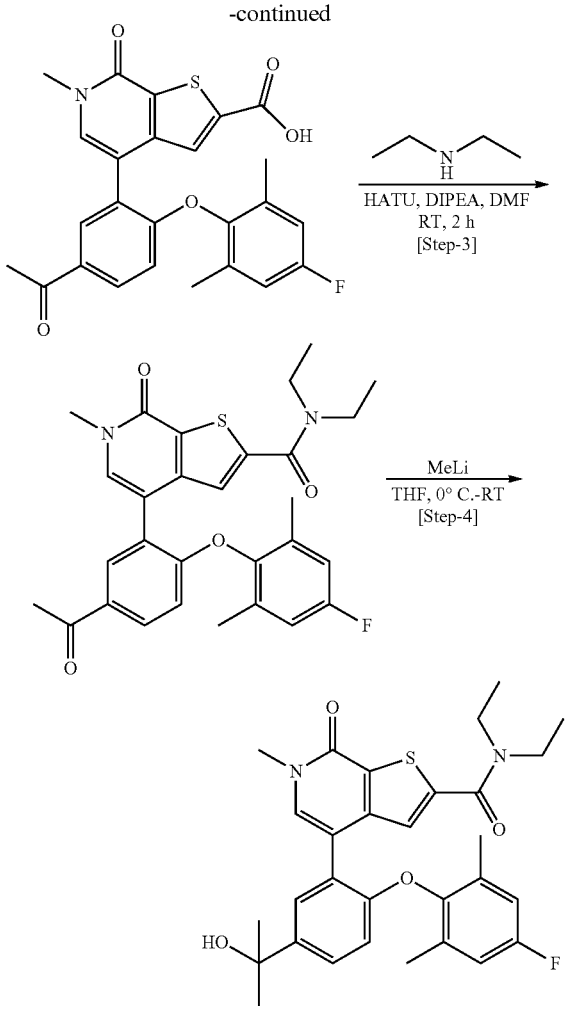

Step 1: Synthesis of methyl 4-(5-acetyl-2-(4-fluoro-2,6-dimethylphenoxy)phenyl)-6-methyl-7-oxo-6,7-dihydrothieno[2,3-c]pyridine-2-carboxylate: Methyl 4-(5-acetyl-2-(4-fluoro-2,6-dimethylphenoxy)phenyl)-6-methyl-7-oxo-6,7-dihydrothieno[2,3-c]pyridine-2-carboxylate (5.0 g, 63%) was prepared following General Procedure 3, Step 1 using methyl 4-bromo-6-methyl-7-oxo-6,7-dihydrothieno[2,3-c]pyridine-2-carboxylate (5 g, 16.55 mmol, 1 eq) and 1-(4-(4-fluoro-2,6-dimethylphenoxy)-3-(4,4,5,5-tetra methyl-1,3,2-dioxaborolan-2-yl)phenyl)ethanone (7.62 g, 19.86 mmol, 1.2 eq). LCMS: 480 [M+1]⁺

Step 2: Synthesis of 4-(5-acetyl-2-(4-fluoro-2,6-dimethylphenoxy)phenyl)-6-methyl-7-oxo-6,7-dihydrothieno[2,3-c]pyridine-2-carboxylic acid: 4-(5-acetyl-2-(4-fluoro-2,6-dimethylphenoxy)phenyl)-6-methyl-7-oxo-6,7-dihydrothieno[2,3-c]pyridine-2-carboxylic acid (0.35 g, 86%) was prepared following General Procedure 2, Step 4 using methyl 4-(5-acetyl-2-(4-fluoro-2,6-dimethylphenoxy)phenyl)-6-methyl-7-oxo-6,7-dihydrothieno[2,3-c]pyridine-2-carboxylate (0.30 g, 0.626 mmol). LCMS: 466 [M+1]⁺

Step 3: Synthesis of 4-(5-acetyl-2-(4-fluoro-2,6-dimethylphenoxy)phenyl)-N,N-diethyl-6-methyl-7-oxo-6,7-dihydrothieno[2,3-c]pyridine-2-carboxamide: To a stirred solution of 4-(5-acetyl-2-(4-fluoro-2,6-dimethylphenoxy)phenyl)-6-methyl-7-oxo-6,7-dihydrothieno[2,3-c]pyridine-2-carboxylic acid (100 mg, 0.215 mmol) in DMF (4 mL) was added HATU (163 mg, 0.43 mmol, 2.0 eq) at 0° C. and the mixture was stirred for 10 min. DIPEA (0.11 mL mg, 0.645 mmol, 3 eq) and diethylamine (31 mg, 0.430 mmol, 2.0 eq) were then added to the mixture and the resultant mixture was stirred at RT for 16 h. The reaction was complete after 16 h and to the mixture was added water (200 mL) and extracted with EtOAc (300 mL). The organic layer was washed with water (100 mL), brine (150 mL) dried over anhydrous $Na_2SO_4$, filtered and concentrated under reduced pressure to afford a crude residue which was purified by CombiFlash Chromatography to afford the title compound (100 mg, 90%). LCMS: 521 [M+1]+

Step 4: Synthesis of N,N-diethyl-4-(2-(4-fluoro-2,6-dimethylphenoxy)-5-(2-hydroxy propan-2-yl)phenyl)-6-methyl-7-oxo-6,7-dihydrothieno[2,3-c]pyridine-2-carboxamide: N,N-diethyl-4-(2-(4-fluoro-2,6-dimethylphenoxy)-5-(2-hydroxy propan-2-yl)phenyl)-6-methyl-7-oxo-6,7-dihydrothieno[2,3-c]pyridine-2-carboxamide (3 mg, 5.8%) was prepared following General Procedure 1, Step 5 using 4-(5-acetyl-2-(4-fluoro-2,6-dimethylphenoxy) phenyl)-N,N-diethyl-6-methyl-7-oxo-6,7-dihydrothieno[2,3-c]pyridine-2-carboxamide (0.050 g, 0.096 mmol). LCMS: 537 [M+1]+; NMR (400 MHz, MeOH-$d_4$): δ 7.65 (s, 1H), 7.56 (d, J=2.6 Hz, 1H), 7.40 (dd, J=2.6, 8.8 Hz, 1H), 7.33 (s, 1H), 6.84 (d, J=8.8 Hz, 2H), 6.42 (d, J=8.3 Hz, 1H), 3.76 (s, 3H), 3.52 (d, J=7.5 Hz, 4H), 2.07-1.95 (m, 6H), 1.60-1.50 (m, 6H), 1.20 (hr. s., 6H).

Example S-26: Synthesis of N-ethyl-7-(2-(4-fluoro-2,6-dimethylphenoxy)-5-(prop-Fen-2-yl)phenyl)-5-methyl-4-oxo-4,5-dihydrothieno[3,2-c]pyridine-2-carboxamide (General Procedure 7) (Compound 156)

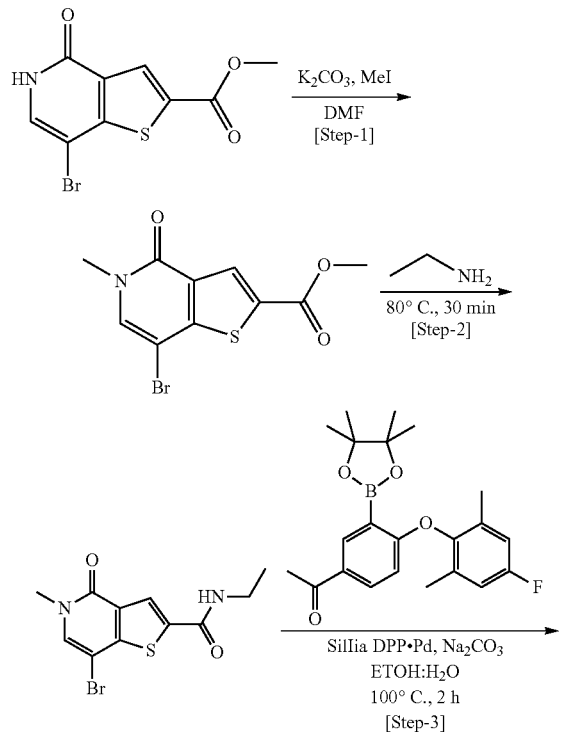

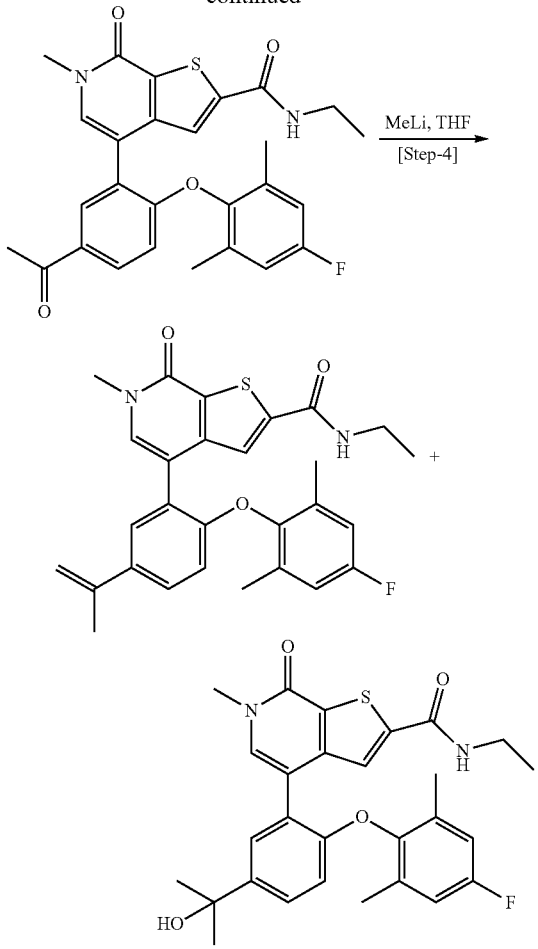

Step 1: Synthesis of Methyl 7-bromo-5-methyl-4-oxo-4,5-dihydrothieno[3,2-c]pyridine-2-carboxylate: To a stirred solution of methyl methyl 7-bromo-4-oxo-4,5-dihydrothieno[3,2-c]pyridine-2-carboxylate (6.7 g, 23.3 mmol) in DMF (60 mL) was added $K_2CO_3$ (4.83 g, 35 mmol, 1.5 eq) at 0° C. slowly over a period of 15 min and the mixture was stirred at same temperature for 30 min. MeI (4.43 mL, 70.3 mmol) was then slowly added to the mixture at 0° C. and the resultant mixture was stirred at RT for 30 min. The reaction was monitored on TLC. Upon completion, the mixture was slowly quenched with ice-cold water (500 mL) and extracted with EtOAc (500 mL×3). The combined organic layers were washed with water (500 mL), brine (150 mL), dried over anhydrous $Na_2SO_4$, filtered and concentrated under reduced pressure to obtain a crude which was triturated with diethyl ether (20 mL) to afford the title compound (5.2 g, 74%). LC-MS: 301 [M]+, 303 [M+2H]+; 1H NMR: (400 MHz, DMSO-$d_6$) δ 8.18 (s, 1H), 8.14 (s, 1H), 3.88 (s, 3H), 3.52 (s, 4H)

Step 2: Synthesis of 7-bromo-N-ethyl-5-methyl-4-oxo-4,5-dihydrothieno[3,2-c]pyridine-2-carboxamide: 7-bromo-N-ethyl-5-methyl-4-oxo-4,5-dihydrothieno[3,2-c]pyridine-2-carboxamide (5.2 g, 96%) was prepared following General Procedure 1, Step 4a using methyl 7-bromo-5-methyl-4-oxo-4,5-dihydrothieno[3,2-c]pyridine-2-carboxylate (5.2 g, 17.27 mmol, 1 eq). LC-MS: 314 [M]+, 316 [M+2H]+; 1H NMR: (400 MHz, DMSO-$d_6$) δ 8.81 (s, 1H), 8.35 (s, 1H), 8.07 (s, 1H), 3.33 (s, 3H), 3.27 (dd, J=5.5, 7.2 Hz, 2H), 1.13 (t, J=7.2 Hz, 3H)

221

Step 3: Synthesis of 7-(5-acetyl-2-(4-fluoro-2,6-dimethylphenoxy)phenyl)-N-ethyl-5-methyl-4-oxo-4,5-dihydrothieno[3,2-c]pyridine-2-carboxamide: 7-(5-acetyl-2-(4-fluoro-2,6-dimethylphenoxy)phenyl)-N-ethyl-5-methyl-4-oxo-4,5-dihydrothieno[3,2-c]pyridine-2-carboxamide (2.0 g, 48%) was prepared following General Procedure 3, Step 1 using 7-bromo-N-ethyl-5-methyl-4-oxo-4,5-dihydrothieno[3,2-c]pyridine-2-carboxamide (2.63 g, 8.34 mmol, 1 eq). LCMS: 493 [M+H]+

Step 4: Synthesis of N-ethyl-7-(2-(4-fluoro-2,6-dimethylphenoxy)-5-(prop-1-en-2-yl)phenyl)-5-methyl-4-oxo-4,5-dihydrothieno[3,2-c]pyridine-2-carboxamide: To a stirred solution of 7-(5-acetyl-2-(4-fluoro-2,6-dimethylphenoxy)phenyl)-N-ethyl-5-methyl-4-oxo-4,5-dihydrothieno[3,2-c]pyridine-2-carboxamide (1.0 g, 2.03 mmol) in anhydrous THF (40 mL) was added methyl lithium (5.0 mL, 8.13 mmol, 4 eq) at 0° C. dropwise and the mixture was stirred at same temperature for 10 min. The reaction was complete after 10 min and the mixture was quenched with saturated NH4Cl solution (50 mL) slowly. The aqueous layer was then extracted with EtOAc (300 mL×2). The combined organic layers were washed with water (100 mL), brine (100 mL), dried over anhydrous Na2SO4, filtered and concentrated under reduced pressure to obtain a crude which was purified by CombiFlash Chromatography to afford N-ethyl-7-(2-(4-fluoro-2,6-dimethylphenoxy)-5-(2-hydroxypropan-2-yl)phenyl)-5-methyl-4-oxo-4,5-dihydro thieno[3,2-c]pyridine-2-carboxamide as a major product and N-ethyl-7-(2-(4-fluoro-2,6-dimethylphenoxy)-5-(prop-1-en-2-yl)phenyl)-5-methyl-4-oxo-4,5-dihydrothieno[3,2-c]pyridine-2-carboxamide (0.0065 g, 0.65%). LCMS: 491 [M+1]+; 1H NMR (400 MHz, DMSO-d6): δ 8.76 (s, 1H), 8.30 (s, 1H), 7.83 (s, 1H), 7.62 (d, J=2.2 Hz, 1H), 7.47 (d, J=6.1 Hz, 1H), 7.02 (d, J=9.2 Hz, 2H), 6.38 (d, J=8.8 Hz, 1H), 5.41 (s, 1H), 5.06 (s, 1H), 3.60 (s, 3H), 3.29-3.19 (m, 2H), 2.10 (s, 3H), 2.03 (s, 6H), 1.11 (t, J=7.2 Hz, 3H)

Example S-27: Synthesis of N-(3-(2-(1H-benzo[d]imidazol-2-yl)-6-methyl-7-oxo-6,7-dihydrothieno[2,3-c]pyridin-4-yl)-4-(4-fluoro-2,6-dimethylphenoxy)phenyl)ethane sulfonamide (Compound 157)

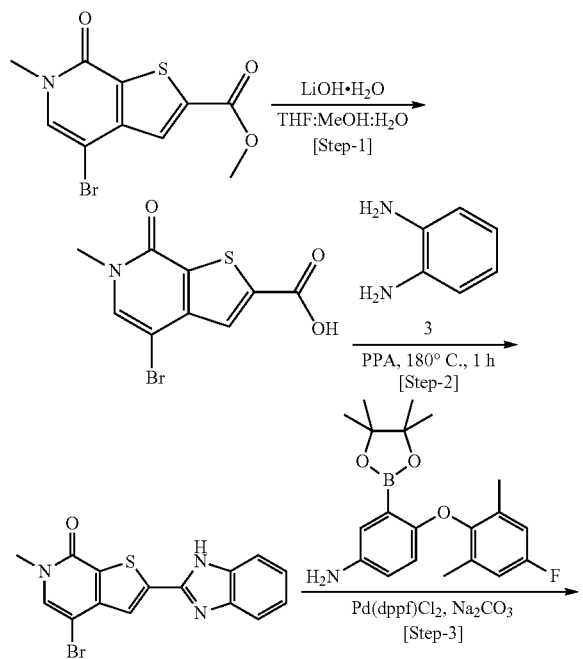

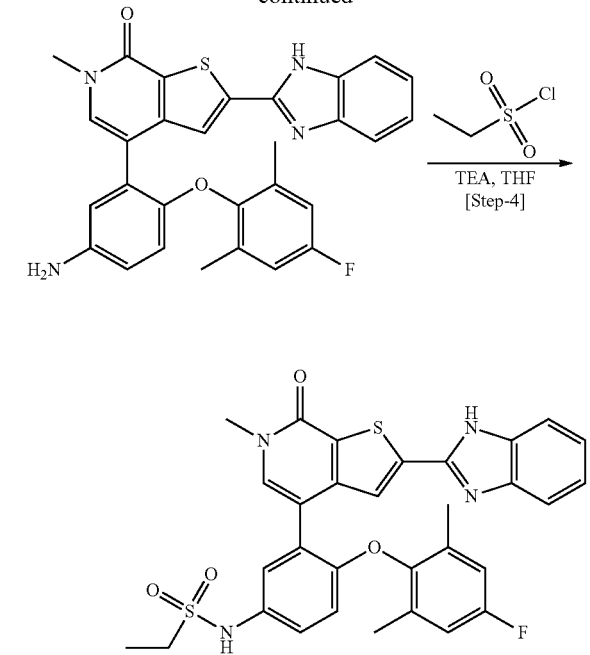

Step 1: Synthesis of 4-bromo-6-methyl-7-oxo-6,7-dihydrothieno[2,3-c]pyridine-2-carboxylic acid: 4-bromo-6-methyl-7-oxo-6,7-dihydrothieno[2,3-c]pyridine-2-carboxylic acid (4 g, 84%) was prepared following General Procedure 2, Step 4 using methyl 4-bromo-6-methyl-7-oxo-6,7-dihydrothieno[2,3-c]pyridine-2-carboxylate (5.0 g, 16.6 mmol). LCMS: 288 [M+H]+, 290 [M+H+2]+

Step 2: Synthesis of 2-(1H-benzo[d]imidazol-2-yl)-4-bromo-6-methylthieno[2,3-c]pyridin-7(6H)-one: 2-(1H-benzo[d]imidazol-2-yl)-4-bromo-6-methylthieno[2,3-c]pyridin-7(6H)-one (0.9 g, 72%) was prepared following General Procedure 6, Step 2 using 4-bromo-6-methyl-7-oxo-6,7-dihydrothieno[2,3-c]pyridine-2-carboxylic acid (1.0 g, 3.47 mmol). LCMS: 360 [M+H]+, 362 [M+H+2]+

Step 3: Synthesis of 4-(5-amino-2-(4-fluoro-2,6-dimethylphenoxy)phenyl)-2-(1H-benzo[d]imidazol-2-yl)-6-methylthieno[2,3-c]pyridin-7(6H)-one: 4-(5-amino-2-(4-fluoro-2,6-dimethylphenoxy)phenyl)-2-(1H-benzo[d]imidazol-2-yl)-6-methylthieno[2,3-c]pyridin-7(6H)-one (120 mg, 24%, off-white solid) was prepared following General Procedure 2, Step 7 using 2-(1H-benzo[d]imidazol-2-yl)-4-bromo-6-methylthieno[2,3-c]pyridin-7(6H)-one (340 mg, 0.947 mmol, 1 eq). LCMS: 511 [M+1]+

Step 4: Synthesis of N-(3-(2-(1H-benzo[d]imidazol-2-yl)-6-methyl-7-oxo-6,7-dihydrothieno[2,3-c]pyridin-4-yl)-4-(4-fluoro-2,6-dimethylphenoxy)phenyl)ethane sulfonamide: N-(3-(2-(1H-benzo[d]imidazol-2-yl)-6-methyl-7-oxo-6,7-dihydrothieno[2,3-c]pyridin-4-yl)-4-(4-fluoro-2,6-dimethylphenoxy)phenyl) ethanesulfonamide (0.016 g, 27%) was prepared following General Procedure 2, Step 8 using 4-(5-amino-2-(4-fluoro-2,6-dimethylphenoxy)phenyl)-2-(1H-benzo[d]imidazol-2-yl)-6-methylthieno[2,3-c]pyridin-7(6H)-one (0.05 g, 0.098 mmol). LCMS: 603 [M+1]+; NMR (400 MHz, DMSO-d6): δ 9.75 (s, 1H), 7.90 (s, 1H), 7.78 (s, 1H), 7.60 (br. s., 2H), 7.30 (d, J=2.6 Hz, 1H), 7.27-7.16 (m, 3H), 6.95 (d, J=8.8 Hz, 2H), 6.46 (d, J=8.8 Hz, 1H), 3.64 (s, 3H), 3.17-3.03 (m, 2H), 2.00 (s, 6H), 1.23 (t, J=1.2 Hz, 3H)

Example S-28: N-(3-(2-(benzo[d]oxazol-2-yl)-6-methyl-7-oxo-6,7-dihydrothieno[2,3-c]pyridin-4-yl)-4-(2,4-difluorophenoxy)phenyl)ethanesulfonamide (Compound 158)

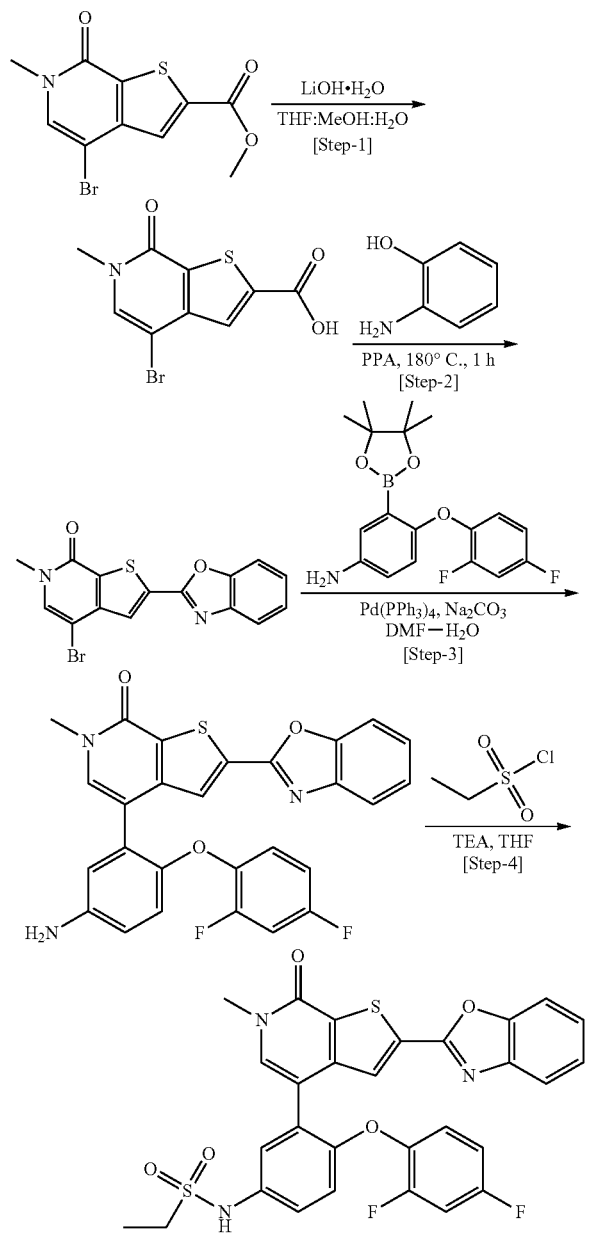

Step 1: Synthesis of 4-bromo-6-methyl-7-oxo-6,7-dihydrothieno[2,3-c]pyridine-2-carboxylic acid: 4-bromo-6-methyl-7-oxo-6,7-dihydrothieno[2,3-c]pyridine-2-carboxylic acid (4 g, 84%) was prepared following General Procedure 2, Step 4 using methyl 4-bromo-6-methyl-7-oxo-6,7-dihydrothieno[2,3-c]pyridine-2-carboxylate (5.0 g, 16.6 mmol). LCMS: 288 [M+H]⁺, 290 [M+H+2]⁺

Step 2: Synthesis of 2-(benzo[d]oxazol-2-yl)-4-bromo-6-methylthieno[2,3-c]pyridin-7(6H)-one: 2-(benzo[d]oxazol-2-yl)-4-bromo-6-methylthieno[2,3-c]pyridin-7(6H)-one (0.5 g, 41%) was prepared following General Procedure 5, Step 2 using 4-bromo-6-methyl-7-oxo-6,7-dihydrothieno[2,3-c]pyridine-2-carboxylic acid (1.0 g, 3.47 mmol). LCMS: 361 [M+H]⁺, 363 [M+H+2]⁺

Step 3: Synthesis of 4-(5-amino-2-(2,4-difluorophenoxy)phenyl)-2-(benzo[d]oxazol-2-yl)-6-methylthieno[2,3-c]pyridin-7(6H)-one: 4-(5-amino-2-(2,4-difluorophenoxy)phenyl)-2-(benzo[d]oxazol-2-yl)-6-methylthieno[2,3-c]pyridin-7(6H)-one (0.105 g, 75%) was prepared following General Procedure 2, Step 7 using 2-(benzo[d]oxazol-2-yl)-4-bromo-6-methylthieno[2,3-c]pyridin-7(6H)-one (0.1 g, 0.278 mmol, 1 eq). LCMS: 502 [M+1]⁺

Step 4: Synthesis of N-(3-(2-(benzo[d]oxazol-2-yl)-6-methyl-7-oxo-6,7-dihydrothieno[2,3-c]pyridin-4-yl)-4-(2,4-difluorophenoxy)phenyl)ethanesulfonamide: N-(3-(2-(benzo[d] oxazol-2-yl)-6-methyl-7-oxo-6,7-dihydrothieno[2,3-c]pyridin-4-yl)-4-(2,4-difluorophenoxy) phenyl)ethanesulfonamide (16 mg, 27%) was prepared following General Procedure 2, Step 8 using 4-(5-amino-2-(2,4-difluorophenoxy)phenyl)-2-(benzo[d]oxazol-2-yl)-6-methylthieno[2,3-c]pyridin-7(6H)-one (0.09 g, 0.17 mmol, 1 eq). LCMS: 594 [M+1]⁺; ¹H NMR (400 MHz, DMSO-d₆): δ 9.90 (s, 1H), 7.81 (s, 3H), 7.85 (s, 1H), 7.56-7.41 (m, 2H), 7.40-7.24 (m, 3H), 7.13 (d, J=5.7 Hz, 1H), 7.03 (d, J=8.3 Hz, 2H), 3.61 (s, 3H), 3.16 (d, J=7.5 Hz, 2H), 1.25 (t, J=7.0 Hz, 3H)

Example S-29: Synthesis of 4-(2-(2,4-difluorophenoxy)-5-(2-hydroxypropan-2-yl)phenyl)-6-methyl-2-(5-methyl-1,3,4-oxadiazol-2-yl)thieno[2,3-c]pyridin-7(6H)-one (Compound 12)

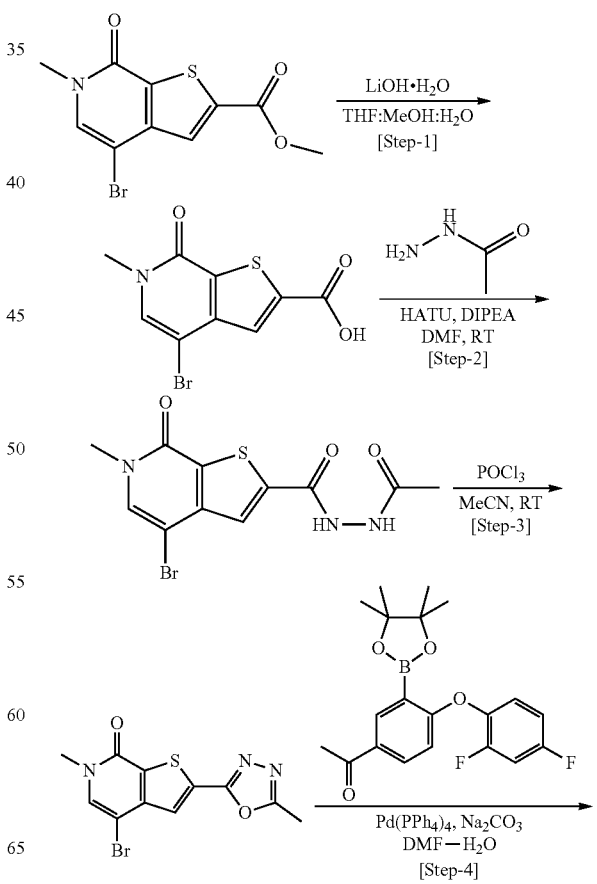

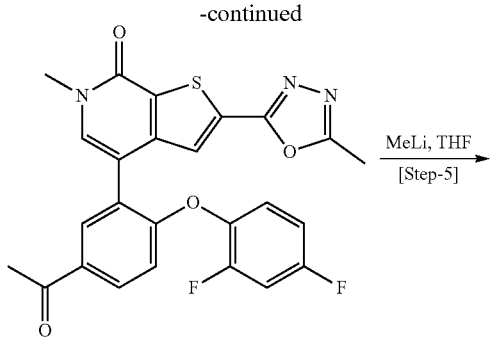

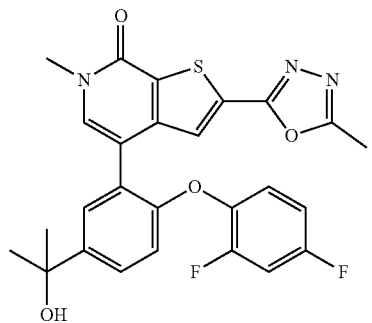

Step 1: Synthesis of 4-bromo-6-methyl-7-oxo-6,7-dihydrothieno[2,3-c]pyridine-2-carboxylic acid: 4-bromo-6-methyl-7-oxo-6,7-dihydrothieno[2,3-c]pyridine-2-carboxylic acid (0.5 g, 52%) was prepared following General Procedure 2, Step 4 using methyl 4-bromo-6-methyl-7-oxo-6,7-dihydrothieno[2,3-c]pyridine-2-carboxylate (1.0 g, 3.3 mmol, 1 eq). LCMS: 288 [M+H]$^+$, 290 [M+H+2]$^+$ Step 2: Synthesis of N'-acetyl-4-bromo-6-methyl-7-oxo-6,7-dihydrothieno[2,3-c]pyridine-2-carbohydrazide: N'-acetyl-4-bromo-6-methyl-7-oxo-6,7-dihydrothieno[2,3-c]pyridine-2-carbohydrazide (0.35 g, 68%) was prepared following General Procedure 2, Step 5 using 4-bromo-6-methyl-7-oxo-6,7-dihydrothieno[2,3-c]pyridine-2-carboxylic acid (0.43 g, 1.49 mmol, 1 eq). LCMS: 344 [M+1]$^+$, 346 [M+H+2]$^+$ Step 3: Synthesis of 4-bromo-6-methyl-2-(5-methyl-1,3,4-oxadiazol-2-yl)thieno[2,3-c]pyridin-7(6H)-one: 4-bromo-6-methyl-2-(5-methyl-1,3,4-oxadiazol-2-yl)thieno[2,3-c]pyridin-7(6H)-one (0.11 g, 58%) was prepared following General Procedure 2, Step 6 using N'-acetyl-4-bromo-6-methyl-7-oxo-6,7-dihydrothieno[2,3-c]pyridine-2-carbohydrazide (0.35 g, 1.023 mmol, 1 eq). LCMS: 326 [M+H]$^+$, 328 [M+H+2]$^+$ Step 4: Synthesis of 4-(5-acetyl-2-(2,4-difluorophenoxy)phenyl)-6-methyl-2-(5-methyl-1,3,4-oxadiazol-2-yl)thieno[2,3-c]pyridin-7(6H)-one: 4-(5-acetyl-2-(2,4-difluorophenoxy)phenyl)-6-methyl-2-(5-methyl-1,3,4-oxadiazol-2-yl)thieno[2,3-c]pyridin-7(6H)-one (0.20 g, 66%) was prepared following General Procedure 4, Step 4 using 4-bromo-6-methyl-2-(5-methyl-1,3,4-oxadiazol-2-yl)thieno[2,3-c]pyridin-7(6H)-one (0.20 g, 0.615 mmol, 1 eq). LCMS: 494 [M+1]$^+$ Step 5: Synthesis of 4-(2-(2,4-difluorophenoxy)-5-(2-hydroxypropan-2-yl)phenyl)-6-methyl-2-(5-methyl-1,3,4-oxadiazol-2-yl)thieno[2,3-c]pyridin-7(6H)-one: 4-(2-(2,4-difluorophenoxy)-5-(2-hydroxypropan-2-yl)phenyl)-6-methyl-2-(5-methyl-1,3,4-oxadiazol-2-yl)thieno[2,3-c]pyridin-7(6H)-one (0.023 g, 12%) was prepared following General Procedure 1, Step 5 using 4-(5-acetyl-2-(2,4-difluorophenoxy)phenyl)-6-methyl-2-(5-methyl-1,3,4-oxadiazol-2-yl)thieno[2,3-c]pyridin-7(6H)-one (0.175 g, 0.354 mmol, 1 eq). LCMS: 510 [M+1]$^+$; NMR (400 MHz, DMSO-d$_6$): δ 7.77 (br. s., 1H), 7.63 (br. s., 1H), 7.58-7.48 (m, 2H), 7.37 (br. s., 1H), 7.12 (br. s., 1H), 7.03 (br. s., 1H), 6.86 (d, J=8.3 Hz, 1H), 5.11 (br. s., 1H), 3.62 (br. s., 3H), 2.58 (br. s., 3H), 1.47 (br. s., 6H).

Example S-30: Synthesis of 7-(2-(2,4-difluorophenoxy)-5-(2-hydroxypropan-2-yl)phenyl)-N-ethyl-5-methyl-4-oxo-4,5-dihydrothieno[3,2-c]pyridine-2-carboxamide (Compound 159)

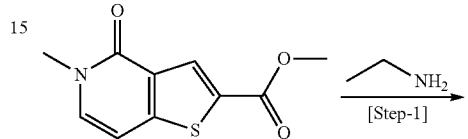

Step 1: Synthesis of 7-bromo-N-ethyl-5-methyl-4-oxo-4,5-dihydrothieno[3,2-c]pyridine-2-carboxamide: 7-bromo-N-ethyl-5-methyl-4-oxo-4,5-dihydrothieno[3,2-c]pyridine-2-carboxamide (0.28 g, 90%) was prepared following General Procedure 1, Step 4a using methyl 7-bromo-5-methyl-4-oxo-4,5-dihydrothieno[3,2-c]pyridine-2-carboxylate (0.3 g, 1 mmol). LCMS: 315 [M+H]$^+$, 317 [M+H+2]$^+$ Step 2. Synthesis of 7-(5-acetyl-2-(2,4-difluorophenoxy)phenyl)-N-ethyl-5-methyl-4-oxo-4,5-dihydrothieno[3,2-c]

pyridine-2-carboxamide: 7-(5-acetyl-2-(2,4-difluorophenoxy) phenyl)-N-ethyl-5-methyl-4-oxo-4,5-dihydrothieno[3,2-c]pyridine-2-carboxamide (0.1 g, 23.4%) was prepared following General Procedure 3, Step 1 using 7-bromo-N-ethyl-5-methyl-4-oxo-4,5-dihydrothieno[3,2-c]pyridine-2-carboxamide (0.28 g, 0.9 mmol, 1 eq) and 1-(4-(2,4-difluorophenoxy)-3-(4,4,5,5-tetramethyl-1,3,2-dioxaborolan-2-yl)phenyl)ethanone (0.43 g, 1.15 mmol, 1.3 eq) LCMS: 483 [M+H]$^+$ Step 3: Synthesis of 7-(2-(2,4-difluorophenoxy)-5-(2-hydroxypropan-2-yl)phenyl)-N-ethyl-5-methyl-4-oxo-4,5-dihydrothieno[3,2-c]pyridine-2-carboxamide: 7-(2-(2,4-difluorophenoxy)-5-(2-hydroxypropan-2-yl)phenyl)-N-ethyl-5-methyl-4-oxo-4,5-dihydrothieno[3,2-c]pyridine-2-carboxamide (0.013 g, 13%) was prepared following General Procedure 1, Step 5 using 7-(5-acetyl-2-(2,4-difluorophenoxy)phenyl)-N-ethyl-5-methyl-4-oxo-4,5-dihydrothieno[3,2-c]pyridine-2-carboxamide (0.1 g, 0.2 mmol, 1 eq) LCMS: 499 [M+H]+; $^1$H NMR (400 MHz, MeOH-d$_4$): δ 8.09 (s, 1H), 7.66 (d, J=2.6 Hz, 1H), 7.62 (s, 1H), 7.56 (dd, J=2.4, 8.6 Hz, 1H), 7.09-6.96 (m, 2H), 6.92 (d, J=8.3 Hz, 1H), 6.84 (br. s., 1H), 3.67 (s, 3H), 3.39 (q, J=7.0 Hz, 2H), 1.57 (s, 6H), 1.22 (t, J=7.2 Hz, 3H).

Example S-31: Synthesis of 7-(2-(4-fluoro-2,6-dimethylphenoxy)-5-(2-hydroxypropan-2-yl)phenyl)-5-methylthieno[3,2-c]pyridin-4(5H)-one (Compound 2.1)

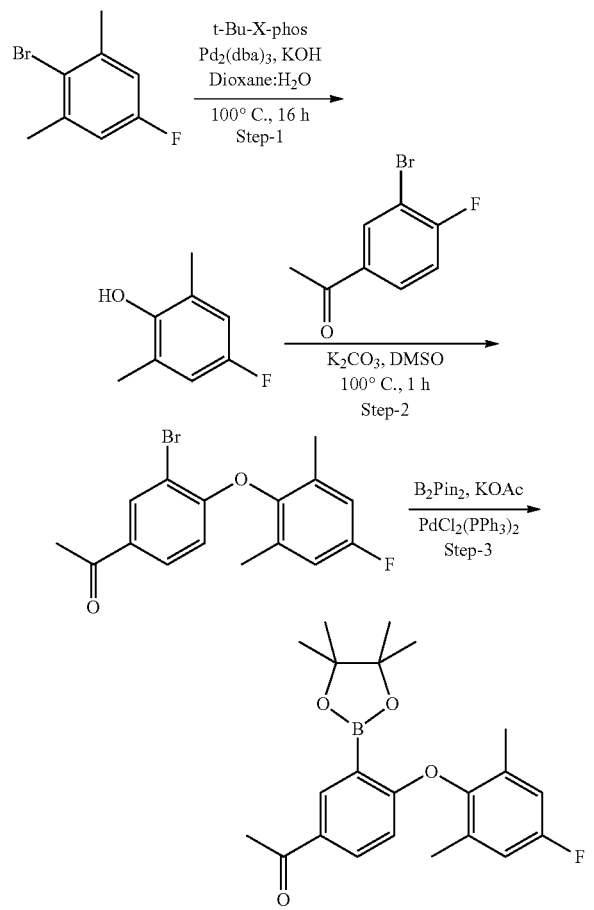

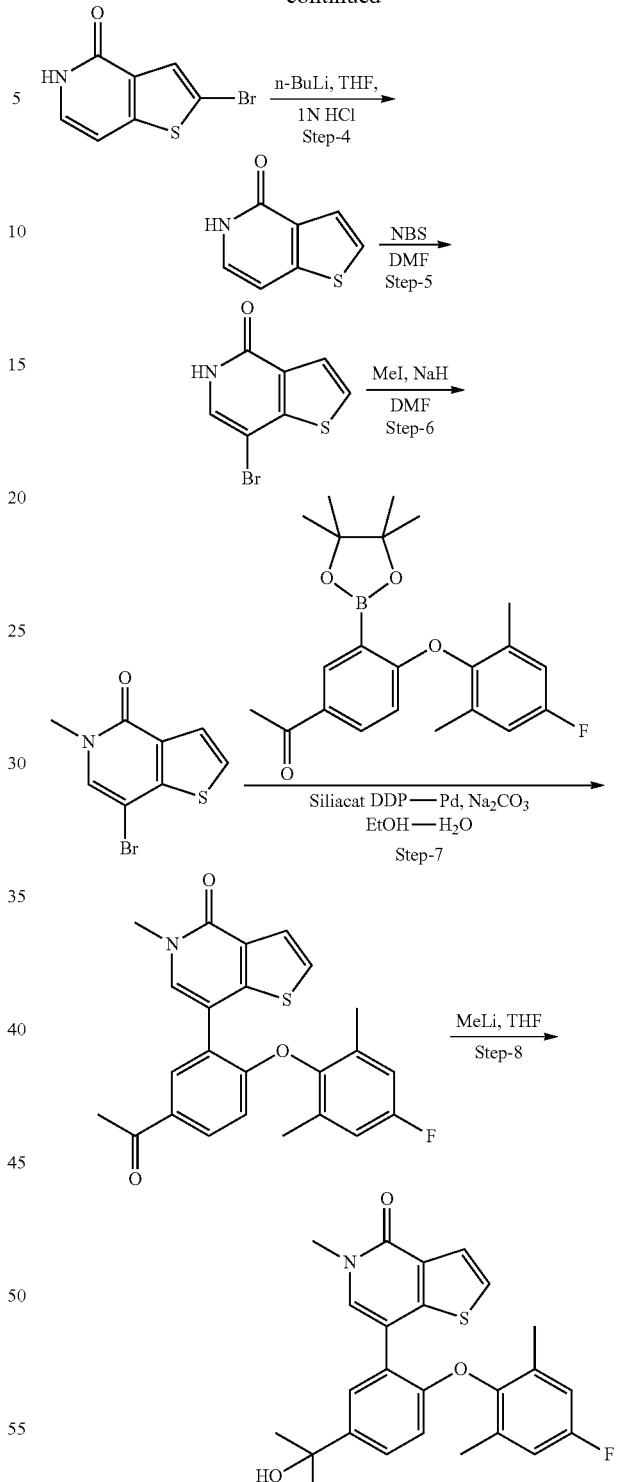

Step 1: Synthesis of 4-fluoro-2,6-dimethylphenol. A solution of 2-bromo-5-fluoro-1,3-dimethylbenzene (5.0 g, 24.7 mmol, 1 eq) in 1,4-dioxane: water (50 mL, 1:1) was added KOH (4.15 g, 74.2 mmol, 3 eq) and the mixture was degassed under nitrogen for 15 min. In another set-up, t-Bu-X-phos (839 mg, 7.98 mmol 0.08 eq) and Pd$_2$(dba)$_3$ (452 mg, 0.49 mmol, 0.08 eq) in 1,4-dioxane:water (20 mL, 1:1) was degassed under nitrogen for 15 min. The contents of the first degassed mixture were transferred into the degassed solution of the second and the mixture was heated at 100° C. and monitored by TLC and LCMS. The reaction was complete after 16 h and the mixture was acidified with 6N—HCl (pH ~2-3) and extracted with EtOAc (700 mL). The organic layer was washed with water (300 mL), brine (200 mL), dried over anhydrous $Na_2SO_4$, filtered and concentrated under reduced pressure to obtain a crude residue which was purified by CombiFlash chromatography to afford the title compound. LCMS: 141 [M+H]$^+$.

Step 2: Synthesis of 1-(3-bromo-4-(4-fluoro-2,6 dimethylphenyl)phenyl)-ethanone. To a solution of 4-fluoro-2,6-dimethylphenol (0.50 g, 3.57 mmol) in DMSO (20 mL) was added $K_2CO_3$ (0.98 g, 7.15 mmol, 2 eq) at RT and the mixture was stirred for 15 min. 1-(3-bromo-4-fluorophenyl) ethanone (0.93 g, 4.28 mmol, 1.2 eq) was then added to the mixture and the resultant mixture was heated 80° C. for 2 h. The reaction was complete after 2 h and to the mixture was added water (200 mL) to obtain a precipitate which was filtered over Büchner funnel; dried under vacuum to afford the title compound. LCMS: 337 [M+H]$^+$, 339 [M+H+2]$^+$.

Step 3: Synthesis of 1-(4-(4-fluoro-2,6-dimethylphenoxy)-3-(4,4,5,5-tetramethyl-1,3,2-dioxaborolan-2-yl)phenyl)ethanone. To a solution of 1-(3-bromo-4-(4-fluoro-2,6-dimethylphenoxy)phenyl)ethanone (0.55 g, 1.63 mmol, 1 eq) in 1,4-dioxane (5 mL), was added $B_2Pin_2$ (0.50 g, 1.96 mmol, 1.2 eq), KOAc (0.48 g, 4.89 mmol, 3 eq), and Pd(dppf)Cl$_2$ (0.12 g, 0.16 mmol, 0.1 eq). The reaction mixture was degassed and purged with $N_2$. Then the mixture was stirred at overnight at 80° C. TLC analysis indicated the reaction was complete. The mixture was concentrated under reduced pressure. The residue was purified by column chromatography on silica gel to afford the title compound.

Step 4: Synthesis of thieno[3,2-c]pyridin-4(5H)-one. To a solution of 2-bromothieno[3,2-c]pyridin-4(5H)-one (3.0 g, 13.04 mmol) in THF (100 mL) was added n-BuLi (1.6 M in n-hexane; 31.4 mL, 52.16 mmol, 4 eq) at −78° C. and the mixture was stirred at same temperature for 2 h. After 2 h, the reaction mixture was slowly quenched with 1N—HCl (3 mL) at 0° C. and extracted with EtOAc (500 mL). The organic layer was washed with water (100 mL), brine (150 mL), dried over anhydrous $Na_2SO_4$, filtered and concentrated under reduced pressure to afford the title compound. LCMS: 152 [M+H]$^+$.

Step 5: Synthesis of 7-bromothieno[3,2-c]pyridin-4(5H)-one: To a stirred solution of thieno[3,2-c]pyridin-4(5H)-one (1.8 g, 11.92 mmol) in DMF (30 mL) was added NBS (2.33 g, 13.11 mmol, 1.2 eq) at 0° C. and the mixture was stirred at RT for 16 h. The reaction was complete after 16 h and to the mixture was added ice-cold water (200 mL) to obtain a precipitate which was filtered over Büchner funnel to afford the title compound. LCMS: 230 [M+H]$^+$, 232 [M+H+2]$^+$.

Step 6: Synthesis of 7-bromo-5-methylthieno[3,2-c]pyridin-4(5H)-one. To a solution of 7-bromothieno[3,2-c]pyridin-4(5H)-one (2.2 g, 9.96 mmol) in DMF (20 mL) was added NaH (60% suspension in mineral oil, 1.19 g, 29.88 mmol, 3 eq) slowly at 0° C. over a period of 20 min and the mixture was stirred at same temperature for 30 min. MeI (1.85 mL, 29.88 mmol, 3 eq) was then added to the mixture slowly 0° C. and the resultant mixture was stirred at RT for 30 min. The reaction was monitored on TLC. Upon completion, the mixture was slowly quenched with ice-cold water (200 mL) and the precipitated solid was filtered over Büchner funnel to afford the title compound. LCMS: 244 [M+H]$^+$, 246 [M+H+2]$^+$.

Step 7: Synthesis of 7-(5-acetyl-2-(4-fluoro-2,6-dimethylphenoxy)phenyl)-5-methyl thieno [3,2-c]pyridin-4(5H)-one. To a stirred solution of 7-bromo-N-ethyl-5-methyl-4-oxo-4,5-dihydrofuro[3,2-c]pyridine-2-carboxamide 7-bromo-5-methylthieno[3,2-c]pyridin-4(5H)-one (0.30 g, 1.23 mmol, 1 eq) in ethanol (18 mL) were added 1-(4-(4-fluoro-2,6-dimethyl phenoxy)-3-(4,4,5,5-tetramethyl-1,3,2-dioxaborolan-2-yl)phenyl)ethanone (0.57 g, 1.47 mmol, 1.2 eq) and $Na_2CO_3$ (0.26 g, 2.45 mmol, 2 eq) dissolved in water (2 mL). Siliacat DPP-Pd (0.30 mmol/g loading; 0.2 g, 0.06 mmol, 0.05 eq) was then added to the mixture and the resultant mixture was then heated at 85° C. for 2 h. The reaction was complete after 2 h and the mixture was filtered through the celite bed, washed with 5% MeOH in DCM (50 mL). The filtrate obtained was concentrated under reduced pressure to obtain a crude residue. The residue obtained was stirred in MeOH (10 mL) for 20 min, filtered over Büchner funnel, dried under vacuum to obtain a solid compound. Then solid obtained was further triturated with diethyl ether (5 mL×2), dried to afford title compound. LCMS: 422 [M+H]$^+$.

Step 8: Synthesis of 7-(2-(4-fluoro-2,6-dimethylphenoxy)-5-(2-hydroxypropan-2-yl)phenyl)-5-methylthieno[3,2-c]pyridin-4(5H)-one. To a stirred solution of 7-(5-acetyl-2-(4-fluoro-2,6-dimethylphenoxy)phenyl)-5-methylthieno[3,2-c]pyridin-4(5H)-one (0.10 g, 0.23 mmol) in anhydrous THF (8 mL) was added methyl lithium (1.6 M in Et$_2$O; 0.9 mL, 1.42 mmol, 6 eq) at 0° C. dropwise and the mixture was stirred at same temperature for 10 min. The progress of the reaction was monitored by TLC. After 10 min and the mixture was quenched with saturated NH$_4$Cl solution (10 mL) slowly. The aqueous layer was then extracted with EtOAc (60 mL×2). The combined organic layers were washed with water (50 mL), brine (30 mL), dried over anhydrous $Na_2SO_4$, filtered and concentrated under reduced pressure to obtain a crude which was purified by reversed phase HPLC to afford the title compound. LCMS: 438 [M+1]$^+$; $^1$H NMR (400 MHz, DMSO-d$_6$): δ 7.67 (s, 1H), 7.63 (d, J=5.3 Hz, 1H), 7.58-7.51 (m, 2H), 7.38 (dd, J=2.4, 8.6 Hz, 1H), 6.99 (d, J=9.2 Hz, 2H), 6.32 (d, J=8.8 Hz, 1H), 5.00 (br s, 1H), 3.60 (s, 3H), 2.03 (s, 6H), 1.43 (s, 6H).

Example S-32: Synthesis of 7-(2-(2,4-difluorophenoxy)-5-(2-hydroxypropan-2-yl)phenyl)-5-methylthieno[3,2-c]pyridin-4(5H)-one (Compound 2.3)

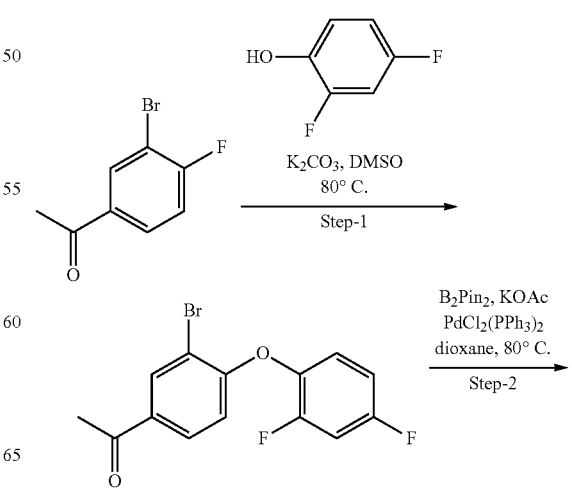

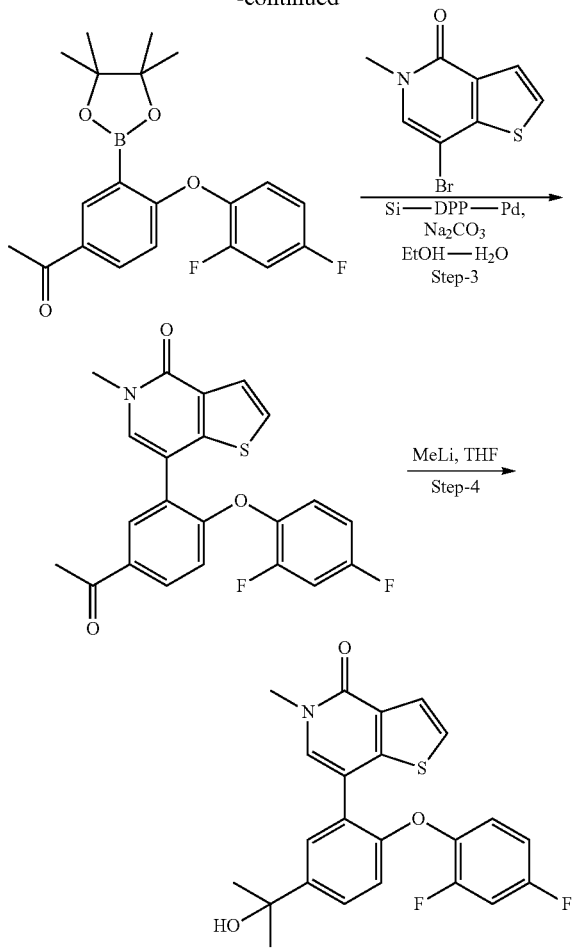

Step 3: Synthesis of 7-(5-acetyl-2-(2,4-difluorophenoxy) phenyl)-5-methylthieno[3,2-c]pyridin-4(5H)-one: The title compound was prepared following Example S-1, step 7 using 7-bromo-5-methylthieno[3,2-c]pyridin-4(5H)-one (0.30 g, 1.23 mmol, 1 eq) and 1-(4-(2,4-difluorophenoxy)-3-(4,4,5,5-tetramethyl-1,3,2-dioxaborolan-2-yl)phenyl) ethanone (0.55 g, 1.47 mmol, 1.2 eq). LCMS: 412 [M+H]$^+$.

Step 4: Synthesis of 7-(2-(2,4-difluorophenoxy)-5-(2-hydroxypropan-2-yl)phenyl)-5-methylthieno[3,2-c]pyridin-4(5H)-one: The title compound was prepared following Example S-1, step 8 using 7-(5-acetyl-2-(2,4-difluorophenoxy)phenyl)-5-methylthieno[3,2-c]pyridin-4(5H)-one (0.14 g, 0.29 mmol, 1 eq). LCMS: 428 [M+1]$^+$. NMR (400 MHz, DMSO-d$_6$): δ 7.67 (d, J=2.6 Hz, 1H), 7.60 (d, J=5.7 Hz, 1H), 7.57-7.47 (m, 3H), 7.00 (dd, J=2.9, 8.6 Hz, 2H), 6.92 (d, J=8.3 Hz, 1H), 6.83 (br s, 1H), 3.68 (s, 3H), 1.57 (s, 6H).

Example S-33: Synthesis of N-(4-(2,4-difluorophenoxy)-3-(5-methyl-4-oxo-4,5-dihydrothieno [3,2-c] pyridin-7-yl)phenyl)ethanesulfonamide (Compound 2.91)

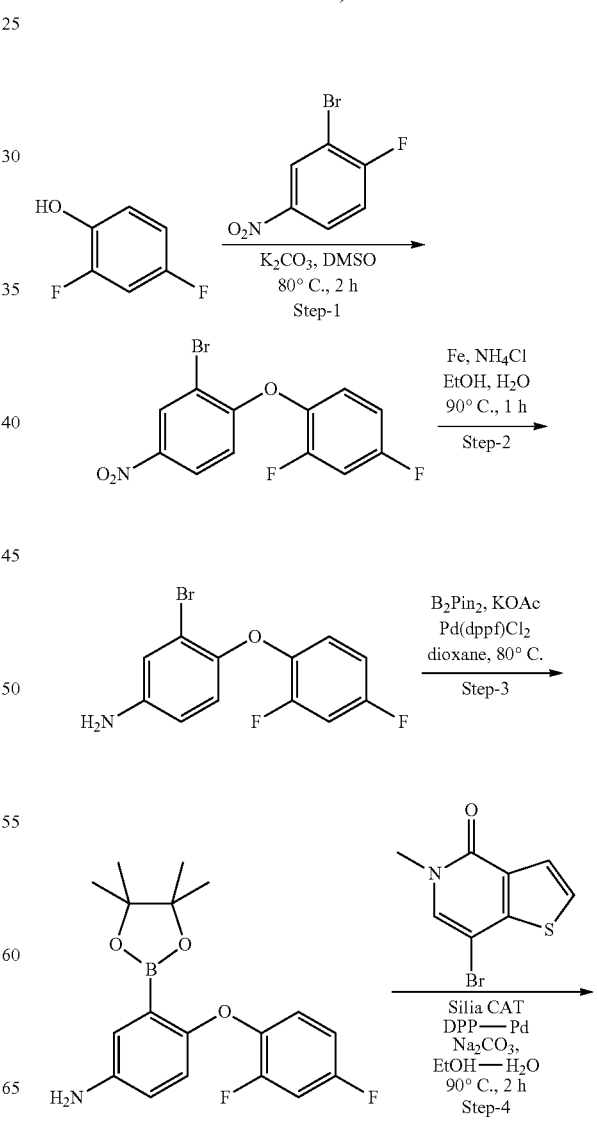

Step 1: Synthesis 1-(3-bromo-4-(2,4-difluorophenoxy) phenyl)ethanone: To a stirred solution of 2,4-difluorophenol (1 g, 7.9 mmol, 1 eq) in DMSO (20 mL) was added K$_2$CO$_3$ (3.2 g, 23 mmol, 3 eq) at RT followed by the addition of 1-(3-bromo-4-fluorophenyl) ethanone (0.98 g, 8.5 mmol, 1.1 eq) and the mixture was heated at 80° C. for 2 h. The reaction was complete after 2 h and to the mixture was added ice-cold water (100 mL) to obtain a precipitate which was filtered over Büchner funnel; dried under vacuum to afford the title compound. LCMS: 327 [M+H]$^+$, 329 [M+H+2]$^+$.

Step 2: Synthesis of 1-(4-(2,4-difluorophenoxy)-3-(4,4,5,5-tetramethyl-1,3,2-dioxaborolan-2-yl)phenyl)ethanone: To a solution of 1-(3-bromo-4-(2,4-difluorophenoxy) phenyl) ethanone (1.0 g, 3.06 mmol, 1 eq) in 1,4-dioxane (20 mL) was added B$_2$Pin$_2$ (1.16 g, 4.6 mmol, 1.5 eq), KOAc (0.9 g, 9.3 mmol, 3 eq) and the mixture was degassed under N$_2$ for 20 min. PdCl$_2$(PPh$_3$)$_2$ (0.22 g, 0.3 mmol, 0.1 eq) was then added to the mixture and the resultant mixture was heated at 80° C. for 16 h. The reaction was monitored by TLC. Upon completion, the mixture was filtered through a pad of Celite and concentrated under reduced pressure. The residue obtained was diluted with water (200 mL) and extracted with EtOAc (250 mL×2). The combined organic layers were washed with water (200 mL), brine (100 mL), dried over anhydrous Na$_2$SO$_4$, filtered and concentrated under reduced pressure to obtain a crude residue which was purified by CombiFlash chromatography to afford the title compound. LCMS: 375 [M+H]$^+$.

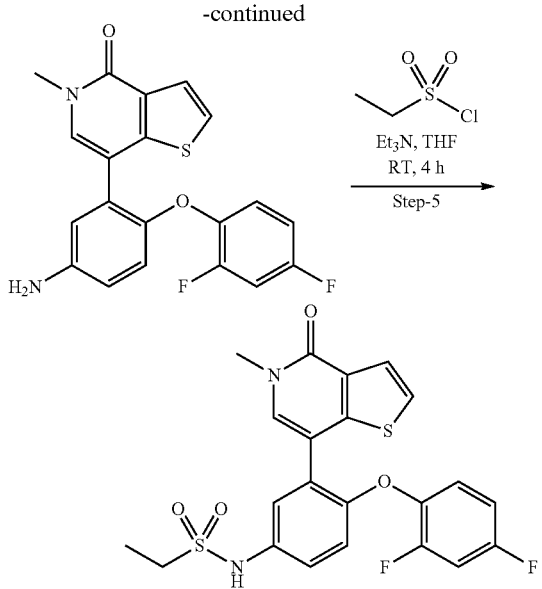

Step 1: Synthesis of 2-bromo-1-(2,4-difluorophenoxy)-4-nitrobenzene: To a stirred solution of 2,4-difluorophenol (3.0 g, 23 mmol, 1 eq) in DMSO (20 mL) was added $K_2CO_3$ (3.0 g, 46 mmol, 2 eq) at RT followed by the addition of 2-bromo-1-fluoro-4-nitrobenzene (5.6 g, 25.3 mmol, 1.1 eq) and the mixture was heated at 100° C. for 1 h. The reaction was complete after 2 h and to the mixture was added ice-cold water (100 mL) to obtain a precipitate which was filtered over Büchner funnel and dried under vacuum to afford the title compound. LCMS: 330 [M+H]$^+$, 332 [M+H+2]$^+$ Step 2: Synthesis of 3-bromo-4-(2,4-difluorophenoxy) aniline: To a solution of 2-bromo-1-(2,4-difluorophenoxy)-4-nitrobenzene (6 g, 18.2 mmol, 1 eq) in ethanol (50 mL), a solution of $NH_4Cl$ (7.8 g, 145.4 mmol, 8 eq) in water (50 mL) was added followed by addition of iron powder (5.1 g, 91 mmol, 5 eq). The resultant mixture was heated at 90° C. for 1 h. The reaction was monitored by TLC. Upon completion, the mixture was filtered through a pad of Celite and concentrated under reduced pressure. The residue obtained was diluted with water (200 mL) and extracted with EtOAc (300 mL×2). The combined organic layers were washed with brine (100 mL), dried over anhydrous $Na_2SO_4$, filtered and concentrated under reduced pressure to obtain a crude residue which was purified by CombiFlash chromatography to afford the title compound. LCMS: 340 [M+H]$^+$, 342 [M+H+2]$^+$ Step 3: Synthesis of 4-(2,4-difluorophenoxy)-3-(4,4,5,5-tetramethyl-1,3,2-dioxaborolan-2-yl)aniline: To a solution of 3-bromo-4-(2,4-difluorophenoxy)aniline (4.0 g, 13.4 mmol, 1 eq) in 1,4-dioxane (40 mL) was added $B_2Pin_2$ (5.1 g, 20.1 mmol, 1.5 eq), KOAc (8.5 g, 33.6 mmol, 2.5 eq) and the mixture was degassed under $N_2$ for 20 min. Pd(dppf)$Cl_2$.DCM (1.1 g, 1.34 mmol, 0.1 eq) was then added to the mixture and the resultant mixture was heated at 80° C. for 16 h. The reaction was monitored by TLC. Upon completion, the mixture was filtered through a pad of Celite and concentrated under reduced pressure. The residue obtained was diluted with water (200 mL) and extracted with EtOAc (250 mL×2). The combined organic layers were washed with water (200 mL), brine (100 mL), dried over anhydrous $Na_2SO_4$, filtered and concentrated under reduced pressure to obtain a crude residue which was purified by CombiFlash chromatography to afford the title compound. $^1$H NMR (400 MHz, DMSO-$d_6$): δ 7.31 (m, 1H), 6.94 (d, J=2.8 Hz, 1H), 6.87 (m, 1H), 6.78 (d, J=8.4 Hz, 1H), 6.71 (dd, J=8.4, 2.8 Hz, 1H), 6.50 (m, 1H), 5.09 (br s, 2H), 1.06 (s, 12H).

Step 4: Synthesis of 7-(5-amino-2-(2,4-difluorophenoxy) phenyl)-5-methylthieno[3,2-c]pyridin-4(5H)-one: To a stirred solution of 7-bromo-5-methylthieno[3,2-c]pyridin-4 (5H)-one (0.15 g, 0.61 mmol, 1 eq) in ethanol (9 mL) were added 4-(2,4-difluorophenoxy)-3-(4,4,5,5-tetramethyl-1,3,2-dioxaborolan-2-yl)aniline (0.32 g, 0.9 mmol, 1.5 eq) and $Na_2CO_3$ (0.13 g, 1.2 mmol, 2 eq) dissolved in water (1 mL). Silia DPP-Pd (0.30 mmol/g loading; 0.6 g, 0.018 mmol, 0.03 eq) was then added to the mixture and the resultant mixture was heated at 90° C. for 2 h. The reaction was complete after 2 h and the mixture was filtered through the celite bed, washed with 5% MeOH in DCM (50 mL) and concentrated to obtain a crude residue which was purified by CombiFlash chromatography to afford the title compound. LCMS: 385 [M+H]$^+$ Step 5: Synthesis of N-(4-(2,4-difluorophenoxy)-3-(5-methyl-4-oxo-4,5-dihydrothieno [3,2-c]pyridin-7-yl)phenyl)ethanesulfonamide: To a stirred solution of 7-(5-amino-2-(2,4-difluorophenoxy) phenyl)-5-methylthieno[3,2-c] pyridin-4(5H)-one (0.15 g, 0.4 mmol, 1.0 eq) in THF (15 mL) was added triethylamine (0.15 g, 1.17 mmol, 3 eq) followed by the addition of ethanesulfonyl chloride (0.13 g, 1 mmol, 2.5 eq) at 0° C. and the resultant mixture was stirred at RT for 4 h. The reaction was complete after 4 h and to the mixture was added water (20 mL) and extracted with EtOAc (30 mL×2). The combined organic layers was washed with saturated $NaHCO_3$ solution (30 mL), brine (25 mL), dried over anhydrous $Na_2SO_4$, filtered and concentrated under reduced pressure to obtain a crude which was purified by prep HPLC to afford the title compound. LCMS: 477 [M+H]$^+$; NMR (400 MHz, MeOH-$d_4$): δ 7.60 (d, J=5.3 Hz, 1H), 7.56 (s, 1H), 7.52 (d, J=5.7 Hz, 1H), 7.45 (d, J=2.6 Hz, 1H), 7.32 (dd, J=2.4, 8.6 Hz, 1H), 7.05-6.93 (m, 3H), 6.82 (hr s, 1H), 3.67 (s, 3H), 3.14 (q, J=7.5 Hz, 2H), 1.35 (t, J=7.5 Hz, 3H).

Example S-34: Synthesis of 7-(2-(2,4-difluorophenoxy)-5-(ethylsulfonamido)phenyl)-N-ethyl-5-methyl-4-oxo-4,5-dihydrothieno[3,2-c]pyridine-2-carboxamide (Compound 160)

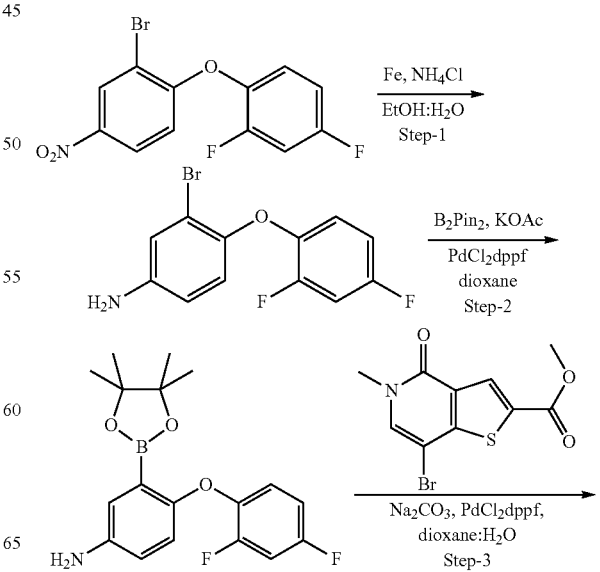

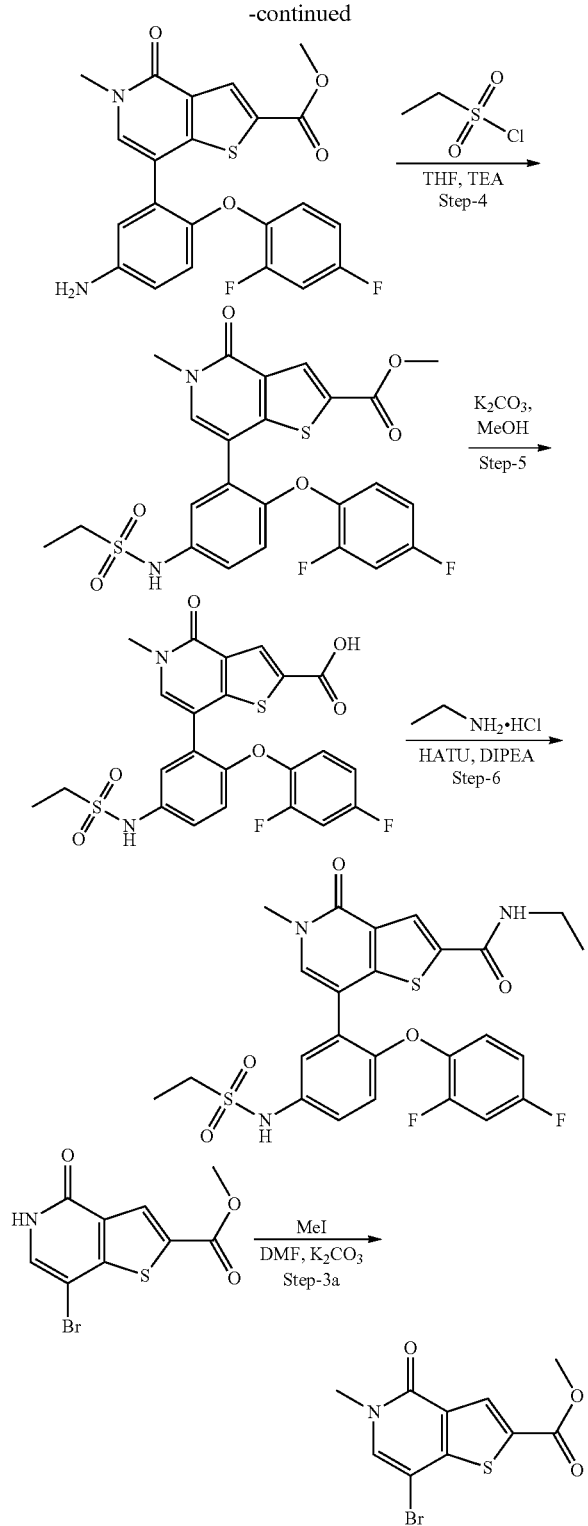

Step 1: Preparation of 3-bromo-4-(2,4-difluorophenoxy) aniline: To a stirred solution of 2-bromo-1-(2,4-difluorophenoxy)-4-nitrobenzene (9 g, 27.24 mmol, 1 eq) in ethanol (60 mL), a solution of NH4Cl (11.7 g, 217.92 mmol, 8 eq) in water (60 mL) was added followed by addition of iron powder (7.56 g, 136.2 mmol, 5 eq). The resultant mixture was heated at 100° C. for 2 h. The progress of the reaction was monitored by TLC & LCMS. After completion, the mixture was filtered through a pad of celite and concentrated under reduced pressure. The residue obtained was diluted with water (200 mL) and extracted with EtOAc (300 mL×2). The combined organic layers were washed with brine (100 mL), dried over anhydrous Na2SO4, filtered and concentrated under reduced pressure to obtain a crude residue which was purified by CombiFlash Chromatography to afford the title compound (6.8 g, 84%). LCMS: 300 [M+H]$^+$, 302 [M+H+2]$^+$ Step 2: Preparation of 4-(2,4-difluorophenoxy)-3-(4,4,5,5-tetramethyl-1,3,2-dioxaborolan-2-yl)aniline: To a stirred solution of 3-bromo-4-(2,4-difluorophenoxy)aniline (4.5 g, 15 mmol, 1 eq) in dioxane (100 mL) were added B2Pin2 (5.7 g, 22.5 mmol, 1.5 eq), KOAc (3.7 g, 37.5 mmol, 2.5 eq) and the mixture was degassed under N2 for 20 min. Pd(dppf)Cl2.DCM (1.1 g, 1.35 mmol, 0.09 eq) was then added to the mixture and the resultant mixture was heated at 80° C. for 16 h. The progress of the reaction was monitored by TLC & LCMS. After completion, the mixture was diluted with EtOAc (250 mL), filtered through a pad of celite and concentrated under reduced pressure to obtain a crude residue which was purified by CombiFlash Chromatography to afford the title compound (3 g, 57%). LCMS: 348 [M+H]$^+$. NMR (400 MHz, DMSO-d$_6$): δ 7.31 (m, 1H), 6.94 (d, J=2.8 Hz, 1H), 6.87 (m, 1H), 6.78 (d, J=8.4 Hz, 1H), 6.71 (dd, J=8.4, 2.8 Hz, 1H), 6.50 (m, 1H), 5.09 (hr s, 2H), 1.06 (s, 12H).

Step 3a: Preparation of methyl 7-bromo-5-methyl-4-oxo-4,5-dihydrothieno[3,2-c]pyridine-2-carboxylate: To a stirred solution of methyl 7-bromo-4-oxo-4,5-dihydrothieno[3,2-c]pyridine-2-carboxylate (3 g, 10.4 mmol, 1 eq) in DMF (30 mL) was added potassium carbonate (2.1 g, 15.6 mmol) at RT and the mixture was stirred for 10 min. Methyl iodide (4.43 g, 31.23 mmol) was then added at 0° C. and the resultant mixture was stirred at RT for 1 h. The progress of the reaction was monitored by TLC & LCMS. After completion, the mixture was diluted with ethyl acetate (300 mL) and washed with water (200 mL×2), brine (50 mL×2), dried over anhydrous Na$_2$SO$_4$, filtered and concentrated under reduced pressure to obtain a crude which was triturated with n-pentane (100 mL×2) to afford the title compound (2.5 g, 79%). LCMS: 302 [M+H]$^+$, 304 [M+H+2]$^+$ Step 3: Preparation of methyl 7-(5-amino-2-(2,4-difluorophenoxy)phenyl)-5-methyl-4-oxo-4,5-dihydrothieno[3,2-c]pyridine-2-carboxylate: To a stirred solution of methyl 7-bromo-5-methyl-4-oxo-4,5-dihydrothieno[3,2-c]pyridine-2-carboxylate (0.7 g, 2.3 mmol, 1 eq) in dioxane (100 mL) were added 4-(2,4-difluorophenoxy)-3-(4,4,5,5-tetramethyl-1,3,2-dioxaborolan-2-yl)aniline (1.61 g, 4.63 mmol, 2 eq), sodium carbonate (0.37 g, 3.46 mmol, 1.5 eq) dissolved in water (3 mL) and the mixture was degassed under nitrogen for 20 min. PdCl$_2$(dppf) (0.084 g, 0.11 mmol, 0.5 eq) was then added to the mixture and the mixture was further degassed for 10 min. The resultant mixture was heated at 80° C. for 4 h. The progress of the reaction was monitored by TLC and LCMS. After completion, the mixture was diluted with DCM (250 mL). The organic layer was washed with water (100 mL), brine (100 mL) dried over anhydrous Na$_2$SO$_4$ and concentrated under reduced pressure to obtain a crude which was purified by CombiFlash Chromatography to afford the title compound (0.6 g, 58%). LCMS: 443 [M+H]$^+$ Step 4: Preparation of methyl 7-(2-(2,4-difluorophenoxy)-5-(ethylsulfonamido)-phenyl)-5-methyl-4-oxo-4,5-dihydrothieno[3,2-c]pyridine-2-carboxylate: To a stirred solution of methyl 7-(5-amino-2-(2,4-difluorophenoxy)phenyl)-5-methyl-4-oxo-4,5-dihydrothieno[3,2-c]pyridine-2- carboxylate (0.5 g, 1.12 mmol, 1 eq) in THF (15 mL) was added Et$_3$N (0.34 g, 3.36 mmol, 3 eq) at 0° C. and the mixture was stirred for 5 min. Ethanesulfonyl chloride (0.5 g, 3.95 mmol, 3.5 eq) was then added to the mixture at 0° C. and the resultant mixture was stirred at RT for 2.5 h. The progress of the reaction was monitored by TLC & LCMS. After completion, the mixture was concentrated under reduced pressure and the residue obtained was diluted with DCM (100 mL) and washed with water (30 mL×2). The organic layer was dried over anhydrous N$_2$SO$_4$, filtered and concentrated under reduced pressure to afford the title compound (0.7 g, crude) which was used in the next step without further purification. LCMS: 535 [M+H]$^+$ Step 5: Preparation of 7-(2-(2,4-difluorophenoxy)-5-(ethylsulfonamido)phenyl)-5-methyl-4-oxo-4,5-dihydrothieno[3,2-c]pyridine-2-carboxylic acid: To a stirred solution of methyl 7-(2-(2,4-difluorophenoxy)-5-(ethylsulfonamido)phenyl)-5-methyl-4-oxo-4,5-dihydrothieno[3,2-c]pyridine-2-carboxylate (0.8 g, 0.66 mmol, 1 eq) in methanol (20 mL) was added potassium carbonate (0.92 g, 6.68 mmol, 10 eq) and the mixture was stirred at RT for 16 h. The progress of the reaction was monitored by TLC and LCMS. After completion, the mixture was filtered and the filtrate was evaporated to dryness. This residue obtained was dissolved in water (20 mL) and washed with diethyl ether (20 mL). The aqueous layer was then acidified with using 1N—HCl (pH 2) at 0° C. and extracted with 5% MeOH:DCM (200 mL×2). The combined organic layers washed with water (30 mL), dried over anhydrous Na$_2$SO$_4$, filtered and concentrated under reduced pressure to afford the title compound (0.4 g, 51%) which was used in the next step without further purification. LCMS: 521 [M+H]$^+$ Step 6: Preparation of 7-(2-(2,4-difluorophenoxy)-5-(ethylsulfonamido)phenyl)-N-ethyl-5-methyl-4-oxo-4,5-dihydrothieno[3,2-c]pyridine-2-carboxamide: To a stirred solution of 7-(2-(2,4-difluorophenoxy)-5-(ethylsulfonamido)phenyl)-5-methyl-4-oxo-4,5-dihydrothieno[3,2-c]pyridine-2-carboxylic acid (0.15 g, 0.28 mmol, 1 eq) in DMF (3 mL) was added HATU (0.16 g, 0.42 mmol, 1.5 eq) at 0° C. and the mixture was stirred at same temperature for 20 min. DIPEA (0.44 g, 3.42 mmol, 6 eq) and ethylamine hydrochloride (182 mg, 1.4 mmol, 5 eq) were then added to the mixture and the resultant mixture was stirred at RT for 3 h. The progress of the reaction was monitored by TLC & LCMS. After completion, the mixture was diluted with water (50 mL) and extracted with 5% MeOH/DCM (50 mL×2). The combined organic layers were washed with water (50 mL×2), and brine (20 mL×2), dried over anhydrous Na$_2$SO$_4$, filtered and concentrated under reduced pressure to obtain a crude which was purified by prep HPLC to afford the title compound (0.02 g, 13%) LCMS: 548 [M+H]$^+$. NMR (400 MHz, DMSO-d$_6$): δ 8.74 (hr. s., 1H), 8.22 (s, 1H), 7.70 (s, 1H), 7.31 (hr. s., 1H), 7.21 (d, J=2.2 Hz, 1H), 7.09 (d, J=2.6 Hz, 1H), 6.95 (d, J=6.6 Hz, 2H), 6.89 (d, J=8.8 Hz, 1H), 3.52 (s, 3H), 3.28-3.20 (m, 2H), 2.95 (d, J=7.5 Hz, 2H), 1.22-1.13 (m, 3H), 1.13-1.05 (m, 3H). It is understood that compounds from Tables-1 and 2 are synthesized using the General Synthetic Schemes 1 to 6 or using the experimental procedures as described in the examples S1-S34 and the steps involved in the synthetic routes are clearly familiar to those skilled in the art, wherein the substituents described in compounds of the Formula (J) or any related formulae where applicable, such as Formula (I), (II), (IIa-1) to (IIa-8), (III), (IIIa-1) to (IIIa-8), (IV), (V), (Va-1) to (Va-11), (VI), or (VIa-1) to (VIa-11), herein can be varied with a choice of appropriate starting materials and reagents utilized in the steps presented.

BIOLOGICAL EXAMPLES

Example B-1

Bromodomain and Extraterminal Domain (BET) Binding Assay

The bromodomain binding assays were performed by Reaction Biology Corp., Malvern, Pa., USA (www.reaction-biology.com). The BET binding assays were conducted in 384 well microplates in assay buffer (50 mM HEPES-HCl, pH 7.5, 100 mM NaCl, 1 mg/ml BSA, 0.05% CHAPS, and 0.5% DMSO) with compounds added as DMSO stocks at a single concentration or with 10-point dose response titrations. BET protein or assay buffer were delivered to the appropriate wells of the microplate. Test compound was then delivered by acoustic technology via a Labcyte Echo550 liquid handler. The microplate was centrifuged for 5 min and pre-incubated for 30 min at RT with gentle shaking. The ligand (histone H4 peptide (1-21) K5/8/12/16Ac-biotin) was delivered and the microplate was again centrifuged for 5 min and allowed to incubate for 30 min at RT with gentle shaking. Donor beads were then added in the absence of light and the microplate was centrifuged and gently shaken. After 5 min, acceptor beads were added in the absence of light and the microplate was centrifuged and gently shaken in the dark for 60 min. The microplate was read using a Perkin Elmer EnSpire Alpha plate reader (λ Ex/λ Em=680/520-620 nm). Percent inhibition was calculated relative to positive and negative controls on a per plate basis. For titration experiments, IC$_{50}$ values were determined by fitting the percent inhibition versus compound concentration.

Final Protein and Ligand Concentrations

| Target | Protein Conc. (nM) | Ligand Conc. (nM) |
|---|---|---|
| BRD2-1 | 40 | 40 |
| BRD2-2 | 120 | 60 |
| BRD3-1 | 30 | 40 |
| BRD3-2 | 75 | 75 |
| BRD4-1 | 20 | 20 |
| BRD4-2 | 130 | 70 |
| BRDT-1 | 60 | 40 |

Compounds described herein were assayed and found to bind to bromodomain and extraterminal domain proteins. BRD4-1 and BRD4-2 IC$_{50}$ for compounds of the invention are shown in Table 3. ND means "not determined."

TABLE 3

BRD4-1 and BRD4-2 IC$_{50}$ (µM)

| Synthesis Example No. | Compound No. | BRD4-1 IC$_{50}$ (µM) | BRD4-2 IC$_{50}$ (µM) |
|---|---|---|---|
| S-1 | 1 | 10.1 | 0.002 |
| S-2 | 2 | ND | 0.001 |
| S-3 | 3 | 2.050 | <0.002 |
| S-4 | 4 | 0.197 | 0.006 |
| S-5 | 5 | 0.744 | 0.018 |
| S-6 | 6 | 1.485 | 0.032 |
| S-7 | 7 | ND | 0.497 |
| S-8 | 8 | 0.094 | 0.074 |
| S-9 | 14 | 1.170 | 0.047 |
| S-10 | 145 | 0.601 | 0.007 |
| S-11 | 146 | 2.922 | 0.002 |

TABLE 3-continued

BRD4-1 and BRD4-2 IC$_{50}$ (µM)

| Synthesis Example No. | Compound No. | BRD4-1 IC$_{50}$ (µM) | BRD4-2 IC$_{50}$ (µM) |
|---|---|---|---|
| S-12 | 13 | 4.942 | 0.009 |
| S-13 | 23 | 1.120 | 0.018 |
| S-14 | 10 | 0.111 | 0.0034 |
| S-15 | 147 | 0.299 | 0.0018 |
| S-16 | 22 | 0.638 | 0.0110 |
| S-17 | 76 | 0.265 | 0.0170 |
| S-18 | 148 | >10 | 0.1027 |
| S-19 | 149 | >10 | 0.1027 |
| S-20 | 150 | 3.595 | 0.0012 |
| S-21 | 151 | 9.380 | 0.0032 |
| S-22 | 152 | 1.492 | 0.0090 |
| S-23 | 153 | >10 | 0.5260 |
| S-24 | 154 | >10 | 0.2836 |
| S-25 | 155 | >10 | 4.066 |
| S-26 | 156 | >10 | 0.7400 |
| S-27 | 157 | >10 | 0.1452 |
| S-28 | 158 | 0.103 | 0.1962 |
| S-29 | 12 | 0.017 | 0.0125 |
| S-30 | 159 | 0.018 | 0.0017 |
| S-31 | 2.1 | 2.495 | 0.0198 |
| S-32 | 2.3 | 0.118 | 0.0285 |
| S-33 | 2.91 | 0.015 | 0.0073 |

ND: not determined

Example B-2

Cell Viability Assays

The effects of test compounds were studied in a cell viability assay in the MV-4-11 human acute myeloid leukemia cell line. The cells were harvested during the logarithmic growth period and counted. Cells were seeded at a count of 15000 cells per well/100 µl. After seeding, cells were incubated at 37° C. 5% CO$_2$ for 1 hr. Cells were treated with test compounds at 8 concentrations within a desired concentration range (e.g. 5 nM-10 µM) for generation of dose response curves by preparing serial dilutions of the test compound in DMSO which were further diluted with culture medium and then added to each well. The plate was further incubated for another 72 hrs in a humidified incubator at 37° C. and 5% CO$_2$. The assay was terminated by addition of Cell Titer-Glo reagent (Promega, Madison, Wis.) at ¼ the volume of total medium per well. Contents were mixed, the plate was incubated for 10 min at room temperature and luminescence was measured. Cell viability data were plotted using GraphPad Prism (GraphPad Software, Inc., San Diego, Calif.). In addition, a nonlinear regression model with a sigmoidal dose response and variable slope within GraphPad Prism was used to calculate the IC$_{50}$ value of individual test compounds. IC$_{50}$ values are given in Table 4.

TABLE 4

Cell Viability IC$_{50}$s for compounds in MV4-11 cells

| Synthesis Example No. | Compound No. | IC$_{50}$ (µM) |
|---|---|---|
| S-1 | 1 | 0.131 |
| S-2 | 2 | 0.111 |
| S-3 | 3 | 0.074 |
| S-4 | 4 | 0.115 |
| S-5 | 5 | 0.597 |
| S-6 | 6 | 1.792 |
| S-7 | 7 | 2.476 |
| S-8 | 8 | 0.379 |
| S-9 | 14 | 0.768 |
| S-10 | 145 | 0.245 |
| S-11 | 146 | 0.084 |
| S-12 | 13 | 0.540 |
| S-13 | 23 | 0.768 |
| S-14 | 10 | 0.126 |
| S-15 | 147 | 0.047 |
| S-16 | 22 | 1.412 |
| S-17 | 76 | 0.879 |
| S-18 | 148 | 1.283 |
| S-19 | 149 | 1.501 |
| S-20 | 150 | 0.193 |
| S-21 | 151 | 0.282 |
| S-22 | 152 | 0.536 |
| S-23 | 153 | 3.830 |
| S-24 | 154 | 2.890 |
| S-27 | 157 | 0.550 |
| S-28 | 158 | 0.560 |
| S-29 | 12 | 0.074 |
| S-31 | 2.1 | 0.470 |
| S-32 | 2.3 | 0.163 |

The effects of test compounds were also studied in the IEC-6 rat intestinal epithelial cell line to assess potential toxicity to non-cancerous cells. The cells were harvested during the logarithmic growth period and counted. In Protocol A, cells were seeded at a count of 3000 cells per well/100 µl in a 96-well plate. After seeding, cells were incubated at 37° C. 5% CO$_2$ for 24 hr. Cells were treated with test compounds at 8 concentrations within a desired concentration range (e.g. 5 nM-10 µM) for generation of dose response curves by preparing serial dilutions of the test compound in DMSO which were further diluted with culture medium and then added to each well. The plate was further incubated for another 96 hrs in humidified incubator at 37° C. and 5% CO$_2$. The assay was terminated by addition of resazurin (#R7017, Sigma). The plate was incubated for 4 hr at 37° C. 5% CO$_2$ and fluorescence was measured using excitation and emission wavelengths of 535 and 590 nm, respectively. Cell viability data were plotted using GraphPad Prism (GraphPad Software, Inc., San Diego, Calif.). In addition, a nonlinear regression model with a sigmoidal dose response and variable slope within GraphPad Prism was used to calculate the IC$_{50}$ value of individual test compounds. Protocol B was the same as Protocol A except that cells were seeded at a count of 4000 cells per well/100 µl in a 96-well plate, and the incubation with test compound was for 48 hrs instead of 96 hrs. IC$_{50}$ values are given in Table 5.

TABLE 5

Cell Viability IC$_{50}$s for compounds in IEC-6 cells

| Synthesis No. | Compound No. | Protocol A IC$_{50}$ (µM) | Protocol B IC$_{50}$ (µM) |
|---|---|---|---|
| S-1 | 1 | 0.266 | 4.91 |
| S-2 | 2 | 0.061 | ND |
| S-3 | 3 | 0.089 | ND |
| S-4 | 4 | 0.048 | 0.283 |
| S-8 | 8 | 0.156 | 0.521 |
| S-10 | 145 | ND | 0.691 |
| S-11 | 146 | ND | 0.729 |
| S-12 | 13 | ND | 2.500 |
| S-13 | 23 | ND | 1.62 |
| S-14 | 10 | ND | 0.780 |

TABLE 5-continued

Cell Viability IC$_{50}$s for compounds in IEC-6 cells

| Synthesis No. | Compound No. | Protocol A IC$_{50}$ (μM) | Protocol B IC$_{50}$ (μM) |
|---|---|---|---|
| S-15 | 147 | ND | 1.770 |

ND: not determined

Other compounds of the invention are also assayed for effect on cell viability. In addition, a panel of BET-sensitive and insensitive cell lines is profiled for effect on cell viability using test compounds. Cells are cultured in the presence of inhibitors at various concentrations for up to 72 hr. For cell viability assays as previously described (Guo Y, et al. 2012. J Hematol Oncol 5:72; Chen Y, et al. 2016. Oncogene 35:2971-8), 0.08 mg/ml XTT (2,3-bis-(2-methoxy-4-nitro-5-sulfophenyl)-2H-tetrazolium-5-carboxanilide) and 8 μM phenazine methyl sulfate (PMS) are added to the cells at the end of the test compound or vehicle treatment duration, and absorbance at 450 nm is measured after 3 hr incubation at 37° C. Assays are performed in triplicates. IC$_{50}$ values are estimated using a non-linear mixed effect model fitting a sigmoid curve to the experimental dose response data (Vis D J, et al. 2016. Pharmacogenomics 17(7):691-700).

Example B-3

Histologic Analysis

The inhibitory effects of test compounds on the growth of cells are demonstrated by Wright-Giemsa staining of cells fixed to glass slides after incubation of the test compound or vehicle with the cells for a certain duration (e.g., 48 h). Morphologic changes of treated cells associated with cell cycle arrest, such as condensed nuclei and shrinking or swollen cell membranes are noted.

Example B-4

In Vivo Efficacy Study

A study to evaluate test compound pharmacodynamics in MV-4-11 systemic leukemia model in NOD SCID mice is conducted. Female NOD SCID mice are inoculated with MV-4-11 cells systemically. Four weeks after cell inoculation, each animal is administered a single IV dose of test compound or vehicle. The dosing volume is 10 mL/kg (0.200 mL/20 g mouse), with volume adjusted according to body weight. Four hours after dosing, animals are sacrificed. Bone marrow and spleen (weight and size are recorded) are dissected, crushed in PBS and made into single cell suspensions for analysis by flow cytometry for the assessment of leukemic engraftment. Western blot analyses of bone marrow and spleen cell extracts with antibody against the housekeeping protein c-Myc are carried out for animals with successful leukemic engraftment.

Example B-5

Mouse Xenograft Model

To examine the in vivo antitumor activity of test compound (as a single agent and in combination with other agents such as enzalutamide) in a castration resistant prostate cancer mouse model, tumor growth experiments are performed in a VCaP cell line mouse xenograft model. Cells are implanted subcutaneously into the flanks of 4-week old male immunodeficient mice (such as nude or SCID mice) and allowed to grow. Tumors are measured using a caliper and tumor volumes calculated using the formula: Tumor volume=(a×b$^2$/2) where 'b' is the smallest diameter and 'a' is the largest diameter. Once the established tumors reach approximately 200 mm$^3$, the tumor-bearing mice are surgically castrated. The mice are stratified into treatment groups once the tumors grow back to the pre-castration size. The treatment groups are, for example: vehicle control, enzalutamide alone, test compound alone, and enzalutamide+test compound at 10 mice per group. The exact treatment groups, drug dose, and dosing schedule are determined according to the specific needs of the study. Tumor growth is monitored, and volume recorded at regular intervals. When the individual tumor of each mouse reaches an approximate endpoint (tumor volume>1,500 mm$^3$), the mouse is sacrificed. The tumor growth inhibition (TGI) is calculated by comparing the control group's tumor measurements with the other study groups once the predetermined endpoint is reached in the control group.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention. All references disclosed herein are hereby incorporated herein by reference.

The invention claimed is:

1. A compound of Formula (J):

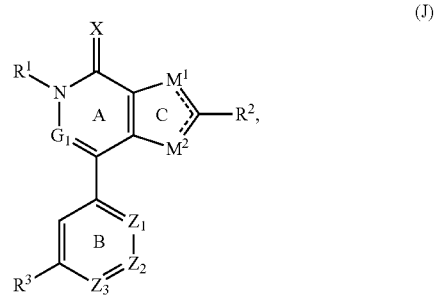

or a tautomer or stereoisomer thereof, or a pharmaceutically acceptable salt of any of the foregoing, wherein:
 each ==== is independently a single bond or double bond;
 X is O or S;
 $R^1$ is hydrogen, $C_1$-$C_3$ alkyl, —($C_1$-$C_3$ alkylene)OH, $C_1$-$C_3$ haloalkyl, or $C_3$-$C_4$ cycloalkyl;
 $G_1$ is $CR^a$, wherein:
  $R^a$ is hydrogen, halogen, or $C_1$-$C_4$ alkyl;
 $Z_1$ is C—$W_1$—$R^c$; wherein:
  each $W_1$ is independently —O— or —$NR^{w1}$—, wherein:
   $R^{w1}$ is hydrogen, $C_3$-$C_6$ cycloalkyl, or $C_1$-$C_4$ alkyl optionally substituted by oxo, —OH, or halogen, and
  $R^c$ is independently $C_3$-$C_6$ cycloalkyl, 4- to 6-membered heterocyclyl, $C_6$-$C_{14}$ aryl, or 5- or 6-membered heteroaryl, each of which is independently optionally substituted by $R^{c1}$, wherein each $R^{c1}$ is independently halogen, $C_1$-$C_4$ alkyl, $C_3$-$C_6$ cycloalkyl, 3- to 6-membered heterocyclyl, cyano, oxo, $C_1$-$C_4$ alkoxy, $C_1$-$C_4$ haloalkoxy, $C_1$-$C_4$ haloalkyl, —$OR^{10}$, —$NR^{10}R^{11}$, —$C(O)NR^{10}R^{11}$, —$NR^{10}C(O)R^{11}$, —$S(O)_2R^{10}$, —$NR^{10}S(O)_2R^{11}$, or —$S(O)_2NR^{10}R^{11}$;

$Z_2$ is C—$W_2$—$R^d$, wherein:
  $W_2$ is —O—, —$NR^{w2}$—, or a bond, wherein:
    $R^{w2}$ is hydrogen, $C_3$-$C_6$ cycloalkyl, or $C_1$-$C_4$ alkyl optionally substituted by oxo, —OH, or halogen, and
  $R^d$ is independently hydrogen, halogen, cyano, 3- to 6-membered heterocyclyl, or $C_1$-$C_4$ alkyl;

$Z_3$ is C—$R^e$, wherein:
  $R^e$ is independently hydrogen, halogen, cyano, 3- to 6-membered heterocyclyl, or $C_1$-$C_4$ alkyl;

$M^1$ is S or $CR^{1a}$;
$M^2$ is S or $CR^{2a}$, provided that
  (1) when $M^1$ is S, then the ═ adjacent to $M^1$ is a single bond and the ═ adjacent to M2 is a double bond,
  (2) when $M^2$ is S, then the ═ adjacent to $M^2$ is a single bond and the ═ adjacent to $M^1$ is a double bond, and
  (3) either $M^1$ or $M^2$ is S;

$R^{1a}$ and $R^{2a}$ are each independently hydrogen, halogen, $C_1$-$C_4$ alkyl, $C_3$-$C_6$ cycloalkyl, 3- to 6-membered heterocyclyl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is independently optionally substituted by $R^{12}$;

$R^2$ is hydrogen, halogen, $C_1$-$C_4$ alkyl, $C_3$-$C_6$ cycloalkyl, 3- to 6-membered heterocyclyl, —($C_1$-$C_3$ alkylene)3- to 6-membered heterocyclyl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$, or —$S(O)_2NR^{10}R^{11}$, each of which is independently optionally substituted by $R^{12}$;

$R^3$ is —$(CH_2)_mNR^{13}S(O)_2R^{14}$ wherein m is 0, 1, 2 or 3; $C_3$-$C_6$ cycloalkyl optionally substituted by halogen, oxo, —CN, or —OH; $C_1$-$C_4$ alkyl substituted by halogen, oxo, —CN, or —OH; or $C_2$-$C_6$ alkenyl;

$R^{10}$ and $R^{11}$ are each independently hydrogen, $C_1$-$C_4$ alkyl, $C_1$-$C_4$ alkoxy, $C_1$-$C_4$ alkenyl, $C_3$-$C_6$ cycloalkyl, $C_6$-$C_{14}$ aryl, 3- to 6-membered heterocyclyl, —($C_1$-$C_3$ alkylene)$C_3$-$C_6$ cycloalkyl, —($C_1$-$C_3$ alkylene) 3- to 6-membered heterocyclyl, —($C_1$-$C_3$ alkylene) $C_6$-$C_{14}$ aryl, —$NR^{15}R^{16}$, or —$C(O)R^{12}$, wherein each of $R^{10}$ and $R^{11}$ is independently optionally substituted by halogen, oxo, —CN, —$CF_3$, —OH, —$NR^{13}R^{14}$, —$C(O)NR^{13}R^{14}$, or $C_1$-$C_4$ alkyl optionally substituted by halogen, oxo, —CN, —$CF_3$, or —OH, or $R^{10}$ and $R^{11}$ are taken together with the atom or atoms to which they are attached to form a 3- to 6-membered heterocyclyl ring optionally substituted by halogen, oxo, —CN, —$CF_3$, —OH, or $C_1$-$C_4$ alkyl optionally substituted by halogen, oxo, —CN, or —OH;

each $R^{12}$ is independently halogen, cyano, $C_1$-$C_4$ haloalkyl, $C_1$-$C_4$ alkoxy, $C_1$-$C_4$ haloalkoxy, —$OR^{15}$, —$NR^{15}R^{16}$, —$C(O)NR^{15}R^{16}$, —$NR^{15}C(O)R^{16}$, —$S(O)_2R^{15}$, —$NR^{15}S(O)_2R^{16}$, —$S(O)_2NR^{15}R^{16}$, $C_3$-$C_6$ cycloalkyl, 3- to 6-membered heterocyclyl, or $C_1$-$C_4$ alkyl, each of which is independently optionally substituted by halogen, oxo, —$CF_3$, —CN, —OH, —$NR^{13}R^{14}$, or —$NR^{13}C(O)R^{14}$;

$R^{13}$ and $R^{14}$ are independently hydrogen, $C_1$-$C_4$ alkyl $C_3$-$C_6$ cycloalkyl, or 3- to 6-membered heterocyclyl, each of which is independently optionally substituted by halogen, oxo, —CN, or —OH, or $R^{13}$ and $R^{14}$ are taken together with the atom or atoms to which they are attached to form a 3- to 6-membered heterocyclyl ring optionally substituted by halogen, oxo, —CN, —OH, or $C_1$-$C_4$ alkyl optionally substituted by halogen, oxo, —CN, or —OH; and each $R^{15}$ and $R^{16}$ are independently hydrogen, $C_1$-$C_4$ alkyl, $C_3$-$C_6$ cycloalkyl, or 3- to 6-membered heterocyclyl, each of which is independently optionally substituted by halogen, oxo, —CN, or —OH, or $R^{15}$ and $R^{16}$ are taken together with the atoms to which they are attached to form a 3- to 6-membered heterocyclyl ring optionally substituted by halogen, oxo, —CN, —OH, or $C_1$-$C_4$ alkyl optionally substituted by halogen, oxo, —CN, or —OH.

2. The compound of claim 1, wherein the compound is a compound of Formula (I):

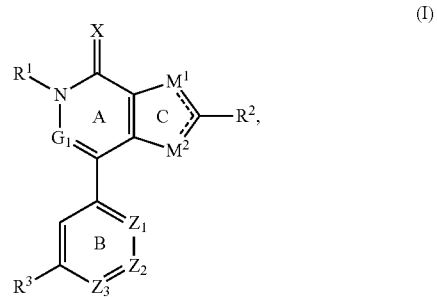

(I)

or a tautomer or stereoisomer thereof, or a pharmaceutically acceptable salt of any of the foregoing, wherein:
each ═ is independently a single bond or double bond;
X is O or S;
$R^1$ is hydrogen, $C_1$-$C_3$ alkyl, —($C_1$-$C_3$ alkylene)OH, $C_1$-$C_3$ haloalkyl, or $C_3$-$C_4$ cycloalkyl;
$G_1$ is $CR^a$, wherein:
  $R^a$ is hydrogen, halogen, or $C_1$-$C_4$ alkyl;
$Z_1$ is C—$W_1$—$R^c$; wherein:
  each $W_1$ is independently —O— or —$NR^{w1}$—, wherein:
    $R^{w1}$ is hydrogen, $C_3$-$C_6$ cycloalkyl, or $C_1$-$C_4$ alkyl optionally substituted by oxo, —OH, or halogen, and
  $R^c$ is independently 4- to 6-membered heterocyclyl, $C_6$-$C_{14}$ aryl, or 5- or 6-membered heteroaryl, each of which is independently optionally substituted by $R^{c1}$, wherein each $R^{c1}$ is independently halogen, $C_1$-$C_4$ alkyl, $C_3$-$C_6$ cycloalkyl, 3- to 6-membered heterocyclyl, cyano, oxo, $C_1$-$C_4$ alkoxy, $C_1$-$C_4$ haloalkoxy, $C_1$-$C_4$ haloalkyl, —$OR^{10}$, —$NR^{10}R^{11}$, —$C(O)NR^{10}R^{11}$, —$NR^{10}C(O)R^{11}$, —$S(O)_2R^{10}$, —$NR^{10}S(O)_2R^{11}$, or —$S(O)_2NR^{10}R^{11}$;

$Z_2$ is C—$W_2$—$R^d$, wherein:
  $W_2$ is —O—, —$NR^{w2}$—, or a bond, wherein:
    $R^{w2}$ is hydrogen, $C_3$-$C_6$ cycloalkyl, or $C_1$-$C_4$ alkyl optionally substituted by oxo, —OH, or halogen, and $R^d$ is independently hydrogen, halogen, cyano, 3- to 6-membered heterocyclyl, or $C_1$-$C_4$ alkyl;

$Z_3$ is C—$R^e$, wherein:

$R^e$ is independently hydrogen, halogen, cyano, 3- to 6-membered heterocyclyl, or $C_1$-$C_4$ alkyl;

$M^1$ is S or $CR^{1a}$;

$M^2$ is S or $CR^{2a}$, provided that (1) when $M^1$ is S, then the ═══ adjacent to $M^1$ is a single bond and the ═══ adjacent to $M^2$ is a double bond, (2) when $M^2$ is S, then the ═══ adjacent to $M^2$ is a single bond and the ═══ adjacent to $M^1$ is a double bond, and (3) at least one of $M^1$ and $M^2$ is not S;

$R^{1a}$ and $R^{2a}$ are each independently hydrogen, halogen, $C_1$-$C_4$ alkyl, $C_3$-$C_6$ cycloalkyl, 3- to 6-membered heterocyclyl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$ or —$S(O)_2NR^{10}R^{11}$, each of which is independently optionally substituted by $R^{12}$;

$R^2$ is halogen, $C_1$-$C_4$ alkyl, $C_3$-$C_6$ cycloalkyl, 3- to 6-membered heterocyclyl, —($C_1$-$C_3$ alkylene)3- to 6-membered heterocyclyl, 5- to 10-membered heteroaryl, cyano, oxo, $C_1$-$C_4$ haloalkyl, $C_1$-$C_4$ alkoxy, $C_1$-$C_4$ haloalkoxy, —$OR^{10}$, —$NR^{10}R^{11}$, —$C(O)OR^{10}$, —$C(O)NR^{10}R^{11}$, —$NR^{10}C(O)R^{11}$, —$S(O)_2R^{10}$, —$NR^{10}S(O)_2R^{11}$, or —$S(O)_2NR^{10}R^{11}$, each of which is independently optionally substituted by $R^{12}$;

$R^3$ is —$(CH_2)_mNR^{13}S(O)_2R^{14}$, $C_3$-$C_6$ cycloalkyl, or $C_1$-$C_4$ alkyl substituted by halogen, oxo, —CN, or —OH, wherein m is 0, 1, 2 or 3;

$R^{10}$ and $R^{11}$ are each independently hydrogen, $C_1$-$C_4$ alkyl, $C_1$-$C_4$ alkoxy, $C_1$-$C_4$ alkenyl, $C_3$-$C_6$ cycloalkyl, 3- to 6-membered heterocyclyl, —($C_1$-$C_3$ alkylene)$C_3$-$C_6$ cycloalkyl, —($C_1$-$C_3$ alkylene) 3- to 6-membered heterocyclyl, —$NR^{15}R^{16}$, or —$C(O)R^{12}$, wherein each of $R^{10}$ and $R^{11}$ is independently optionally substituted by halogen, oxo, —CN, —$CF_3$, —OH, —$NR^{13}R^{14}$, —$C(O)NR^{13}R^{14}$, or $C_1$-$C_4$ alkyl optionally substituted by halogen, oxo, —CN, —$CF_3$, or —OH, or $R^{10}$ and $R^{11}$ are taken together with the atom or atoms to which they are attached to form a 3- to 6-membered heterocyclyl ring optionally substituted by halogen, oxo, —CN, —$CF_3$, —OH, or $C_1$-$C_4$ alkyl optionally substituted by halogen, oxo, —CN, or —OH;

each $R^{12}$ is independently halogen, cyano, $C_1$-$C_4$ haloalkyl, $C_1$-$C_4$ alkoxy, $C_1$-$C_4$ haloalkoxy, —$OR^{15}$, —$NR^{15}R^{16}$, —$C(O)NR^{15}R^{16}$, —$NR^{15}C(O)R^{16}$, —$S(O)_2R^{15}$, —$NR^{15}S(O)_2R^{16}$, —$S(O)_2NR^{15}R^{16}$, $C_3$-$C_6$ cycloalkyl, 3- to 6-membered heterocyclyl, or $C_1$-$C_4$ alkyl, each of which is independently optionally substituted by halogen, oxo, —$CF_3$, —CN, —OH, —$NR^{13}R^{14}$, or —$NR^{13}C(O)R^{14}$;

$R^{13}$ and $R^{14}$ are independently hydrogen, $C_1$-$C_4$ alkyl $C_3$-$C_6$ cycloalkyl, or 3- to 6-membered heterocyclyl, each of which is independently optionally substituted by halogen, oxo, —CN, or —OH, or $R^{13}$ and $R^{14}$ are taken together with the atom or atoms to which they are attached to form a 3- to 6-membered heterocyclyl ring optionally substituted by halogen, oxo, —CN, —OH, or $C_1$-$C_4$ alkyl optionally substituted by halogen, oxo, —CN, or —OH; and each $R^{15}$ and $R^{16}$ are independently hydrogen, $C_1$-$C_4$ alkyl, $C_3$-$C_6$ cycloalkyl, or 3- to 6-membered heterocyclyl, each of which is independently optionally substituted by halogen, oxo, —CN, or —OH, or $R^{15}$ and $R^{16}$ are taken together with the atoms to which they are attached to form a 3- to 6-membered heterocyclyl ring optionally substituted by halogen, oxo, —CN, —OH, or $C_1$-$C_4$ alkyl optionally substituted by halogen, oxo, —CN, or —OH.

3. The compound of claim 1, or a tautomer or stereoisomer thereof, or a pharmaceutically acceptable salt of any of the foregoing, wherein the compound is of Formula (II),

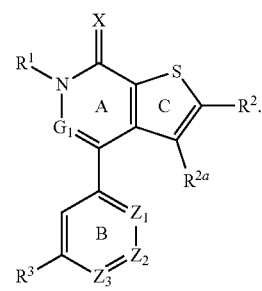

(II)

4. The compound of claim 1, or a tautomer or stereoisomer thereof, or a pharmaceutically acceptable salt of any of the foregoing, wherein the compound is of Formula (III),

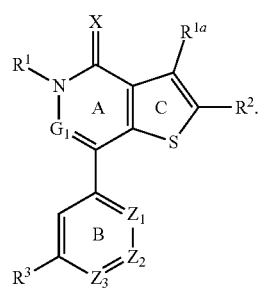

(III)

5. The compound of claim 1, or a tautomer or stereoisomer thereof, or a pharmaceutically acceptable salt of any of the foregoing, wherein X is O.

6. The compound of claim 1, or a tautomer or stereoisomer thereof, or a pharmaceutically acceptable salt of any of the foregoing, wherein $G_1$ is CH.

7. The compound of claim 1, or a tautomer or stereoisomer thereof, or a pharmaceutically acceptable salt of any of the foregoing, wherein $Z^1$ is C—$W_1$—$R^c$ and $R^c$ is $C_6$-$C_{14}$ aryl optionally substituted by $R^{c1}$.

8. The compound of claim 7, or a tautomer or stereoisomer thereof, or a pharmaceutically acceptable salt of any of the foregoing, wherein R' is phenyl optionally substituted by halogen or $C_1$-$C_4$ alkyl.

9. The compound of claim 1, or a tautomer or stereoisomer thereof, or a pharmaceutically acceptable salt of any of the foregoing, wherein $Z_2$ is CH.

10. The compound of claim 1, or a tautomer or stereoisomer thereof, or a pharmaceutically acceptable salt of any of the foregoing, wherein $Z_3$ is CH.

11. The compound of claim 1, or a tautomer or stereoisomer thereof, or a pharmaceutically acceptable salt of any of the foregoing, wherein $R^1$ is $C_1$-$C_3$ alkyl.

12. The compound of claim 1, or a tautomer or stereoisomer thereof, or a pharmaceutically acceptable salt of any of the foregoing, wherein $R^2$ is —$C(O)NR^{10}R^{11}$, 5- to 10-membered heteroaryl, —($C_1$-$C_3$ alkylene)3- to 6-membered heterocyclyl, or $C_1$-$C_4$ alkyl, each of which is independently optionally substituted by $R^{12}$.

13. The compound of claim 12, or a tautomer or stereoisomer thereof, or a pharmaceutically acceptable salt of any of the foregoing, wherein $R^2$ is —C(O)NR$^{10}$R$^{11}$ which is optionally substituted by $R^{12}$, wherein $R^{10}$ and $R^{11}$ are each independently hydrogen, $C_1$-$C_4$ alkyl, or $C_3$-$C_6$ cycloalkyl, or $R^{10}$ and $R^{11}$ are taken together with the atom or atoms to which they are attached to form a 3- to 6-membered heterocyclyl ring optionally substituted by halogen.

14. The compound of claim 12, or a tautomer or stereoisomer thereof, or a pharmaceutically acceptable salt of any of the foregoing, wherein $R^2$ is 5- to 10-membered heteroaryl optionally substituted by $R^{12}$.

15. The compound of claim 1, or a tautomer or stereoisomer thereof, or a pharmaceutically acceptable salt of any of the foregoing, wherein $R^3$ is —(CH$_2$)$_m$NR$^{13}$S(O)$_2$R$^{14}$ or $C_1$-$C_4$ alkyl substituted by halogen, oxo, —CN, or —OH.

16. The compound of claim 1, or a tautomer or stereoisomer thereof, or a pharmaceutically acceptable salt of any of the foregoing, wherein $R^3$ is —(CH$_2$)$_m$NR$^{13}$S(O)$_2$R$^{14}$.

17. The compound of claim 1, or a tautomer or stereoisomer thereof, or a pharmaceutically acceptable salt of any of the foregoing, wherein $R^3$ is

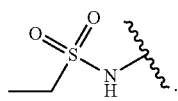

18. The compound of claim 1, or a tautomer or stereoisomer thereof, or a pharmaceutically acceptable salt of any of the foregoing, wherein $R^3$ is $C_1$-$C_4$ alkyl substituted by —OH.

19. The compound of claim 18, or a tautomer or stereoisomer thereof, or a pharmaceutically acceptable salt of any of the foregoing, wherein $R^3$ is

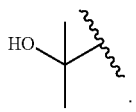 [SMILES: *C(C)(C)O]

20. The compound of claim 1, or a tautomer or stereoisomer thereof, or a pharmaceutically acceptable salt of any of the foregoing, wherein $R^{1a}$ is hydrogen.

21. The compound of claim 1, or a tautomer or stereoisomer thereof, or a pharmaceutically acceptable salt of any of the foregoing, wherein $R^{2a}$ is hydrogen.

22. The compound of claim 1, wherein the compound is selected from the group consisting of:

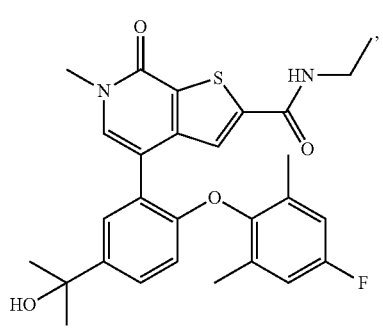

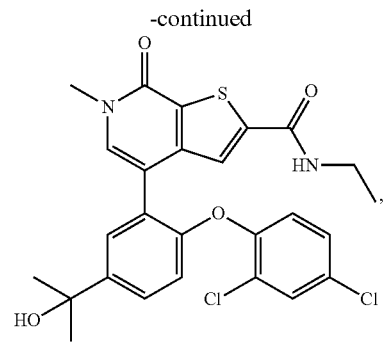

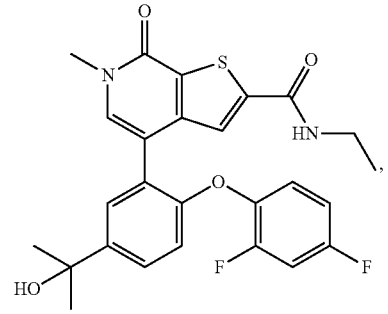

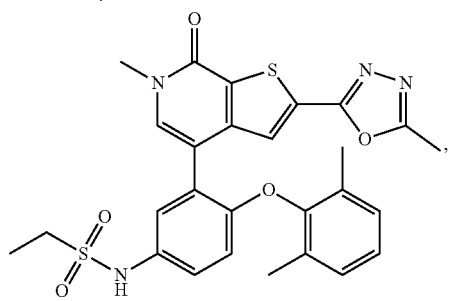

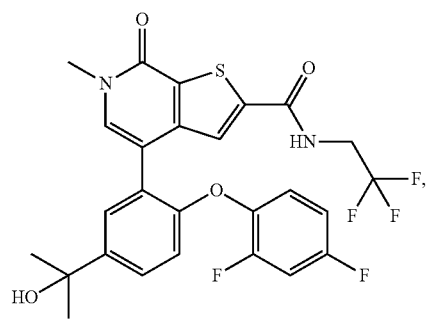

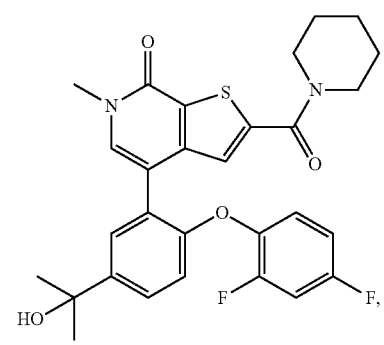

249
-continued
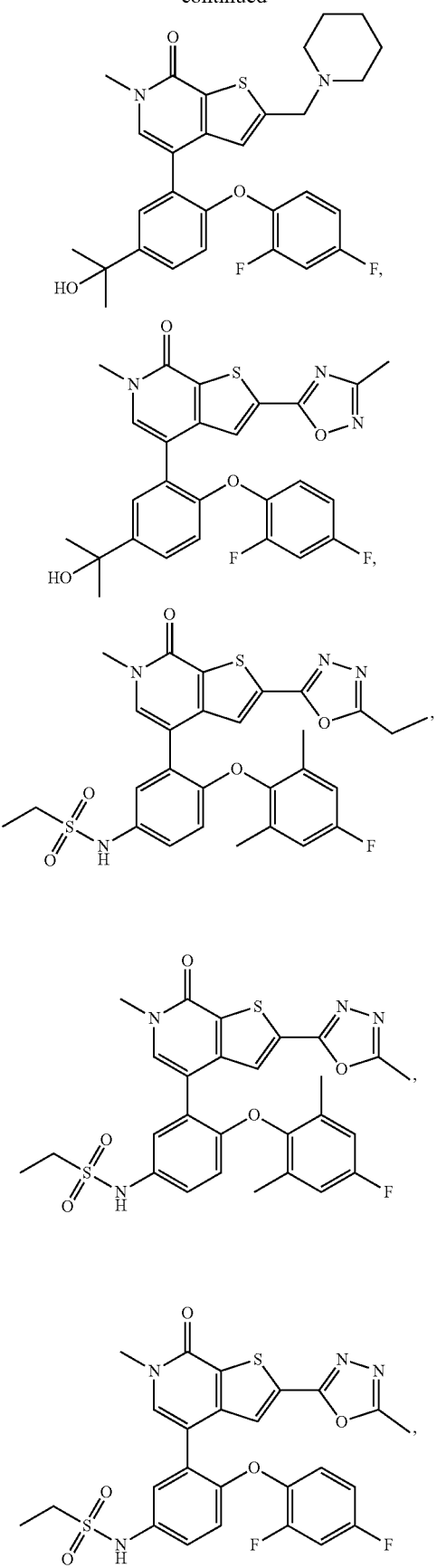
250
-continued
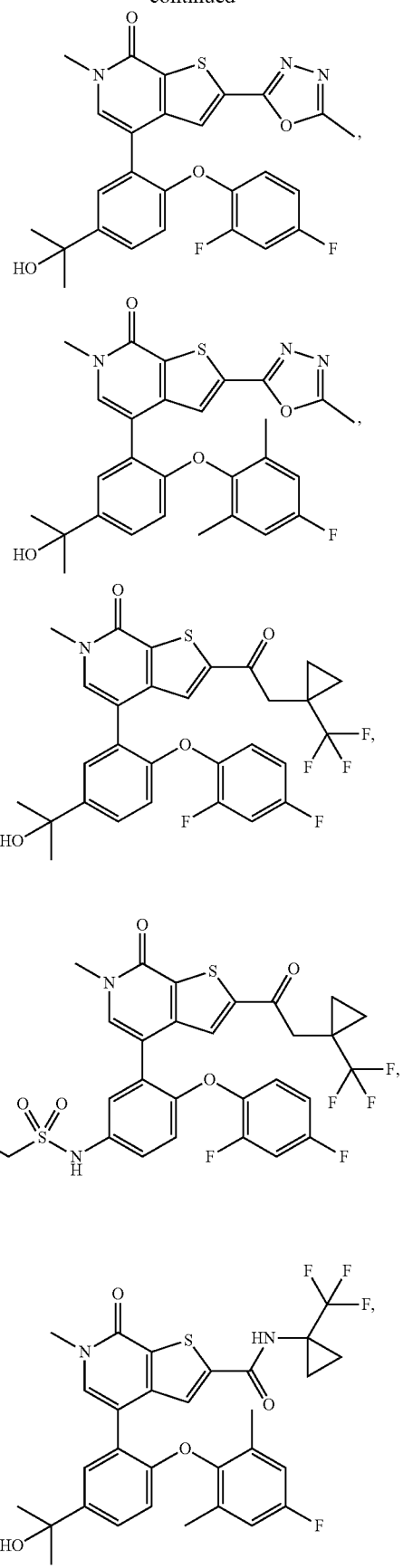

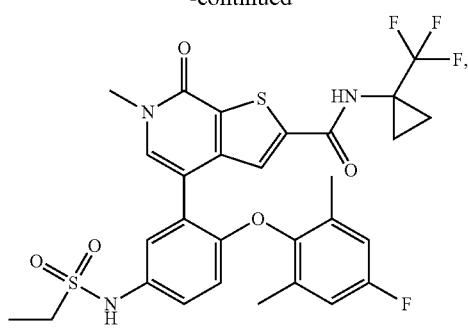
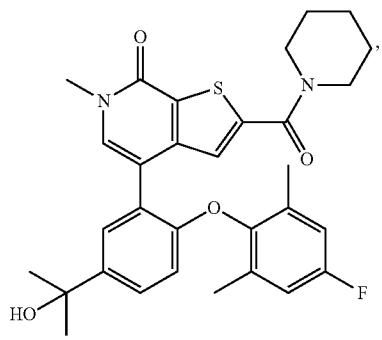
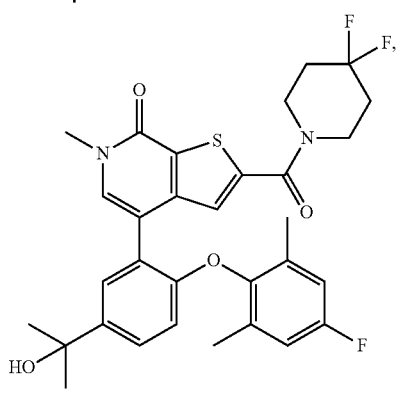
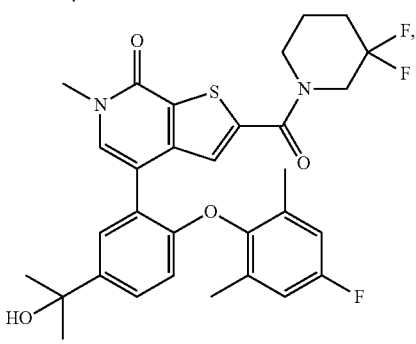
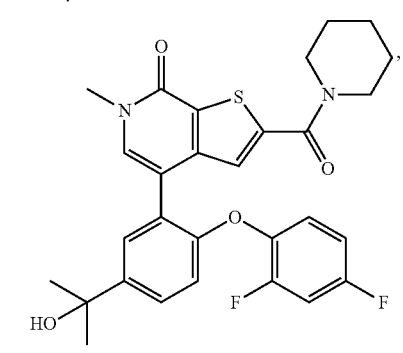
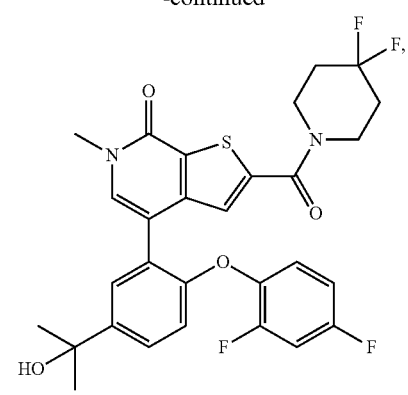
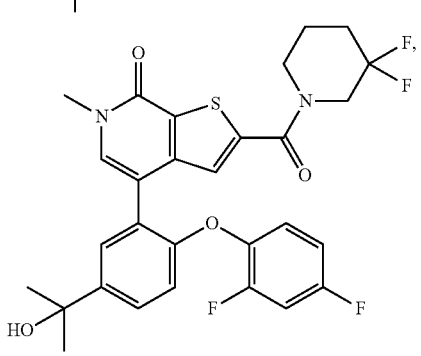
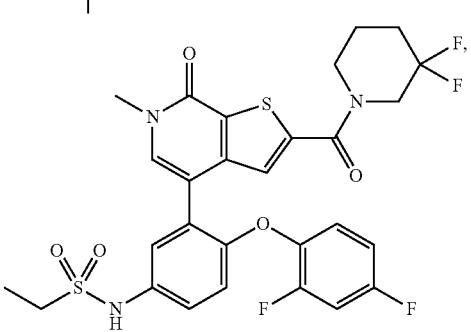
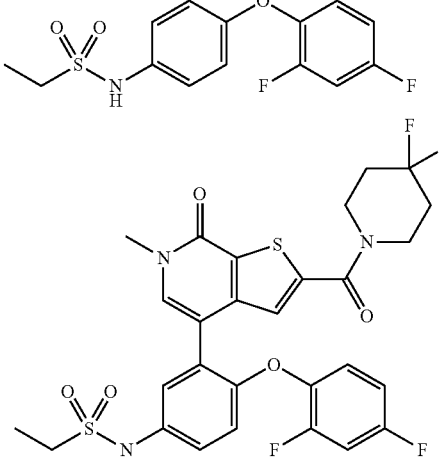
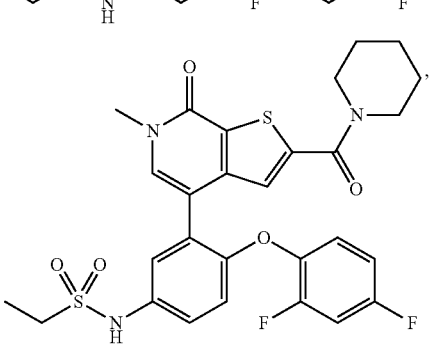

253
-continued
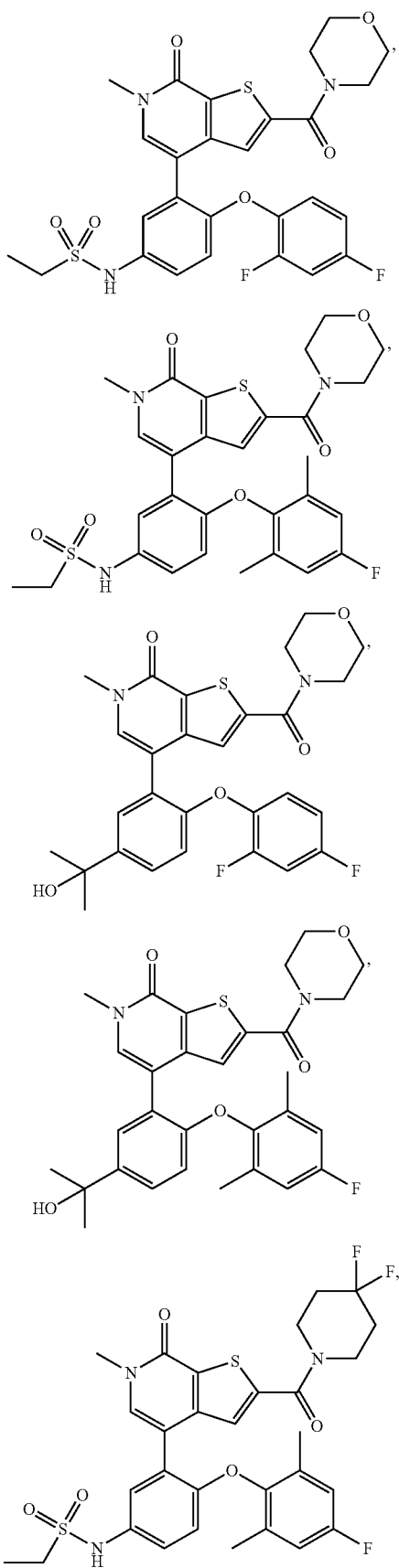
254
-continued
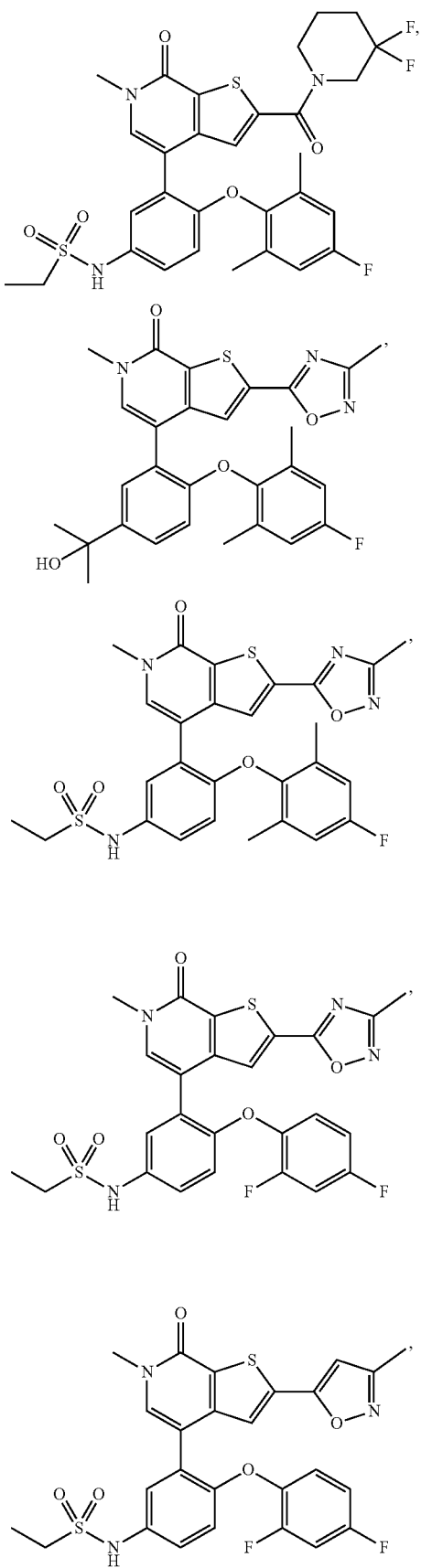

255
-continued
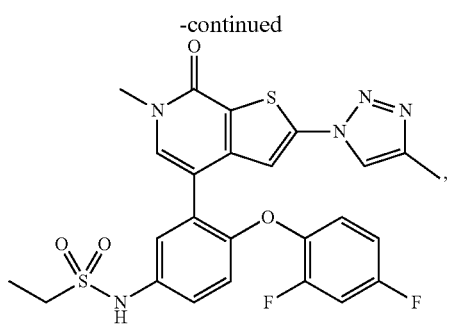
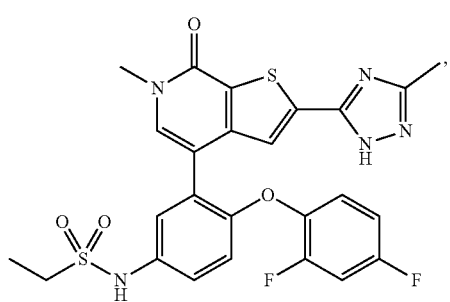
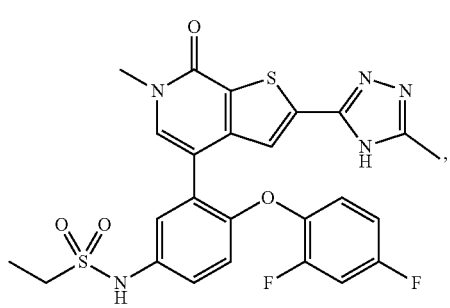
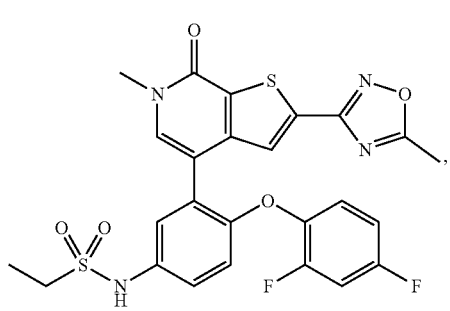
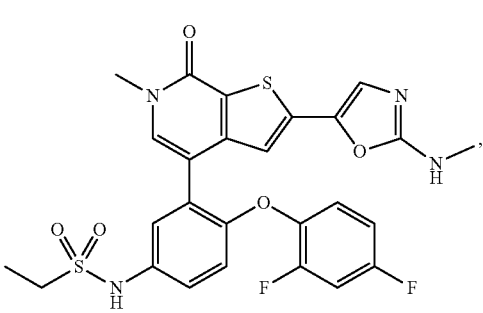
256
-continued
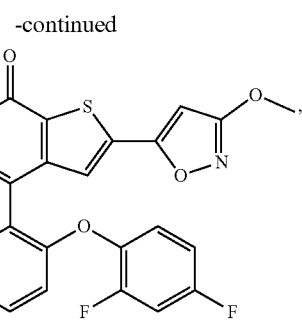
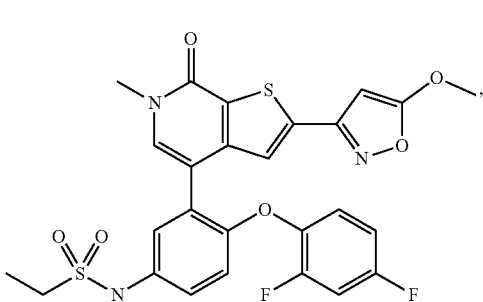
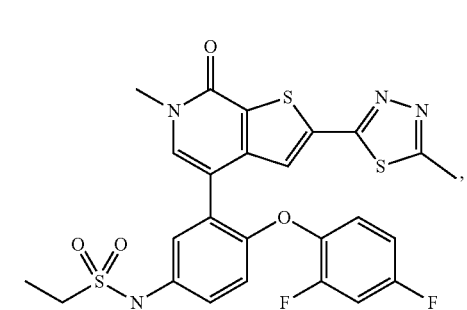
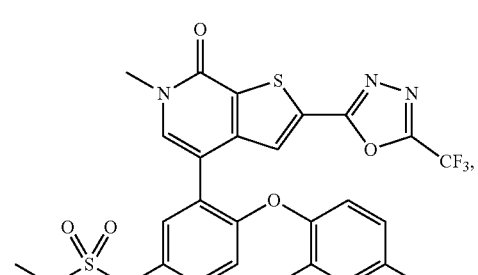
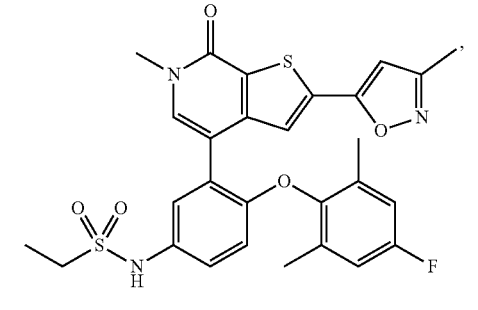

257
-continued
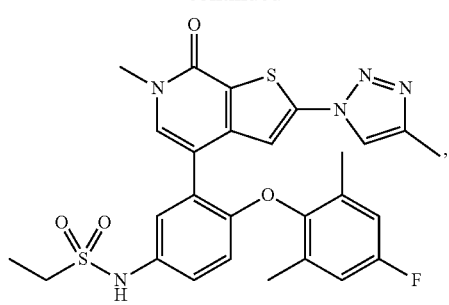
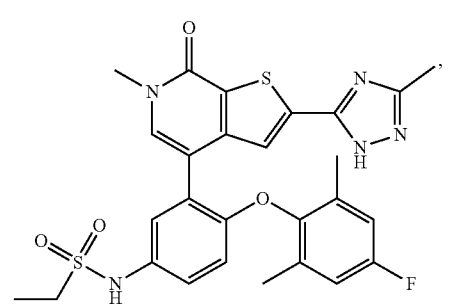
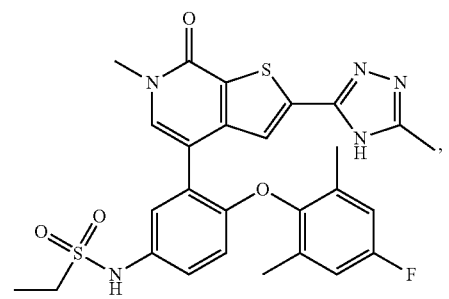
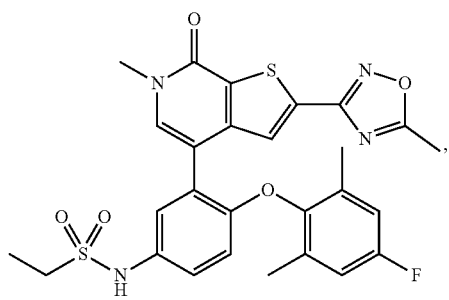
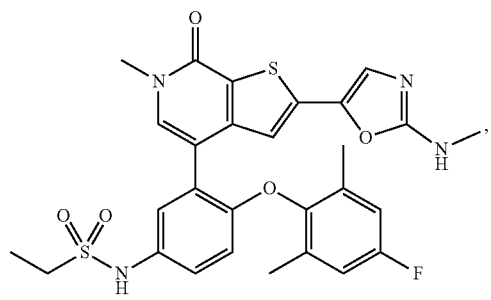
258
-continued
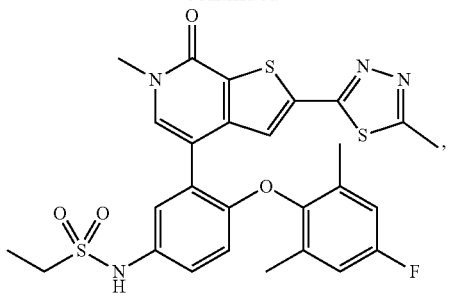
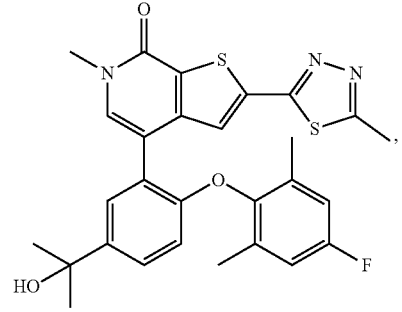
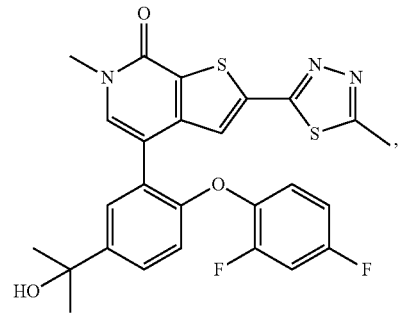
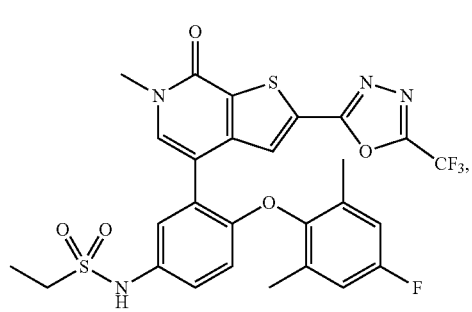
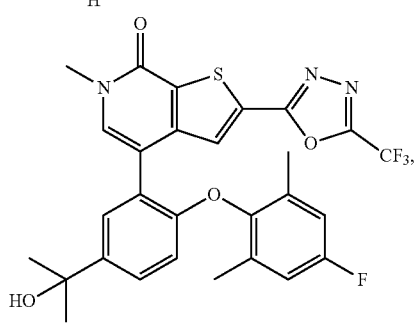

259
-continued
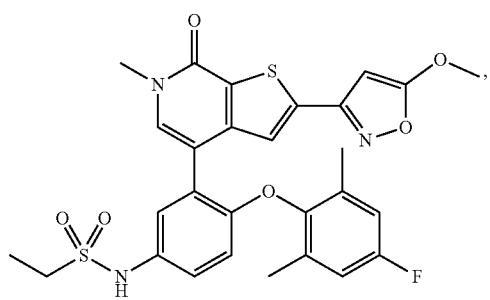
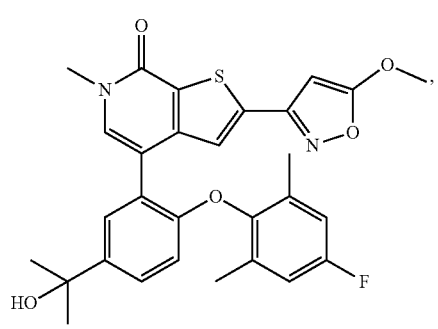
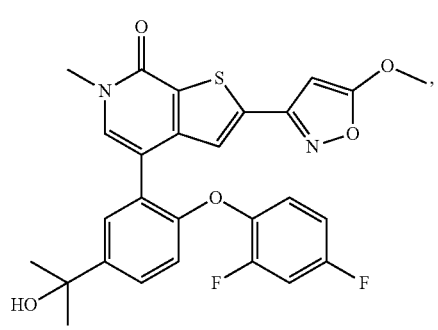
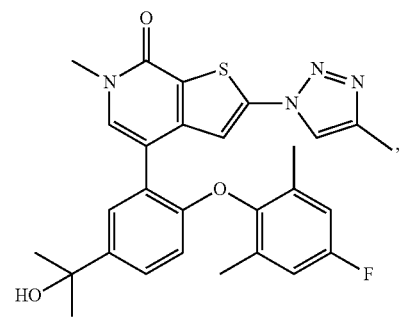
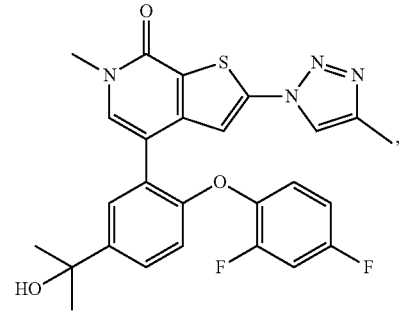
260
-continued
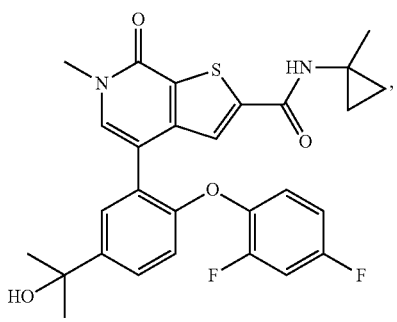
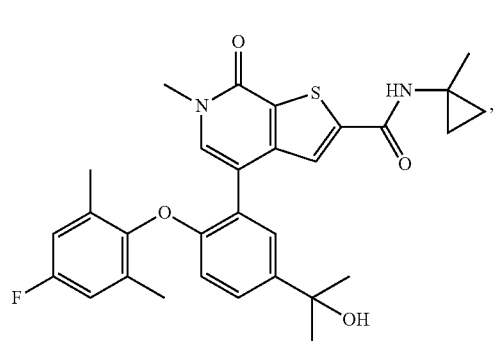
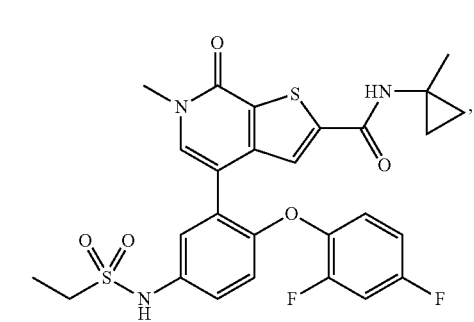
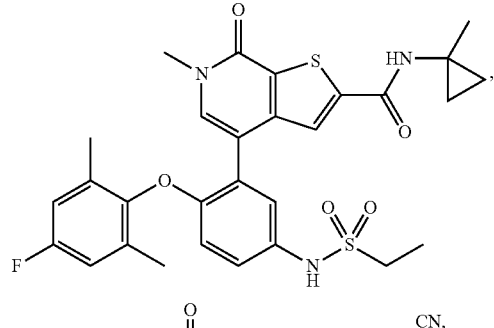
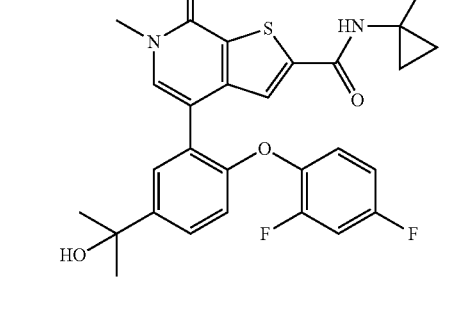

261
-continued
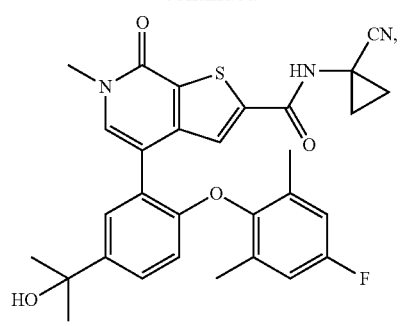
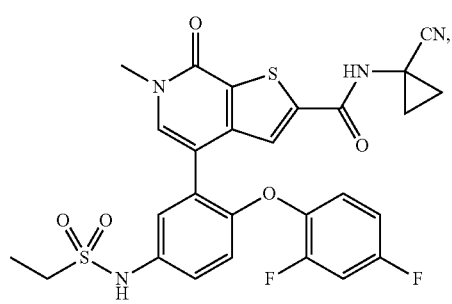
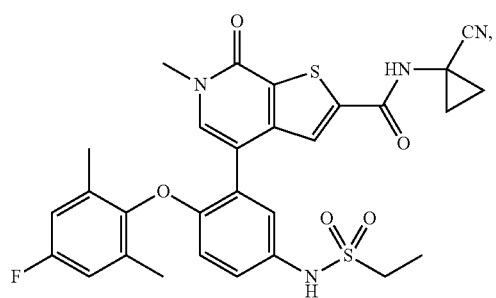
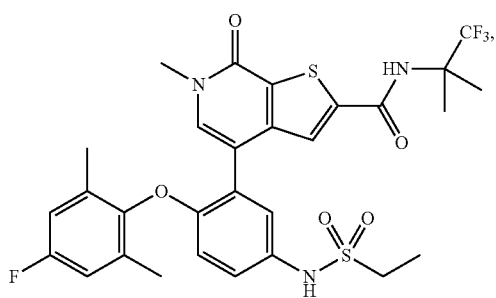
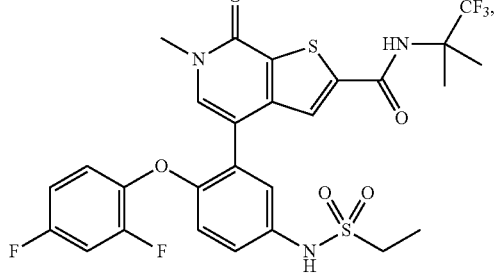
262
-continued
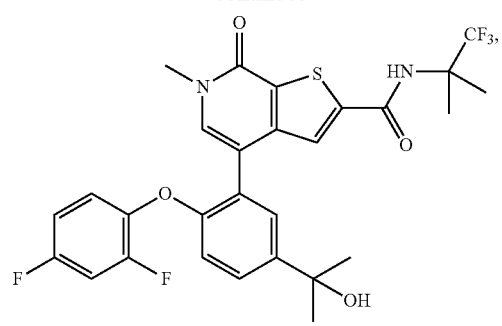
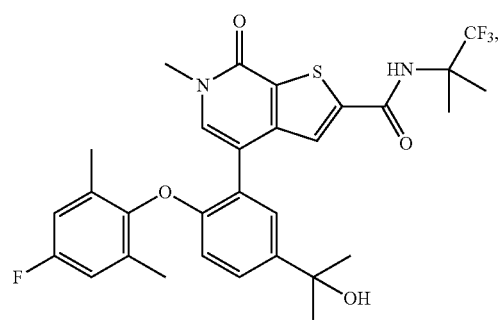
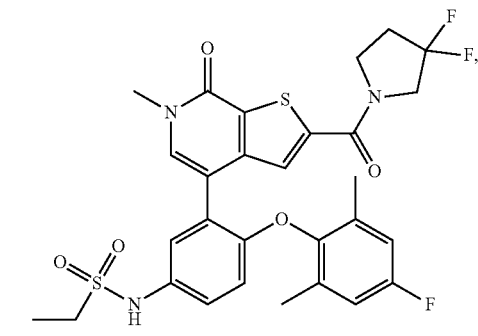
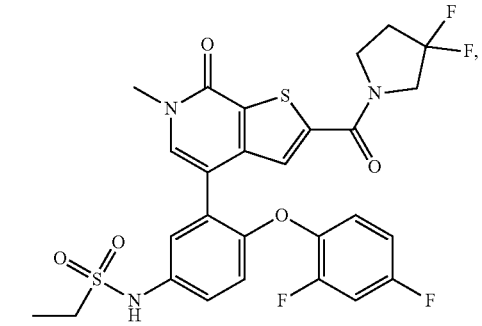
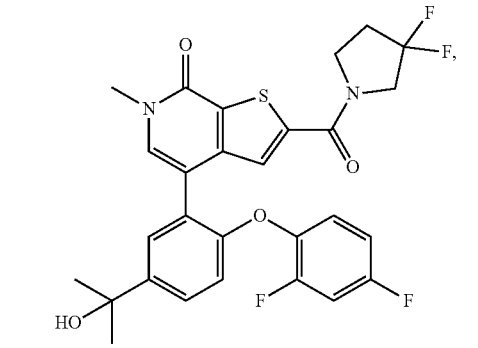

263
-continued
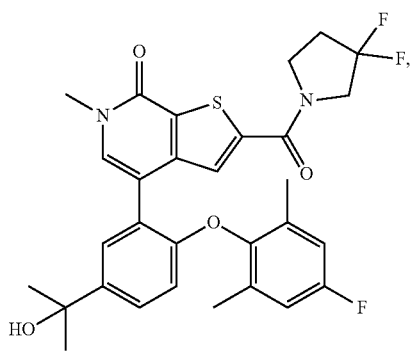
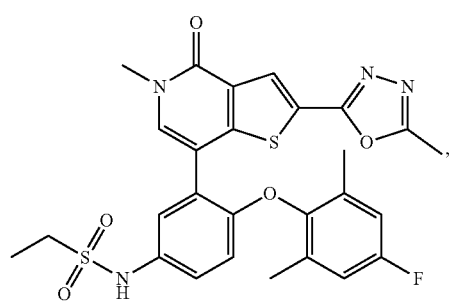
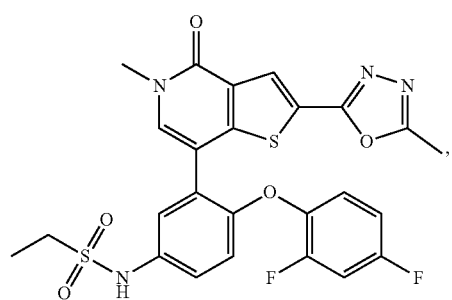
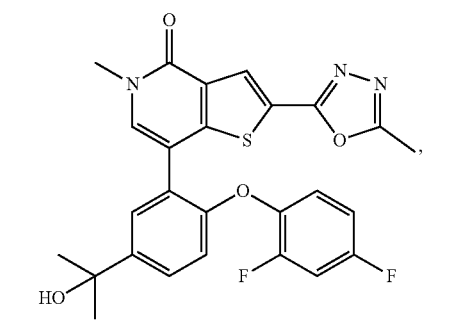
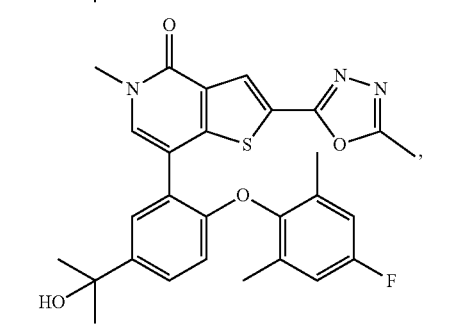
264
-continued
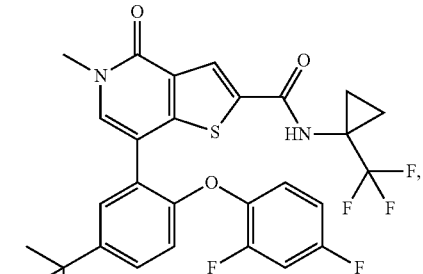
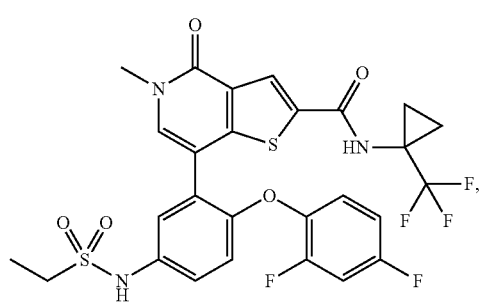
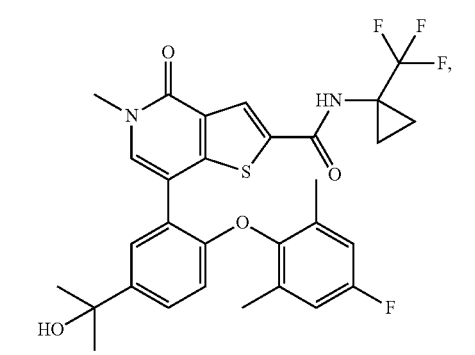
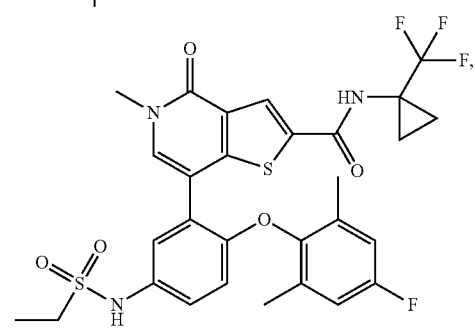
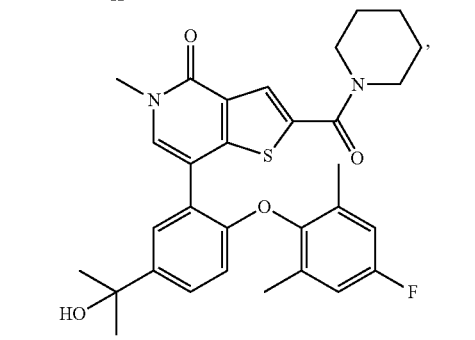

265
-continued
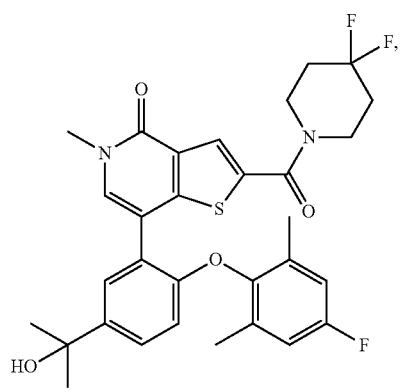
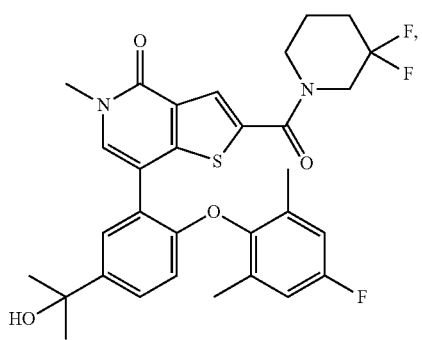
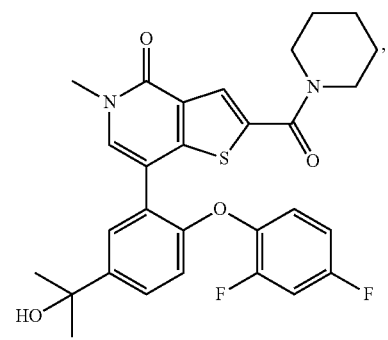
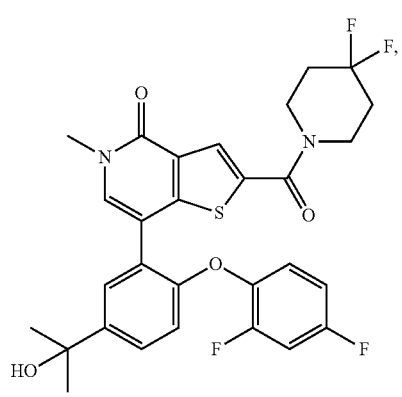
266
-continued
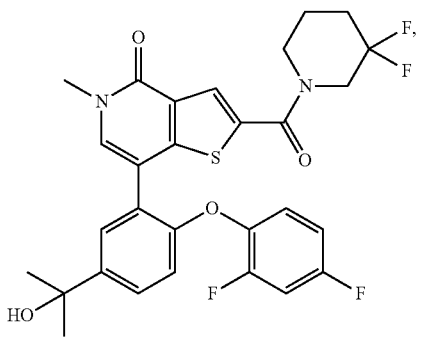
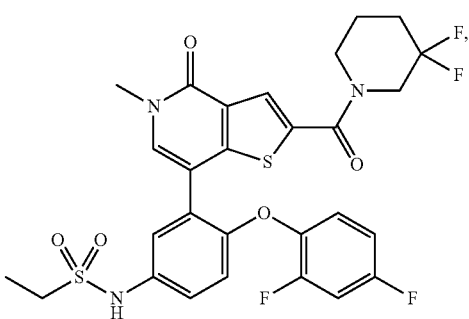
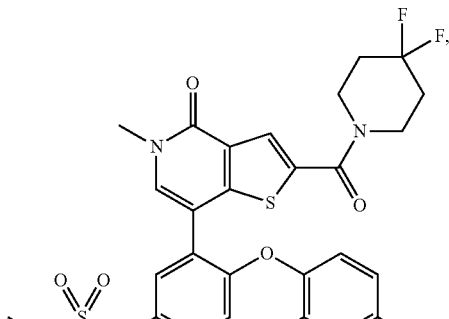
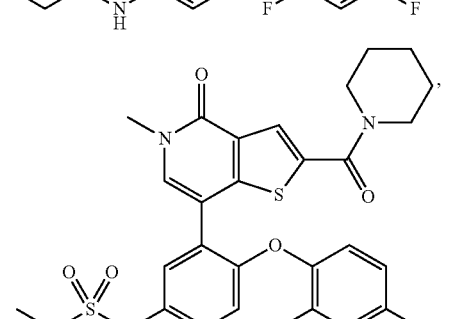
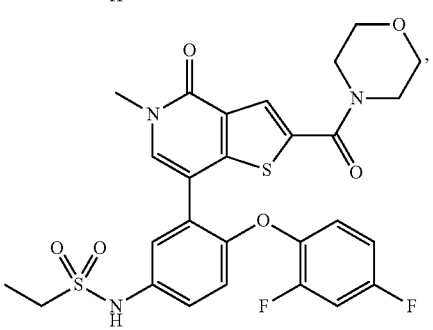

267
-continued
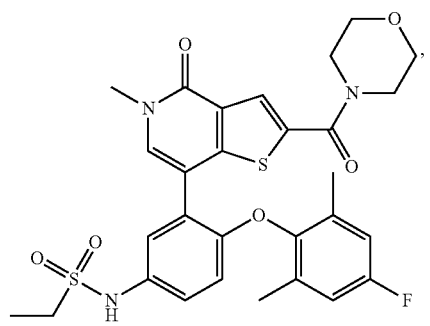
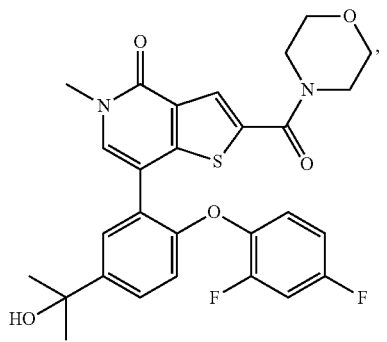
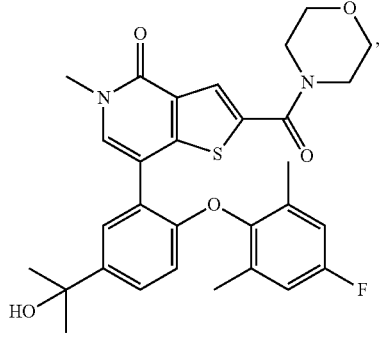
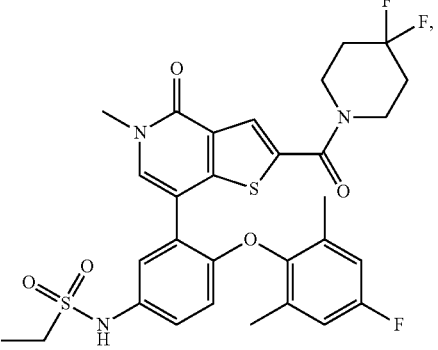
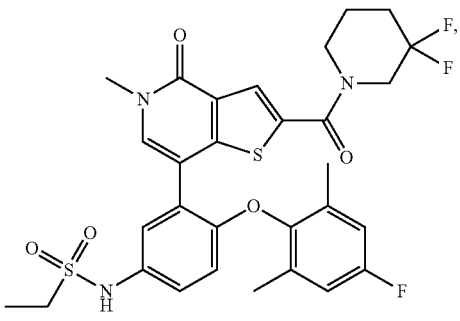
268
-continued
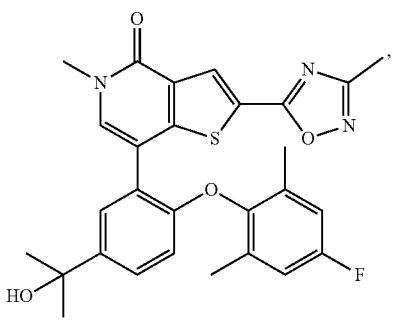
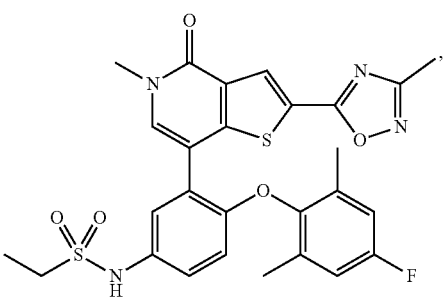
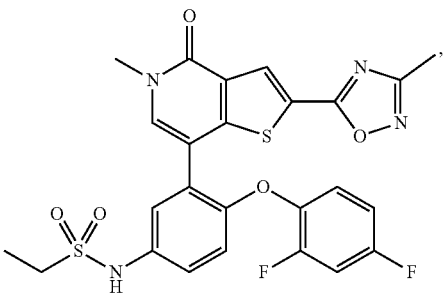
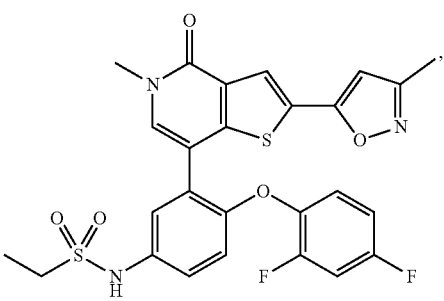
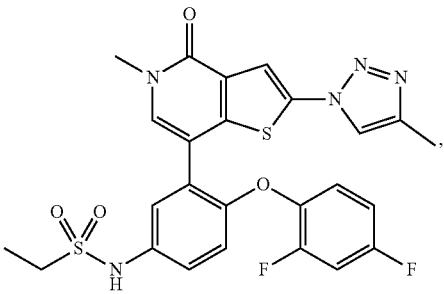

269
-continued
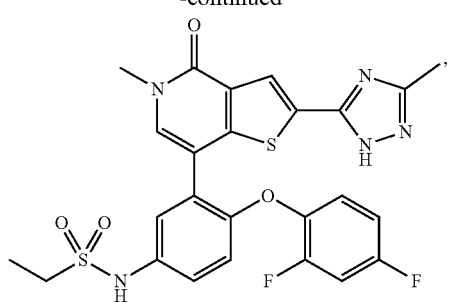
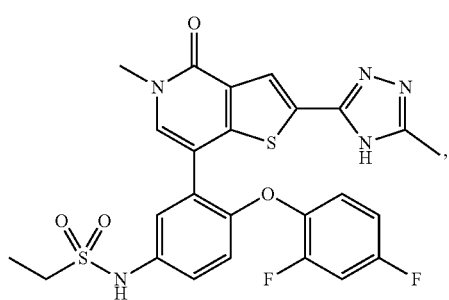
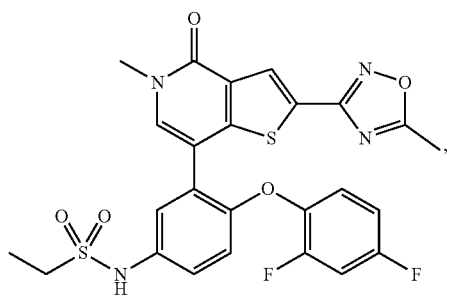
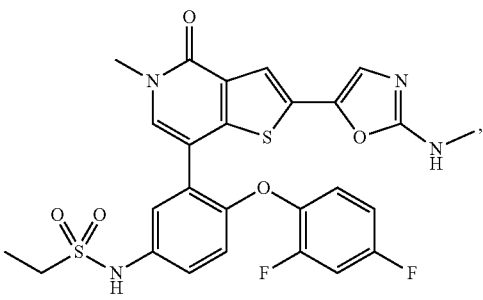
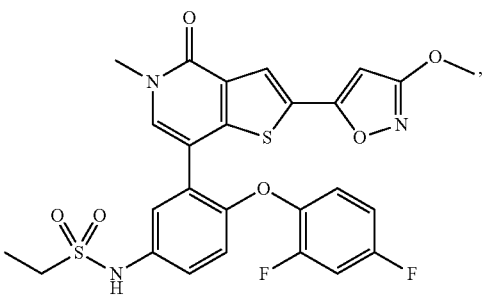
270
-continued
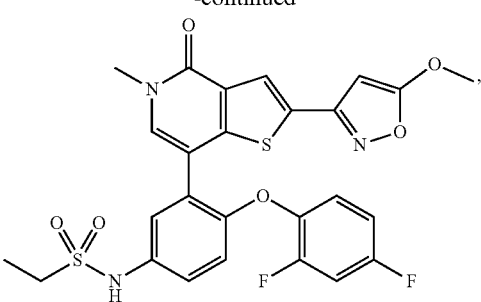
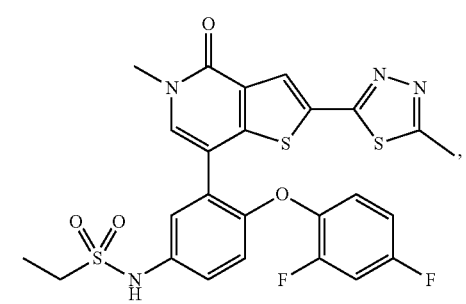
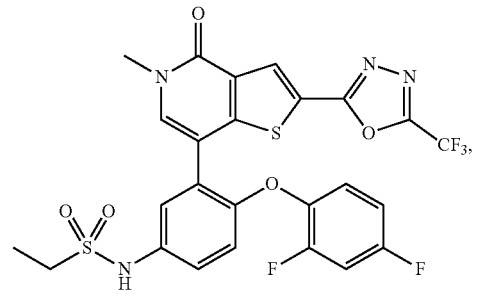
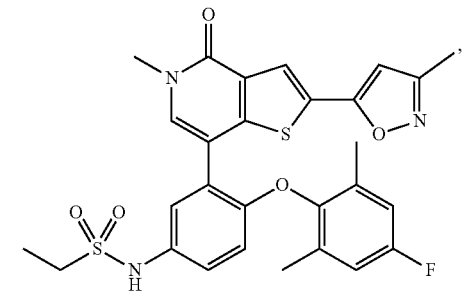
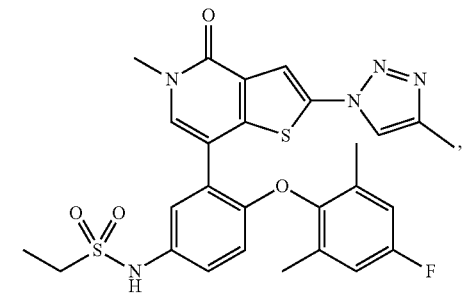

271
-continued
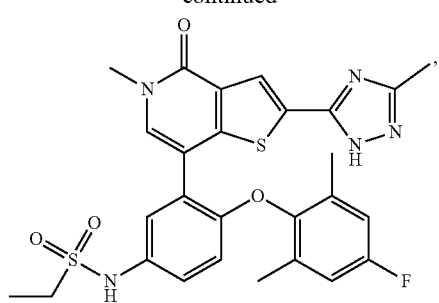
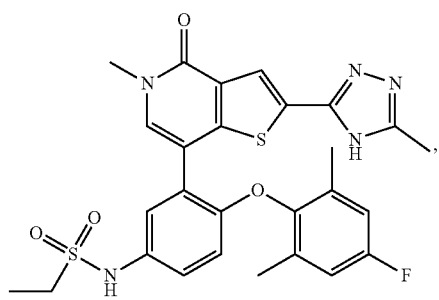
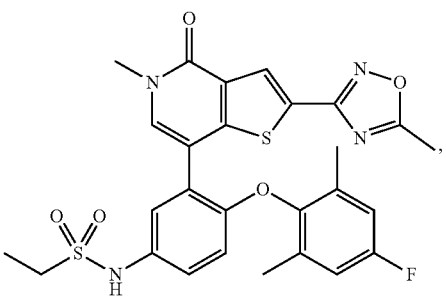
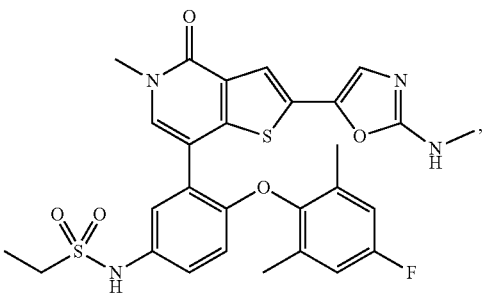
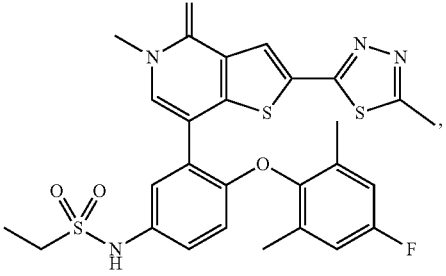
272
-continued
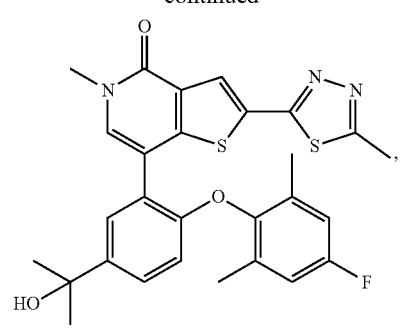
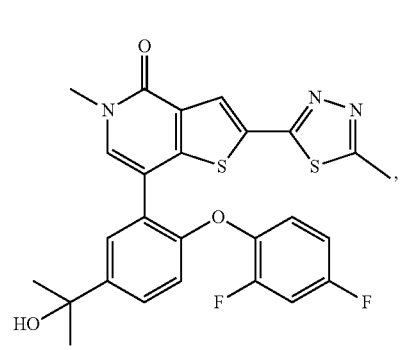
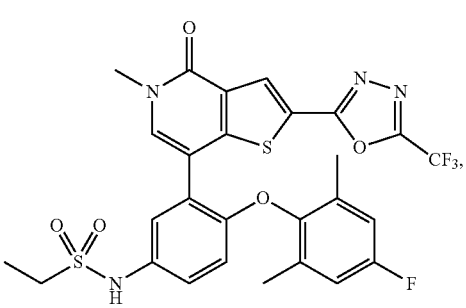
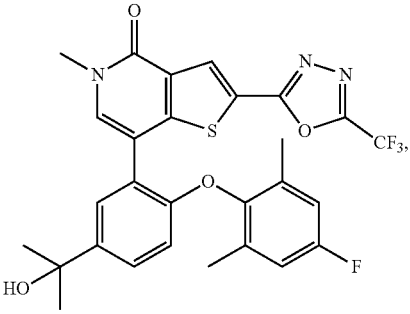
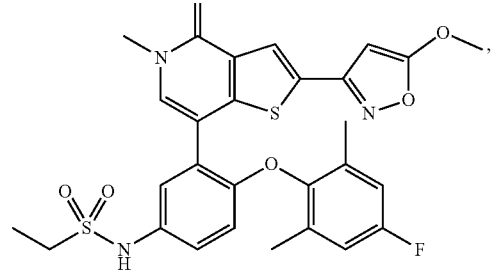

273
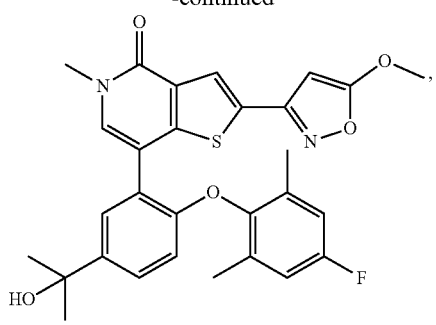
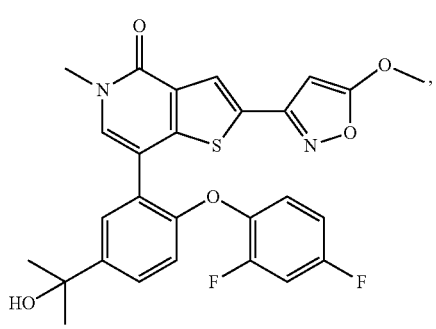
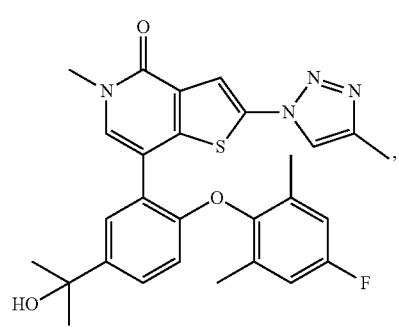
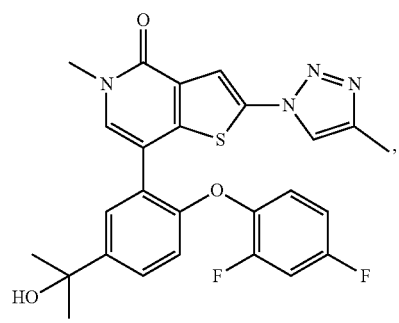
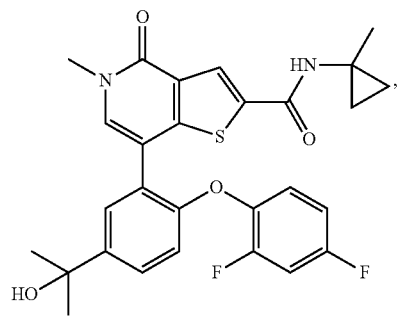
274
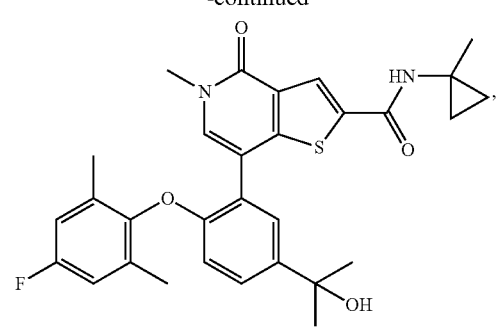
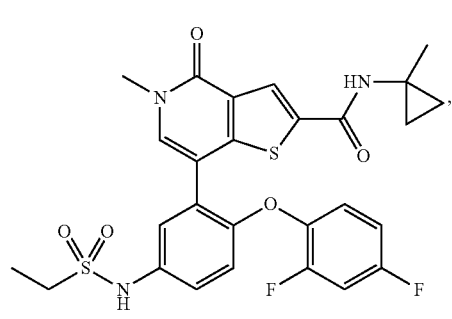
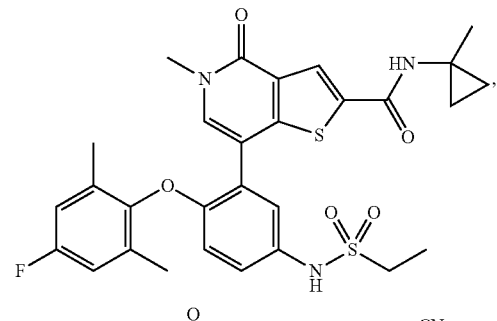
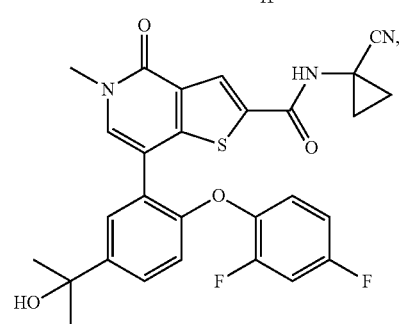
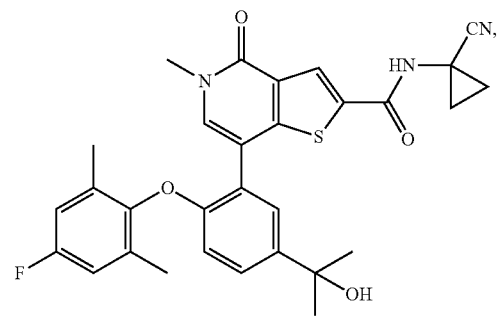

275
-continued
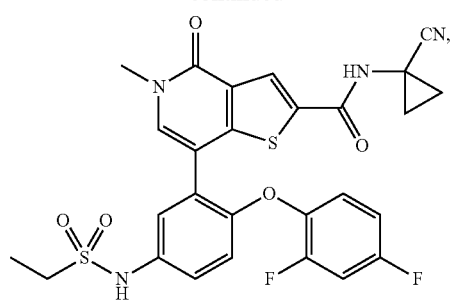
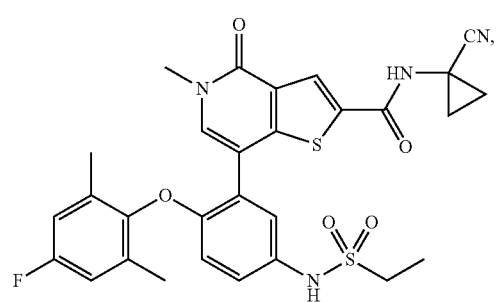
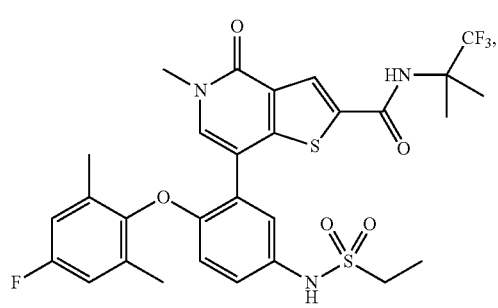
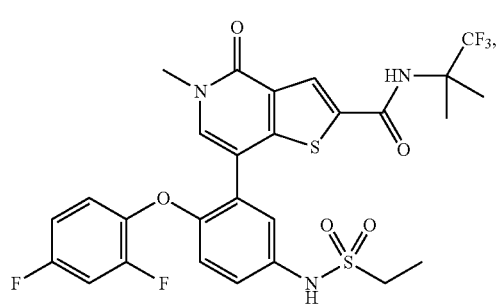
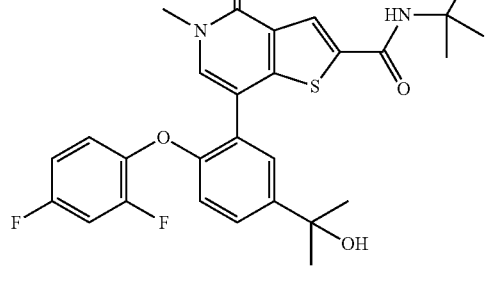
276
-continued
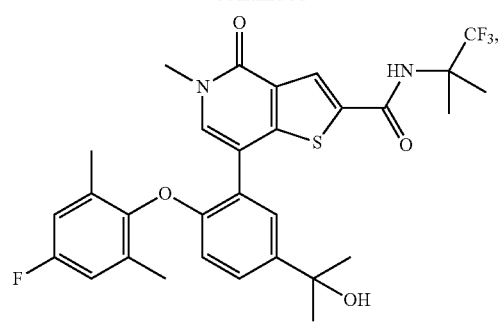
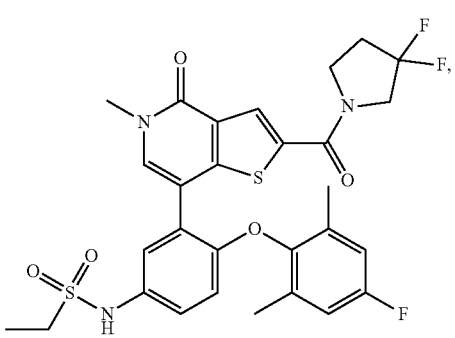
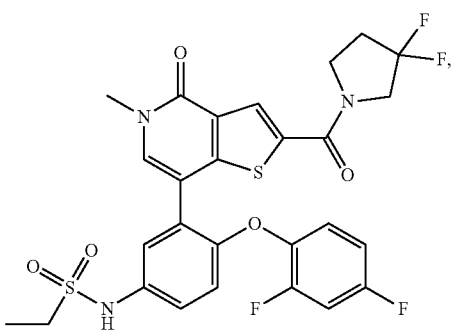
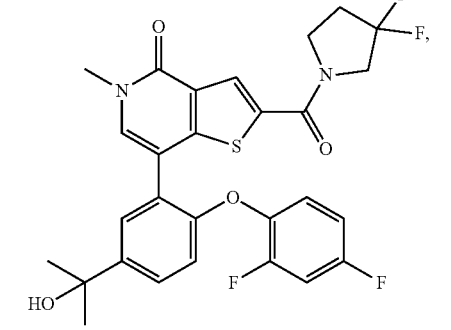
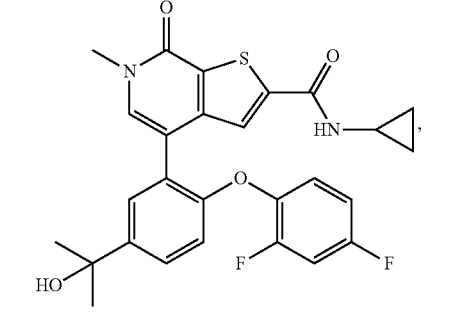

277
-continued
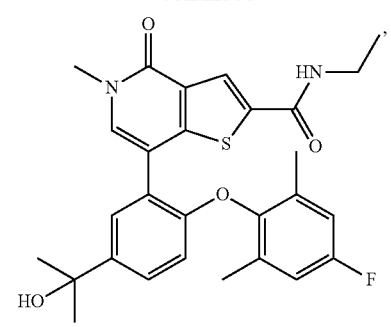
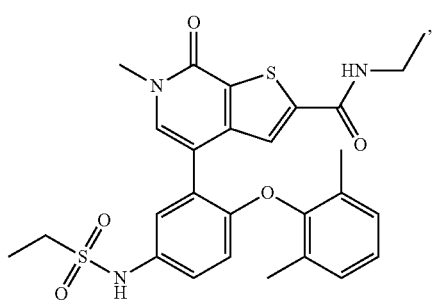
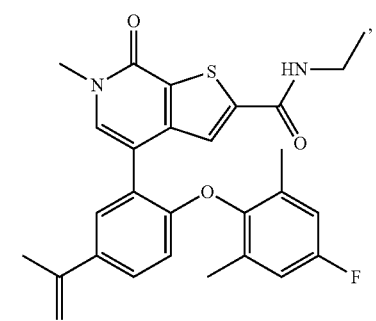
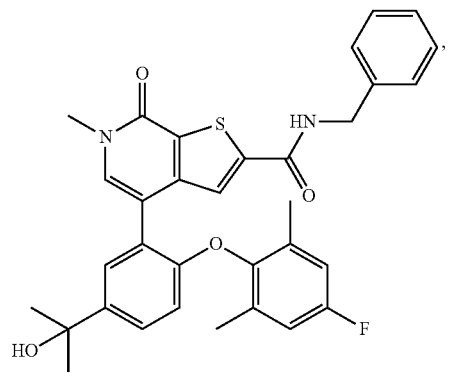
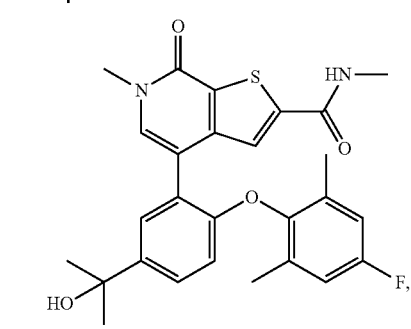
278
-continued
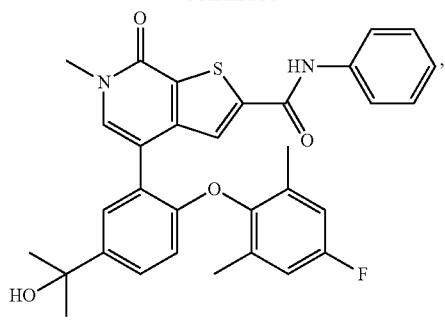
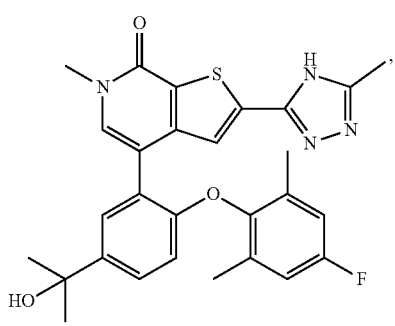
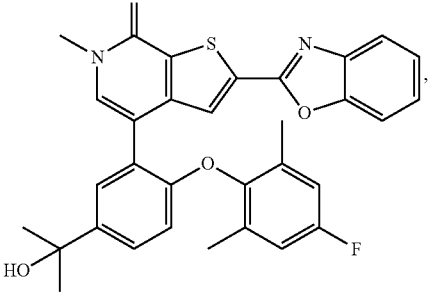
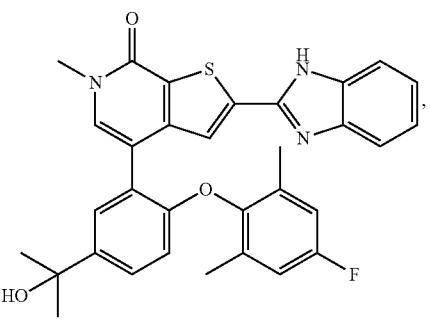
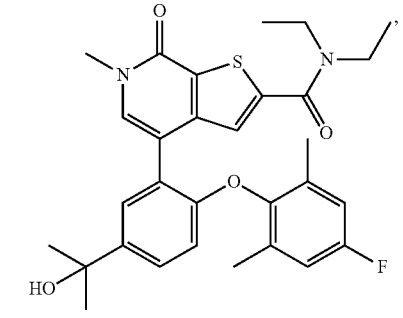

279
-continued
280
-continued
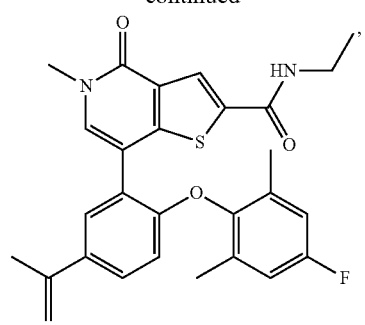
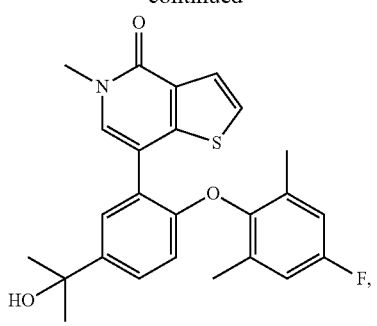
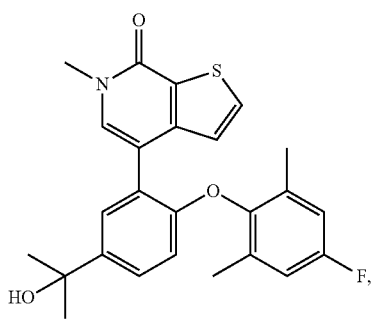

-continued
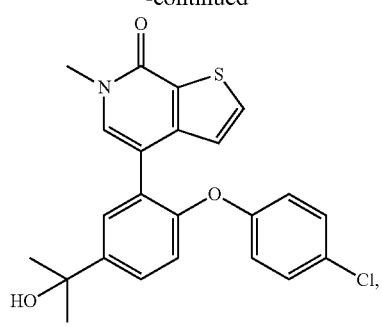
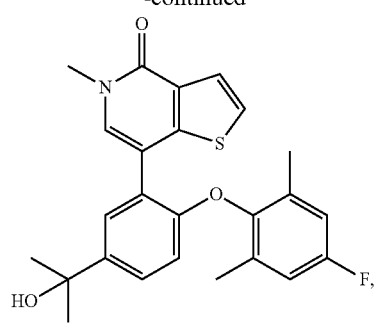

283
-continued
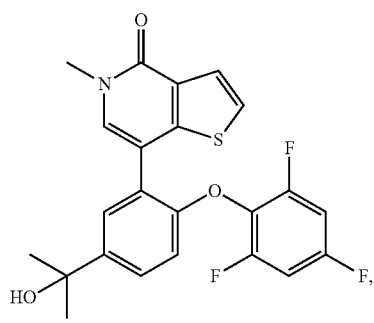
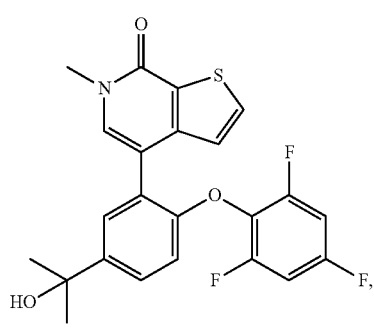
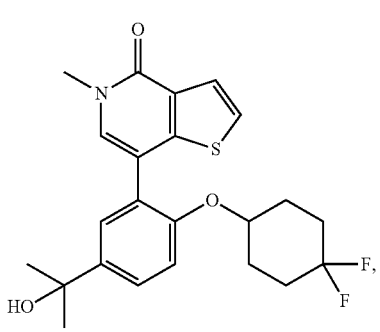
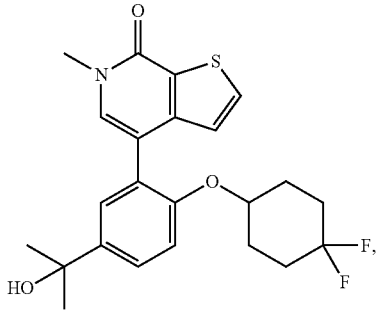
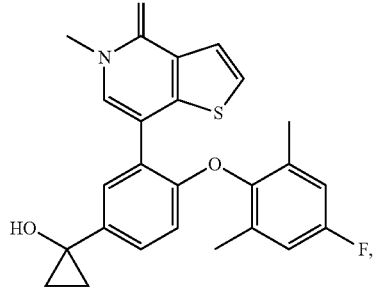
284
-continued
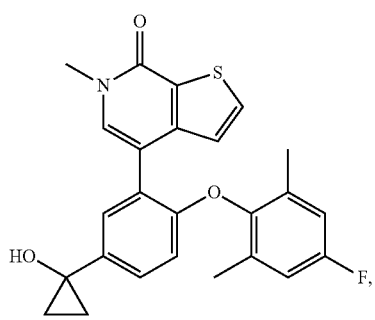
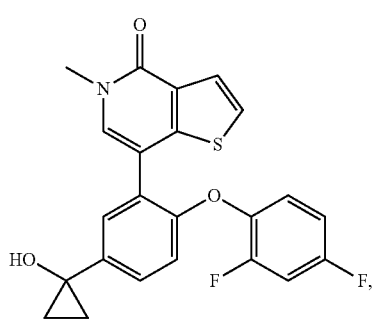
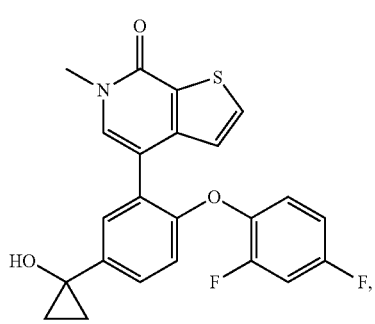
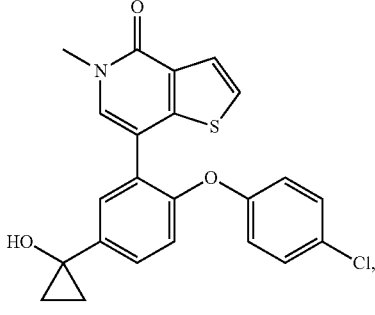
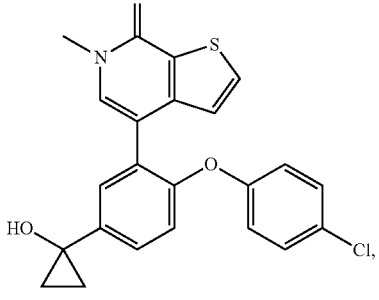

285
-continued
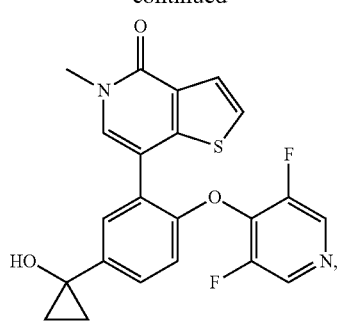
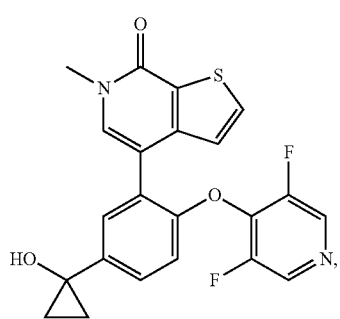
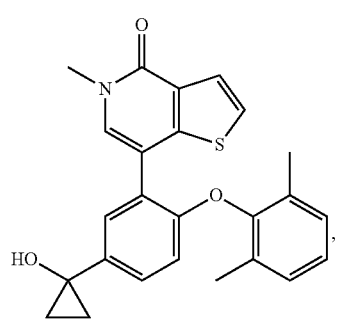
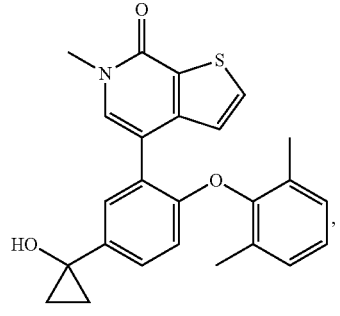
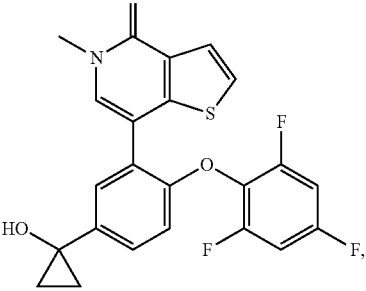
286
-continued
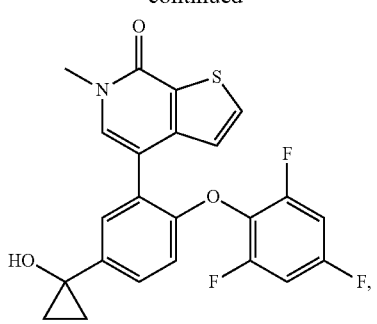
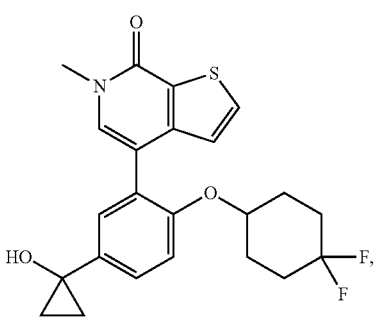
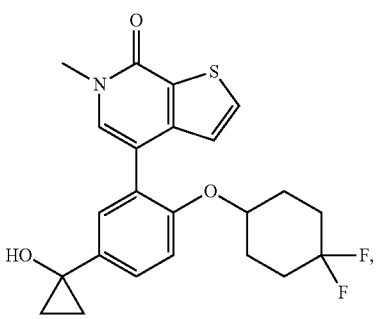
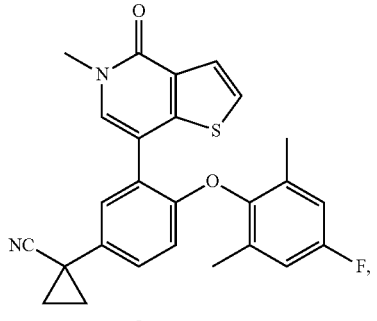
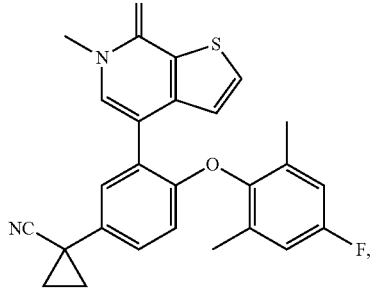

287
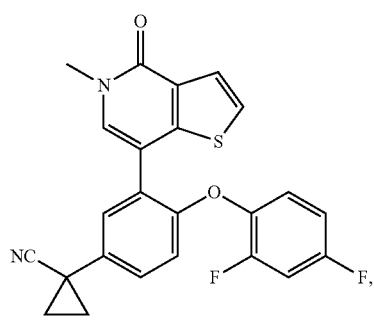
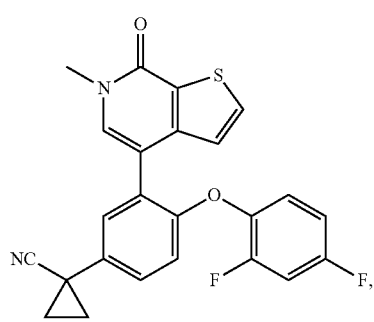
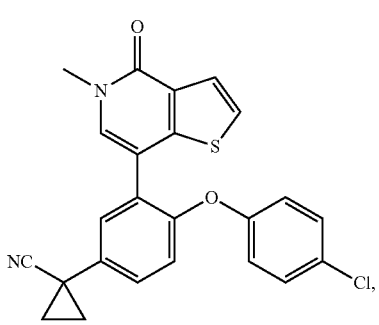
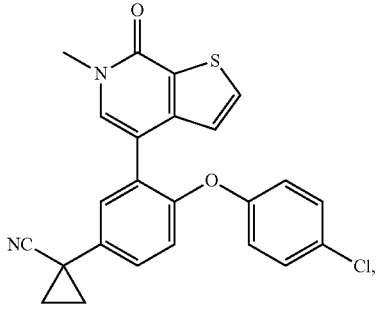
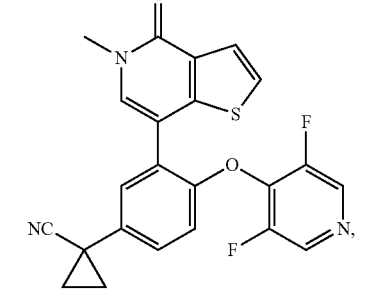
288
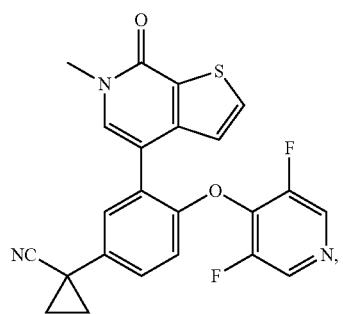
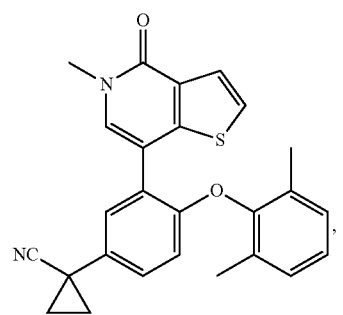
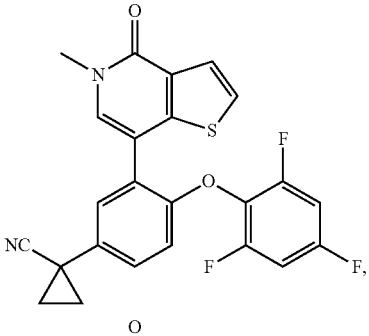
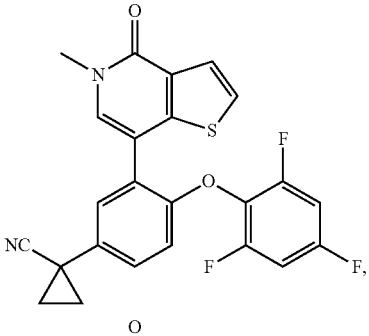
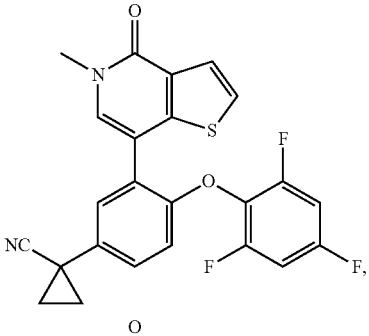

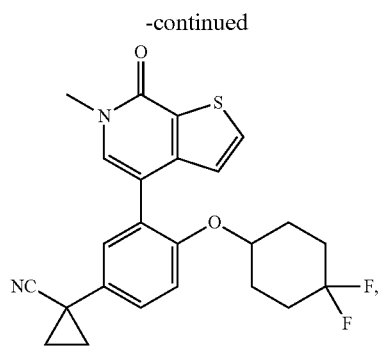
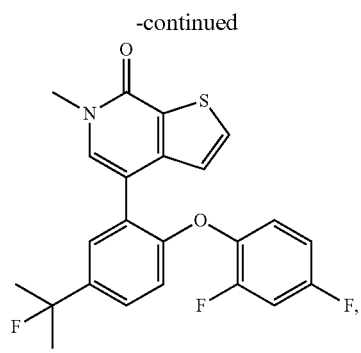

291
-continued
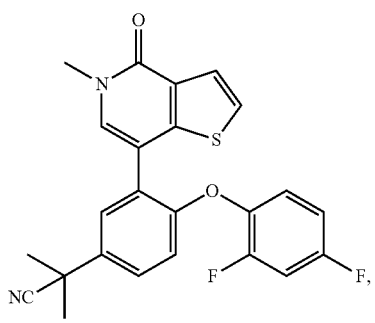
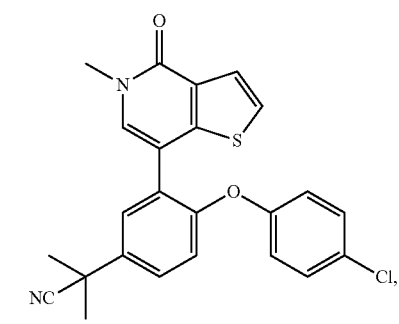
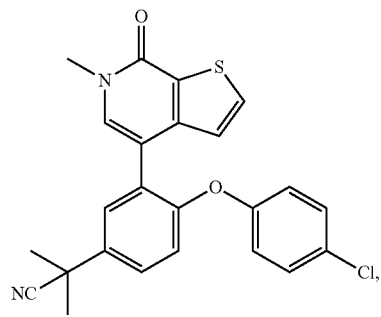
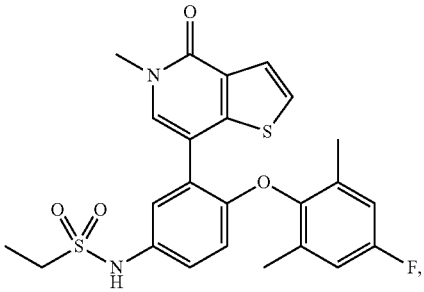
292
-continued
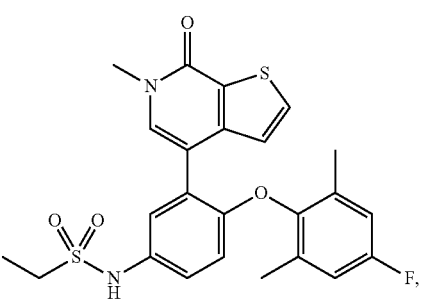
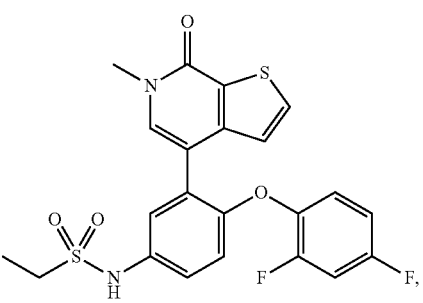
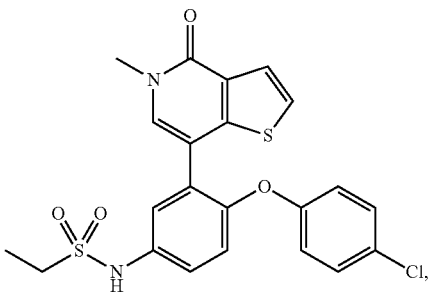
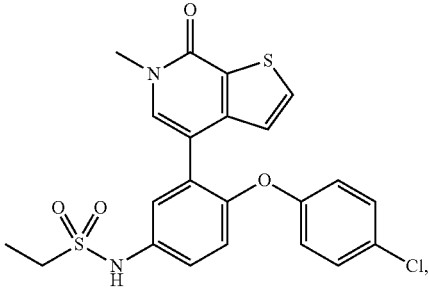

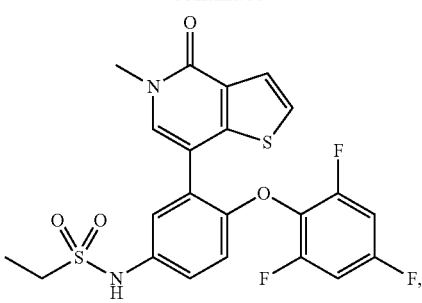

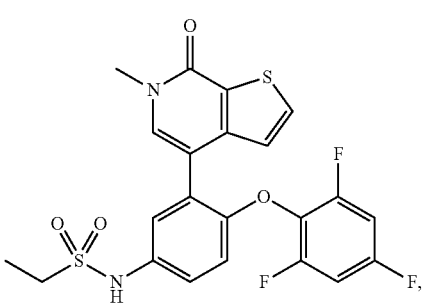

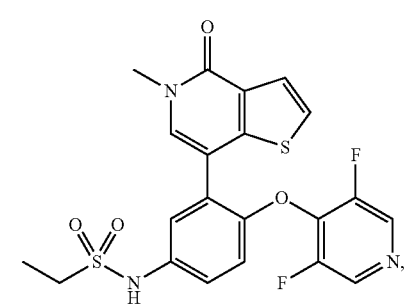

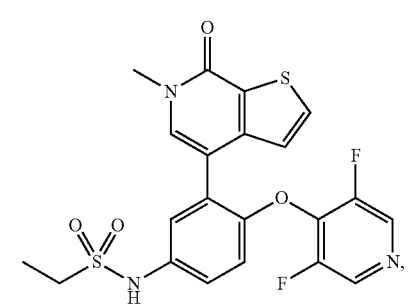

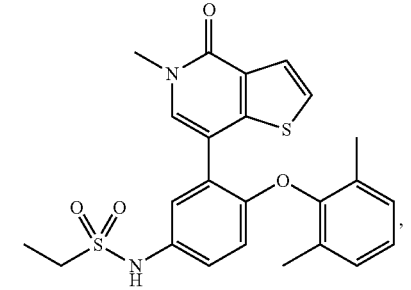

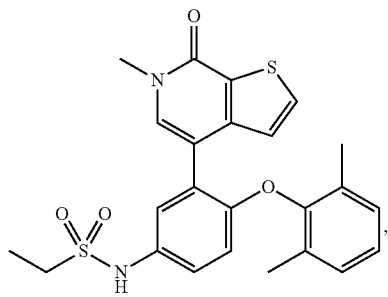

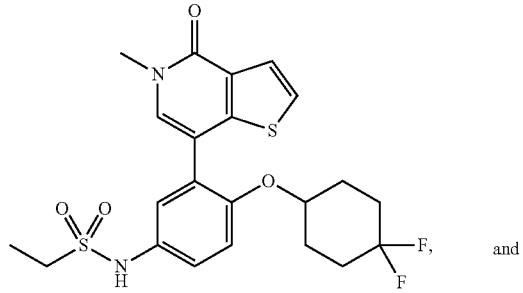

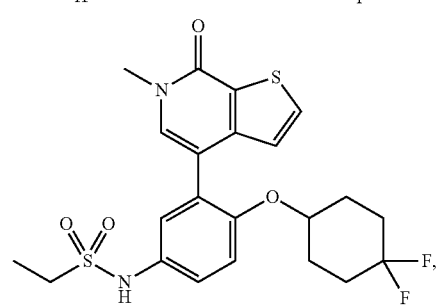

or a pharmaceutically acceptable salt of any of the foregoing.

23. A pharmaceutical composition comprising the compound of claim 1, or a tautomer or stereoisomer thereof, or a pharmaceutically acceptable salt of any of the foregoing, and a pharmaceutically acceptable carrier.

24. A kit comprising the compound of claim 1, or a tautomer or stereoisomer thereof, or a pharmaceutically acceptable salt of any of the foregoing.

25. The compound of claim 22, or a pharmaceutically acceptable salt thereof, wherein the compound is

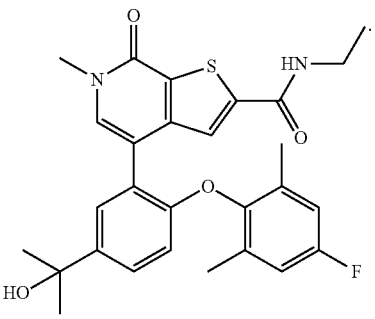 [SMILES: CCNC(=O)c1cc2c(-c3cc(C(C)(C)O)ccc3Oc3c(C)cc(F)cc3C)cn(C)c(=O)c2s1]

26. The compound of claim 22, or a pharmaceutically acceptable salt thereof, wherein the compound is

27. The compound of claim 22, or a pharmaceutically acceptable salt thereof, wherein the compound is

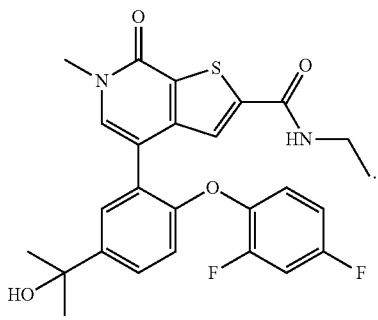 [SMILES: CCNC(=O)c1cc2c(-c3cc(C(C)(C)O)ccc3Oc3ccc(F)cc3F)cn(C)c(=O)c2s1]

28. The compound of claim 22, or a pharmaceutically acceptable salt thereof, wherein the compound is

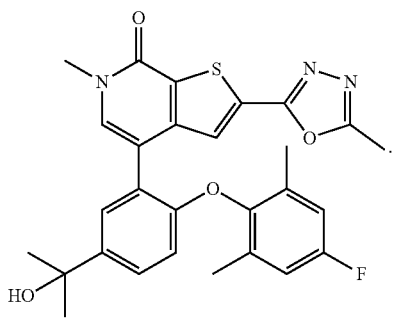 [SMILES: Cc1nnc(-c2cc3c(-c4cc(C(C)(C)O)ccc4Oc4c(C)cc(F)cc4C)cn(C)c(=O)c3s2)o1]

29. The compound of claim 22, or a pharmaceutically acceptable salt thereof, wherein the compound is

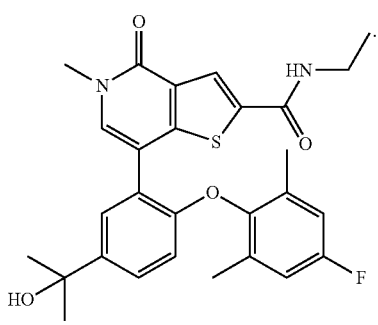 [SMILES: CCNC(=O)c1cc2c(=O)n(C)cc(-c3cc(C(C)(C)O)ccc3Oc3c(C)cc(F)cc3C)c2s1]

30. The compound of claim 22, or a pharmaceutically acceptable salt thereof, wherein the compound is

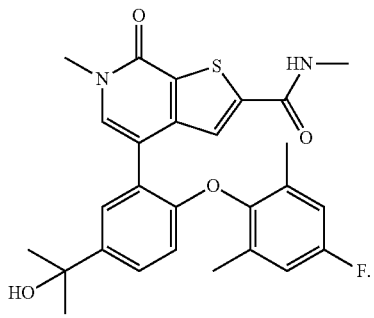 [SMILES: CNC(=O)c1cc2c(-c3cc(C(C)(C)O)ccc3Oc3c(C)cc(F)cc3C)cn(C)c(=O)c2s1]

31. The compound of claim 22, or a pharmaceutically acceptable salt thereof, wherein the compound is

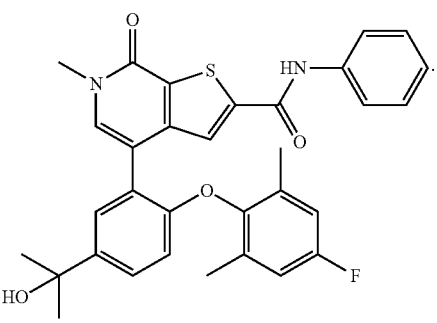 [SMILES: Cc1cc(F)cc(C)c1Oc1ccc(C(C)(C)O)cc1-c1cn(C)c(=O)c2sc(C(=O)Nc3ccccc3)cc12]

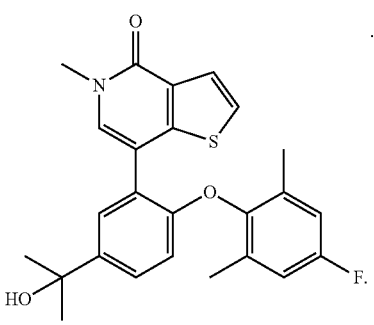 [SMILES: Cc1cc(F)cc(C)c1Oc1ccc(C(C)(C)O)cc1-c1cn(C)c(=O)c2ccsc12]

\* \* \* \* \*